US012497625B2

(12) United States Patent
Glasscock et al.

(10) Patent No.: US 12,497,625 B2
(45) Date of Patent: Dec. 16, 2025

(54) RIBOREGULATED SWITCHABLE FEEDBACK PROMOTER SYSTEMS AND METHODS

(71) Applicants: Northwestern University, Evanston, IL (US); Cornell University, Ithaca, NY (US)

(72) Inventors: Cameron J. Glasscock, Chicago, IL (US); Julius B. Lucks, Chicago, IL (US); Danielle Tullman Ercek, Wilmette, IL (US); Keith Tyo, Evanston, IL (US); Bradley W. Biggs, Evanston, IL (US)

(73) Assignees: Northwestern University, Evanston, IL (US); Cornell University, Ithaca, NY (US)

( * ) Notice: Subject to any disclaimer, the term of this patent is extended or adjusted under 35 U.S.C. 154(b) by 1149 days.

(21) Appl. No.: 17/202,202

(22) Filed: Mar. 15, 2021

(65) Prior Publication Data

US 2021/0198678 A1 Jul. 1, 2021

Related U.S. Application Data

(63) Continuation-in-part of application No. PCT/US2019/051133, filed on Sep. 13, 2019.

(60) Provisional application No. 62/730,720, filed on Sep. 13, 2018.

(51) Int. Cl.
*C12N 15/70* (2006.01)

(52) U.S. Cl.
CPC ........ *C12N 15/70* (2013.01); *C12N 2830/001* (2013.01)

(58) Field of Classification Search
CPC .............. C12N 15/70; C12N 2830/001; C12N 2310/11; C12N 2310/113; C12N 15/63; C12N 15/113
See application file for complete search history.

(56) References Cited

U.S. PATENT DOCUMENTS

| | | | | |
|---|---|---|---|---|
| 4,683,195 | A | 7/1987 | Mullis | |
| 4,683,202 | A | 7/1987 | Mullis | |
| 4,897,355 | A | 1/1990 | Eppstein | |
| 4,946,787 | A | 8/1990 | Eppstein | |
| 5,049,386 | A | 9/1991 | Eppstein | |
| 5,494,810 | A | 2/1996 | Barany | |
| 7,396,664 | B2 | 7/2008 | Daly | |
| 2012/0070870 | A1 | 3/2012 | Way | |
| 2017/0183664 | A1 | 6/2017 | Lucks | |
| 2017/0204477 | A1 | 7/2017 | Green | |
| 2019/0218624 | A1 * | 7/2019 | Green | C12Q 1/68 |
| 2021/0163947 | A1 | 6/2021 | Silverman | |
| 2021/0164059 | A1 | 6/2021 | Jewett | |

FOREIGN PATENT DOCUMENTS

| | | | | |
|---|---|---|---|---|
| WO | 1991016024 | A1 | 10/1991 | |
| WO | 1991017424 | A1 | 11/1991 | |
| WO | WO-2017040829 | A1 * | 3/2017 | C12N 15/67 |

OTHER PUBLICATIONS

Ehrt (Nucleic acids research 33.2 (2005): e21-e21) (Year: 2005).*
Mitosch (Institute of Science and Technology Austria, Klosterneuburg, Austria, 2017) (Year: 2017).*
Weber, W. et al. Inducible product gene expression technology tailored to bioprocess engineering. Current Opinion in Biotechnology (2007). doi:10.1016/j.copbio.2007.09.002.
Wetmur, 1991, Critical Review in Biochem. and Mol. Biol. 26(3/4):227-259.
Xu, P., et al. Improving fatty acids production by engineering dynamic pathway regulation and metabolic control. Proc. Natl. Acad. Sci. U. S. A. (2014). doi:10.1073/pnas.1406401111.
Zhang et al., "Design of a dynamic sensor-regulator system for production of chemicals and fuels derived from fatty acids," Nat. Biotechnol., Mar. 25, 2012;30(4):354-9.
Aertsen, A. et al. Stress and how bacteria cope with death and survival. Critical Reviews in Microbiology (2004). doi:10.1080/10408410490884757.
Ajikumar, P. K. et al. Isoprenoid pathway optimization for Taxol precursor overproduction in *Escherichia coli*. Science (2010). doi:10.1126/science.1191652.
Beaucage, S. L., et al. "Deoxynucleoside phosphoramidites—a new class of key intermediates for deoxypolynucleotide synthesis." Tetrahedron letters 22.20 (1981): 1859-1862.
Belliveau, N. M. et al. Systematic approach for dissecting the molecular mechanisms of transcriptional regulation in bacteria. Proc. Natl. Acad. Sci. (2018). doi:10.1073/pnas.1722055115.
Biggs, B. W. et al. Overcoming heterologous protein interdependency to optimize P450-mediated Taxol precursor synthesis in *Escherichia coli*. Proc. Natl. Acad. Sci. (2016). doi:10.1073/pnas.1515826113.
Biggs, B. W., et al. Multivariate modular metabolic engineering for pathway and strain optimization. Current Opinion in Biotechnology (2014). doi:10.1016/j.copbio.2014.05.005.
Boyarskiy et al., "Transcriptional feedback regulation of efflux protein expression for increased tolerance to and production of n-butanol." Metab. Eng. Jan. 2016;33:130-137.

(Continued)

*Primary Examiner* — Anne M. Gussow
*Assistant Examiner* — Kyle T Rega
(74) *Attorney, Agent, or Firm* — Casimir Jones, S.C.; Rikki A. Hullinger

(57) ABSTRACT

Disclosed are systems and methods that include and utilize engineered riboregulated switchable feedback promoters (rSFPs). The disclosed systems and methods include and utilize as a component one or more expression cassettes. At least one expression cassette of the disclosed systems and methods comprises a promoter operably linked to DNA encoding an RNA switch located 3' of the promoter and a target gene or operon located 3' of the DNA encoding the RNA switch, where the RNA switch regulates expression of the target gene. Suitable promoters may include stress responsive promoters. The disclosed systems and methods may include and utilize a second expression cassette that includes an inducible promoter for expressing an RNA effector of the RNA switch in the first expression cassette.

10 Claims, 51 Drawing Sheets

Specification includes a Sequence Listing.

(56) References Cited

OTHER PUBLICATIONS

Brockman, I. M. et al. Dynamic metabolic engineering: New strategies for developing responsive cell factories. Biotechnol. J. (2015). doi:10.1002/biot.201400422.
Brown, E. L., et al. "[8] Chemical synthesis and cloning of a tyrosine tRNA gene." Methods in Enzymology. vol. 68. Academic Press, 1979. 109-151.
Carothers, J. M., et al. Model-driven engineering of RNA devices to quantitatively program gene expression. Science (2011). doi:10.1126/science.1212209.
Ceroni, F. et al. Burden-driven feedback control of gene expression. Nat. Methods (2018). doi:10.1038/nmeth.4635.
Chang, M. C. Y., et al. Engineering *Escherichia coli* for production of functionalized terpenoids using plant P450s. Nat. Chem. Biol. (2007). doi:10.1038/nchembio875.
Chappell et al., "Creating small transcription activating RNAs," Nat. Chem. Biol., Mar. 2015;11(3):214-20.
Chappell, J., et al. "Computational design of small transcription activating RNAs for versatile and dynamic gene regulation." Nature communications 8.1 (2017): 1-12.
Dahl et al., "Engineering dynamic pathway regulation with stress-response promoters," Nat. Biotechnol. Nov. 2013;31(11):1039-46.
Engebrecht, J. et al. Identification of genes and gene products necessary for bacterial bioluminescence. Proc. Natl. Acad. Sci. U. S. A. (1984). doi:10.1073/pnas.81.13.4154.
Farmer, W. R. et al. Improving lycopene production in *Escherichia coli* by engineering metabolic control. Nat. Biotechnol. (2000). doi:10.1038/75398.
Glasscock, C. et al. Inducible feedback promoters for dynamic gene regulation. Engineering Biology Research Consortium Fall Retreat, Sep. 13-14, 2018.
Glasscock, C. J. et al. A flow cytometric approach to engineering *Escherichia coli* for improved eukaryotic protein glycosylation. Metab. Eng. (2018). doi:10.1016/j.ymben.2018.04.014.
Goodchild, J. "Conjugates of oligonucleotides and modified oligonucleotides: a review of their synthesis and properties." Bioconjugate Chemistry 1.3 (1990): 165-187.
Green, A. A., et al. "Toehold switches: de-novo-designed regulators of gene expression." Cell 159.4 (2014): 925-939.
Gupta et al., "Dynamic regulation of metabolic flux in engineered bacteria using a pathway-independent quorum-sensing circuit," Nat. Biotechnol., Mar. 2017;35(3):273-279.
International Searching Authority. International Search Report and Written Opinion for application PCT/US2019/051133. Mailed on Dec. 19, 2019. 7 pages.
Isabella, V. M. et al. Development of a synthetic live bacterial therapeutic for the human metabolic disease phenylketonuria. Nat. Biotechnol. (2018). doi:10.1038/nbt.4222.
Jones, J. A. et al. EPathOptimize: A combinatorial approach for transcriptional balancing of metabolic pathways. Sci. Rep. (2015). doi:10.1038/srep11301.
Keasling, J. D. Manufacturing molecules through metabolic engineering. Science (2010). doi:10.1126/science.1193990.
Kim, E. M. et al. Autonomous control of metabolic state by a quorum sensing (QS)-mediated regulator for bisabolene production in engineered *E. coli*. Metab. Eng. (2017). doi:10.1016/j.ymben.2017.11.004.
Leonard, E. et al. Engineering of artificial plant cytochrome P450 enzymes for synthesis of isoflavones by *Escherichia coli*. Appl. Environ. Microbiol. (2007). doi:10.1128/AEM.01411-07.
Lo, T.-M., et al. "A two-layer gene circuit for decoupling cell growth from metabolite production." Cell systems 3.2 (2016): 133-143.
Lutz, R. et al. "Independent and tight regulation of transcriptional units in *Escherichia coli* via the LacR/O, the TetR/O and AraC/I1-I2 regulatory elements." Nucleic Acids Research 25.6 (1997): 1204.
Malinowski, J. J. Two-phase partitioning bioreactors in fermentation technology. Biotechnology Advances (2001). doi:10.1016/S0734-9750(01)00080-5.
Meier, I., et al. Differential regulation of the Tn10-encoded tetracycline resistance genes tetA and tetR by the tandem tet operators O1 and O2. EMBO J. (1988). doi:10.1002/j.1460-2075.1988.tb02846.x.
Minogue, T. D., et al. "The autoregulatory role of EsaR, a quorum-sensing regulator in *Pantoea stewartii* ssp. stewartii: evidence for a repressor function." Molecular microbiology 44.6 (2002): 1625-1635.
Moser, F. et al. "Dynamic control of endogenous metabolism with combinatorial logic circuits." Molecular systems biology 14.11 (2018): e8605.
Mutalik, V. K. et al. "Precise and reliable gene expression via standard transcription and translation initiation elements." Nature methods 10.4 (2013): 354-360.
Narang, S. A. et al. "[6] Improved phosphotriester method for the synthesis of gene fragments." Methods in Enzymology. vol. 68. Academic Press, 1979. 90-98.
Nielsen, J. et al. Engineering Cellular Metabolism. Cell (2016). doi:10.1016/j.cell.2016.02.004.
Owczarzy, R., et al. "Predicting stability of DNA duplexes in solutions containing magnesium and monovalent cations." Biochemistry 47.19 (2008): 5336-5353.
Papenfort, K. et al. Quorum sensing signal-response systems in Gramnegative bacteria. Nature Reviews Microbiology (2016). doi:10.1038/nrmicro.2016.89.
Smanski, M. J. et al. Functional optimization of gene clusters by combinatorial design and assembly. Nat. Biotechnol. (2014). doi:10.1038/nbt.3063.
St-Pierre, F. et al. One-step cloning and chromosomal integration of DNA. ACS Synth. Biol. (2013). doi:10.1021/sb400021j.
Sun, J., et al. Metabolite damage and repair in metabolic engineering design. Metabolic Engineering (2017). doi:10.1016/j.ymben.2017.10.006.
Tan, C., et al. Emergent bistability by a growth-modulating positive feedback circuit. Nat. Chem. Biol. (2009). doi:10.1038/nchembio.218.
Tan, S. Z. et al. Dynamic pathway regulation: recent advances and methods of construction. Current Opinion in Chemical Biology (2017). doi:10.1016/j.cbpa.2017.10.004.
Tatusova, T.A. et al. (1999), "Blast 2 sequences—a new tool for comparing protein and nucleotide sequences", FEMS Microbiol Lett. 174:247-250.
Tsao, C. Y., et al. Autonomous induction of recombinant proteins by minimally rewiring native quorum sensing regulon of *E. coli*. Metab. Eng. (2010). doi:10.1016/j.ymben.2010.01.002.
Valderrama-Rincon, J. D. et al. An engineered eukaryotic protein glycosylation pathway in *Escherichia coli*. Nat. Chem. Biol. (2012). doi:10.1038/nchembio.921.
Van Dien, S. From the first drop to the first truckload: Commercialization of microbial processes for renewable chemicals. Current Opinion in Biotechnology (2013). doi:10.1016/j.copbio.2013.03.002.
Venayak, N., et al. Engineering metabolism through dynamic control. Current Opinion in Biotechnology (2015). doi:10.1016/j.copbio.2014.12.022.
Watstein, D. M., et al. Precise metabolic engineering of carotenoid biosynthesis in *Escherichia coli* towards a low-cost biosensor. Metab. Eng. (2015). doi:10.1016/j.ymben.2015.06.007.

* cited by examiner

STAR
mCherry
Fold Act. @ 6 hrs = 30.1
Fold Act. @ 6 hrs = 94.3
Fold Act. @ 6 hrs = 49.8
0 ng/mL aTc
100 ng/mL aTc
Time (hrs)
FL/OD x 10⁴(au)

SEQUENCE LISTING

<160> NUMBER OF SEQ ID NOS: 38

<210> SEQ ID NO 1
<211> LENGTH: 1074
<212> TYPE: DNA
<213> ORGANISM: Artificial Sequence
<220> FEATURE:
<223> OTHER INFORMATION: synthetic

<400> SEQUENCE: 1
gaattctaaa gatctttttc tctatcactg atagggagtg gtaaaataac tctatcaacg 60
atagagtgtc aacaaaaatt aggaattaat gatgtcgaga ttagataaaa gtaaagtgat 120
taacagcgca ttagagctgc ttaatgaggt cggaatcgaa ggtttaacaa cccgtaaact 180
cgcccagaag ctaggtgtag agcagcctac attgtattgg catgtaaaaa ataagcgggc 240
tttgctcgac gccttagcca ttgagatgtt agataggcac catactcact tttgcccttt 300
agaaggggaa agctggcaag atttttacg taataacgct aaaagtttta gatgtgcttt 360
actaagtcat cgcgatggag caaaagtaca tttaggtaca cggcctacag aaaaacagta 420
tgaaactctc gaaaatcaat tagccttttt atgccaacaa ggtttttcac tagagaatgc 480
attatatgca ctcagcgctg tggggcattt tactttaggt tgcgtattgg aagatcaaga 540
gcatcaagtc gctaaagaag aaagggaaac acctactact gatagtatgc cgccattatt 600
acgacaagct atcgaattat ttgatcacca aggtgcagag ccagccttct tattcggcct 660
tgaattgatc atatgcggat tagaaaaaca acttaaatgt gaaagtgggt cttaataaca 720
ctgatagtgc tagtgtagat cactactaga gccaggcatc aaataaaacg aaaggctcag 780
tcgaaagact gggcctttcg ttttatctgt tgtttgtcgg tgaacgctct ctactagagt 840
cacactggct caccttcggg tgggcctttc tgcgtttata tactagagtc cctatcagtg 900
atagagattg acatccctat cagtgataga gatactgagc actgaactgt atacattccc 960
cgcaggataa gagtaagtga gagtaggtag agattgagga tggggatctc aaagcccgcc 1020
gaaaggcggg cttttttttg gatccttact cgagtctaga ctgcaggctt cctc 1074

<210> SEQ ID NO 2
<211> LENGTH: 208
<212> TYPE: DNA
<213> ORGANISM: Artificial Sequence
<220> FEATURE:
<223> OTHER INFORMATION: synthetic

<400> SEQUENCE: 2
ctaaagatct atatactaga gacctgtagg atcgtacagg tttacgcaag aaaatggttt 60
gttatagtcg aataaatgaa ctgtatacat tccccgcagg ataagagtaa gtgagagtag 120
gtagagattg aggatgggga tctcaaagcc cgccgaaagg cgggcttttt tttggatcct 180
tactcgagtc tagactgcag gcttcctc 208

<210> SEQ ID NO 3
<211> LENGTH: 1437
<212> TYPE: DNA
<213> ORGANISM: Artificial Sequence
<220> FEATURE:
<223> OTHER INFORMATION: synthetic

<400> SEQUENCE: 3
cgatcatcct gttacggaat attacattgc aacatttacg cgcaaaaact aatccgcatt 60
cttattgcgg attagttttt tcttagctaa tagcacaatt ttcatactat tttttggcat 120

```
tctggatgtc tgaaagaaga ttttgtgcca ggtcgataaa gtttccatca gaaacaaaat    180

ttccgtttag ttaatttaaa tataaggaaa tcatataaat agattaaaat tgctgtaaat    240

atcatcacgt ctctatggaa atatgacggt gttcacaaag ttccttaaat tttacttttg    300

gttacatatt ttttcttttt gaaaccaaat ctttatcttt gtagcacttt cacggtagcg    360

aaacgttagt ttgaatggaa agatgcctgc agacacataa agacaccaaa ctctcatcaa    420

tagttccgta aatttttatt gacagaactt attgacggca gtggcaggtg tcataaaaaa    480

aaccatgagg gtaataaata ccatcctcaa tctctaccta ctctcactta ctcttatcct    540

gcggggaatg tatacagttc atgtatatat tccccgcttt ttttttggat ctaggaggaa    600

ggatctatgg cgagtagcga agacgttatc aaagagttca tgcgtttcaa agttcgtatg    660

gaaggttccg ttaacggtca cgagttcgaa atcgaaggtg aaggtgaagg tcgtccgtac    720

gaaggtaccc agaccgctaa actgaaagtt accaaaggtg gtccgctgcc gttcgcttgg    780

gacatcctgt ccccgcagtt ccagtacggt tccaaagctt acgttaaaca cccggctgac    840

atcccggact acctgaaact gtccttcccg gaaggtttca aatgggaacg tgttatgaac    900

ttcgaagacg gtggtgttgt taccgttacc caggactcct ccctgcaaga cggtgagttc    960

atctacaaag ttaaactgcg tggtaccaac ttcccgtccg acggtccggt tatgcagaaa   1020

aaaaccatgg gttgggaagc ttccaccgaa cgtatgtacc cggaagacgg tgctctgaaa   1080

ggtgaaatca aaatgcgtct gaaactgaaa gacggtggtc actacgacgc tgaagttaaa   1140

accacctaca tggctaaaaa accggttcag ctgccgggtg cttacaaaac cgacatcaaa   1200

ctggacatca cctcccacaa cgaagactac accatcgttg aacagtacga acgtgctgaa   1260

ggtcgtcact ccaccggtgc ttaaggatcc aaactcgagt aaggatctcc aggcatcaaa   1320

taaaacgaaa ggctcagtcg aaagactggg cctttcgttt tatctgttgt ttgtcggtga   1380

acgctctcta ctagagtcac actggctcac cttcgggtgg gcctttctgc gtttata      1437
```

<210> SEQ ID NO 4
<211> LENGTH: 3396
<212> TYPE: DNA
<213> ORGANISM: Artificial Sequence
<220> FEATURE:
<223> OTHER INFORMATION: synthetic

<400> SEQUENCE: 4

```
atggctctgt tattagcagt ttttttagc atcgctttga gtgcaattgc cgggatcttg     60

ctgttgctcc tgctgtttcg ctcgaaacgt catagtagcc tgaaattacc tccgggcaaa    120

ctgggcattc cgtttatcgg tgagtccttt attttttttgc gcgcgctgag gagcaattct    180

ctggaacagt tctttgatga acgtgtgaag aagttcggcc tggtatttaa aacgtccctt    240

atcggtcacc cgacggttgt cctgtgcggg cccgcaggta atcgcctcat cctgagcaac    300

gaagaaaagc tggtacagat gtcctggccg gcgcagttta tgaagctgat gggagagaac    360

tcagttgcga cccgccgtgg tgaagatcac attgttatgc gctccgcgtt ggcaggcttt    420

ttcggcccgg gagctctgca atcctatatc ggcaagatga acacggaaat ccaaagccat    480

attaatgaaa agtggaaagg gaaggacgag gttaatgtct taccccctggt gcgggaactg    540

gtttttaaca tcagcgctat tctgttcttt aacatttacg ataagcagga acaagaccgt    600

ctgcacaagt tgttagaaac cattctggta ggctcgtttg ccttaccaat tgatttaccg    660

ggtttcgggt ttcaccgcgc tttacaaggt cgtgcaaaac tcaataaaat catgttgtcg    720
```

-continued

```
cttattaaaa aacgtaaaga ggacttacag tcgggatcgg ccaccgcgac gcaggacctg    780
ttgtctgtgc ttctgacttt ccgtgatgat aagggcaccc cgttaaccaa tgacgaaatc    840
ctggacaact ttagctcact gcttcacgcc tcttacgaca ccacgactag tccaatggct    900
ctgattttca aattactgtc aagtaaccct gaatgctatc agaaagtcgt gcaagagcaa    960
ctcgagattc tgagcaataa ggaagaaggt gaagaaatta cctggaaaga tcttaaggcc   1020
atgaaataca cgtggcaggt tgcgcaggag acacttcgca tgtttccacc ggtgttcggg   1080
accttccgca aagcgatcac ggatattcag tatgacggat acacaatccc gaaaggttgg   1140
aaactgttgt ggactaccta tagcactcat cctaaggacc tttacttcaa cgaaccggag   1200
aaatttatgc ctagtcgttt cgatcaggaa ggcaaacatg ttgcgcccta taccttcctg   1260
ccctttggag gcggtcagcg gagttgtgtg ggttgggagt tctctaagat ggagattctc   1320
ctcttcgtgc atcatttcgt gaaaacattt tcgagctata ccccggtcga tcccgatgaa   1380
aaaatttccg gcgatccact gccgccgtta ccgagcaaag ggttttcaat caaactgttc   1440
cctcgtccgg gcagcaccgg atcccgccgt ggtggaagtg atacacagaa gcccgccgta   1500
cgtcccacac ctcttgttaa agaagaggac gaagaagaag aagatgatag cgccaagaaa   1560
aaggtcacaa tattttttgg cacccagacc ggcaccgccg aaggtttcgc aaaggcctta   1620
gctgaggaag caaaggcacg ttatgaaaag gcggtattta aagtcgtgga tttggataac   1680
tatgcagcgg atgacgaaca gtacgaagag aagttgaaaa aggaaaagct agcgttcttc   1740
atgctcgcca cctacggtga cggcgaaccg actgataatg ccgctcgctt ttataaatgg   1800
tttctcgagg gtaaagagcg cgagccatgg ttgtcagatc tgacttatgg cgtgtttggc   1860
ttaggtaacc gtcagtatga acactttaac aaggtcgcga aagcggtgga cgaagtgctc   1920
attgaacaag gcgccaaacg tctggtaccg gtagggcttg gtgatgatga tcagtgcatt   1980
gaggacgact tcactgcctg gagagaacaa gtgtggcctg agctggatca gctcttacgt   2040
gatgaagatg acgagccgac gtctgcgacc ccgtacacgg cggctattcc agaataccgg   2100
gtggaaatct acgactcagt agtgtcggtc tatgaggaaa cccatgcgct gaaacaaaat   2160
ggacaagccg tatacgatat ccaccacccg tgtcgcagca acgtggcagt acgtcgtgag   2220
ctgcataccc cgctgtcgga tcgtagttgt attcatctgg aattcgatat tagtgatact   2280
gggttaatct atgagacggg cgaccacgtt ggagttcata ccgagaattc aattgaaacc   2340
gtggaagaag cagctaaact gttaggttac caactggata caatcttcag cgtgcatggg   2400
gacaaggaag atggaacacc attgggcggg agtagcctgc caccgccgtt tccggggccc   2460
tgcacgctgc ggacggcgct ggcacgttac gcggacctgc tgaaccctcc gcgcaaagcc   2520
gccttcctgg cactggccgc acacgcgtca gatccggctg aagctgaacg ccttaaattt   2580
ctcagttctc cagccggaaa agacgaatac tcacagtggg tcactgcgtc ccaacgcagc   2640
ctcctcgaga ttatggccga attccccagc gcgaaaccgc cgctgggagt gtttttcgcc   2700
gcaatagcgc cgcgcttgca acctaggtat tatagcatct cctcctcccc gcgtttcgcg   2760
ccgtctcgta tccatgtaac gtgcgcgctg gtctatggtc ctagccctac ggggcgtatt   2820
cataaaggtg tgtgcagcaa ctggatgaag aattctttgc cctccgaaga aacccacgat   2880
tgcagctggg caccggtctt tgtgcgccag tcaaacttta aactgcccgc cgattcgacg   2940
acgccaatcg tgatggttgg acctggaacc ggcttcgctc catttcgcgg cttccttcag   3000
gaacgcgcaa aactgcagga agcgggcgaa aaattgggcc cggcagtgct gtttttttggg   3060
tgccgcaacc gccagatgga ttacatctat gaagatgagc ttaagggtta cgttgaaaaa   3120
```

ggtattctga cgaatctgat cgttgcattt tcacgagaag gcgccaccaa agagtatgtt 3180
cagcacaaga tgttagagaa agcctccgac acgtggtctt taatcgccca gggtggttat 3240
ctgtatgttt gcggtgatgc gaagggtatg gccagagacg tacatcgcac cctgcataca 3300
atcgttcagg aacaagaatc cgtagactcg tcaaaagcgg agtttttagt caaaaagctg 3360
caaatggatg gacgctactt acgggatatt tggtaa 3396

<210> SEQ ID NO 5
<211> LENGTH: 1701
<212> TYPE: DNA
<213> ORGANISM: Artificial Sequence
<220> FEATURE:
<223> OTHER INFORMATION: synthetic

<400> SEQUENCE: 5
ttgacaatta atcatccggc tcgtaatgtt tgtggagggc ccaagttcac ttaaaaagga 60
gatcaacaat gaaagcaatt ttcgtactga aacatcttaa tcatgctaag gaggttttct 120
aatgatgctt gaactgtttg acgtcagtta cgaagaactg caaaccaccc gttcagaaga 180
actttataaa cttcgcaaga aaacatttag cgatcgtctg ggatgggaag tcatttgcag 240
tcagggaatg gagtccgatg aatttgatgg gcccggtaca cgttatattc tgggaatctg 300
cgaaggacaa ttagtgtgca gcgtacgttt taccagcctc gatcgtccca acatgatcac 360
gcacactttt cagcactgct tcagtgatgt caccctgccc gcctatggta ccgaatccag 420
ccgttttttt gtcgacaaag cccgcgcacg tgcgctgtta ggtgagcact accctatcag 480
ccaggtcctg tttttagcga tggtgaactg ggcgcaaaat aatgcctacg gcaatatcta 540
tacgattgtc agccgcgcga tgttgaaaat tctcactcgc tctggctggc aaatcaaagt 600
cattaaagag gctttcctga ccgaaaagga acgtatctat ttgctgacgc tgccagcagg 660
tcaggatgac aagcagcaac tcggtggtga tgtggtgtca cgtacgggct gtccgcccgt 720
cgcagtcact acctggccgc tgacgctgcc ggtctgatac tagagaaaga ggagaaatac 780
tagatgaaaa acataaatgc cgacgacaca tacagaataa ttaataaaat taaagcttgt 840
agaagcaata atgatattaa tcaatgctta tctgatatga ctaaaatggt acattgtgaa 900
tattatttac tcgcgatcat ttatcctcat tctatggtta aatctgatat ttcaatccta 960
gataattacc ctaaaaaatg gaggcaatat tatgatgacg ctaatttaat aaaatatgat 1020
cctatagtag attattctaa ctccaatcat tcaccaatta attggaatat atttgaaaac 1080
aatgctgtaa ataaaaaatc tccaaatgta attaaagaag cgaaaacatc aggtcttatc 1140
actgggttta gtttccctat tcatacggct aacaatggct tcggaatgct tagttttgca 1200
cattcagaaa aagacaacta tatagatagt ttatttttac atgcgtgtat gaacatacca 1260
ttaattgttc cttctctagt tgataattat cgaaaaataa atatagcaaa taataaatca 1320
aacaacgatt taaccaaaag agaaaaagaa tgtttagcgt gggcatgcga aggaaaaagc 1380
tcttgggata tttcaaaaat attaggttgc agtgagcgta ctgtcacttt ccatttaacc 1440
aatgcgcaaa tgaaactcaa tacaacaaac cgctgccaaa gtatttctaa agcaatttta 1500
acaggagcaa ttgattgccc atactttaaa aattaatcta gaggatccaa actcgagtaa 1560
ggatctccag gcatcaaata aaacgaaagg ctcagtcgaa agactgggcc tttcgtttta 1620
tctgttgttt gtcggtgaac gctctctact agagtcacac tggctcacct tcgggtgggc 1680
ctttctgcgt ttatacctag g 1701

<210> SEQ ID NO 6
<211> LENGTH: 8
<212> TYPE: DNA
<213> ORGANISM: Artificial Sequence
<220> FEATURE:
<223> OTHER INFORMATION: synthetic

<400> SEQUENCE: 6 aggaggaa 8

<210> SEQ ID NO 7
<211> LENGTH: 11
<212> TYPE: DNA
<213> ORGANISM: Artificial Sequence
<220> FEATURE:
<223> OTHER INFORMATION: synthetic

<400> SEQUENCE: 7
aagaggagaa a 11

<210> SEQ ID NO 8
<211> LENGTH: 54
<212> TYPE: DNA
<213> ORGANISM: Artificial Sequence
<220> FEATURE:
<223> OTHER INFORMATION: synthetic

<400> SEQUENCE: 8
tccctatcag tgatagagat tgacatccct atcagtgata gagatactga gcac 54

<210> SEQ ID NO 9
<211> LENGTH: 55
<212> TYPE: DNA
<213> ORGANISM: Artificial Sequence
<220> FEATURE:
<223> OTHER INFORMATION: synthetic

<400> SEQUENCE: 9
acctgtagga tcgtacaggt ttacgcaaga aaatggtttg ttatagtcga ataaa 55

<210> SEQ ID NO 10
<211> LENGTH: 35
<212> TYPE: DNA
<213> ORGANISM: Artificial Sequence
<220> FEATURE:
<223> OTHER INFORMATION: synthetic

<400> SEQUENCE: 10
tttatagcta gctcagccct tggtacaatg ctagc 35

<210> SEQ ID NO 11
<211> LENGTH: 200
<212> TYPE: DNA
<213> ORGANISM: Artificial Sequence
<220> FEATURE:
<223> OTHER INFORMATION: synthetic

<400> SEQUENCE: 11
aatctgtgac accgaaaatg ttagatttag gtttcacctt gtcaccgggc ggatctattt 60
aagcccacaa atttgaagta gctcacactt atacacttaa ggcatggatg gatattgctt 120
ctgatattgt ccggctggac aatgttaccg ataacagtta cccgtaacat ttttaattct 180
tgtattgtgg gggcaccact 200

<210> SEQ ID NO 12
<211> LENGTH: 500
<212> TYPE: DNA
<213> ORGANISM: Artificial Sequence
<220> FEATURE:
<223> OTHER INFORMATION: synthetic

<400> SEQUENCE: 12
cgatcatcct gttacggaat attacattgc aacatttacg cgcaaaaact aatccgcatt 60
cttattgcgg attagttttt tcttagctaa tagcacaatt ttcatactat tttttggcat 120
tctggatgtc tgaaagaaga ttttgtgcca ggtcgataaa gtttccatca gaaacaaaat 180
ttccgtttag ttaatttaaa tataaggaaa tcatataaat agattaaaat tgctgtaaat 240
atcatcacgt ctctatggaa atatgacggt gttcacaaag ttccttaaat tttacttttg 300
gttacatatt ttttcttttt gaaaccaaat ctttatcttt gtagcacttt cacggtagcg 360
aaacgttagt ttgaatggaa agatgcctgc agacacataa agacaccaaa ctctcatcaa 420
tagttccgta aatttttatt gacagaactt attgacggca gtggcaggtg tcataaaaaa 480
aaccatgagg gtaataaata 500

<210> SEQ ID NO 13
<211> LENGTH: 500
<212> TYPE: DNA
<213> ORGANISM: Artificial Sequence
<220> FEATURE:
<223> OTHER INFORMATION: synthetic

<400> SEQUENCE: 13
attagcggcc tcggctgcgg ctatttaccc cgttatctgg cgcaacgttt tctcgatagt 60
ggcgcgttaa tcgagaagaa agtggtcgcc caaactctct ttgaacccgt ctggattggc 120
tggaacgaac agaccgcagg acttgccagt ggctggtggc gggatgaaat tttagcaaat 180
agtgcgatcg ccggtgttta tgcaaaatct gatgacggaa aatcagccat ttaaagaaaa 240
attattctga caagcctctc attctcttgt catttccccc ccatttaggc acaatgcgcc 300
gctgtcaaaa aatgactaaa aaccgacgtt tcatcagcgt cggttatttt ttgcttcaaa 360
ccaatcattc ataccaagag gccgggcttc gtaccggata gatatttact aaaaatcgac 420
agttgttgtc gctgaggaat ccaaaaaaat ggggcaattt tttgcttacg cgacggttat 480
caccgtaaag gagaatgacc 500

<210> SEQ ID NO 14
<211> LENGTH: 500
<212> TYPE: DNA
<213> ORGANISM: Artificial Sequence
<220> FEATURE:
<223> OTHER INFORMATION: synthetic

<400> SEQUENCE: 14
aacggataag acgggcataa atgaggaaga aatggcgcgc cctgcaggat tcgaacctgc 60
ggcccacgac ttagaagttc ctagaacgac attttaagtc aacaacttac cgcgccatct 120
ctgcgctcac acgtcccact acctcaaaac atgtaaagcc ttgcaagcca ttgcgaggcc 180
ttatgtgtct cagttttgtc cctctttttt gtactaaaaa acatagtaat tgaggataaa 240
cctcatgcta ttttcgctta tatgcctcta aaggcatggc acttaaatag ataaaagcac 300
cacaaaagca taaaaaaacc acacagtaaa accgaaatat gaaacaataa cagataatta 360
aaccaaaaac agatagcgca ttgtgataat cattcaatac taaacaaaat ataaacagtg 420
gagcaatatg taattgactc attaagttag atataaaaaa tacatattca atcattaaaa 480
cgattgaatg gagaactttt 500

<210> SEQ ID NO 15
<211> LENGTH: 500
<212> TYPE: DNA
<213> ORGANISM: Artificial Sequence
<220> FEATURE:
<223> OTHER INFORMATION: synthetic

<400> SEQUENCE: 15
ggcgaaactc ttcaacacta ccctgcggat gatgcgggca ataatagata ccatccagat 60
cgacatctcg gtccgccagc gaccagtcca tccactcggt cagcgtttca aactgtgctt 120
cggtaaattt accgcgagca atgccagact ggttggttac taccaccagc gcaaagccca 180 tttttttag ctcgcgcatg gcgtcaataa caccgtcgat aaattcaaag ttgtcgatct 240
catggacata gccgtgatcg acattaatgg tgccatcacg gtcaagaaaa attgcgggta 300
cgctcttcgc caccttttat agctccttaa taaggcatgt gacgctagta tcgcatgttt 360
cgacctgcaa gaaagtgctc ttcgcataaa cctgattgat ttagacgtct ggatgcctta 420
acatccattt cattgacggc gttgcccgtt tcaggcattc gagatgccac gactaactta 480
atgacgataa taaataatca 500

<210> SEQ ID NO 16
<211> LENGTH: 500
<212> TYPE: DNA
<213> ORGANISM: Artificial Sequence
<220> FEATURE:
<223> OTHER INFORMATION: synthetic

<400> SEQUENCE: 16
gattattgaa ctgttgttca agcgtggttt cctgaccaaa aaagggcgct atatccactc 60
caccgacgcc ggaaaagcgc tattccattc gctgccggag atggcgacgc gaccggacat 120
gaccgcgcac tgggaatcgg tgctgacgca aatcagcgaa aagcagtgtc gctatcagga 180
ctttatgcag ccgctggtgg ggacgctata tcagcttatt gatcaagcca aacgtacgcc 240
ggtgcggcag tttcgcggca ttgtggctcc gggcagtggt ggcagtgctg ataagaaaaa 300
ggctgcaccg cgtaaacgta gtgcgaaaaa aagtccgcca gcagatgaag tcggaagcgg 360
ggcgatagcg taagcgagtg aatctttcgt gctattcgag tcatattctg aaatatccag 420
cggatcaaga aaattcgttg gatatttttt ttgcatggat aaaattatcg cctctaaagt 480
atgtaataac agggaatgtg 500

<210> SEQ ID NO 17
<211> LENGTH: 500
<212> TYPE: DNA
<213> ORGANISM: Artificial Sequence
<220> FEATURE:
<223> OTHER INFORMATION: synthetic

<400> SEQUENCE: 17 ggtcttttg atatgcgaga tgtacttgat ctcaataatt tgtaaccaca aaatatttgt 60
tatggtgcaa aaataacaca tttaatttat tgattataaa gggctttaat ttttggccct 120 tttattttg gtgttatgtt tttaaattgt ctataagtgc caaaaattac atgttttgtc 180 ttctgtttt gttgttttaa tgtaaatttt gaccatttgg tccactttt tctgctcgtt 240 tttatttcat gcaatcttct tgctgcgcaa gcgttttcca gaacaggtta gatgatcttt 300
ttgtcgctta atgcctgtaa aacatgcatg agccacaaaa taatataaaa aatcccgcca 360
ttaagttgac ttttagcgcc catatctcca gaatgccgcc gtttgccaga aattcgtcgg 420
taagcagatt tgcattgatt tacgtcatca ttgtgaatta atatgcaaat aaagtgagtg 480
aatattctct ggagggtgtt 500

<210> SEQ ID NO 18
<211> LENGTH: 500
<212> TYPE: DNA
<213> ORGANISM: Artificial Sequence
<220> FEATURE:
<223> OTHER INFORMATION: synthetic

<400> SEQUENCE: 18
cgtttgctct gcttctgcgc ggtttgcaaa cacgcggctg taagacgcgg tgcagtcgga 60
gttgtccata atggtgccaa catccataca gcagcaaacc ggggtttcat cagcactaca 120
tttactcatc gttgatttcc tctgtatgtg cacccaaggt gccagataaa cgttgtggat 180
attttacgct tccggaaagt gctgctccag ttgttaattc tgcaaaatcg gataagtgac 240
cgaaatcaca cttaaaaatg atctaaaaca aaattcaccc gaatccatga gtgcgccacc 300
tccaaatttt gccagctgga tcgcgtttct tagatcatat ttgaaaaaag atagaaacat 360
acttgcaaca ttccagctgg tccgacctat actctcgcca ctggtctgat ttctaagatg 420
tacctcagac cctacacttc gcgctcctgt tacagcacgt aacatagttt gtataaaaat 480
aaatcattga ggttatggtc 500

<210> SEQ ID NO 19
<211> LENGTH: 500
<212> TYPE: DNA
<213> ORGANISM: Artificial Sequence
<220> FEATURE:
<223> OTHER INFORMATION: synthetic

<400> SEQUENCE: 19
taccgttgtg ccaattctgc gtgcgggtct tggtatgatg gacggtgtgc tggaaaacgt 60
tccgagcgcg cgcatcagcg ttgtcggtat gtaccgtaat gaagaaacgc tggagccggt 120
accgtacttc cagaaactgg tttctaacat cgatgagcgt atggcgctga tcgttgaccc 180
aatgctggca accggtggtt ccgttatcgc gaccatcgac ctgctgaaaa aagcgggctg 240
cagcagcatc aaagttctgg tgctggtagc tgcgccagaa ggtatcgctg cgctggaaaa 300
agcgcacccg gacgtcgaac tgtataccgc atcgattgat cagggactga acgagcacgg 360
atacattatt ccgggcctcg gcgatgccgg tgacaaaatc tttggtacga aataaagaat 420
aaaaataatt aaagccgact ttaagagtcg gcttttttttt gagtaaagcg cctataacac 480
ataatacaga ggataatact 500

<210> SEQ ID NO 20
<211> LENGTH: 500
<212> TYPE: DNA
<213> ORGANISM: Artificial Sequence
<220> FEATURE:
<223> OTHER INFORMATION: synthetic

<400> SEQUENCE: 20
cggaaatggg ttcatcagtg aaatggcgaa tggagcgatg gccacaaata agttcaatgg 60
ttggcgtcat tatctttttc tctttctgaa cgtgaatatt gcggtggacg gttcatcagc 120
tgtggggcaa gacgttttgc cacctgaaga ataaccacca ccgcagcggg aagcatgagc 180
aaaacaccga gaaaaatcat cagaatctgc acttctggcc gagaaaatgg ctcaggcagc 240
gacagggagt cgcttaccga cagcagcgcc accgccagta gcatcattcc gataaattcc 300
agtatcaaca cgcctttagg caatttaccg atcgcgcgca tacgcttccc tctgcaaagt 360
gagccttcag tctaaaactt ttcactgtat tgtgtttaac agttatagct tttagcaatt 420
aatgcaacag gttaaaccta ctttcagcga atacatttta gcgtgatcat tacaggcata 480
aatctatgag gagagaaata 500

<210> SEQ ID NO 21
<211> LENGTH: 500
<212> TYPE: DNA
<213> ORGANISM: Artificial Sequence
<220> FEATURE:
<223> OTHER INFORMATION: synthetic

<400> SEQUENCE: 21
catttaactg gcgaagcgat gacggaaacg cgcaatgtgc tgattgaagc ggcacgaata 60
acgcgcggtg aaatccgtcc tctggcccag gccgatgccg ctgaactgga tgcgttgatt 120
gtgccggggg ggtttggcgc ggcgaagaat ttaagcaatt ttgccagtct tggtagcgaa 180
tgcaccgttg accgtgaatt aaaggcgctg gcacaagcga tgcatcaggc cggaaaaccg 240
cttggtttta tgtgtattgc cccggcgatg ctgccgaaaa ttttcgattt cccgctgcgt 300
ttgaccatcg gtactgatat cgataccgca gaagtgctgg aagagatggg cgcggagcat 360
gtgccgtgtc ctgtcgatga tatcgtggtt gatgaagaca ataagattgt caccacccca 420
gcatatatgc tggcgcagaa cattgcagaa gcggcgagcg gcattgataa gctggtttcc 480
cgcgtgctgg ttctggctga 500

<210> SEQ ID NO 22
<211> LENGTH: 500
<212> TYPE: DNA
<213> ORGANISM: Artificial Sequence
<220> FEATURE:
<223> OTHER INFORMATION: synthetic

<400> SEQUENCE: 22
tcaagaaata cgcatcttat agaaacgtcc tatgataggt tgaaatcaag agaaatcaca 60
tttcagcaat acagggaaaa tcttgctaaa gcaggagttt tccgatggat tacaaatatc 120
cacgaacata aaagatatta ctatacccttt gataattcat tactatttac tgagagcatt 180
cagaacacta cacaaatctt tccacgctaa atcataacgt ccggtttctt ccgtgtcagc 240
accggggtgt tggcataata caatacatgt acgcgctaaa ccctgtgtgc atcgttttta 300
attattcccg gacactcccg cagagaagtt ccccgtcagg gctgtggaca tagttaatcc 360
gggaatacaa tgacgattca tcgcacctgg catacattaa taaatattaa caatatgaaa 420
tttcaactca ttgtttaggg tttgtttaat tttctacaca tacgattctg cgaacttcaa 480
aaagcatcgg gaataacacc 500

<210> SEQ ID NO 23
<211> LENGTH: 500
<212> TYPE: DNA
<213> ORGANISM: Artificial Sequence
<220> FEATURE:
<223> OTHER INFORMATION: synthetic

<400> SEQUENCE: 23
cagactttat tattacacca ccgctatttg tgctgaatcc ggcaaatgag aatctgttac 60
gcattatgta cattggagcg ccgttggcga aagacagaga aacccttttc ttcactagcg 120
tacgggcagt cccttcaaca acgaagcgga aagagggaaa taccctgaag attgccacac 180
aaagcgtcat caaacttttc tggcgaccaa aaggtttagc gtatccctta ggcgaggctc 240
cggcgaaact gcgttgcact tcgtcagctg acatggttac ggtcagtaac ccaacacctt 300
atttcattac cctgacagac ctgaaaatag gtggaaaagt agttaaaaat caaatgattt 360
ccccctttga taaataccaa ttttctctgc caaagggggc caaaaatagc agcgtaacgt 420
atcgaaccat caatgactac ggggcggaaa cgccgcaact caactgtaaa tcgtaagccg 480
tcttcagtta agagagcgag 500

<210> SEQ ID NO 24
<211> LENGTH: 500
<212> TYPE: DNA
<213> ORGANISM: Artificial Sequence
<220> FEATURE:
<223> OTHER INFORMATION: synthetic

<400> SEQUENCE: 24
taggctggcg tgttgactcc cggcttggcg atctccgacc ctgggcgcaa atcagctata 60
accagcaatt tggcgagaat atctggaagg cgcaatcagg cctgagccgg atgacggcga 120
caaaccagaa cggcaactgg ctggatgtca ccgtaggcgc tgatatgttg ctcaatcaaa 180
atattgccgc ctatgccgcg ctaactcagg cagaaaatac cactaataat agcgactatc 240
tgtatacgat gggggttagc gccagatttt aacgtaacag tcacaattga aaccattaaa 300
taacaatagt tgtggcgata gtgggtgcta acttaccaaa taataaattt ggtgaataat 360
tgtcgcgtca ttcattcctg aactaaggca tttcattccg ttctgatggc atttcatgcc 420
gtttttcccc aggcataaag tgcacttcgt tatggttgtc ggcagagatt tttccttttt 480
attactgcag gaatactgcc 500

<210> SEQ ID NO 25
<211> LENGTH: 500
<212> TYPE: DNA
<213> ORGANISM: Artificial Sequence
<220> FEATURE:
<223> OTHER INFORMATION: synthetic

<400> SEQUENCE: 25
gcgtttgttg ataccggcat cggtccgctc atcgtcaatg gtcgagtccg caaagtgatt 60
gcttcacata tcggcaccaa cccggaaaca ggtcggcgca tgatatctgg tgagatggac 120
gtcgttctgg tgccgcaagg tacgctaatc gagcaaattc gctgtggtgg agctggactt 180
ggtggttttc tcaccccaac gggtgtcggc accgtcgtag aggaaggcaa acagacactg 240
acactcgacg gtaaaacctg gctgctcgaa cgcccactgc gcgccgacct ggcgctaatt 300
cgcgctcatc gttgcgacac acttggcaac ctgacctatc aacttagcgc ccgcaacttt 360
aaccccctga tagcccttgc ggctgatatc acgctggtag agccagatga actggtcgaa 420
accggcgagc tgcaacctga ccatattgtc acccctggtg ccgttatcga ccacatcatc 480
gtttcacagg agagcaaata 500

<210> SEQ ID NO 26
<211> LENGTH: 500
<212> TYPE: DNA

<213> ORGANISM: Artificial Sequence
<220> FEATURE:
<223> OTHER INFORMATION: synthetic

<400> SEQUENCE: 26
ggattattaa gtggctgtgc cagccataat gaaaatgcca gtttactggc gaaaaaacag 60
gcgcaaaata tcagccaaaa cctgccgatt aaatctgcgg gatatacctt agtgctggcg 120
caaagtagcg gcacaacggt aaaaatgacc attatcagcg aagcgggtac acaaaccacg 180
cagacgcctg acgccttttt aaccagctat caacgacaaa tgtgcgctga cccgacggtg 240
aaattaatga tcactgaggg aattaattac agcataacga ttaatgatac acgtacaggt 300
aaccagtatc agcggaaact ggatcgtacc acctgtggaa tagtcaaagc ataacgtcgg 360
gtagatataa attggcgcgg gttgttttc gtgacgcacg aatttatctc attcaatggc 420
tgacaaaaat tcgtcacact cttaaccaga gacaatctct taatacagac aaagagcatc 480
tgcgaaaaat tgcacgcggg 500

<210> SEQ ID NO 27
<211> LENGTH: 500
<212> TYPE: DNA
<213> ORGANISM: Artificial Sequence
<220> FEATURE:
<223> OTHER INFORMATION: synthetic

<400> SEQUENCE: 27
cgggctggag gacgacggtc agatcagcgc caaaatcaac gggcggattt tcccgcttaa 60
cggcaagcgt aactatctcc cgctctctcc ctatggaaga tatgaggtgg agttacagaa 120
cagcaaaaac tcactcgaca gttacgatat cgtcagcggc cgcaaaagtc gtctgactct 180
ctatccaggc aatgtcgctg tcattgagcc agaggtgaag cagatggtta ccgtctccgg 240
tcgtatccgt gcggaagacg gcacactgct ggctaacgca cggattaaca accatatcgg 300
ccgaacccga accgatgaaa acggcgagtt tgtcatggac gtggataaga aatacccccac 360 tatcgatttt cgctacagtg gcaataaaac ctgcgaagtg gctctggaac tcaaccaggc 420
gcgcggtgcc gtctgggtcg gtgatgtggt ctgcagcggc ctctcatcgt gggcggcggt 480
gacgcagaca ggagaagaga 500

<210> SEQ ID NO 28
<211> LENGTH: 500
<212> TYPE: DNA
<213> ORGANISM: Artificial Sequence
<220> FEATURE:
<223> OTHER INFORMATION: synthetic

<400> SEQUENCE: 28
gggacagaat ttaccgtccg ccagcaggat aatttcacgc agcttgacgt gcagcagcac 60
gctgtggaag tgcttctcgc cagtgccccc gcgcaaaaac gcatcgtgaa cgctggtgaa 120
agcctgcagt tcagcgcctc tgagtttggc gcagtgaaac cgctggatga cgagagtaca 180
agctggacga aggacatcct gagcttcagc gataaaccgc tgggtgaggt gatagccacg 240
ctaacccgtt accgcaacgg cgtgctgcgc tgcgatcccg ccgttgccgg gctgcgcctg 300
agcgggacgt tcccgctgaa aaataccgat gcgatcctga acgttatcgc gcaaacgctt 360
cccgttaaaa ttcagtctat tacgcggtac tggataaaca tttcaccact gtaaggaaaa 420
taattcttat ttcgattgtc ctttttaccc ttctcgttcg actcatagct gaacacaaca 480
aaaatgatga tggggaaggt 500

<210> SEQ ID NO 29
<211> LENGTH: 1074
<212> TYPE: DNA
<213> ORGANISM: Artificial Sequence
<220> FEATURE:
<223> OTHER INFORMATION: Synthetic Construct

<400> SEQUENCE: 29
gaattctaaa gatctttttc tctatcactg atagggagtg gtaaaataac tctatcaacg 60
atagagtgtc aacaaaaatt aggaattaat gatgtcgaga ttagataaaa gtaaagtgat 120
taacagcgca ttagagctgc ttaatgaggt cggaatcgaa ggtttaacaa cccgtaaact 180
cgcccagaag ctaggtgtag agcagcctac attgtattgg catgtaaaaa ataagcgggc 240
tttgctcgac gccttagcca ttgagatgtt agataggcac catactcact tttgcccttt 300
agaaggggaa agctggcaag atttttttacg taataacgct aaaagtttta gatgtgcttt 360
actaagtcat cgcgatggag caaaagtaca tttaggtaca cggcctacag aaaaacagta 420
tgaaactctc gaaaatcaat tagccttttt atgccaacaa ggtttttcac tagagaatgc 480
attatatgca ctcagcgctg tggggcattt tactttaggt tgcgtattgg aagatcaaga 540
gcatcaagtc gctaaagaag aaagggaaac acctactact gatagtatgc cgccattatt 600
acgacaagct atcgaattat ttgatcacca aggtgcagag ccagccttct tattcggcct 660
tgaattgatc atatgcggat tagaaaaaca acttaaatgt gaaagtgggt cttaataaca 720
ctgatagtgc tagtgtagat cactactaga gccaggcatc aaataaaacg aaaggctcag 780
tcgaaagact gggcctttcg ttttatctgt tgtttgtcgg tgaacgctct ctactagagt 840
cacactggct caccttcggg tgggcctttc tgcgtttata tactagagtc cctatcagtg 900
atagagattg acatccctat cagtgataga gatactgagc actgaactgt atacattccc 960
cgcaaagaca caggacagga caggcagata gataggatag aggggatctc aaagcccgcc 1020
gaaaggcggg ctttttttttg gatccttact cgagtctaga ctgcaggctt cctc 1074

<210> SEQ ID NO 30
<211> LENGTH: 208
<212> TYPE: DNA
<213> ORGANISM: Artificial Sequence
<220> FEATURE:
<223> OTHER INFORMATION: Synthetic Construct

<400> SEQUENCE: 30
ctaaagatct atatactaga gacctgtagg atcgtacagg tttacgcaag aaaatggttt 60
gttatagtcg aataaatgaa ctgtatacat tccccgcaaa gacacaggac aggacaggca 120
gatagatagg atagagggga tctcaaagcc cgccgaaagg cgggcttttt tttggatcct 180
tactcgagtc tagactgcag gcttcctc 208

<210> SEQ ID NO 31
<211> LENGTH: 1664
<212> TYPE: DNA
<213> ORGANISM: Artificial Sequence
<220> FEATURE:
<223> OTHER INFORMATION: Synthetic Construct

<400> SEQUENCE: 31
ttaatactct ctccgctacg cagtgttgta gatcaattgc gcactatcat tgaaataatt 60
acctgctagt gattatttca acctactgaa tttcatctaa tttttttcac tctatggcaa 120

```
attagccatt tcaaacatta tcatggctga tattttccgt agtcaggttt aatgttttaa    180

aagtgctgtg ggaaagtgaa caaagagttc cgtaagcgtt gatgctatgg gcggttaaat    240

aagtaatccg ggttcatttt tttgcaactg gcgttgatta cattgcataa atatccgtgt    300

ctccagacgc tatataaaaa cctgaagaca tgaatgcgtt atttactcag gtaatttcaa    360

tgcgttaaaa gaaagctggc aatccaattg ccagcttaag tcgaaacaag gagactcgat    420

atttaaatcg gattacattt taactttagt aatattcttc agagatcaca aactggttat    480

tgataactta ttcttgggca gtaatccgca aacgttaact ttttgtttgc tatttacaag    540

ctgataacaa ccaggaatct tacttaggat caatatatgg agtgcgtgat ggataaatct    600

gaagtattga ttagtgttaa tagacgtatt agttcacgaa gggtaaagtt cttataggcg    660

tttactatat tgaacaacga ttcggacaag gatgtaaata atgaaaagga tgacatattc    720

gaaacgacct ctatcctatc tatctgcctg tcctgtcctg tgtctttgcg gggaatgtat    780

acagttcatg tatatattcc ccgctttttt tttggatcta ggaggaagga tctatggcga    840

gtagcgaaga cgttatcaaa gagttcatgc gtttcaaagt tcgtatggaa ggttccgtta    900

acggtcacga gttcgaaatc gaaggtgaag gtgaaggtcg tccgtacgaa ggtacccaga    960

ccgctaaact gaaagttacc aaaggtggtc cgctgccgtt cgcttgggac atcctgtccc   1020

cgcagttcca gtacggttcc aaagcttacg ttaaacaccc ggctgacatc ccggactacc   1080

tgaaactgtc cttcccggaa ggtttcaaat gggaacgtgt tatgaacttc gaagacggtg   1140

gtgttgttac cgttacccag gactcctccc tgcaagacgg tgagttcatc tacaaagtta   1200

aactgcgtgg taccaacttc ccgtccgacg gtccggttat gcagaaaaaa accatgggtt   1260

gggaagcttc caccgaacgt atgtacccgg aagacggtgc tctgaaaggt gaaatcaaaa   1320

tgcgtctgaa actgaaagac ggtggtcact acgacgctga agttaaaacc acctacatgg   1380

ctaaaaaacc ggttcagctg ccgggtgctt acaaaaccga catcaaactg gacatcacct   1440

cccacaacga agactacacc atcgttgaac agtacgaacg tgctgaaggt cgtcactcca   1500

ccggtgctta aggatccaaa ctcgagtaag gatctccagg catcaaataa aacgaaaggc   1560

tcagtcgaaa gactgggcct ttcgttttat ctgttgtttg tcggtgaacg ctctctacta   1620

gagtcacact ggctcacctt cgggtgggcc tttctgcgtt tata                    1664
```

<210> SEQ ID NO 32
<211> LENGTH: 3396
<212> TYPE: DNA
<213> ORGANISM: Artificial Sequence
<220> FEATURE:
<223> OTHER INFORMATION: Synthetic Construct

<400> SEQUENCE: 32

```
atggctctgt tattagcagt ttttttagc atcgctttga gtgcaattgc cgggatcttg      60

ctgttgctcc tgctgtttcg ctcgaaacgt catagtagcc tgaaattacc tccgggcaaa    120

ctgggcattc cgtttatcgg tgagtccttt attttttgc gcgcgctgag gagcaattct     180

ctggaacagt tctttgatga acgtgtgaag aagttcggcc tggtatttaa aacgtccctt    240

atcggtcacc cgacggttgt cctgtgcggg cccgcaggta atcgcctcat cctgagcaac    300

gaagaaaagc tggtacagat gtcctggccg gcgcagttta tgaagctgat gggagagaac    360

tcagttgcga cccgccgtgg tgaagatcac attgttatgc gctccgcgtt ggcaggcttt    420

ttcggcccgg gagctctgca atcctatatc ggcaagatga acacggaaat ccaaagccat    480

attaatgaaa agtggaaagg gaaggacgag gttaatgtct taccccctggt gcgggaactg    540
```

```
gtttttaaca tcagcgctat tctgttcttt aacatttacg ataagcagga acaagaccgt    600
ctgcacaagt tgttagaaac cattctggta ggctcgtttg ccttaccaat tgatttaccg    660
ggtttcgggt ttcaccgcgc tttacaaggt cgtgcaaaac tcaataaaat catgttgtcg    720
cttattaaaa aacgtaaaga ggacttacag tcgggatcgg ccaccgcgac gcaggacctg    780
ttgtctgtgc ttctgacttt ccgtgatgat aagggcaccc cgttaaccaa tgacgaaatc    840
ctggacaact ttagctcact gcttcacgcc tcttacgaca ccacgactag tccaatggct    900
ctgattttca aattactgtc aagtaaccct gaatgctatc agaaagtcgt gcaagagcaa    960
ctcgagattc tgagcaataa ggaagaaggt gaagaaatta cctggaaaga tcttaaggcc   1020
atgaaataca cgtggcaggt tgcgcaggag acacttcgca tgtttccacc ggtgttcggg   1080
accttccgca aagcgatcac ggatattcag tatgacggat acacaatccc gaaaggttgg   1140
aaactgttgt ggactaccta tagcactcat cctaaggacc tttacttcaa cgaaccggag   1200
aaatttatgc ctagtcgttt cgatcaggaa ggcaaacatg ttgcgcccta taccttcctg   1260
ccctttggag gcggtcagcg gagttgtgtg ggttgggagt tctctaagat ggagattctc   1320
ctcttcgtgc atcatttcgt gaaaacattt tcgagctata ccccggtcga tcccgatgaa   1380
aaaatttccg gcgatccact gccgccgtta ccgagcaaag ggttttcaat caaactgttc   1440
cctcgtccgg gcagcaccgg atcccgccgt ggtggaagtg atacacagaa gcccgccgta   1500
cgtcccacac ctcttgttaa agaagaggac gaagaagaag aagatgatag cgccaagaaa   1560
aaggtcacaa tattttttgg cacccagacc ggcaccgccg aaggtttcgc aaaggcctta   1620
gctgaggaag caaaggcacg ttatgaaaag gcggtattta aagtcgtgga tttggataac   1680
tatgcagcgg atgacgaaca gtacgaagag aagttgaaaa aggaaaagct agcgttcttc   1740
atgctcgcca cctacggtga cggcgaaccg actgataatg ccgctcgctt ttataaatgg   1800
tttctcgagg gtaaagagcg cgagccatgg ttgtcagatc tgacttatgg cgtgtttggc   1860
ttaggtaacc gtcagtatga acactttaac aaggtcgcga aagcggtgga cgaagtgctc   1920
attgaacaag gcgccaaacg tctggtaccg gtagggcttg gtgatgatga tcagtgcatt   1980
gaggacgact tcactgcctg gagagaacaa gtgtggcctg agctggatca gctcttacgt   2040
gatgaagatg acgagccgac gtctgcgacc ccgtacacgg cggctattcc agaataccgg   2100
gtggaaatct acgactcagt agtgtcggtc tatgaggaaa cccatgcgct gaaacaaaat   2160
ggacaagccg tatacgatat ccaccacccg tgtcgcagca acgtggcagt acgtcgtgag   2220
ctgcataccc cgctgtcgga tcgtagttgt attcatctgg aattcgatat tagtgatact   2280
gggttaatct atgagacggg cgaccacgtt ggagttcata ccgagaattc aattgaaacc   2340
gtggaagaag cagctaaact gttaggttac caactggata caatcttcag cgtgcatggg   2400
gacaaggaag atggaacacc attgggcggg agtagcctgc caccgccgtt tccggggccc   2460
tgcacgctgc ggacggcgct ggcacgttac gcggacctgc tgaaccctcc gcgcaaagcc   2520
gccttcctgg cactggccgc acacgcgtca gatccggctg aagctgaacg ccttaaattt   2580
ctcagttctc cagccggaaa agacgaatac tcacagtggg tcactgcgtc ccaacgcagc   2640
ctcctcgaga ttatggccga attccccagc gcgaaaccgc cgctgggagt gtttttcgcc   2700
gcaatagcgc cgcgcttgca acctaggtat tatagcatct cctcctcccc gcgtttcgcg   2760
ccgtctcgta tccatgtaac gtgcgcgctg gtctatggtc ctagccctac ggggcgtatt   2820
cataaaggtg tgtgcagcaa ctggatgaag aattctttgc cctccgaaga aacccacgat   2880
```

tgcagctggg caccggtctt tgtgcgccag tcaaacttta aactgcccgc cgattcgacg 2940
acgccaatcg tgatggttgg acctggaacc ggcttcgctc catttcgcgg cttccttcag 3000
gaacgcgcaa aactgcagga agcgggcgaa aaattgggcc cggcagtgct gtttttgggg 3060
tgccgcaacc gccagatgga ttacatctat gaagatgagc ttaagggtta cgttgaaaaa 3120
ggtattctga cgaatctgat cgttgcattt tcacgagaag gcgccaccaa agagtatgtt 3180
cagcacaaga tgttagagaa agcctccgac acgtggtctt taatcgccca gggtggttat 3240
ctgtatgttt gcggtgatgc gaagggtatg gccagagacg tacatcgcac cctgcataca 3300
atcgttcagg aacaagaatc cgtagactcg tcaaaagcgg agtttttagt caaaaagctg 3360
caaatggatg gacgctactt acgggatatt tggtaa 3396

<210> SEQ ID NO 33
<211> LENGTH: 10486
<212> TYPE: DNA
<213> ORGANISM: Artificial Sequence
<220> FEATURE:
<223> OTHER INFORMATION: Synthetic Construct

<400> SEQUENCE: 33
ttaatactct ctccgctacg cagtgttgta gatcaattgc gcactatcat tgaaataatt 60
acctgctagt gattatttca acctactgaa tttcatctaa ttttttcac tctatggcaa 120 attagccatt tcaaacatta tcatggctga tattttccgt agtcaggttt aatgttttaa 180
aagtgctgtg ggaaagtgaa caaagagttc cgtaagcgtt gatgctatgg gcggttaaat 240
aagtaatccg ggttcatttt tttgcaactg gcgttgatta cattgcataa atatccgtgt 300
ctccagacgc tatataaaaa cctgaagaca tgaatgcgtt atttactcag gtaatttcaa 360
tgcgttaaaa gaaagctggc aatccaattg ccagcttaag tcgaaacaag gagactcgat 420
atttaaatcg gattacattt taactttagt aatattcttc agagatcaca aactggttat 480
tgataactta ttcttgggca gtaatccgca aacgttaact ttttgtttgc tatttacaag 540
ctgataacaa ccaggaatct tacttaggat caatatatgg agtgcgtgat ggataaatct 600
gaagtattga ttagtgttaa tagacgtatt agttcacgaa gggtaaagtt cttataggcg 660
tttactatat tgaacaacga ttcggacaag gatgtaaata atgaaaagga tgacatattc 720
gaaacgacct ctatcctatc tatctgcctg tcctgtcctg tgtctttgcg gggaatgtat 780
acagttcatg tatatattcc ccgctttttt tttggatctt aggaggaata taaaatgaaa 840
aattgtgtca tcgtcagtgc ggtacgtact gctatcggta gttttaacgg ttcactcgct 900
tccaccagcg ccatcgacct gggggcgaca gtaattaaag ccgccattga acgtgcaaaa 960
atcgattcac aacacgttga tgaagtgatt atgggtaacg tgttacaagc cgggctgggg 1020
caaaatccgg cgcgtcaggc actgttaaaa agcgggctgg cagaaacggt gtgcggattc 1080
acggtcaata aagtatgtgg ttcgggtctt aaaagtgtgg cgcttgccgc ccaggccatt 1140
caggcaggtc aggcgcagag cattgtggcg gggggtatgg aaaatatgag tttagccccc 1200
tacttactcg atgcaaaagc acgctctggt tatcgtcttg gagacggaca ggtttatgac 1260
gtaatcctgc gcgatggcct gatgtgcgcc acccatggtt atcatatggg gattaccgcc 1320
gaaaacgtgg ctaaagagta cggaattacc cgtgaaatgc aggatgaact ggcgctacat 1380
tcacagcgta aagcggcagc cgcaattgag tccggtgctt ttacagccga aatcgtcccg 1440
gtaaatgttg tcactcgaaa gaaaaccttc gtcttcagtc aagacgagtt cccgaaagcg 1500
aactcaacgg ctgaagcgtt aggtgcattg cgcccggcct tcgataaagc aggaacagtc 1560
accgctggga acgcgtctgg tattaacgac ggtgctgccg ctctggtgat tatggaagaa 1620
tctgcggcgc tggcagcagg ccttaccccc ctggctcgca ttaaaagtta tgccagcggt 1680
ggcgtgcccc ccgcattgat gggtatgggg ccagtacctg ccacgcaaaa agcgttacaa 1740
ctggcggggc tgcaactggc ggatattgat ctcattgagg ctaatgaagc atttgctgca 1800
cagttccttg ccgttgggaa aaacctgggc tttgattctg agaaagtgaa tgtcaacggc 1860
ggggccatcg cgctcgggca tcctatcggt gccagtggtg ctcgtattct ggtcacacta 1920
ttacatgcca tgcaggcacg cgataaaacg ctggggctgg caacactgtg cattggcggc 1980
ggtcagggaa ttgcgatggt gattgaacgg ttgaattgag gatcttgaat taaggaggac 2040
agctaaatga aactctcaac taaactttgt tggtgtggta ttaaaggaag acttaggccg 2100
caaaagcaac aacaattaca caatacaaac ttgcaaatga ctgaactaaa aaaacaaaag 2160
accgctgaac aaaaaaccag acctcaaaat gtcggtatta aaggtatcca aatttacatc 2220
ccaactcaat gtgtcaacca atctgagcta gagaaatttg atggcgtttc tcaaggtaaa 2280
tacacaattg gtctgggcca aaccaacatg tcttttgtca atgacagaga agatatctac 2340
tcgatgtccc taactgtttt gtctaagttg atcaagagtt acaacatcga caccaacaaa 2400
attggtagat tagaagtcgg tactgaaact ctgattgaca agtccaagtc tgtcaagtct 2460
gtcttgatgc aattgtttgg tgaaaacact gacgtcgaag gtattgacac gcttaatgcc 2520
tgttacggtg gtaccaacgc gttgttcaac tctttgaact ggattgaatc taacgcatgg 2580
gatggtagag acgccattgt agtttgcggt gatattgcca tctacgataa gggtgccgca 2640
agaccaaccg gtggtgccgg tactgttgct atgtggatcg gtcctgatgc tccaattgta 2700
tttgactctg taagagcttc ttacatggaa cacgcctacg atttttacaa gccagatttc 2760
accagcgaat atccttacgt cgatggtcat ttttcattaa cttgttacgt caaggctctt 2820
gatcaagttt acaagagtta ttccaagaag gctatttcta aagggttggt tagcgatccc 2880
gctggttcgg atgctttgaa cgttttgaaa tatttcgact acaacgtttt ccatgttcca 2940
acctgtaaat tggtcacaaa atcatacggt agattactat ataacgattt cagagccaat 3000
cctcaattgt tcccagaagt tgacgccgaa ttagctactc gcgattatga cgaatcttta 3060
accgataaga acattgaaaa aacttttgtt aatgttgcta agccattcca caaagagaga 3120
gttgcccaat ctttgattgt tccaacaaac acaggtaaca tgtacaccgc atctgtttat 3180
gccgcctttg catctctatt aaactatgtt ggatctgacg acttacaagg caagcgtgtt 3240
ggtttatttt cttacggttc cggtttagct gcatctctat attcttgcaa aattgttggt 3300
gacgtccaac atattatcaa ggaattagat attactaaca aattagccaa gagaatcacc 3360
gaaactccaa aggattacga agctgccatc gaattgagag aaaatgccca tttgaagaag 3420
aacttcaaac ctcaaggttc cattgagcat ttgcaaagtg gtgtttacta cttgaccaac 3480
atcgatgaca aatttagaag atcctacgat gttaaaaaat gaggatctaa aataaggagg 3540
attacactat ggttttaacc aataaaacag tcatttctgg atcgaaagtc aaaagtttat 3600
catctgcgca atcgagctca tcaggacctt catcatctag tgaggaagat gattcccgcg 3660
atattgaaag cttggataag aaaatacgtc ctttagaaga attagaagca ttattaagta 3720
gtggaaatac aaaacaattg aagaacaaag aggtcgctgc cttggttatt cacggtaagt 3780
tacctttgta cgctttggag aaaaaattag gtgatactac gagagcggtt gcggtacgta 3840
ggaaggctct ttcaattttg gcagaagctc ctgtattagc atctgatcgt ttaccatata 3900
aaaattatga ctacgaccgc gtatttggcg cttgttgtga aaatgttata ggttacatgc 3960
ctttgcccgt tggtgttata ggccccttgg ttatcgatgg tacatcttat catataccaa 4020
tggcaactac agagggttgt ttggtagctt ctgccatgcg tggctgtaag gcaatcaatg 4080
ctggcggtgg tgcaacaact gttttaacta aggatggtat gacaagaggc ccagtagtcc 4140
gtttcccaac tttgaaaaga tccggtgcct gtaagatatg gttagactca gaagagggac 4200
aaaacgcaat taaaaaagct tttaactcta catcaagatt tgcacgtctg caacatattc 4260
aaacttgtct agcaggagat ttactcttca tgagatttag aacaactact ggtgacgcaa 4320
tgggtatgaa tatgatttct aaaggtgtcg aatactcatt aaagcaaatg gtagaagagt 4380
atggctggga agatatggag gttgtctccg tttctggtaa ctactgtacc gacaaaaaac 4440
cagctgccat caactggatc gaaggtcgtg gtaagagtgt cgtcgcagaa gctactattc 4500
ctggtgatgt tgtcagaaaa gtgttaaaaa gtgatgtttc cgcattggtt gagttgaaca 4560
ttgctaagaa tttggttgga tctgcaatgg ctgggtctgt tggtggattt aacgcacatg 4620
cagctaattt agtgacagct gttttcttgg cattaggaca agatcctgca caaaatgttg 4680
aaagttccaa ctgtataaca ttgatgaaag aagtggacgg tgatttgaga atttccgtat 4740
ccatgccatc catcgaagta ggtaccatcg gtggtggtac tgttctagaa ccacaaggtg 4800
ccatgttgga cttattaggt gtaagaggcc cgcatgctac cgctcctggt accaacgcac 4860
gtcaattagc aagaatagtt gcctgtgccg tcttggcagg tgaattatcc ttatgtgctg 4920
ccctagcagc cggccatttg gttcaaagtc atatgaccca caacaggaaa cctgctgaac 4980
caacaaaacc taacaatttg gacgccactg atataaatcg tttgaaagat gggtccgtca 5040
cctgcattaa atcctgagga tctaggaggt taattggatg tcattaccgt tcttaacttc 5100
tgcaccggga aaggttatta tttttggtga acactctgct gtgtacaaca agcctgccgt 5160
cgctgctagt gtgtctgcgt tgagaaccta cctgctaata agcgagtcat ctgcaccaga 5220
tactattgaa ttggacttcc cggacattag ctttaatcat aagtggtcca tcaatgattt 5280
caatgccatc accgaggatc aagtaaactc ccaaaaattg gccaaggctc aacaagccac 5340
cgatggcttg tctcaggaac tcgttagtct tttggacccg ttgttagctc aactatccga 5400
atccttccac taccatgcag cgttttgttt cctgtatatg tttgtttgcc tatgccccca 5460
tgccaagaat attaagtttt ctttaaagtc tactttaccc atcggtgctg ggttgggctc 5520
aagcgcctct atttctgtat cactggcctt agctatggcc tacttggggg ggttaatagg 5580
atctaatgac ttggaaaagc tgtcagaaaa cgataagcat atagtgaatc aatgggcctt 5640
cataggtgaa aagtgtattc acggtacccc ttcaggaata gataacgctg tggccactta 5700
tggtaatgcc ctgctatttg aaaaagactc acataatgga acaataaaca caaacaattt 5760
taagttctta gatgatttcc cagccattcc aatgatccta acctatacta ggattccaag 5820
gtctacaaaa gaccttgttg ctcgcgttcg tgtgttggtc accgagaaat ttcctgaagt 5880
tatgaagcca attctagatg ccatgggtga atgtgcccta caaggcttag agatcatgac 5940
taagttaagt aaatgtaaag gcaccgatga cgaggctgta gaaactaata atgaactgta 6000
tgaacaacta ttggaattga taagaataaa tcatggactg cttgtctcaa tcggtgtttc 6060
tcatcctgga ttagaactta ttaaaaatct gagcgatgat ttgagaattg gctccacaaa 6120
acttaccggt gctggtggcg gcggttgctc tttgactttg ttacgaagag acattactca 6180
agagcaaatt gacagcttca aaaagaaatt gcaagatgat tttagttacg agacatttga 6240
aacagacttg ggtgggactg gctgctgttt gttaagcgca aaaaatttga ataaagacct 6300
taaaatcaaa tccctagtat tccaattatt tgaaaataaa actaccacaa agcaacaaat 6360
tgacgatcta ttattgccag gaaacacgaa tttaccatgg acttcatagg gatcttaagg 6420
aggataccct atgtcagagt tgagagcctt cagtgcccca gggaaagcgt tactagctgg 6480
tggatattta gttttagata caaaatatga agcatttgta gtcggattat cggcaagaat 6540
gcatgctgta gcccatcctt acggttcatt gcaagggtct gataagtttg aagtgcgtgt 6600
gaaaagtaaa caatttaaag atggggagtg gctgtaccat ataagtccta aaagtggctt 6660
cattcctgtt tcgataggcg gatctaagaa ccctttcatt gaaaaagtta tcgctaacgt 6720
atttagctac tttaaaccta acatggacga ctactgcaat agaaacttgt tcgttattga 6780
tattttctct gatgatgcct accattctca ggaggatagc gttaccgaac atcgtggcaa 6840
cagaagattg agttttcatt cgcacagaat tgaagaagtt cccaaaacag ggctgggctc 6900
ctcggcaggt ttagtcacag ttttaactac agctttggcc tcctttttg tatcggacct 6960
ggaaaataat gtagacaaat atagagaagt tattcataat ttagcacaag ttgctcattg 7020
tcaagctcag ggtaaaattg gaagcgggtt tgatgtagcg gcggcagcat atggatctat 7080
cagatataga agattcccac ccgcattaat ctctaatttg ccagatattg gaagtgctac 7140
ttacggcagt aaactggcgc atttggttga tgaagaagac tggaatatta cgattaaaag 7200
taaccattta ccttcgggat taactttatg gatgggcgat attaagaatg gttcagaaac 7260
agtaaaactg gtccagaagg taaaaaattg gtatgattcg catatgccag aaagcttgaa 7320
aatatataca gaactcgatc atgcaaattc tagatttatg gatggactat ctaaactaga 7380
tcgcttacac gagactcatg acgattacag cgatcagata tttgagtctc ttgagaggaa 7440
tgactgtacc tgtcaaaagt atcctgaaat cacagaagtt agagatgcag ttgccacaat 7500
tagacgttcc tttagaaaaa taactaaaga atctggtgcc gatatcgaac ctcccgtaca 7560
aactagctta ttggatgatt gccagacctt aaaaggagtt cttacttgct taatacctgg 7620
tgctggtggt tatgacgcca ttgcagtgat tactaagcaa gatgttgatc ttagggctca 7680
aaccgctaat gacaaaagat ttctaaggt tcaatggctg gatgtaactc aggctgactg 7740
gggtgttagg aaagaaaaag atccggaaac ttatcttgat aaatagggat ctaggaggat 7800
tatgagatga ccgtttacac agcatccgtt accgcacccg tcaacatcgc aacccttaag 7860
tattggggga aaagggacac gaagttgaat ctgcccacca attcgtccat atcagtgact 7920
ttatcgcaag atgacctcag aacgttgacc tctgcggcta ctgcacctga gtttgaacgc 7980
gacactttgt ggttaaatgg agaaccacac agcatcgaca atgaaagaac tcaaaattgt 8040
ctgcgcgacc tacgccaatt aagaaaggaa atggaatcga aggacgcctc attgcccaca 8100
ttatctcaat ggaaactcca cattgtctcc gaaaataact ttcctacagc agctggttta 8160
gcttcctccg ctgctggctt tgctgcattg gtctctgcaa ttgctaagtt ataccaatta 8220
ccacagtcaa cttcagaaat atctagaata gcaagaaagg ggtctggttc agcttgtaga 8280
tcgttgtttg gcggatacgt ggcctgggaa atgggaaaag ctgaagatgg tcatgattcc 8340
atggcagtac aaatcgcaga cagctctgac tggcctcaga tgaaagcttg tgtcctagtt 8400
gtcagcgata ttaaaaagga tgtgagttcc actcagggta tgcaattgac cgtggcaacc 8460
tccgaactat ttaaagaaag aattgaacat gtcgtaccaa agagatttga agtcatgcgt 8520
aaagccattg ttgaaaaaga tttcgccacc tttgcaaagg aaacaatgat ggattccaac 8580
tctttccatg ccacatgttt ggactctttc cctccaatat tctacatgaa tgacacttcc 8640

```
aagcgtatca tcagttggtg ccacaccatt aatcagtttt acggagaaac aatcgttgca   8700

tacacgtttg atgcaggtcc aaatgctgtg ttgtactact tagctgaaaa tgagtcgaaa   8760

ctctttgcat ttatctataa attgtttggc tctgttcctg gatgggacaa gaaatttact   8820

actgagcagc ttgaggcttt caaccatcaa tttgaatcat ctaactttac tgcacgtgaa   8880

ttggatcttg agttgcaaaa ggatgttgcc agagtgattt taactcaagt cggttcaggc   8940

ccacaagaaa caaacgaatc tttgattgac gcaaagactg gtctaccaaa ggaataagga   9000

tctaggaggt aatgataatg caaacggaac acgtcatttt attgaatgca cagggagttc   9060

ccacgggtac gctggaaaag tatgccgcac acacggcaga cacccgctta catctcgcgt   9120

tctccagttg gctgtttaat gccaaaggac aattattagt tacccgccgc gcactgagca   9180

aaaaagcatg gcctggcgtg tggactaact cggtttgtgg gcacccacaa ctgggagaaa   9240

gcaacgaaga cgcagtgatc cgccgttgcc gttatgagct tggcgtggaa attacgcctc   9300

ctgaatctat ctatcctgac tttcgctacc gcgccaccga tccgagtggc attgtggaaa   9360

atgaagtgtg tccggtattt gccgcacgca ccactagtgc gttacagatc aatgatgatg   9420

aagtgatgga ttatcaatgg tgtgatttag cagatgtatt acacggtatt gatgccacgc   9480

cgtgggcgtt cagtccgtgg atggtgatgc aggcgacaaa tcgcgaagcc agaaaacgat   9540

tatctgcatt tacccagctt aaataaggat ctaggaggtt actcatatgg actttccgca   9600

gcaactcgaa gcctgcgtta agcaggccaa ccaggcgctg agccgtttta tcgccccact   9660

gccctttcag aacactcccg tggtcgaaac catgcagtat ggcgcattat taggtggtaa   9720

gcgcctgcga cctttcctgg tttatgccac cggtcatatg ttcggcgtta gcacaaacac   9780

gctggacgca cccgctgccg ccgttgagtg tatccacgct tactcattaa ttcatgatga   9840

tttaccggca atggatgatg acgatctgcg tcgcggtttg ccaacctgcc atgtgaagtt   9900

tggcgaagca aacgcgattc tcgctggcga cgctttacaa acgctggcgt tctcgatttt   9960

aagcgatgcc gatatgccgg aagtgtcgga ccgcgacaga atttcgatga tttctgaact  10020

ggcgagcgcc agtggtattg ccggaatgtg cggtggtcag gcattagatt tagacgcgga  10080

aggcaaacac gtacctctgg acgcgcttga gcgtattcat cgtcataaaa ccggcgcatt  10140

gattcgcgcc gccgttcgcc ttggtgcatt aagcgccgga gataaaggac gtcgtgctct  10200

gccggtactc gacaagtatg cagagagcat cggccttgcc ttccaggttc aggatgacat  10260

cctggatgtg gtgggagata ctgcaacgtt gggaaaacgc cagggtgccg accagcaact  10320

tggtaaaagt acctaccctg cacttctggg tcttgagcaa gcccggaaga aagcccggga  10380

tctgatcgac gatgcccgtc agtcgctgaa acaactggct gaacagtcac tcgatacctc  10440

ggcactggaa gcgctagcgg actacatcat ccagcgtaat aaataa                  10486
```

<210> SEQ ID NO 34
<211> LENGTH: 3133
<212> TYPE: DNA
<213> ORGANISM: Artificial Sequence
<220> FEATURE:
<223> OTHER INFORMATION: Synthetic Construct

<400> SEQUENCE: 34

```
ctcggtacca aattccagaa aagaggcctc ccgaaagggg ggcctttttt cgttttggtc     60

ctactggcgc gcctcagtca gagtattgac ttaaagtcta acctatagga ccgttacagc    120

catcgagagc tgcgagactg tcgccggatg tgtatccgac ctgacgatgg cccaaaaggg    180

ccgaaacagt cctctacaaa taattttgtt taaatcaatt cacctgcgtg aaaatggtag    240
```

```
atttaagaac tttaggatat tcacagcagc aacaggaaaa gatcaagccc aaagttaggt    300
cgacagtcgc gcagcatcac gaagcgctgg ttggtcatgg gtttacacat gcccacatcg    360
tagccttatc gcagcaccct gcagcccttg gcacggtcgc cgtcaagtac caggacatga    420
ttgcggcgtt gccggaagcc acacatgagg cgatcgtcgg tgtggggaaa cagtggagcg    480
gagcccgagc gcttgaggcc ctgttgacgg tcgcgggaga gctgagaggg cctccccttc    540
agctggacac gggccagttg ctgaagatcg cgaagcgggg aggagtcacg gcggtcgagg    600
cggtgcacgc gtggcgcaat gcgctcacgg gagcacccct caatctgacc ccggatcagg    660
tggttgcgat cgccagtaat ggcggaggca aacaagcact cgaaactgta cagcgcctcc    720
tgccggtact gtgccaagat catggcttga cgcctgagca agtcgtagct attgcatcaa    780
acatcggtgg taaacaggcg ctggaaaccg tacaacgatt actccctgtc ttatgccagg    840
cacacggtct gacccccgac caagttgtag ccattgcgtc taatggcggc gggaaacagg    900
ccctggaaac ggtccaacgt ctgttacccg ttctgtgtca ggctcacggt ctgacccctg    960
cccaggtagt tgcaattgcc agcaacatcg gcgggaaaca agcgctggag actgtgcagc   1020
gtctgctccc tgtgttatgc caagatcatg ggctcactcc ggatcaggtg gtggccatcg   1080
cttccaatat tggcggtaaa caggcgctgg agacagtgca acgactttta cctgttctct   1140
gccaggatca tggtctaact cccgagcagg tcgtcgccat cgcctctcat gacggcggga   1200
aacaagcgtt ggaaactgtc cagcgactcc tgccggtttt gtgccaggcc cacgggctta   1260
ctcctgacca ggtagttgcg atcgcgtcaa atgggggtgg caaacaagcc ctcgaaaccg   1320
tgcaacgcct gctgcccgtc ttgtgccaag ctcatgggct gactccggcg caagtagtcg   1380
cgattgcgag ccacgatggc ggtaagcagg cactggaaac ggttcagcgc ctgctcccgg   1440
ttctatgcca ggatcacggc ctgaccccgg accaggtcgt cgcgatcgcg tcaaatatcg   1500
gtggcaaaca agctttggag acagtacagc gcctgttacc agtgctttgc caggaccatg   1560
gtctgacccc tgagcaagta gtggcgatcg cttctaatat tgggggcaaa caagcgctgg   1620
aaacagtaca gcgtctgtta ccggtcctat gccaggcaca tggcctgacc cctgatcagg   1680
tggtagccat tgccagtcat gatggcggta aacaggcgct tgagactgtc caacgtctgc   1740
tgccggtcct ctgtcaggct catggcctga cgccagctca agtcgtggct atcgcttcgc   1800
atgatggcgg aaaacaggca ctggagactg tgcagcgact gttgccagtt ctgtgtcagg   1860
atcacggttt aactccggac caggtggtcg ctattgcgtc gaatgggggc ggtaaacaag   1920
cgctggaaac tgtgcaacgt ttgctcccag ttctgtgcca ggaccatggg ctgactccgg   1980
aacaggtagt ggccattgct tctaatattg gtgggaaaca ggcgctggaa accgtgcagc   2040
gcctgcttcc agtgctttgc caggcccatg gcctgacgcc agatcaggtg gttgctatag   2100
ccagcaatgg cggcggtaaa caggccctcg aaaccgtcca gcgcctgctc cctgtgctgt   2160
gccaggccca tgggcttacc ccagcgcaag tagtggcgat tgcgtctaat attggtggta   2220
aacaggcgtt ggagactgta caacgcctgc tgccagtttt atgccaagat catggtctga   2280
cccctgagca ggtagtggct attgcatcca acaacggggg cagacccgca ctggagtcaa   2340
tcgtggccca gctttcgagg ccggaccccg cgctggccgc actcactaat gatcatcttg   2400
tagcgctggc ctgcctcggc ggacgacccg ccttggatgc ggtgaagaag gggctcccgc   2460
acgcgcctgc attgattaag cggaccaaca gaaggattcc cgagaggaca tcacatcgag   2520
tggcagatca cgcgcaagtg gtccgcgtgc tcggattctt ccagtgtcac tcccaccccg   2580
```

-continued

```
cacaagcgtt cgatgacgcc atgactcaat ttggtatgtc gagacacgga ctgctgcagc   2640

tctttcgtag agtcggtgtc acagaactcg aggcccgctc gggcacactg cctcccgcct   2700

cccagcggtg ggacaggatt ctccaagcga gcggtatgaa acgcgcgaag ccttcaccta   2760

cgtcaactca gacacctgac caggcgagcc ttcatgcgtt cgcagactcg ctggagaggg   2820

atttggacgc gccctcgccc atgcatgaag gggaccaaac tcgcgcgtca taataggttt   2880

cagccaaaaa acttaagacc gccggtcttg tccactacct tgcagtaatg cggtggacag   2940

gatcggcggt tttcttttct cttctcaagc ttatcccgaa aatttatcaa aaagagtatt   3000

gacttataac tcaacctata ggatacttac agccatcgag agctgcgcca tcctcaatct   3060

ctacctactc tcacttactc ttatcctgcg gggaatgtat acagttcatg tatatattcc   3120

ccgctttttt ttt                                                      3133


<210> SEQ ID NO 35
<211> LENGTH: 20
<212> TYPE: DNA
<213> ORGANISM: Artificial Sequence
<220> FEATURE:
<223> OTHER INFORMATION: Synthetic Construct

<400> SEQUENCE: 35

tttaagaagg agatatacat                                                 20


<210> SEQ ID NO 36
<211> LENGTH: 35
<212> TYPE: DNA
<213> ORGANISM: Artificial Sequence
<220> FEATURE:
<223> OTHER INFORMATION: Synthetic Construct

<400> SEQUENCE: 36

ttgacagcta gctcagtcct aggtataata ctagt                                35


<210> SEQ ID NO 37
<211> LENGTH: 45
<212> TYPE: DNA
<213> ORGANISM: Artificial Sequence
<220> FEATURE:
<223> OTHER INFORMATION: Synthetic Construct

<400> SEQUENCE: 37

aaaaagagta ttgacttcgc atctttttgt acctataatg tgtgg                     45


<210> SEQ ID NO 38
<211> LENGTH: 35
<212> TYPE: DNA
<213> ORGANISM: Artificial Sequence
<220> FEATURE:
<223> OTHER INFORMATION: Synthetic Construct

<400> SEQUENCE: 38

ttgacaatta atcatccggc tcgtaattta tgtgg                                35
```

RIBOREGULATED SWITCHABLE FEEDBACK PROMOTER SYSTEMS AND METHODS

CROSS-REFERENCE TO RELATED PATENT APPLICATIONS

The present application is a Continuation-In-Part Application of International Application PCT/US2019/051133, having an international filing date of Sep. 13, 2019, and which claims the benefit of priority under 35 U.S.C. § 119 (e) to U.S. Provisional Patent Application 62/730,720, filed on Sep. 13, 2018. The content of each of the aforementioned patent documents is incorporated herein by reference in its entirety.

REFERENCE TO A SEQUENCE LISTING

The content of the ASCII text file of the sequence listing named "44062.502 SQL_ST25.txt" which is 53,790 bytes in size was created on Dec. 12, 2024 and electronically submitted herewith the application is incorporated herein by reference in its entirety.

BACKGROUND

The present invention is related to systems and methods for engineering gene expression systems. The systems and methods include and utilize engineered riboregulated switchable feedback promoters. The systems and methods maybe utilized for controlling gene expression and increasing performance in bioprocess systems using dynamic regulation of metabolic pathways.

Dynamic pathway regulation has emerged as a promising strategy in metabolic engineering for improved system productivity and yield, and continues to grow in sophistication. Bacterial stress-response promoters allow dynamic gene regulation using the host's natural transcriptional networks, but lack the flexibility to control the expression timing and overall magnitude of pathway genes. Here, we report a strategy that uses engineered riboregulated switchable feedback promoters (rSFPs) comprising RNA transcriptional regulators to introduce another layer of control over the output of natural stress-response promoters. This new class of promoters can be utilized in gene expression cassettes and can be modularly activated using a variety of mechanisms, from manual induction to quorum sensing.

Here, we describe work in which we developed and applied rSFPs to regulate a toxic cytochrome P450 enzyme in the context of a Taxol precursor biosynthesis pathway and achieved 2.4× fold higher titers than titers from the best reported strain. In addition, we describe work in which we applied rSFPs to regulate expression of a pathway for amorphadiene production and achieved increased production and genetic stability over previously developed strains. We envision that rSFPs will become a valuable tool for flexible and dynamic control of gene expression in metabolic engineering, protein and biologic production, and many other applications.

SUMMARY

Disclosed are systems and methods that include and utilize engineered riboregulated switchable feedback promoters (rSFPs). The disclosed systems and methods include and utilize as a component one or more expression cassettes.

The systems and methods typically include and utilize at least one expression cassette, the expression cassette comprising a promoter operably linked to DNA encoding an RNA switch located 3' of the promoter and a target gene located 3' of the DNA encoding the RNA switch, where the RNA switch regulates expression of the target gene. Suitable promoters may include stress responsive promoters. The promoter of the described gene expression cassettes may be referred to as a riboregulated switchable feedback promoter (rSFP).

In some embodiments, the RNA switch of the expression cassette is selected from the group consisting of: (i) a target sequence for a small transcription activating RNA (STAR RNA); (ii) a toehold switch; and a (iii) riboswitch. In further embodiments, the RNA switch is a target sequence for a STAR RNA and the system further comprises an expression cassette for the STAR RNA, where the expression cassette for the STAR RNA comprises an inducible promoter operably linked to DNA encoding the STAR RNA. In even further embodiment, the RNA switch is a toehold switch and the system further comprises an expression cassette for a trigger RNA for the toehold switch, where the expression cassette for the trigger RNA comprises an inducible promoter operably linked to DNA encoding the trigger RNA. Suitable inducible promoters for expressing an effector for the RNA switch such as STAR RNA or trigger RNA may be induced by effectors including, but not limited to a chemical inducer, cell density, and substrate accumulation.

Also disclosed are vectors comprising the disclosed expression cassettes. In some embodiments of the disclosed systems and methods, a single vector comprises the expression cassette comprising a promoter operably linked to DNA encoding an RNA switch located 3' of the promoter and a target gene or operon located 3' of the DNA encoding the RNA switch, and an expression cassette that expresses an effector for the RNA switch. In other embodiments, separate vectors comprise the expression cassette comprising a promoter operably linked to DNA encoding an RNA switch located 3' of the promoter and a target gene located 3' of the DNA encoding the RNA switch, and an expression cassette that expresses an effector for the RNA switch.

Also disclosed are cells comprising the disclosed riboregulated switchable feedback promoter systems. In some embodiments, the expression cassettes are integrated in the genomes of the disclosed cells. In other embodiments, the expression cassettes are present in one or more episomal vectors. Exemplary cells may include prokaryotic cells.

BRIEF DESCRIPTION OF THE FIGURES

(FIG. 1A) Riboregulated switchable feedback promoters (rSFPs) are composed of a natural stress-response promoter and an RNA transcriptional switch that allows control over the output of native stress-mediated transcriptional networks. (FIG. 1B) Schematic of the small transcription activating RNA (STAR) transcriptional switch mechanism used in rSFPs. A Target DNA sequence (switch symbol) is placed 3' of a stress-response promoter. The transcribed Target RNA is designed to fold into an intrinsic transcription terminator hairpin, composed of a hairpin structure followed immediately by a poly uracil sequence. The formation of this terminator hairpin causes RNA polymerase (RNAP) to terminate transcription upstream of the gene to be regulated (gene OFF). A separately transcribed STAR RNA can bind to both the linear region and the 5' half of the terminator hairpin of the Target RNA, preventing its formation and allowing transcription elongation of the downstream gene (gene ON). In this way the output of the stress-response promoter is controlled by STAR expression, which adds an additional layer of regulation to that present within the stress-mediated transcriptional network that governs expression at the stress-response promoter. (FIG. 1C) Illustration of expression control enabled by rSFPs. Natural stress-response promoters (dashed line) can exhibit dynamic behaviors in response to stress but are fixed with regards to user-defined timing and overall expression magnitude. rSFPs use the additional layer of regulation to resolve this issue and allow control of timing and overall expression magnitude by gating transcriptional output with a trans-acting RNA regulatory switch. (FIG. 1D) Characterization of rSFP variants containing unique envelope stress-response promoters. $P_{L,TetO1}$ inducible STAR expression is used to activate rSFPs containing a natural stress-response promoter upstream of a STAR Target sequence, a ribosome binding site, and a red fluorescent protein (mCherry) coding sequence. Fluorescence characterization was performed on *E. coli* transformed with plasmids encoding each rSFP controlling mCherry expression in the absence and presence of 100 ng/ml aTc. (FIG. 1E) rSFPs enable titration of natural stress-response promoter output. Fluorescence characterization performed on *E. coli* cells containing rSFPs controlling mCherry expression under different levels of aTc induction. Data in d, e represent mean values in units of arbitrary fluorescence/optical density (FL/OD) and error bars represent s.d. of at least n=7 biological replicates. * indicate a statistically significant difference in FL/OD by a two-tailed Welch's t-test (*=P<0.05, **=P<0.005).

(FIG. 2A) Taxol biosynthesis schematic depicting an abbreviated overview of the Taxol precursor pathway involving the toxic cytochrome P450 725A4 (CYP725A4) enzyme. In the *E. coli* strain Tax1, the methylerythritol phosphate (MEP) pathway and taxadiene synthase/geryanlgeranyl diphosphate (GGPP) synthase (TG) module convert glyceraldehyde-3-phosphate (G3P) and pyruvate (PYR) into the 20-carbon backbone taxa-4 (5),11 (12)-diene (taxadiene). Taxadiene is oxygenated by the membrane-anchored CYP725A4 fused with its reductase partner (tcCPR) to form taxadiene-5α-ol. rSFPs utilizing envelope stress-response promoters are applied to control the expression of CYP725A4/tcCPR. IPP=isopentenyl diphosphate, DMAP=dimethylallyl diphosphate. (FIG. 2B) Plasmids used for CYP725A4/tcCPR expression in *E. coli* Tax1. CYP725A4/tcCPR is expressed from a standard IPTG-inducible $P_{Trc}$ promoter in either a low copy (p5Trc, SC101) or medium copy (p10Trc, pACYC) plasmid, or from rSFPs with various $P_{stress}$ promoters encoded on a p15a plasmid. $P_{L,TetO1}$-STAR was used to activate rSFP expression. rSFPs allow CYP725A4/tcCPR expression to be controlled by externally supplied aTc and feedback-regulated by the natural stress response pathways. p5Trc is a gold standard CYP725A4/tcCPR expression system from previously reported optimization efforts. (FIG. 2C) Titers of fermentations with empty *E. coli* Tax1 and *E. coli* Tax1 containing low copy p5Trc (the previous gold standard) or medium copy p10Trc expression of CYP725A4/tcCPR. Addition of p5Trc to *E. coli* Tax1 enables production of oxygenated taxanes at a cost to overall taxane production, while addition of p10Trc eliminates nearly all taxane production presumably due to the toxicity of CYP725A4/tcCPR expression. (FIG. 2D) Titers of fermentations with *E. coli* Tax1 containing CYP725A4/tcCPR under control of rSFPs. Dashed line represents production of oxygenated taxanes from p5Trc. The $P_{ompF}$ rSFP resulted in ~2.2× fold greater oxygenated taxanes (~23.5 mg/L) and ~2.8× fold greater overall taxanes (29.8 mg/L) than the p5Trc strain that is the previous gold standard. Data in c, d represent mean values of fermentation titers after 96 hrs and error bars represent s.d. of at least n=5 biological replicates.

(FIG. 3A) Plasmids used for CYP725A4/tcCPR expression from rSFPs with $P_{stress}$ promoters encoded on a p15a plasmid in *E. coli* Tax1. $P_{L,TetO1}$-STAR was used to activate rSFP expression. (FIG. 3B) Conditions of aTc induction level and timing used for rSFP CYP725A4/tcCPR expression optimization. (FIG. 3C, FIG. 3D) Induction level and timing optimization of fermentations with *E. coli* Tax1 containing the $P_{metN}$ (c) or $P_{ompF}$ (d) rSFP controlling CYP725A4/tcCPR. Heatmap shows the average oxygenated taxane titers for different combinations of aTc concentration and time of induction. (FIG. 3E, FIG. 3F) Titers of fermentations with *E. coli* Tax1 containing the $P_{metN}$ (e) or $P_{ompF}$ (f) rSFP before (100 ng/ml aTc at 0 hrs) and after induction optimization. Dashed line represents production of oxygenated taxanes from p5Trc. Data in c, d, e, f represent mean values of fermentation titers after 96 hrs and error bars represent s.d. of at least n=3 biological replicates. * indicate a statistically significant difference in oxygenated taxane production by a two-tailed Welch's t-test (*=P<0.05, **=P<0.005).

(FIG. 4A) Schematic showing quorum-sensing (QS) activation of rSFPs to allow autonomous control of pathway expression. LuxR is activated by C6-HSL produced by the EsaI HSL synthase upon sufficient accumulation due to an increase in cell density. LuxR activation results in STAR production from the $P_{Lux}$ promoter, thereby activating rSFP expression. (FIG. 4B) Fluorescence experiments showing autonomous activation of $P_{ompF}$ and $P_{metN}$ rSFPs, configured to control mCherry expression, over time. Fluorescence is only significant with the Tax1-QS strain containing a chromosomal LuxR/EsaI expression cassette, but not with the parent Tax1 strain. (FIG. 4C, FIG. 4D) Titers of oxygenated taxadiene fermentations in *E. coli* Tax1 strains containing the $P_{metN}$ (c) or $P_{ompF}$ (d) rSFP controlling CYP725A4/tcCPR expression. Left: in *E. coli* Tax1 (without QS insert) containing a $P_{L,TetO1}$-STAR plasmid induced by aTc; middle: in *E. coli* Tax1 containing a $P_{Lux}$-STAR plasmid; right: in *E. coli* Tax1-QS containing a $P_{Lux}$-STAR plasmid activated by EsaI produced HSL. QS-activated rSFPs obtained similar titers to the unoptimized PL, Tet01-STAR activated rSFPs, but without any external interventions. Dashed line represents production of oxygenated taxanes from p5Trc FIG. 2C. Data in b represent mean values in units of arbitrary fluorescence/optical density (FL/OD) and error bars represent s.d. of at least n=7 biological replicates. Data in c represent mean values of fermentation titers after 96 hrs and error bars represent s.d. of at least n=3 biological replicates.

(FIG. 7A) Schematic of plasmids used for fluorescence characterization of rSFP stress response. $P_{L,TetO1}$-STAR was used to activate expression from select rSFP plasmids. p10Trc was used to induce CYP275A4/tcCPR stress in comparison with an empty vector. Monitoring rSFP controlled expression of mCherry then allows the response to CYP275A4/tcCPR stress to be characterized. (FIG. 7B) Fluorescence characterization of cells containing select $P_{L,TetO1}$-STAR activated rSFPs controlling mCherry expression with 100 ng/ml aTc, and either an empty vector or the p10Trc vector to express CYP725A4/tcCPR and induce membrane stress. Fluorescence values were normalized to the empty vector control and error bars represent standard error of the mean. Experiments were performed as in main FIG. 1*d* except 20 μL of each overnight culture were added to 490 μL of R-media containing selective antibiotics and grown for 4 h at 22C to closely mimic hungate fermentations. 100 ng/mL aTc was added after 4 hrs growth. After another 6 hrs of growth at 22C, 100 μL were sampled for characterization by bulk fluorescence measurements. Pcon=PJ23115. Data represent mean values of fermentation titers and error bars represent standard error of the mean (s.e.m) of at least n=7 biological replicates.

(FIG. 14A) Commonly used constitutive promoters can be manually tuned to alter gene expression levels but are not designed to respond to sources of toxicity, stress, and other biological signals. (FIG. 14B) Natural stress-response promoter and engineered feedback promoter systems use regulatory networks to enable responsiveness to sources of toxicity, stress, and other biological signals, but gene expression timing and tuning is difficult to manipulate. (FIG. 14C) A switchable feedback promoter (SFP) integrates external control with feedback-responsive promoters, allowing induction timing and tuning with inducible regulators and autonomous quorum sensing systems. (FIG. 14D) A riboregulated SFP (rSFP) is composed of a feedback-responsive promoter and an RNA transcriptional switch. (FIG. 14E) Schematic of the small transcription activating RNA (STAR) mechanism. A target sequence (switch symbol) is placed downstream of a feedback-responsive promoter. The transcribed target RNA is designed to fold into an intrinsic transcription terminator hairpin that causes RNA polymerase to terminate transcription upstream of the gene to be regulated (gene OFF). A separately transcribed STAR RNA can bind to the target RNA, preventing hairpin formation and allowing transcription elongation (gene ON).

(FIG. 15A) Time-course characterization of the PgadE rSFP. Fluorescence characterization was performed on *E. coli* DH1 transformed with plasmids encoding the PgadE rSFP controlling mCherry expression in the absence and presence of 100 ng/ml aTc added at 0 hrs or 4 hrs. (FIG. 15B) The P gadE rSFP under different aTc induction levels measured after 6 hrs of growth. (FIG. 15C) Responsiveness of the PgadE rSFP to FPP accumulation. Fluorescence characterization was performed on *E. coli* DH1 transformed with a $P_{LTetO\text{-}1}$ inducible STAR plasmid and a plasmid encoding the PgadE rSFP controlling mCherry expression in the absence and presence of 100 ng/mL aTc added at inoculation. Plasmids were co-expressed with pMevT-MBIS (FPP production) or pMevT-MBIS ΔMPD (no FPP production) induced with IPTG at 2.5 hrs. Reduced endpoint expression was observed for P gadE rSFP with pMevT-MBIS. Lines in a-c represent mean values in units of arbitrary fluorescence/optical density (FL/OD) and shaded areas represent mean values +/−s.d. of at least n=16 biological replicates. Points represent individual data points for each condition. FPP, farnesyl pyrophosphate. MPD, mevalonate pyrophosphate decarboxylase.

(FIG. 16A) Characterization of rSFP variants containing unique envelope stress-response promoters. $P_{LTetO\text{-}1}$ inducible STAR expression is used to activate rSFPs containing a natural stress-response promoter upstream of a STAR target sequence, a ribosome binding site, and a red fluorescent protein (mCherry) coding sequence. (FIG. 16B) Fluorescence characterization was performed on *E. coli* Tax1 transformed with plasmids encoding each rSFP controlling mCherry expression in the absence and presence of 100 ng/mL aTc added at inoculation. Data in (b) represent mean values in units of arbitrary fluorescence/optical density (FL/OD) and error bars represent s.d. of n=9 biological replicates. * indicate a statistically significant difference in FL/OD by a Welch's t-test (two-tailed, unequal variances) (*=P<0.05, **=P<0.005) between no aTc and 100 ng/ml aTc conditions. P values for each condition are reported in Table 15. Points represent individual data points for each condition.

(FIG. 17A) Schematic of plasmids used for fluorescence characterization of rSFP stress response. PJ23119-STAR8 was used to constitutively activate expression from select rSFP plasmids. PBAD-Pg1B was used to induce Pg1B stress. Monitoring rSFP controlled expression of mCherry then allows the response to Pg1B stress to be characterized. (FIG. 17B) Fluorescence characterization of cells containing select PJ23119-STAR activated rSFPs controlling mCherry expression, and PBAD-Pg1B induced with either 0 μg/mL or 200 μg/mL L-arabinose. Pconstitutive=PJ23115. Overall expression levels differed significantly from FIG. 3 in media conditions used for Pg1B expression (see methods). Bars represent mean values in units of arbitrary fluorescence/optical density (FL/OD) and error bars represent s.d. of n=16 biological replicates. Individual data points represent FL/OD data.

(FIG. 18A) Architecture of a STAR-regulated constitutive promoter (shaded red) and the stabilized rSFP. Expression activation is mediated by the inducible system $P_{LTetO\text{-}1}$-STAR vector in both cases. The stabilized rSFP uses a previously developed co-expressed TALE repressor[27] that counters changes in gene expression from higher plasmid DNA copy number resulting in outputs that are uniform across different plasmids. Constructs were cloned into SC101 plasmid variants with a range of copy numbers. (FIG. 18B) Fluorescence characterization of the stabilized rSFP system. Experiments were performed on *E. coli* transformed with plasmids encoding the stabilized rSFP controlling sfGFP expression in the absence and presence of 100 ng/ml aTc for the STAR-regulated constitutive promoter and stabilized rSFP for each SC101 plasmid. Bars in (b) represent mean values in units of molecules of equivalent fluorescein (MEFL) determined by flow cytometry and error bars represent s.d. of n=11 biological replicates. Filled points represent individual data points of MEFL.

(FIG. 19A) Amorphadiene biosynthesis schematic depicting control of the MevT-MBIS pathway with the PgadE rSFP. The MevT module produces mevalonate from Acetyl-CoA and the MBIS module produces FPP from mevalonate. Amorphadiene synthase (ADS) converts FPP to amorphadiene. (FIG. 19B) Fermentation titers with *E. coli* DH1 containing pTrc-ADS and MevT-MBIS under control of the unregulated PgadE promoter or PgadE rSFP in the absence or presence of 100 ng/ml aTc added at inoculation. Fermentations were performed in supplemented M9 minimal media with 0.5 mM IPTG added at inoculation to induce ADS expression. Bars in b represent mean values of amorphadiene titers measured with GCMS after 72 hrs of fermentation and error bars represent s.d. of n=6 biological replicates. Points represent individual data points of amorphadiene.

(FIG. 20A) Taxol biosynthesis schematic depicting an abbreviated overview of the Taxol precursor pathway involving the toxic cytochrome P450 (CYP) 725A4 enzyme. In the *E. coli* strain Tax1, the methylerythritol phosphate (MEP) pathway and taxadiene synthase/geryanlgeranyl diphosphate (GGPP) synthase (TS) module convert glyceraldehyde-3-phosphate (G3P) and pyruvate (PYR) into the 20-carbon backbone taxa-4 (5),11 (12)-diene (taxadiene). Taxadiene is oxygenated by the CYP725A4/tcCPR fusion enzyme to form taxadiene-5cx-ol. CYP725A4/tcCPR was initially expressed from a standard IPTG-inducible $P_{Trc}$ promoter in either a low copy (p5Trc) or medium copy (p10Trc) plasmid. IPP=isopentenyl diphosphate, DMAPP=dimethylallyl diphosphate. (FIG. 20B) rSFPs are applied to control CYP725A4/tcCPR utilizing the $P_{LTetO\text{-}1}$-STAR vector. (FIG. 20C) Fermentation titers with *E. coli* Tax1 containing an empty vector (-), p5Trc, p10Trc, or an rSFP plasmid for expression of CYP725A4/tcCPR with 100 ng/ml aTc added at inoculation. Dashed line represents production of oxygenated taxanes from p5Trc. Bars in c represent mean values of taxane titers measured with GCMS after 96 hrs of fermentation and error bars represent s.d. of at least n=4 biological replicates. Filled points represent individual data points of overall taxanes or individual data points of oxygenated taxanes.

FIGS. 21A-12E show induction optimization of the best performing taxadiene oxygenation rSFP strains. (FIG. 21A) Conditions of aTc induction level and timing used for rSFP CYP725A4/tcCPR expression optimization. (FIG. 21B, FIG. 21C) Induction level and timing optimization of fermentations with *E. coli* Tax1 containing the (b) $P_{metN}$ or (c) $P_{ompF}$ rSFP controlling CYP725A4/tcCPR. Heatmaps show mean values of oxygenated taxane titers measured with GCMS for different combinations of aTc concentration and induction time after 96 hrs of fermentation.

(FIG. 22A) Schematic showing the $P_{Lux}$ rSFP activation system in the presence of EsaI and LuxR to allow autonomous control of pathway expression. LuxR is activated by C6-HSL produced by the EsaI HSL synthase upon sufficient accumulation due to an increase in cell density. LuxR activation results in STAR production from the $P_{Lux}$ promoter, thereby activating rSFP expression. (FIG. 22B, FIG. 22C) Fluorescence experiments showing autonomous activation of mCherry expression over time with (b) the PgadE rSFP transformed in *E. coli* DH1 or *E. coli* DH1-QS and (c) the $P_{ompF}$ rSFP transformed in *E. coli* Tax1 or *E. coli* Tax1-QS. Lines in b, c represent mean values in units of arbitrary fluorescence/optical density (FL/OD) and shaded areas represent mean values +/−s.d. of at least n=9 biological replicates. Points represent individual data points for each condition.

(FIG. 23A) Schematic showing the $P_{Lux}$ rSFP activation system in the presence of EsaI and LuxR to allow autonomous control of pathway expression. (FIG. 23B) Amorphadiene fermentation titers with the PgadE rSFP controlling MevT-MBIS expression and pTrc-ADS. Left: *E. coli* DH1 (without QS insert) containing a $P_{LTetO\text{-}1}$-STAR plasmid induced by aTc; middle: *E. coli* DH1 containing a $P_{Lux}$-STAR plasmid; right: *E. coli* DH1-QS containing a $P_{Lux}$-STAR plasmid. (FIG. 23C) Oxygenated taxadiene fermentation titers with the $P_{ompF}$ rSFP controlling CYP725A4/tcCPR expression. Left, middle, and right bars contain same conditions as a, but for oxygenated taxadiene fermentations in *E. coli* Tax1. Dashed line represents production of oxygenated taxanes from p5Trc in FIG. 7C. Bars in a represent mean values amorphadiene titers measured with GCMS after 72 hrs of fermentation and error bars represent s.d. of n=6 biological replicates. Color filled points represent individual data points. Bars in b represent mean values taxane titers measured with GCMS after 96 hrs of fermentation and error bars represent s.d. of n=4 biological replicates. Filled points represent individual data points of overall taxanes or t individual data points of oxygenated taxanes.

(FIG. 24A) Schematic of plasmids used for fluorescence characterization of STAR-regulated constitutive promoter response to FPP-induced stress. (FIG. 24B) Fluorescence characterization was performed on *E. coli* DH1 transformed with a $P_{LTetO\text{-}1}$ inducible STAR plasmid and a plasmid encoding the $P_{Con}$ rSFP controlling mCherry expression in the absence) and presence of 100 ng/ml aTc added at inoculation. Plasmids were co-expressed with pMevT-MBIS (FPP production, red) or pMevT-MBIS ΔMPD (no FPP production) induced with IPTG at 2.5 hrs. pMevT-MBIS DMPD is defective in pyrophosphate decarboxylase activity involved in conversion of mevalonate to FPP. All data were normalized to the endpoint expression level of the +aTc, pMevT-MBIS ΔMPD condition. Lines represent mean values in units of arbitrary fluorescence/optical density (FL/OD) and shaded areas represent mean values +/−s.d. of at least n=16 biological replicates. Points represent individual data points for each condition.

(FIG. 26A) $P_{LTetO\text{-}1}$ inducible STAR expression is used to activate rSFPs containing a natural stress-response promoter upstream of a STAR target sequence, a ribosome binding site, and a red fluorescent protein (mCherry) coding sequence. (FIG. 26B) rSFPs enable titration of natural stress-response promoter output. Fluorescence characterization performed on *E. coli* Tax1 cells containing rSFPs controlling mCherry expression under different levels of aTc added at inoculation. (FIG. 26C) Characterization of rSFP variants over time. Fluorescence characterization was performed on *E. coli* Tax1 transformed with plasmids encoding each rSFP in b controlling mCherry expression in the presence of 100 ng/mL aTc added at inoculation. (FIG. 26D) Fluorescence characterization of select unregulated stress-response promoter in the absence of aTc. Color coding in c and d are the same as in b. Individual data points represent fluorescence measurements in units of arbitrary fluorescence/optical density (FL/OD). The inset is provided for better comparison with SI FIG. 16C. Lines represent mean values of FL/OD and shaded areas represent mean +/−s.d. of at least n=7 biological replicates.

(FIG. 27A) Fold activation (ON/OFF) of the STAR-regulated constitutive promoter or stabilized rSFP on different copy number SC101 variants. Fluorescence characterization was performed on *E. coli* TG1 transformed with plasmids encoding each STAR-regulated constitutive promoter or stabilized rSFP controlling mCherry expression and PLTet0-1-STAR in the absence and presence of 100 ng/ml aTc. (FIG. 27B) Comparison of robust coefficient of variation (Robust CV) for STAR-regulated constitutive promoters and stabilized rSFPs. Stabilized rSFPs have lower cell-to-cell variability at high plasmid copy number, as expected due to the incorporation of negative feedback. Individual data points in a represent fold activation calculated as MEFL for each colony grown with 100 ng/ml aTc divided by MEFL of the same colony without aTc. Bars represent mean fold activation and error bars represent s.d. of n=11 biological replicates. Individual data points in b represent robust CV calculated over the flow cytometry distribution of each individual measurement using FlowJo 10.7.1 software. Bars represent mean robust CV's and error bars represent s.d. of n=11 biological replicates.

FIG. 28C shows titers of fermentations after 72 hrs with *E. coli* DH1 containing pADS and MevT-MBIS under control of the stabilized promoter rSFP. $P_{LTetO\text{-}1}$-STAR was used to regulate PgadE expression in the absence and presence of 100 ng/mL aTc added at inoculation. Bars represent mean titers of amorphadiene measured with GC-MS and error bars represent s.d. of n=6 biological replicates. Color filled points represent individual data points of amorphadiene titers. P indicates results of a Welch's t-test (two-tailed, unequal variances) between no aTc and 100 ng/ml aTc conditions.

(FIG. 30A) Schematic of plasmids used for fluorescence characterization of rSFP stress response. $P_{LTetO\text{-}1}$-STAR was used to activate expression from select rSFP plasmids. p10Trc was used to induce CYP275A4/tcCPR stress in comparison with an empty vector. Monitoring rSFP controlled expression of mCherry then allows the response to CYP275A4/tcCPR stress to be characterized. (FIG. 30B) Fluorescence characterization of cells containing PLTet0-1-STAR activated rSFPs controlling mCherry expression with 100 ng/ml aTc, and either an empty vector or the p10Tre vector to express CYP725A4/tcCPR and induce membrane stress. Experiments were performed as in main FIG. 3B except 10 μL of each overnight culture were added to 490 μL of R-media containing selective antibiotics and grown for 4 h at 22C to closely mimic hungate fermentations. 100 ng/mL aTc was added after 4 hrs growth. After another 6 hrs of growth at 22C, 100 μL were sampled for characterization by bulk fluorescence measurements. $P_{con}$=PJ23115. Bars represent mean values in units of arbitrary fluorescence/optical density (FL/OD) and error bars represent s.d. of at least n=7 biological replicates. Individual data points represent FL/OD data. * indicate a statistically significant difference in FL/OD between the p10trc and empty vector condition by a Welch's t-test (two-tailed, unequal variances) (** P=0.0000261).

DETAILED DESCRIPTION

Figure 1A:
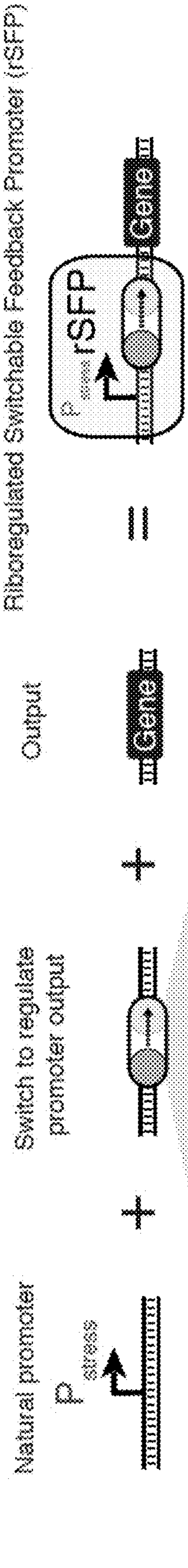
FIGS. 1A-1E show riboregulated switchable feedback promoters.

The present invention is described herein using several definitions, as set forth below and throughout the application.

Unless otherwise specified or indicated by context, the terms "a", "an", and "the" mean "one or more." For example, "a system," "a method," "a protein," "a vector," "a domain," "a binding site," and "an RNA" should be interpreted to mean "one or more systems," "one or more methods," "one or more proteins," "one or more vectors," "one or more domains," "one or more binding sites," and "one or more RNAs," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, “about” and “approximately” will mean plus or minus ≤10% of the particular term and “substantially” and “significantly” will mean plus or minus >10% of the particular term.

As used herein, the terms “include” and “including” have the same meaning as the terms “comprise” and “comprising” in that these latter terms are “open” transitional terms that do not limit claims only to the recited elements succeeding these transitional terms. The term “consisting of,” while encompassed by the term “comprising,” should be interpreted as a “closed” transitional term that limits claims only to the recited elements succeeding this transitional term. The term “consisting essentially of,” while encompassed by the term “comprising,” should be interpreted as a “partially closed” transitional term which permits additional elements succeeding this transitional term, but only if those additional elements do not materially affect the basic and novel characteristics of the claim.

As used herein, the terms “regulation” and “modulation” may be utilized interchangeably and may include “promotion” and “induction.” For example, a switch that regulates or modulates expression of a target gene may promote and/or induce expression of expression of the target gene. In addition, the terms “regulation” and “modulation” may be utilized interchangeably and may include “inhibition” and “reduction.” For example, a switch that regulates or modulates expression of a target gene may inhibit and/or reduce expression of expression of the target gene.

Polynucleotides and Uses Thereof

The terms “polynucleotide,” “polynucleotide sequence,” “nucleic acid” and “nucleic acid sequence” refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

The terms “nucleic acid” and “oligonucleotide,” as used herein, may refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms “nucleic acid”, “oligonucleotide” and “polynucleotide”, and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1 (3): 165-187, incorporated herein by reference.

Regarding polynucleotide sequences, the terms “percent identity” and “% identity” refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including “blastn,” that is used to align a known polynucleotide sequence with other polynucleotide sequences from a variety of databases. Also available is a tool called “BLAST 2 Sequences” that is used for direct pairwise comparison of two nucleotide sequences. “BLAST 2 Sequences” can be accessed and used interactively at the NCBI website. The “BLAST 2 Sequences” tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, “variant,” “mutant,” or “derivative” may be defined as a nucleic acid sequence having at least 50% sequence identity to the particular nucleic acid sequence over a certain length of one of the nucleic acid sequences using blastn with the “BLAST 2 Sequences” tool available at the National Center for Biotechnology Information’s website. (See Tatiana A. Tatusova, Thomas L. Madden (1999), “Blast 2 sequences—a new tool for comparing protein and nucleotide sequences”, FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, *E. coli*, plants, and other host cells.

A “recombinant nucleic acid” is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence", "target region", and "target nucleic acid," as used herein, are synonymous and may refer to a region or sequence of a nucleic acid which is to be hybridized and/or bound by another nucleic acid (e.g., a target sequence that is bound by a STAR RNA and/or a target sequence that is bound by a trigger RNA for a Toehold switch) . . .

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning-A Laboratory Manual, Cold Spring Harbor Laboratory, Cold Spring Harbor, New York; Wetmur, 1991, Critical Review in Biochem. and Mol. Biol. 26 (3/4): 227-259; and Owczarzy et al., 2008, Biochemistry, 47:5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly$(A)_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, RNA polymerases of bacteriophages (e.g. T3 RNA polymerase, T7 RNA polymerase, SP6 RNA polymerase), and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, "expression template" refers to a nucleic acid that serves as substrate for transcribing at least one RNA. Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

"Transformation" or "transfection" describes a process by which exogenous nucleic acid (e.g., DNA or RNA) is introduced into a recipient cell. Transformation or transfection may occur under natural or artificial conditions according to various methods well known in the art, and may rely on any known method for the insertion of foreign nucleic acid sequences into a prokaryotic or eukaryotic host cell. The method for transformation or transfection is selected based on the type of host cell being transformed and may include, but is not limited to, bacteriophage or viral infection or non-viral delivery. Methods of non-viral delivery of nucleic acids include lipofection, nucleofection, microinjection, electroporation, heat shock, particle bombardment, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam.TM. and Lipofectin.TM.). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term "transformed cells" or "transfected cells" includes stably transformed or transfected cells in which the inserted DNA is capable of replication either as an autonomously replicating plasmid or as part of the host chromosome, as well as transiently transformed or transfected cells which express the inserted DNA or RNA for limited periods of time.

The polynucleotide sequences contemplated herein may be present in expression vectors. For example, the vectors may comprise a polynucleotide encoding an ORF of a protein operably linked to a promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter operably linked to a polynucleotide that encodes a protein. A "heterologous promoter" refers to a promoter that is not the native or endogenous promoter for the protein or RNA that is being expressed.

As used herein, "expression" refers to the process by which a polynucleotide is transcribed from a DNA template (such as into mRNA or another RNA transcript) and/or the process by which a transcribed mRNA is subsequently translated into peptides, polypeptides, or proteins. Transcripts and encoded polypeptides may be collectively referred to as "gene product."

The term "vector" refers to some means by which nucleic acid (e.g., DNA) can be introduced into a host organism or host tissue. There are various types of vectors including plasmid vector, bacteriophage vectors, cosmid vectors, bacterial vectors, and viral vectors. As used herein, a "vector" may refers to a recombinant nucleic acid that has been engineered to express a heterologous polypeptide (e.g., the fusion proteins disclosed herein). The recombinant nucleic acid typically includes cis-acting elements for expression of the heterologous polypeptide.

In the methods contemplated herein, a host cell may be transiently or non-transiently transfected (i.e., stably transfected) with one or more vectors described herein. A cell transfected with one or more vectors described herein may be used to establish a new cell line comprising one or more vector-derived sequences. In the methods contemplated herein, a cell may be transiently transfected with the components of a system as described herein (such as by transient transfection of one or more vectors), and modified through the activity of a complex, in order to establish a new cell line comprising cells containing the modification but lacking any other exogenous sequence.

Peptides, Polypeptides, and Proteins

As used herein, the terms "protein" or "polypeptide" or "peptide" may be used interchangeable to refer to a polymer of amino acids. Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids.

A "protein" as contemplated herein typically comprises a polymer of naturally or non-naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The proteins disclosed herein may include "wild type" proteins and variants, mutants, and derivatives thereof. As used herein the term "wild type" is a term of the art understood by skilled persons and means the typical form of an organism, strain, gene or characteristic as it occurs in nature as distinguished from mutant or variant forms. As used herein, a "variant, "mutant," or "derivative" refers to a protein molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a mutant or variant molecule may one or more insertions, deletions, or substitution of at least one amino acid residue relative to a reference polypeptide.

Regarding proteins, a "deletion" refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide). A "variant," "mutant," or "derivative" of a reference polypeptide sequence may include a deletion relative to the reference polypeptide sequence.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full-length polypeptide. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, variants, or described herein may have one or more functional or biological activities exhibited by a reference polypeptide (e.g., one or more functional or biological activities exhibited by wild-type protein).

The disclosed proteins may be substantially isolated or purified. The term “substantially isolated or purified” refers to proteins that are removed from their natural environment, and are at least 60% free, preferably at least 75% free, and more preferably at least 90% free, even more preferably at least 95% free from other components with which they are naturally associated.

Riboregulated Switchable Feedback Promoter Systems and Methods

Disclosed are systems and methods that include and utilize engineered riboregulated switchable promoters (rSFPs). The disclosed systems and methods include and utilize as a component one or more expression cassettes. In some embodiments, the disclosed systems and methods utilize a first expression cassette and a second expression cassette as further described.

The systems and methods typically include and utilize at least a first expression cassette, the first expression cassette comprising a promoter operably linked to DNA encoding an RNA switch located 3' of the promoter and a target gene located 3' of the DNA encoding the RNA switch, where the RNA switch regulates expression of the target gene. Suitable promoters may include stress responsive promoters. The promoter of the disclosed expression cassettes, systems, and methods may be referred to as a riboregulated switchable feedback promoter (rSFP).

In some embodiments, suitable promoters may include, but are not limited to stress responsive promoters that are regulated by an effector selected from the group consisting of metabolites including toxic metabolites, proteins, RNAs, responses to cellular conditions such as pH, temperature, ion levels, or $O_2$ levels, extracellular quorum-sensing signals, membrane stresses, unfolded protein stress responses, and stresses caused by reactive oxygen species (ROS). In some embodiments, suitable promoters may include any natural promoter that is regulated by an endogenous temporal gene expression network and exhibits a temporal pattern of gene expression. In other embodiments, suitable stress responsive promoters are selected from promoters for any of gntK, yhjX, uraA, ycbS, ataA, mtgA, ecpD, grxA, ybcU, fecA, fadL, b1762, carA, ompT, yeeF, metN, ompF, gadE.

In some embodiments, the disclosed systems, expression cassettes, and/or methods include and/or utilize one or more RNA switches selected from the group consisting of: (i) a target sequence for a small transcription activating RNA (STAR RNA); (ii) a toehold switch; and a (iii) riboswitch. Typically, the RNA switch is an RNA element that can be positively regulated to induce expression of the target gene.

In some embodiments, the RNA switch is a target sequence for a STAR RNA and the system further comprises a second expression cassette for the STAR RNA, where the second expression cassette for the STAR RNA comprises an inducible promoter operably linked to DNA encoding the STAR RNA. Suitable inducible promoters for the second expression cassette of this embodiment may include promoters that are induced by an effector selected from the group consisting of a chemical inducer, cell density, light, temperature, pH, $O_2$ levels, substrate accumulation, and any natural promoter that is regulated by the host's endogenous transcriptional network. Suitable effectors for the inducible promoter of the second expression cassette further may include, but are not limited to n-butanol accumulation, glucose depletion, geranylgeranyl pyrophosphate accumulation, farnesyl-pyrophophate accumulation, anhydrotetracycline (aTc), isopropyl β-D-1-thiogalactopyranoside (IPTG), L-arabinose, light, temperature, $O_2$ levels, pH, light, ion levels, membrane stresses, unfolded protein stress responses, stress caused by reactive oxygen species (ROS), and N-acyl-homoserine lactone (AHL) accumulation at high cell density.

In further embodiments, the RNA switch is a toehold switch and the system further comprises a second expression cassette for a trigger RNA for the toehold switch, where the second expression cassette for the trigger RNA comprises an inducible promoter operably linked to DNA encoding the trigger RNA. Suitable inducible promoters for the second expression cassette of this embodiment may include promoters that are induced by an effector selected from the group consisting of a chemical inducer, cell density, light, temperature, pH, $O_2$ levels, substrate accumulation, and any natural promoter that is regulated by the host's endogenous transcriptional network. Suitable effectors for the inducible promoter of the second expression cassette further may include, but are not limited to n-butanol accumulation, glucose depletion, geranylgeranyl pyrophosphate accumulation, farnesyl pyrophosphate accumulation, anhydrotetracycline (aTc), isopropyl β-D-1-thiogalactopyranoside (IPTG), L-arabinose, light, temperature, $O_2$ levels, pH, light, ion levels, membrane stresses, unfolded protein stress responses, stress caused by reactive oxygen species (ROS), and N-acyl-homoserine lactone (AHL) accumulation at high cell density.

Also disclosed are vectors comprising the disclosed expression cassettes. Suitable vectors may include episomal vectors such as plasmid vectors. In some embodiments of the disclosed systems and methods, a single vector comprises both of the first expression cassette described above (i.e., a first expression cassette a promoter operably linked to DNA encoding an RNA switch located 3' of the promoter and a target gene located 3' of the DNA encoding the RNA switch), and the second expression cassette described above (i.e., a second expression cassette that expresses an effector for the RNA switch). In other embodiments of the disclosed systems and methods, separate vectors comprise the first expression cassette described above (i.e., a first expression cassette a promoter operably linked to DNA encoding an RNA switch located 3' of the promoter and a target gene located 3' of the DNA encoding the RNA switch), and the second expression cassette described above (i.e., a second expression cassette that expresses an effector for the RNA switch).

Also disclosed are cells comprising the disclosed riboregulated switchable feedback promoter systems. In some embodiments, the expression cassettes are integrated in the genomes of the disclosed cells. In other embodiments, the expression cassettes are present in one or more episomal vectors such as episomal plasmids. Exemplary cells may include prokaryotic cells, include bacteria suitable for large-scale production methods.

Illustrative Embodiments

The following embodiments are illustrative and should not be interpreted to limit the scope of the claimed subject matter.

Embodiment 1. A riboregulated switchable feedback promoter system comprising an expression cassette, the expression cassette comprising a promoter operably linked to DNA encoding an RNA switch located 3' of the promoter and a target gene or operon located 3' of the DNA encoding the RNA switch.

Embodiment 2. The system of embodiment 1, wherein the promoter is a stress responsive promoter.

Embodiment 3. The system of embodiment 2, wherein the stress responsive promoter is selected from promoters for any of gntK, yhjX, uraA, ycbS, ataA, mtgA, ecpD, grxA, ybcU, fecA, fadL, b1762, carA, ompT, yeeF, metN, ompF, and gadE.

Embodiment 4. The system of any of the foregoing embodiments, wherein the promoter is regulated by an effector selected from the group consisting of metabolites including toxic metabolites, proteins, RNAs, responses to cellular conditions such as pH, temperature, ion levels, or $O_2$ levels, extracellular quorum-sensing signals, membrane stresses, unfolded protein stress responses, and stresses caused by reactive oxygen species (ROS).

Embodiment 5. The system of embodiment 1, where the promoter is transcriptionally regulated by an endogenous temporal gene expression network.

Embodiment 6. The system of any of embodiments 1-5, wherein the system comprises one or more RNA switches selected from the group consisting of: (i) a transcriptional terminator and a target sequence for a small transcription activating RNA (STAR RNA); (ii) a toehold switch comprising a target sequence for a trigger RNA; and (iii) a riboswitch.

Embodiment 7. The system of embodiment 6, wherein the RNA switch is a target sequence for a STAR RNA and the system further comprises an expression cassette for the STAR RNA, wherein the expression cassette for the STAR RNA comprises an inducible promoter operably linked to DNA encoding the STAR RNA.

Embodiment 8. The system of embodiment 7, wherein the RNA switch is a toehold switch and the system further comprises an expression cassette for a trigger RNA for the toehold switch, wherein the expression cassette for the trigger RNA comprises an inducible promoter operably linked to DNA encoding the trigger RNA.

Embodiment 9. The system of embodiment 8 or 9, wherein the inducible promoter for the STAR or trigger RNA is induced by an effector selected from the group consisting of a chemical inducer, cell density, light, temperature, pH, $O_2$ levels, substrate accumulation, or an endogenous temporal gene expression network.

Embodiment 10. The system of embodiment 9, wherein the effector is selected from n-butanol accumulation, glucose depletion, geranylgeranyl pyrophosphate accumulation, farnesyl-pyrophosphate accumulation, anhydrotetracycline (aTc), isopropyl β-D-1-thiogalactopyranoside (IPTG), L-arabinose, light, temperature, $O_2$, pH, light, ion levels, membrane stresses, unfolded protein stress responses, stress caused by reactive oxygen species (ROS), and N-acyl-homoserine lactone (AHL) accumulation at high cell density Embodiment 11. The system of any of the foregoing embodiment wherein the expression cassette or expression cassettes are present in one or more vectors.

Embodiment 12. A cell comprising the system or one or more components of any system of any of the foregoing embodiments.

Embodiment 13. The cell of embodiment 12, wherein the cell is a prokaryotic cell.

Embodiment 14. The cell of claim 12, wherein the system or the one or more components of the system are integrated into the genome of the cell (e.g., to provide a recombinant cell).

EXAMPLES

The following Examples are illustrative and should not be interpreted to limit the scope of the claimed subject matter.

Example 1

Title-Compositions for Synthetic Regulation of Natural Promoters and Uses Thereof

TECHNICAL FIELD

The technical field relates to methods for controlling gene expression and increasing bioprocess performance using dynamic regulation of metabolic pathways.

Abstract

Metabolic engineering—the manipulation of microorganisms for the purpose of biochemical production—continues to mature as an environmentally friendly and potentially sustainable alternative to traditional petroleum-based production of important compounds including foods, fuels, and pharmaceuticals. However, optimizing the production for commercial scale bioprocessing is complex and often requires many engineering cycles to develop systems that help the microorganisms overcome the inhibitory burdens of compound production at high yield. In this disclosure, a new tool for microorganism optimization and gene expression control is described, called a riboregulated switchable feedback promoter (rSFP), that will accelerate and simplify optimization by utilizing and controlling a microorganism's natural ability to sense and optimize its metabolism against product stresses. rSFPs are developed and applied to the production of different industrially relevant molecules to ensure relevance across diverse metabolic engineering applications.

Applications

Applications of the disclosed technology include, but are not limited to: (i) Controlled dynamic regulation of gene expression in response to environmental cues, endogenous cellular signals, exogenous signals and stresses in bacteria, where gene expression includes expression of metabolic pathway enzymes, protein production, therapeutic proteins, RNA molecules, reporter genes, and the like; (ii) Signal integration of multiple environmental cues and stresses in bacteria to dynamically control gene expression; (iii) Specific applications to metabolic engineering, biochemical production, and bioprocess optimization include but are not limited to: (a) Regulation of membrane-bound enzymes, such as cytochrome P450s, in response to cellular stress; (b) Regulation of membrane transporters, such as efflux pumps, in response to cellular stress; and (c) Regulation of metabolic pathway enzymes in response to toxic intermediates and products; and (iv) Plug-and-play inducible control and signal integration of natural bacterial promoters (such as stress response promoters, two-component sensors) for any purpose in metabolic pathways, bioprocesses, bioremediation, live therapeutics in the microbiome, and health and environmental diagnostics; (v) Signal integration of biosensors and quorum-sensing signals with natural bacterial promoters for metabolic engineering applications; (vi) Optimization of metabolic pathway titers, preparation of seed trains for biochemical production and bioprocess optimization; and (vii) Controlled expression of toxic proteins.

Advantages

Existing technologies use stress response promoters to dynamically control expression of genes in response to stresses. rSFPs provide an extra layer of user control over stress response promoters that enable signal integration with common inducible promoters, quorum-sensing signals, and metabolite biosensors. Existing technologies also use quorum sensing signals and biosensors to control gene expression in metabolic pathways. However, these systems are often unable to integrate multiple inputs. rSFPs enable integration of more than two dynamic signals for control of gene expression. Existing technologies also use large libraries of static gene regulation elements (Promoters, RBSs, etc.) to tune expression levels of pathway enzymes. However, these result in expression levels that are constant and do not adaptively change in response to cellular conditions. rSFPs provide timing control and adaptive responses to cellular conditions by enabling integration of multiple dynamic signals for control of gene expression.

Brief Summary of the Technology

In some embodiments, rSFP systems utilize two expression cassettes that are cloned into expression vectors or into a host genome. In a first expression cassette, a natural stress promoter, or any natural promoter from the host, is placed 5' of the target gene or operon that is the target for regulation. Between the natural promoter and the target gene, a "TARGET" sequence is placed that will be transcribed into the 5' end of the mRNA. In some embodiments, this TARGET sequence contains a transcriptional terminator and the target sequence for a STAR RNA. In this embodiment, the second expression cassette then comprises an inducible promoter, a quorum-sensing promoter, or a biosensor promoter controlling expression of a STAR RNA. When the rSFP system is activated (such as upon induction of expression of STAR RNA with a small molecule inducer of the inducible promoter for the STAR RNA) the STAR RNA is expressed and disrupts folding of the transcriptional terminator downstream of the stress promoter for the target gene. This process enables controlled target gene expression from the natural promoter sequence by allowing full length transcription of the target gene to occur only in the presence of the induction signal for expression of the STAR RNA. FIG. 1 illustrates an rSFP as described.

Technical Description

In some embodiments, IFP systems utilize two expression cassettes that are cloned into expression vectors or into a host genome. In a first expression cassette, a natural stress promoter, or any natural promoter from the host, is placed 5' of the target gene that is the target for regulation. Between the natural promoter and the target gene, a "TARGET" sequence is placed that will be transcribed into the 5' end of the mRNA. In some embodiments, this TARGET sequence contains a transcriptional terminator and the target sequence for a STAR RNA. In this embodiment, the second expression cassette then comprises an inducible promoter, a quorum-sensing promoter, or a biosensor promoter controlling expression of a STAR RNA. When the IFP system is activated (such as upon induction of expression of STAR RNA with a small molecule inducer of the inducible promoter for the STAR RNA) the STAR RNA is expressed and disrupts folding of the transcriptional terminator downstream of the stress promoter for the target gene. This process enables controlled target gene expression from the natural promoter sequence by allowing full length transcription of the target gene to occur only in the presence of the induction signal for expression of the STAR RNA. FIG. 1 illustrates an IFP as described.

The STAR RNA and TARGET sequence of the aforementioned embodiment can be replaced with toehold activating RNAs that activate translation of target genes when the appropriate target sequence is placed 5' of the gene and 3' of the natural promoter. In this embodiment, the toehold activating RNAs then are expressed from the second expression cassette comprising an inducible promoter, a quorum-sensing promoter, or a biosensor promoter controlling expression of the toehold activating RNAs, and the TARGET sequence for STAR RNA is replaced with a target sequence for toehold activating RNAs.

In a further embodiment, a riboswitch could be placed downstream of the natural promoter for another alternative configuration of an rSFP. This configuration only requires one expression cassette because riboswitches are most often cis-regulated and act on transcription, translation, or both. If the natural promoter is feedback regulated by a stress response or metabolite, this method will allow inducible control of the riboswitch to be combined with the natural activity of the promoter. In addition, this configuration allows titration of the magnitude of expression from the natural promoter.

Previous Solutions and Commercialization

Some have attempted to statically control gene expression with constitutive promoters and 5' untranslated regions. Others have utilized quorum-sensing to dynamically control gene expression in a cell-density dependent manner or biosensors to dynamically control gene expression in response to metabolite accumulation. These attempts utilized natural stress response promoters to dynamically control enzyme expression in response to stresses but did not incorporate additional user control or signal integration.

Commercially, stress and burden in microbial production hosts is a significant issue that reduces productivity. rSFPs enable implementation of dynamic regulation to control enzyme expression in response to stress or burden.

Long development times for microbial bioprocesses are the result of intensive expression tuning and retuning. rSFPs sidestep this arduous problem by allowing dynamic inputs of both feedback and extrinsic controls.

rSFPs also can be utilized in screening methods for new biosynthetic pathways of enzyme homologs in heterologous hosts that would otherwise prove too toxic to be successfully expressed with existing technologies. rSFPs also can be utilized in methods for optimizing expressions levels under static expression conditions.

Because rSFPs can be utilized to modulate expression of a target product, rSFPs also can be utilized to overexpress proteins and RNAs that would otherwise be toxic to a bacterial culture. rSFPs therefore can be utilized to express otherwise toxic proteins and RNAs.

Patent References

U.S. Published Application No. 2017/0183664, "SMALL RNAs (sRNA) THAT ACTIVATE TRANSCRIPTION," Julius B. Lucks, James Chappell, and Melissa Takahashi.

U.S. Published Application No. 2017/0204477, "COMPOSITION COMPRISING RIBOREGULATORS AND METHODS OF USE THEREOF," Alexander A. Green, Peng Yin, James J. Collins, and Jongmin Kim.

U.S. Published Application No. 2012/0070870, "METHODS AND MOELCULE FOR YIELD IMPORVEMENT INVOLVING METABOLI ENGINEERING," Jeffrey C. Way and Joseph H. Day.

Non-Patent References

Chappell et al., "Computational design of small transcription activating RNAs for versatile and dynamic gene regulation," Nat. Communications 8, 19 Oct. 2017, Article number 1051.

Chappell et al., "Creating small transcription activating RNAs," Nat. Chem. Biol., 2015 March;11 (3): 214-20.

Dahl et al., "Engineering dynamic pathway regulation with stress-response promoters," Nat. Biotechnol. 2013 November;31 (11): 1039-46.

Boyarskiy et al., "Transcriptional feedback regulation of efflux protein expression for increased tolerance to and production of n-butanol." Metab. Eng. 2016 January;33: 130-137.

Green et al., "Toehold Switches: De-Novo-Designed Regulators of Gene Expression," Cell, Volume 159, Issue 4, P925-939, Nov. 6, 2014.

Gupta et al., "Dynamic regulation of metabolic flux in engineered bacteria using a pathway-independent quorum-sensing circuit," Nat. Biotechnol., 2017 March;35 (3): 273-279.

Zhang et al., "Design of a dynamic sensor-regulator system for production of chemicals and fuels derived from fatty acids," Nat. Biotechnol., 2012 Mar. 25;30 (4): 354-9.

Example 2

Title-Dynamic Control of Pathway Expression with Riboregulated Switchable Promoters Abstract Dynamic pathway regulation has emerged as a promising strategy in metabolic engineering for improved system productivity and yield, and continues to grow in sophistication. Bacterial stress-response promoters allow dynamic gene regulation using the host's natural transcriptional networks, but lack the flexibility to control the expression timing and overall magnitude of pathway genes. Here, we report a strategy that uses RNA transcriptional regulators to introduce another layer of control over the output of natural stress-response promoters. This new class of gene expression cassette, called a riboregulated switchable feedback promoter (rSFP), can be modularly activated using a variety of mechanisms, from manual induction to quorum sensing. We develop and apply rSFPs to regulate a toxic cytochrome P450 enzyme in the context of a Taxol precursor biosynthesis pathway and show this leads to 2.4× fold higher titers than from the best reported strain. We envision that rSFPs will become a valuable tool for flexible and dynamic control of gene expression in metabolic engineering, protein and biologic production, and many other applications.

INTRODUCTION

Sustainable production of chemicals and materials in microbes through metabolic engineering[1,2] is a long-standing focus of synthetic biology. A primary challenge in metabolic engineering is the burden and toxicity on engineered cells owing to heterologous enzyme expression and unnecessary intracellular accumulation of toxic pathway intermediates[3,4]. This deleterious effect to the host often results in a loss to productivity and yield, creating a pressing need for strategies that can alleviate or avoid these pitfalls. This is nontrivial because each pathway can present unique cellular stresses, making it difficult to find generalizable solutions.

Synthetic biologists have sought to alleviate pathway toxicity by using dynamic pathway regulation to precisely tune the level and timing of enzyme expression[5-8]. These systems are designed to adaptively adjust enzyme expression in response to changes in growth phase, cellular stress, fermentation conditions, and pathway intermediate concentrations so that they maintain an optimal concentration of enzymes that can vary over time. In order to implement these designs, synthetic biologists have created synthetic feedback networks that dynamically control gene expression using regulatory parts, such as engineered transcription factors[9-11] or ligand-induced ribozymes[12], that respond to relevant cues.

While these systems represent important advances, synthetic feedback networks are often difficult to construct because the sensors required for specific inputs are hard to design or source from nature, and the added burden of expressing regulatory components can itself negatively impact the host[13]. Ultimately, this means that synthetic feedback networks require considerable additional engineering to match the specific requirements of every application. On the other hand, nature has evolved stress-responsive feedback networks that are already compatible with host cells. This is a result of the fact that microbial cells persist and thrive in changing environments due to their ability to sense and respond to stresses and environmental conditions[14]. Much of this ability is encoded within regulatory elements called stress-response promoters that integrate signals from complex and interconnected transcriptional networks to modulate mRNA synthesis in response to specific cellular stresses[15]. This creates the possibility of using stress-response promoters to regulate heterologous pathway expression as a means to implement genetic feedback networks that lead to improvements in productivity and yield. In fact, synthetic biologists have used stress-response promoters to control pathway expression, leading to notable improvements to productivity and yield for protein expression[16] and industrially important pathways, such as the artemisinin precursor amorphadiene[17] and n-butanol[18]. However, stress-response promoters have not been widely adopted, as their complexity makes it difficult to fine-tune their behavior for specific applications. As their function is determined by the complex topologies of natural genetic networks, there are no simple methods to tune either the timing or overall magnitude of their transcriptional outputs-two key parameters that are important for optimizing metabolic pathway productivity and yield[19].

Figure 1B:
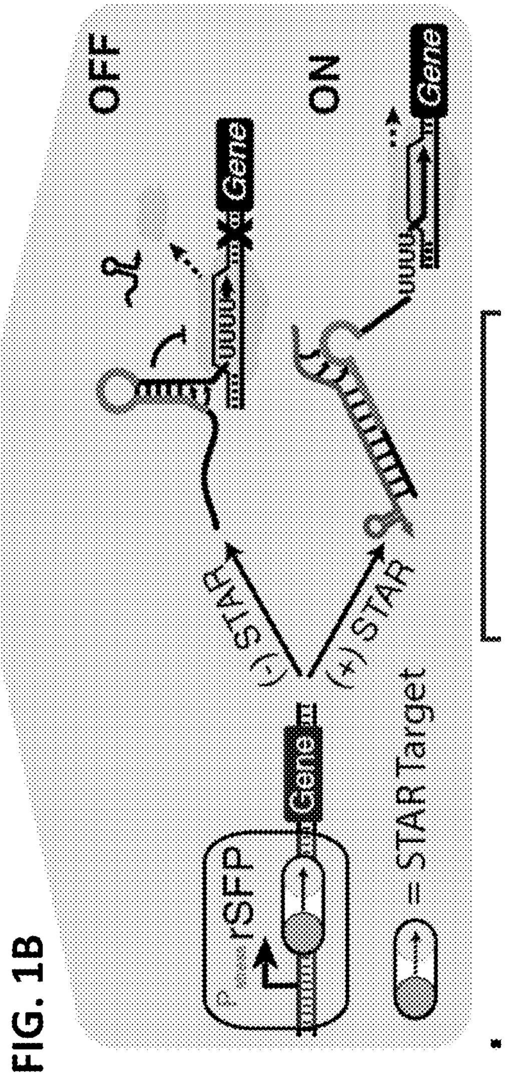
Figure 1C:
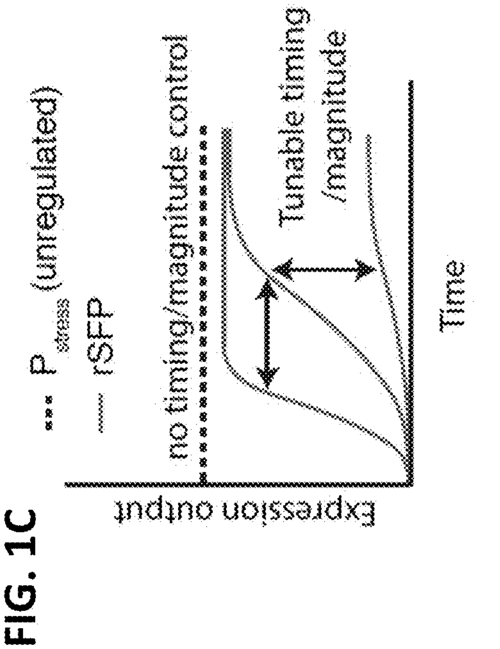

To address this limitation, we sought to create a new regulatory motif called a switchable feedback promoter (SFP) that combines the feedback properties of natural stress-response promoters with regulators that offer control of the timing and overall magnitude of transcriptional outputs (FIG. 1A-C). The SFP concept is general, and can be implemented in several ways including engineering transcription factor operator sites within the stress-response promoter region[20]. However, the architecture of many stress-response promoters is still unknown, making the rational design of transcription factor-based SFPs difficult. Instead, we utilized trans-acting synthetic RNA regulators[21,22], which can be configured to control transcription in the case of small transcription activating RNAs (STARs)[21], or translation in the case of toehold switches[22]. The key feature of both STARs and toehold switches is that they have well-defined composition rules such that they can be inserted into a gene expression construct without modification or disruption of the desired promoter sequence. In this way, riboregulated SFPs (rSFPs) can be created by inserting a STAR or toehold target binding region 3' of a natural stress-response promoter (FIG. 1B). By default, when transcribed, these RNA sequences fold into structures that block gene expression. However, binding of the trans-acting STAR or toehold trigger RNA changes these structures to allow gene expression. This enables the timing and overall magnitude of the rSFP output to be controlled with any strategy that can regulate the expression of the trans-acting RNA (FIG. 1C). These regulators have additional advantages that make inclusion in rSFPs promising, including the availability of large libraries of orthogonal STARs and toehold switches with a range of functional properties (ON/OFF levels)[22,23] and their having compact DNA footprints (<100 nts). Furthermore, they have been shown to control gene expression in a variety of contexts, including within metabolic pathways[23].

Here we report the creation and characterization of a library of STAR-mediated rSFPs, and their application to optimizing the yield of a metabolic pathway that produces an oxygenated taxane precursor to the anticancer drug Taxol. We first show that we can create a library of 17 rSFPs by interfacing STARs with natural *Escherichia coli* stress-response promoters and placing trans-acting STAR production under control of an inducible promoter. We then applied rSFPs to control the expression of a plant cytochrome P450 that is known to cause envelope stress[24] in the context of a pathway that produces an oxygenated Taxol precursor[25]. By screening rSFPs for oxygenated taxane production, we were able to find multiple rSFPs that showed improvement in both overall and oxygenated taxane titers compared to the previously reported best strain. We next used the external control of rSFPs to systematically optimize both timing and expression level to ultimately find pathway conditions that produce 25.4 mg/L of oxygenated taxanes and 39.0 mg/L of total taxanes, representing a 2.4× and a 3.6× fold improvement over the current state-of-the-art, respectively. To demonstrate the use of other control points for rSFPs, we next sought to interface them with a quorum sensing system and show that quorum sensing rSFPs offer completely autonomous pathway expression regulation with yields similar to our fully optimized system without costly external inducers.

Overall, rSFPs are a novel and general strategy to achieve dynamic regulation of metabolic pathway enzymes and we envision them to be broadly useful for introducing controllable stress-response promoters in many synthetic biology applications.

Results

Riboregulated switchable feedback promoters (rSFPs) enable tunable outputs from stress-response promoters. We chose to build rSFPs with STARs because they exhibit low leak and high dynamic range comparable to exemplary protein-based regulators[23]. STARs activate transcription by disrupting the folding pathway of a terminator hairpin sequence, called a Target, that is placed upstream of the gene to be regulated (FIG. 1B). In the absence of a STAR, the Target region folds into an intrinsic terminator hairpin which stops transcription before reaching the downstream gene. When present, a STAR RNA can bind to the 5' portion of the terminator hairpin, preventing its formation, and allowing transcription. rSFPs are then created by inserting a Target sequence 3' of a candidate stress-response promoter. In this way, the introduction of the STAR/Target adds an additional layer of control to the stress-response promoter, effectively gating its transcriptional output through the additional regulation of STAR RNA expression, which can be controlled using a variety of mechanisms, including manual inducible promoters or quorum-sensing systems.

Figure 1D:
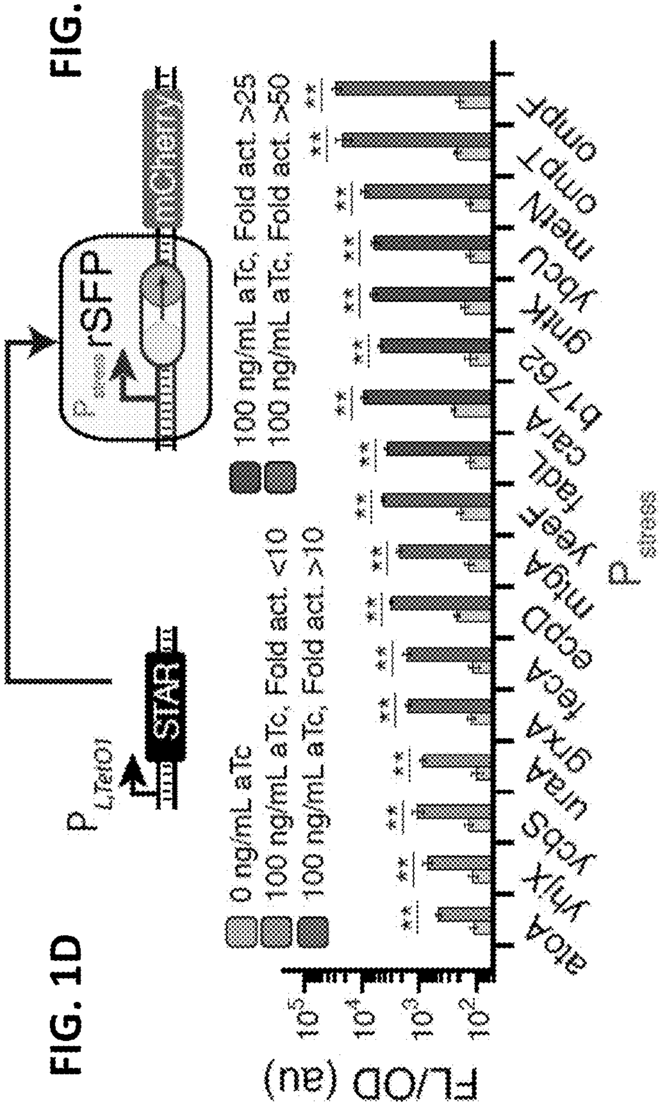
Figure 1E:
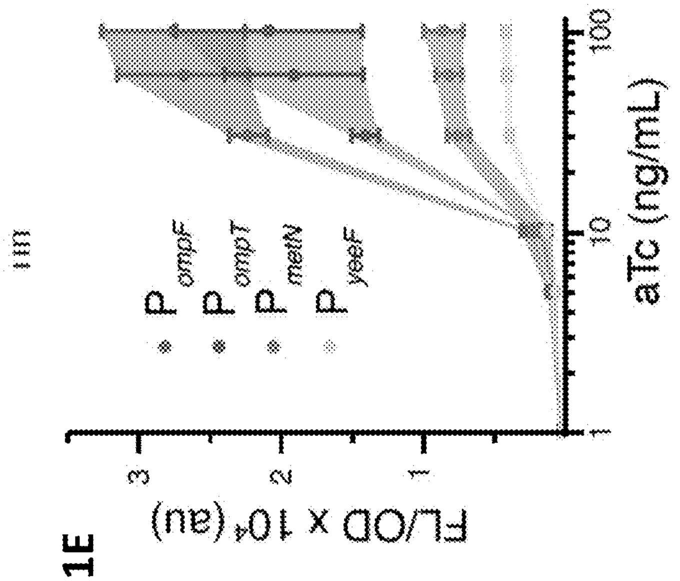
Figure 2A:
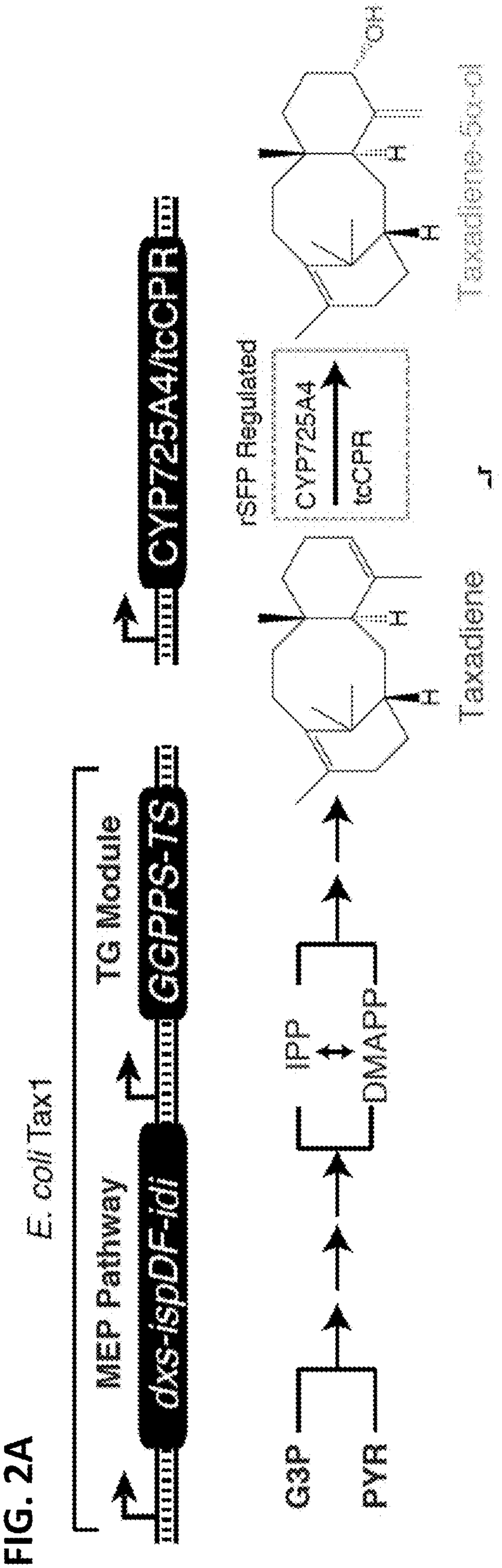
FIGS. 2A-2D show rSFPs enhance productivity of a Taxol precursor synthesis pathway in *E. coli*.
Figure 5:
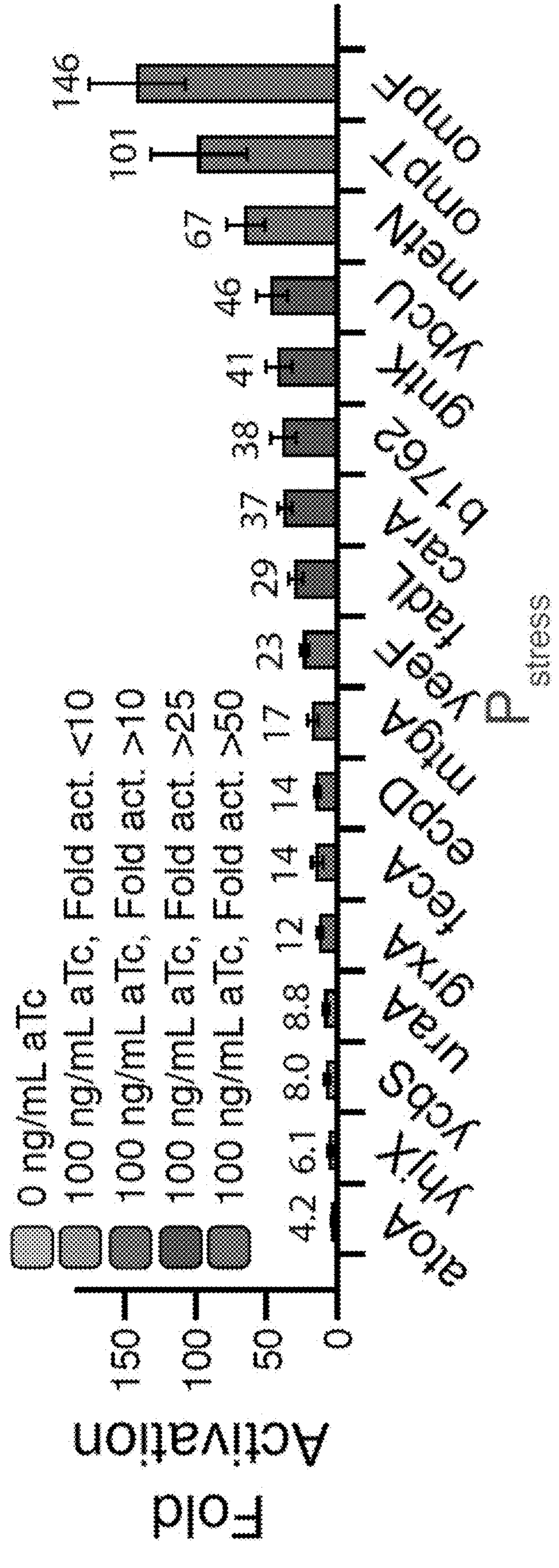
FIG. 5 shows fold activation (ON/OFF) of rSFP variants containing unique envelope stress-response promoters. Fluorescence characterization was performed on *E. coli* transformed with plasmids encoding each rSFP controlling mCherry expression and PL,TetO1-STAR in the absence and presence of 100 ng/mL aTc. Data represent mean values in units of arbitrary fluorescence/optical density (FL/OD) and error bars represent s.d. of at least n=7 biological replicates. Mean fold activation for each rSFP variant is indicated above each bar.

Our initial rSFP designs utilized a previously developed STAR[23] under the well-characterized inducible system TetR/$P_{L,TetO1}$[20] interfaced with a library of 17 putative membrane stress-responsive promoters[17,18]. These promoters were chosen as several had been previously identified to regulate a biofuel transporter protein in *E. coli*[18], and could be valuable for dynamic regulation of membrane proteins in metabolic pathways. To construct and characterize these rSFPs, a STAR Target sequence was cloned immediately 3' of each promoter to regulate expression of an mCherry reporter, and its cognate STAR was cloned in a second $P_{L,TetO1}$ plasmid. Plasmids were transformed into *E. coli* and fluorescence was measured with and without the presence of the $P_{LTetO1}$ inducer anhydrotetracycline (aTc) at saturating levels (100 ng/ml). We found that induction of $P_{L,TetO1}$-STAR resulted in significant activation from all members of the stress-response promoter library (FIG. 1D), exemplifying the modularity of the rSFP concept. We also observed that 8 library members were activated by greater than 25× fold in the presence of aTc, with a maximum activation of nearly 150× fold (FIG. 5). We next selected a set of high-performing rSFPs and characterized their transfer functions by titrating levels of aTc and found that all exhibited a similar transfer function shape, though with different maximal activation levels (FIG. 1E). This is evidence that the transfer function of the $P_{L,TetO1}$ regulatory system can be overlaid on a range of stress response promoters through the STAR intermediate. Overall these results demonstrated that we can create a library of rSFPs that provide tunable control of gene expression level by selecting different stress-response promoters and manipulating inducer concentration.

rSFPs enhance production of an oxygenated Taxol precursor. We next tested the ability of rSFPs to regulate expression of a challenging metabolic pathway enzyme. As a model system, we chose a portion of the anticancer drug Paclitaxel's biosynthesis pathway that has been previously reconstituted in *E. coli*[24]. Specifically, we focused on the first P450-mediated step where taxadiene is oxygenated by the membrane anchored cytochrome P450 CYP725A4 (FIG. 2A). This system is an ideal test bed for the use of rSFPs because CYP725A4 expression causes membrane stress due to lipid anchoring of an N-terminal domain. This stress appears to reduce pathway productivity and makes pathway optimizations extremely difficult[24]. The sensitivity of product titers to expression level of CYP725A4 must be carefully managed, as too low expression will create a bottleneck in oxygenated taxane synthesis, but too high expression will also suppress synthesis due to stress. Previous reports to optimize this system required significant experimental effort[24], exemplifying the importance of new pathway engineering strategies, but also providing a competitive benchmark for comparison with rSFPs. Furthermore, this problematic expression is not unique to CYP725A4, but extends to many P450's[26,27], along with other classes of proteins such as transporters[18] and glycosylation enzymes[28,29]. Therefore, the system is a model challenge for testing the concept of using rSFPs to leverage external control of natural stress-response promoters to maintain pathway expression in a narrow optimal range.

Figure 2B:
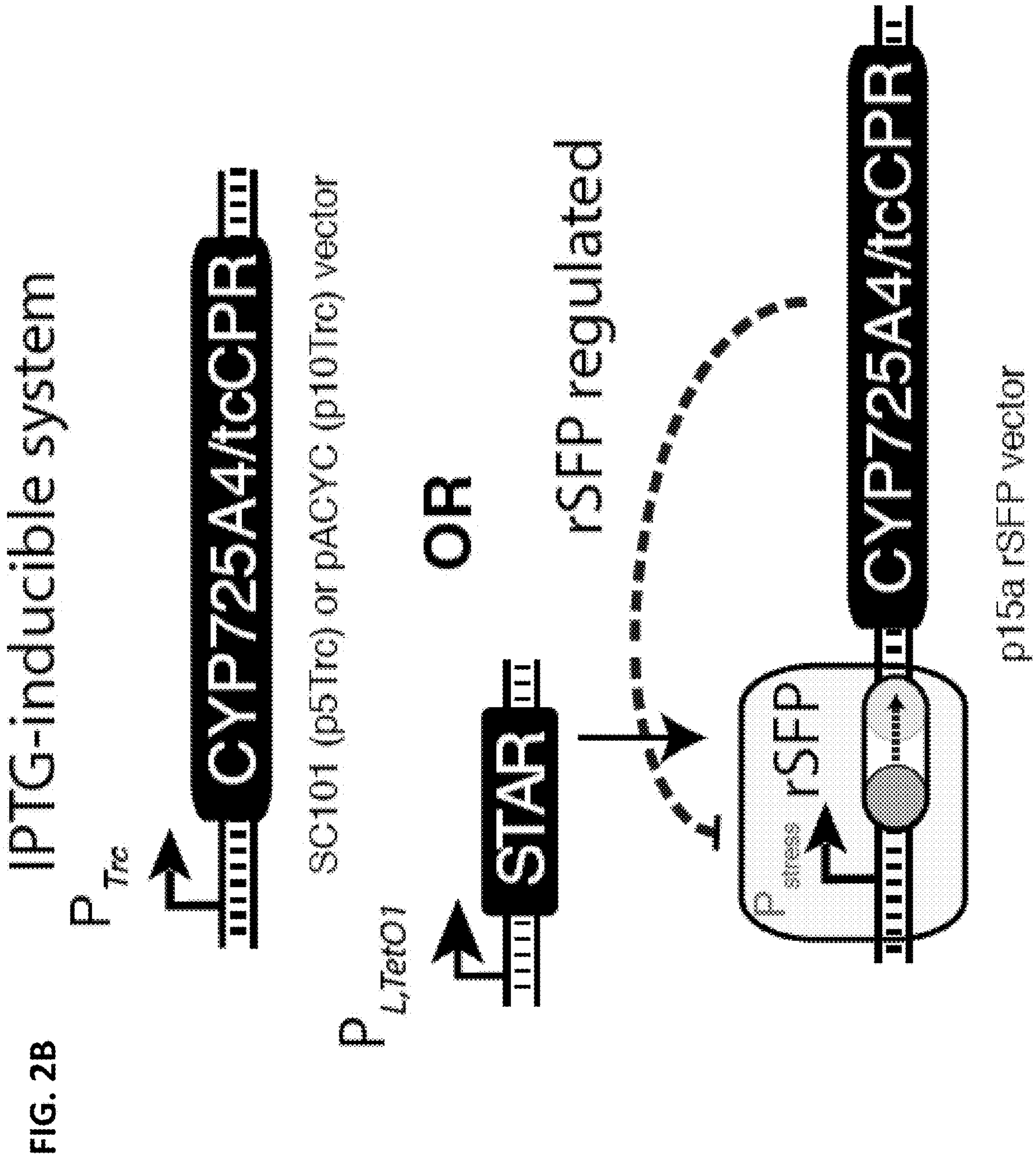

Previous work has shown that expression level of a CYP725A4/tcCPR reductase fusion is critical to achieving high titers of oxygenated taxanes in *E. coli*[24]. A previously optimized low-copy expression vector (p5Trc-CYP725A4/tcCPR) (FIG. 2B) transformed into the *E. coli* Tax1 strain containing genomic modifications to maximize the synthesis of the taxadiene precursor, produces ~11 mg/L of oxygenated taxanes, albeit with a loss to total taxane production.

Figure 2D:
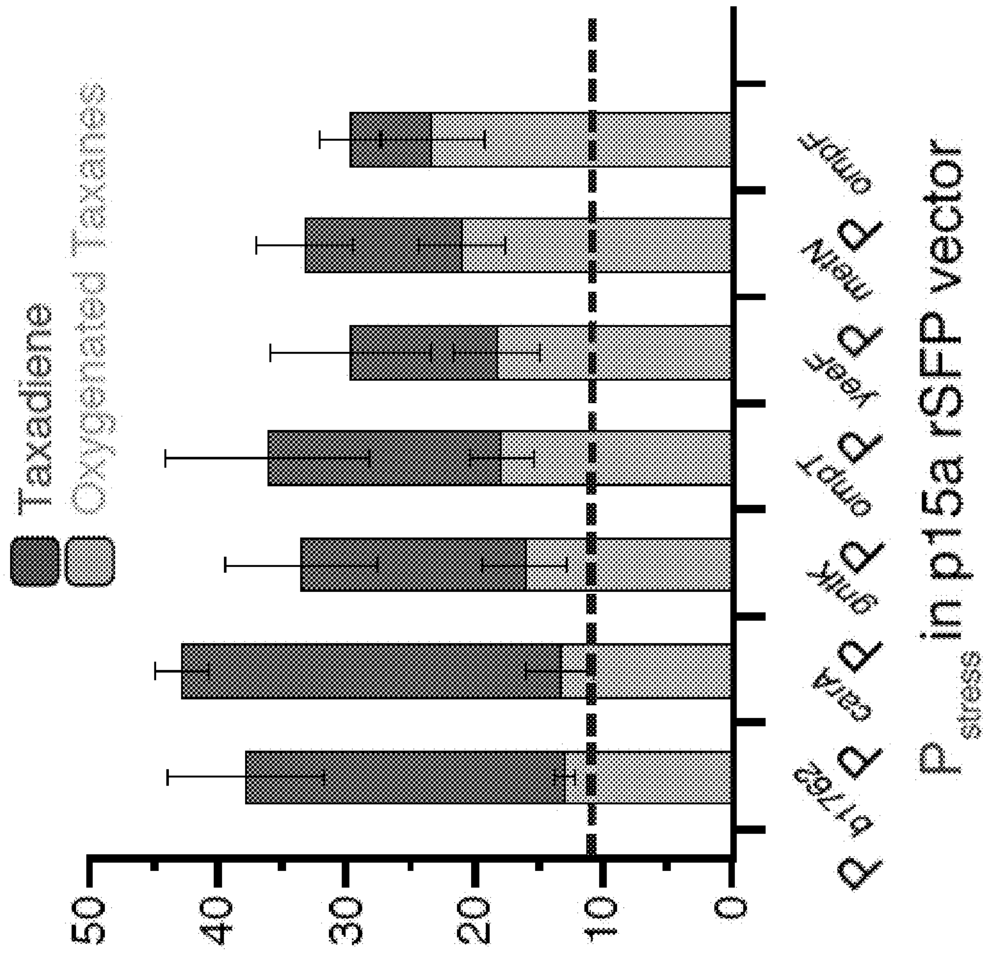
Figure 2C:
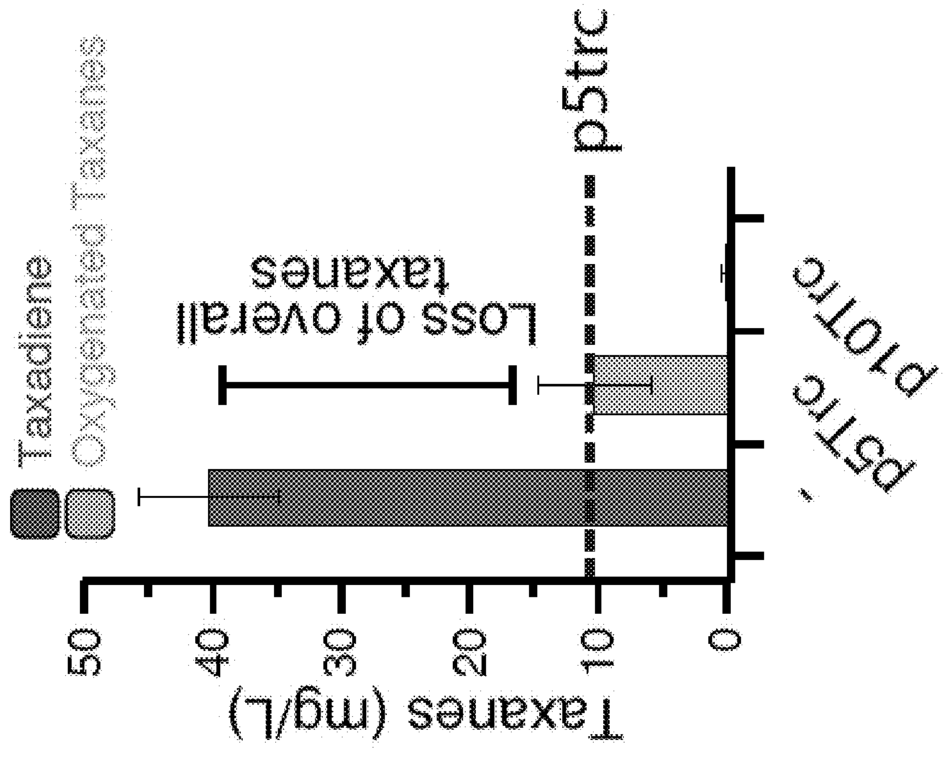

However, increasing expression of the enzyme using a medium copy expression vector (p10Trc) does not increase titer, but causes a complete loss of pathway productivity (FIG. 2C), presumably due to the enzyme's membrane stress crossing a critical threshold and triggering a global response.

Figure 6:
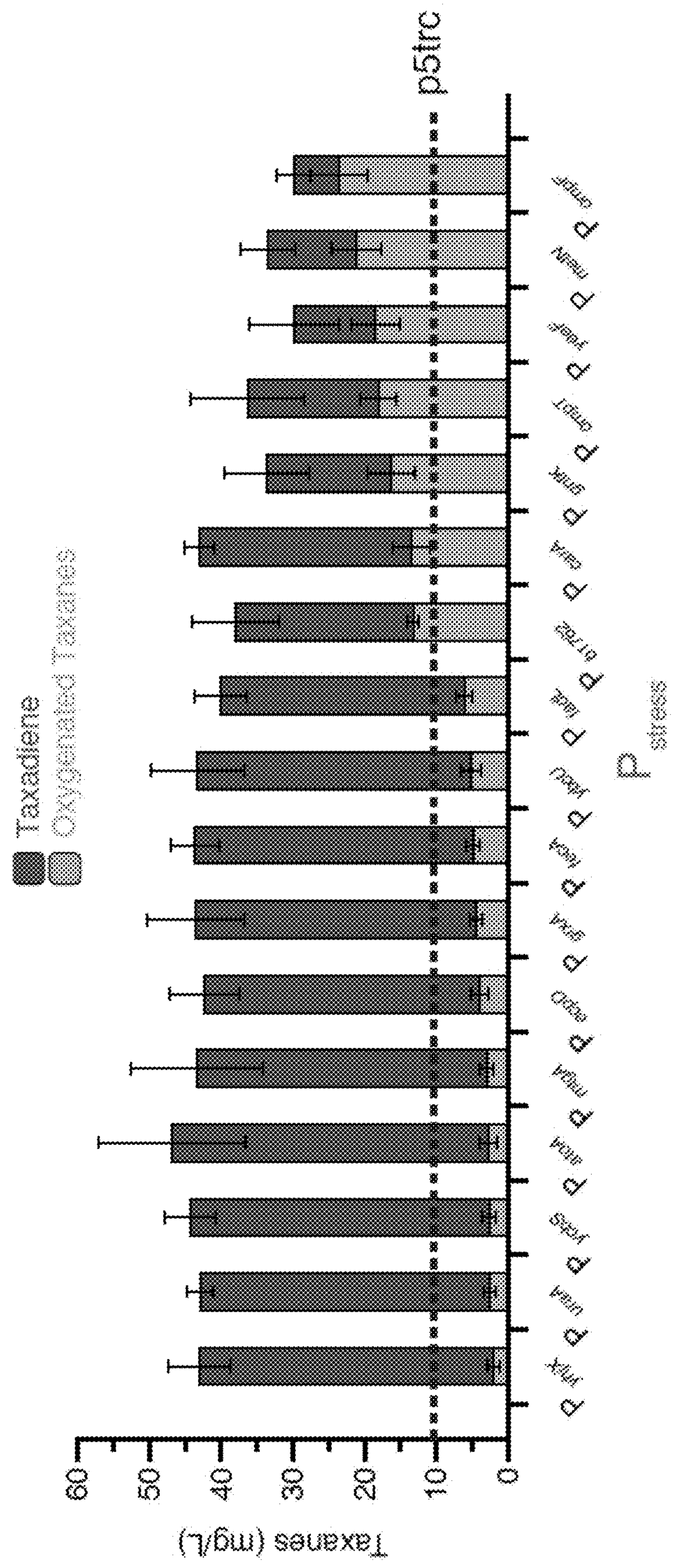
FIG. 6 shows titers of fermentations after 96 hrs with *E. coli* Tax1 containing CYP725A4/tcCPR under control of complete rSFP library and $P_{L,TetO1}$-STAR with addition of 100 ng/mL aTc at inoculation. Dashed line represents production of oxygenated taxanes from p5Trc in FIG. 2C. Data represent mean values measured with GC-MS and error bars represent s.d. of at least n=5 biological replicates.

We hypothesized we could achieve greater pathway productivity over the p5Trc benchmark strain by identifying putative envelope stress rSFPs for control of CYP725A4/tcCPR. To test this, the CYP725A4/tcCPR coding sequence was introduced into each one of the 17 rSFP constructs. *E. coli* Tax1 was transformed with each rSFP construct and the $P_{L,TetO1}$-STAR plasmid and each tested in the context of taxadiene oxygenation fermentations with addition of 100 ng/mL aTc at inoculation. Using this approach, we found that several performed well against the p5Trc benchmark strain (FIG. 6). In particular, 7 of the rSFPs had greater titers of oxygenated taxanes than the p5Trc strain (FIG. 2D), with all also improving overall taxane production. Furthermore, the $P_{ompF}$ rSFP resulted in ~2.2× fold greater oxygenated taxanes (~23.5 mg/L) and ~2.8× fold greater overall taxanes (29.8 mg/L) than the p5Trc strain, clearly showing the benefit of rSFP pathway regulation.

Figure 7A:
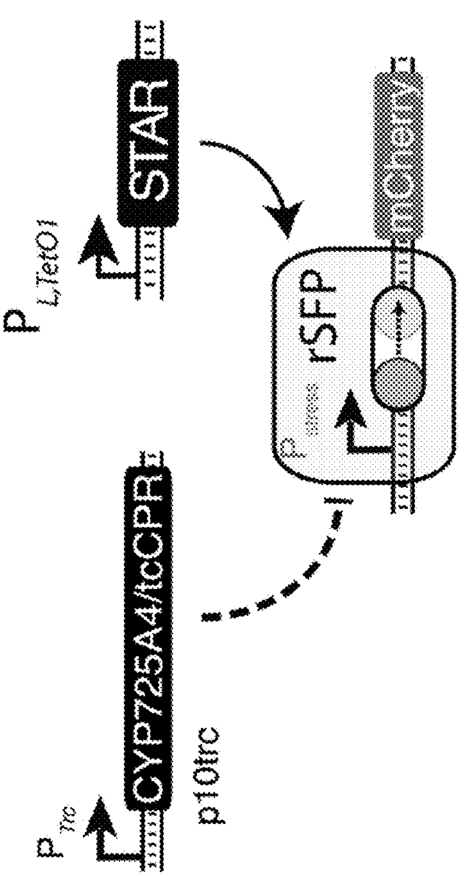
FIGS. 7A-7B show analysis of feedback-responsiveness of selected stress-response promoters to CYP725A4/tcCPR stress.
Figure 7B:
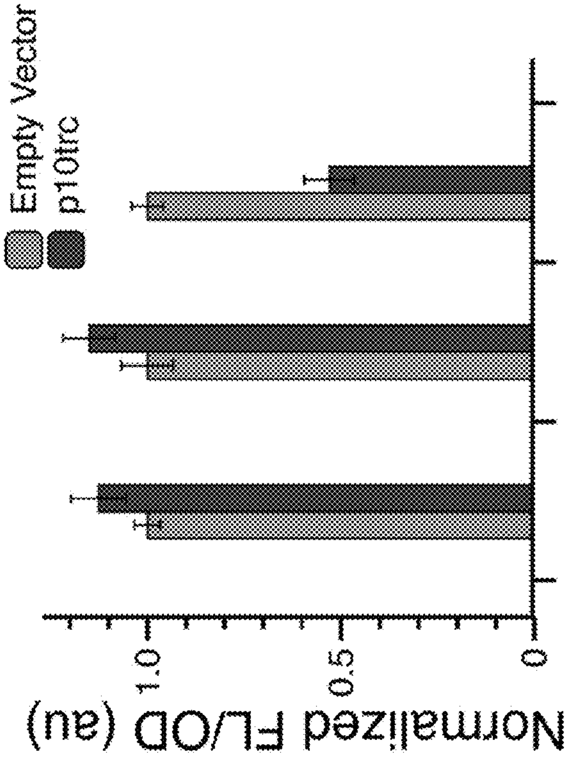

To confirm that rSFPs can indeed be feedback regulated by CYP725A4/tcCPR stress, we performed fluorescence analysis of *E. coli* cells containing plasmids for rSFP expression of an mCherry reporter with the top two performing stress-response promoters and the p10Trc plasmid separately expressing CYP725A4/tcCPR, in order to monitor changes in rSFP expression caused by membrane stress (FIG. 7A). We observed reduced expression from $P_{ompF}$ when p10Trc was present in place of an empty vector (FIG. 7B), suggesting that it is indeed responsive to CYP725A4/tcCPR induced stress. On the other hand, a constitutive promoter control had no response as expected. Interestingly, the $P_{metN}$ rSFP did not exhibit a reduced expression in response to CYP725A4/tcCPR expression, indicating that not all rSFPs respond to stresses in the same way, as we expected for a diverse set of natural stress-response promoters.

Figure 3A:
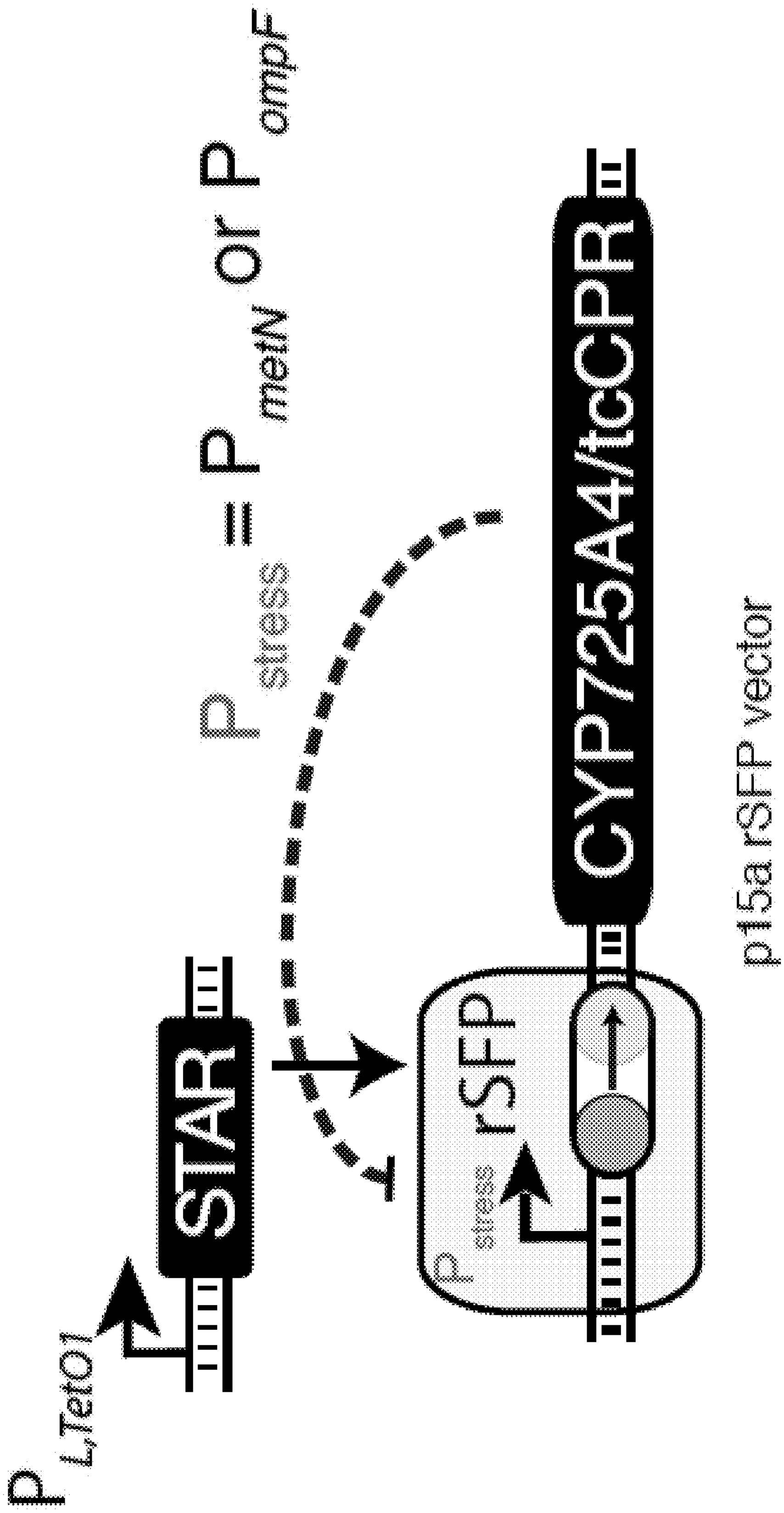
FIGS. 3A-3F show external control of rSFPs enable optimization of induction level and timing from stress-response promoters.
Figure 3B:
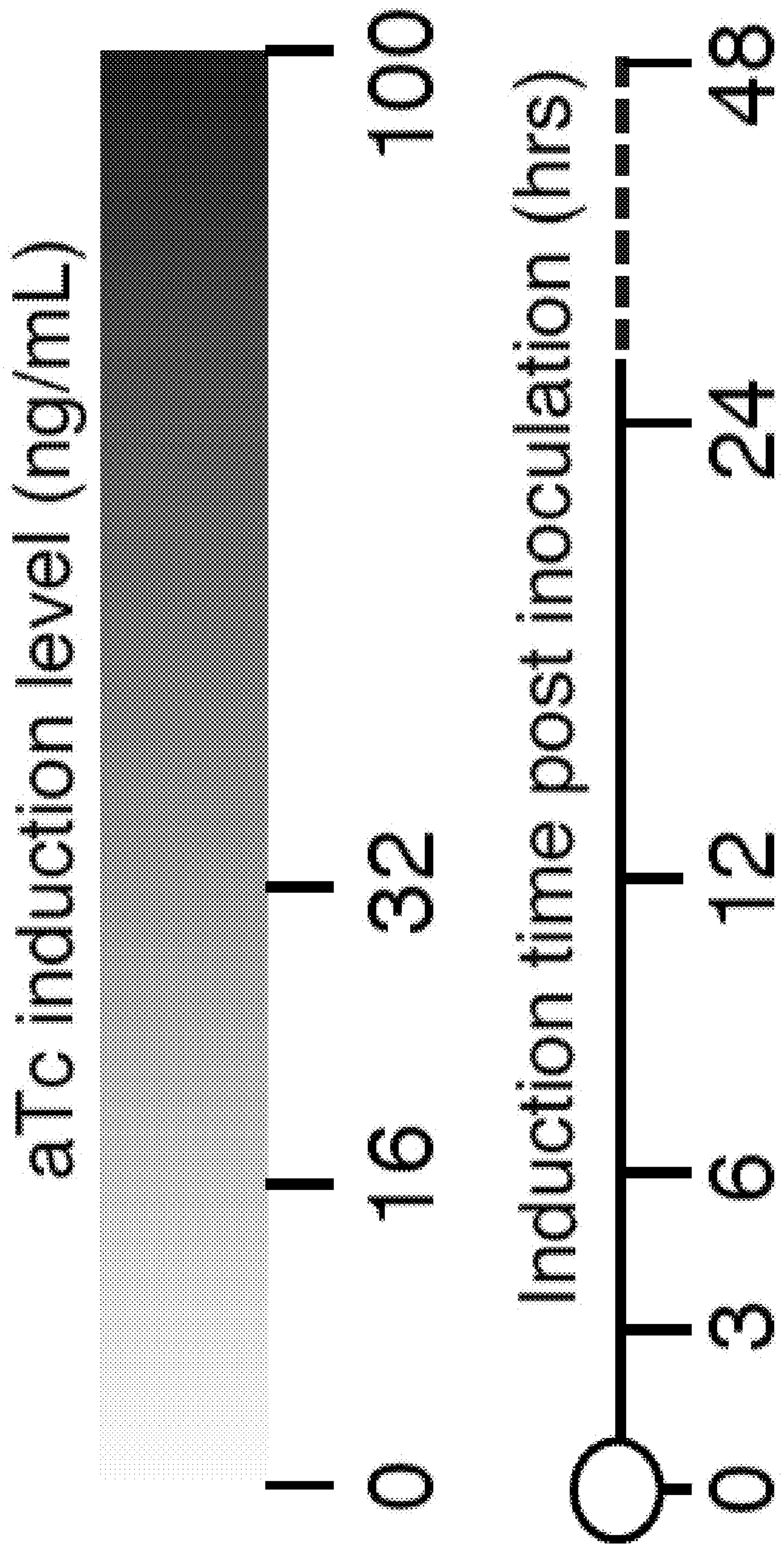
Figures 3C, 3D:
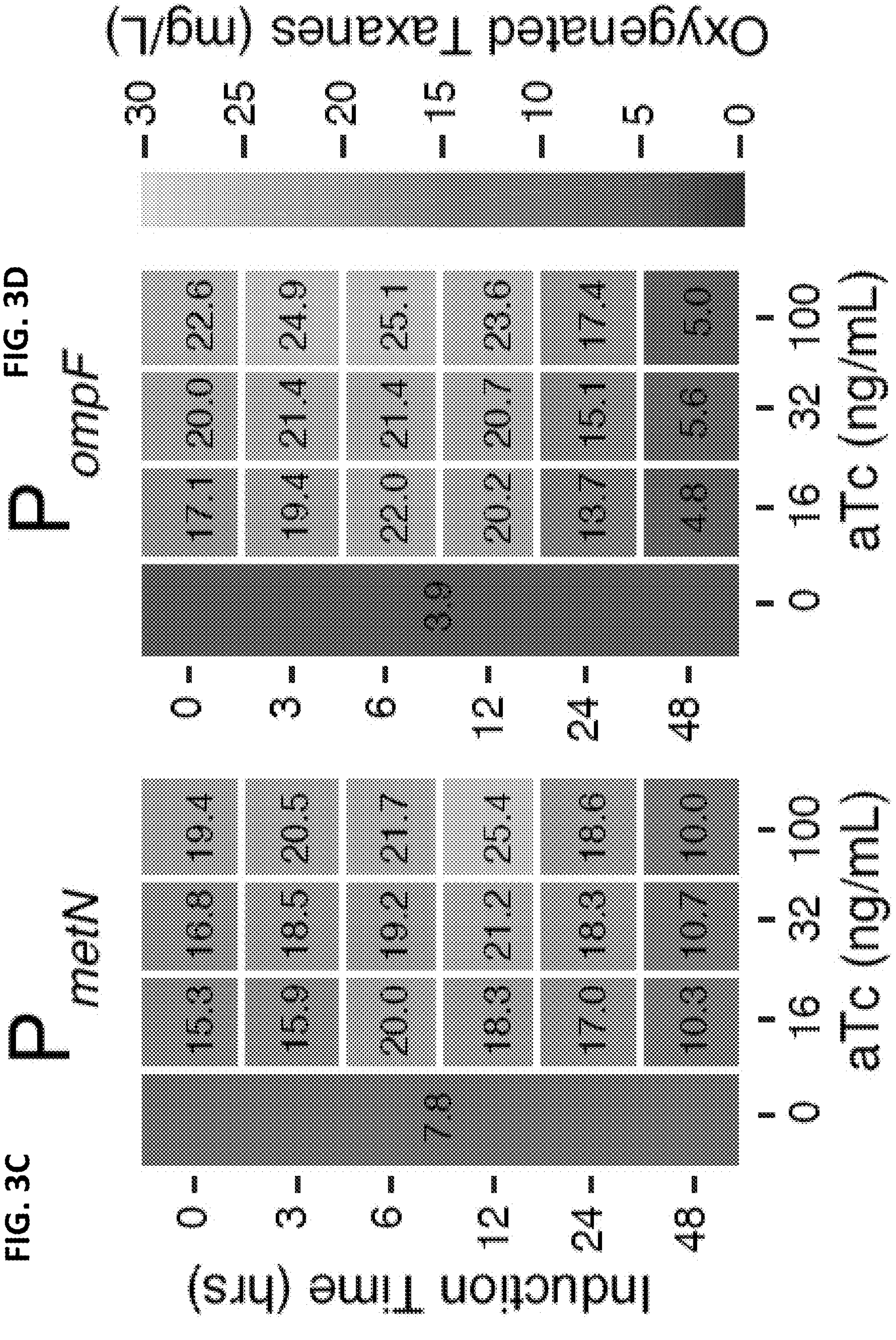
Figures 3E, 3F:
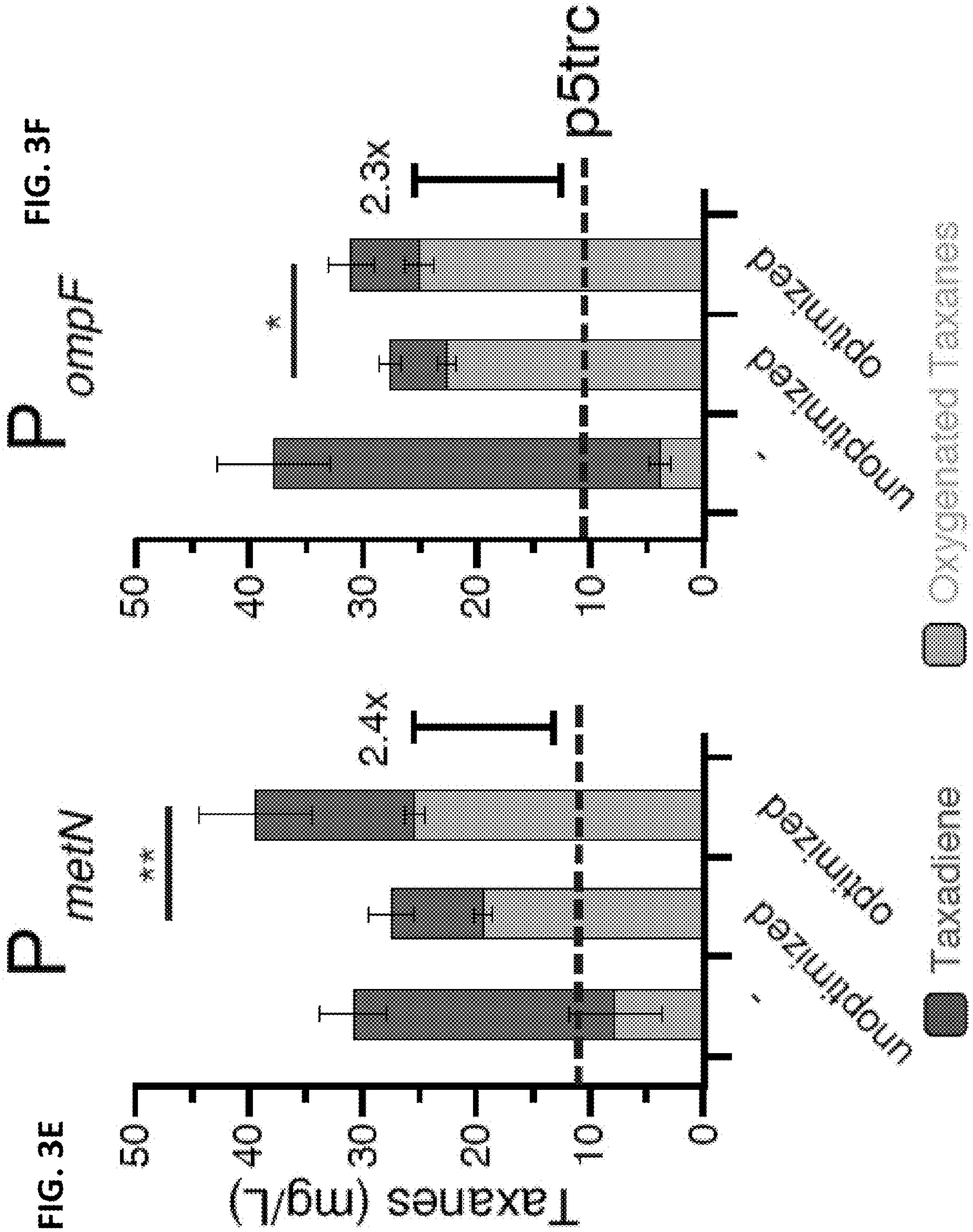

Overall these results show that rSFPs can be effectively used to optimize overall pathway expression and that they can exhibit the dynamic feedback behaviors of incorporated stress-response promoters.

rSFPs allow further pathway optimization through the control of expression timing and overall magnitude. Having shown significant improvements in taxadiene oxygenation with rSFPs, we next sought to test how the external control offered by rSFPs can be used to further optimize induction level and timing of stress-response promoter activity. To test this, we selected the two best rSFP systems and performed a matrix of aTc induction at four levels (0, 16, 32, and 100 ng/mL aTc), which were added at six different induction times (0, 3, 6, 12, 24, 48 hrs) post fermentation inoculation (FIG. 3A-B). We found that oxygenated taxane production with both rSFPs was indeed sensitive to induction level and timing (FIG. 3C,D) and that late induction of $P_{metN}$ and $P_{ompF}$ rSFPs could improve final titers of oxygenated taxanes even further to 25.4 and 25.1 mg/L, respectively, and overall taxanes to 39.0 and 31.0 mg/L (FIG. 3E,F), representing an overall 2.4× and 2.3× fold improvement over the previous gold standard benchmark in terms of oxygenated taxanes, and 3.6× and 2.9× fold improvements in terms of overall taxanes. These results demonstrate that rSFPs can be implemented to enable rapid tuning of expression timing and overall magnitude of stress-response promoter output to further enhance fermentation titers.

Figure 4A:
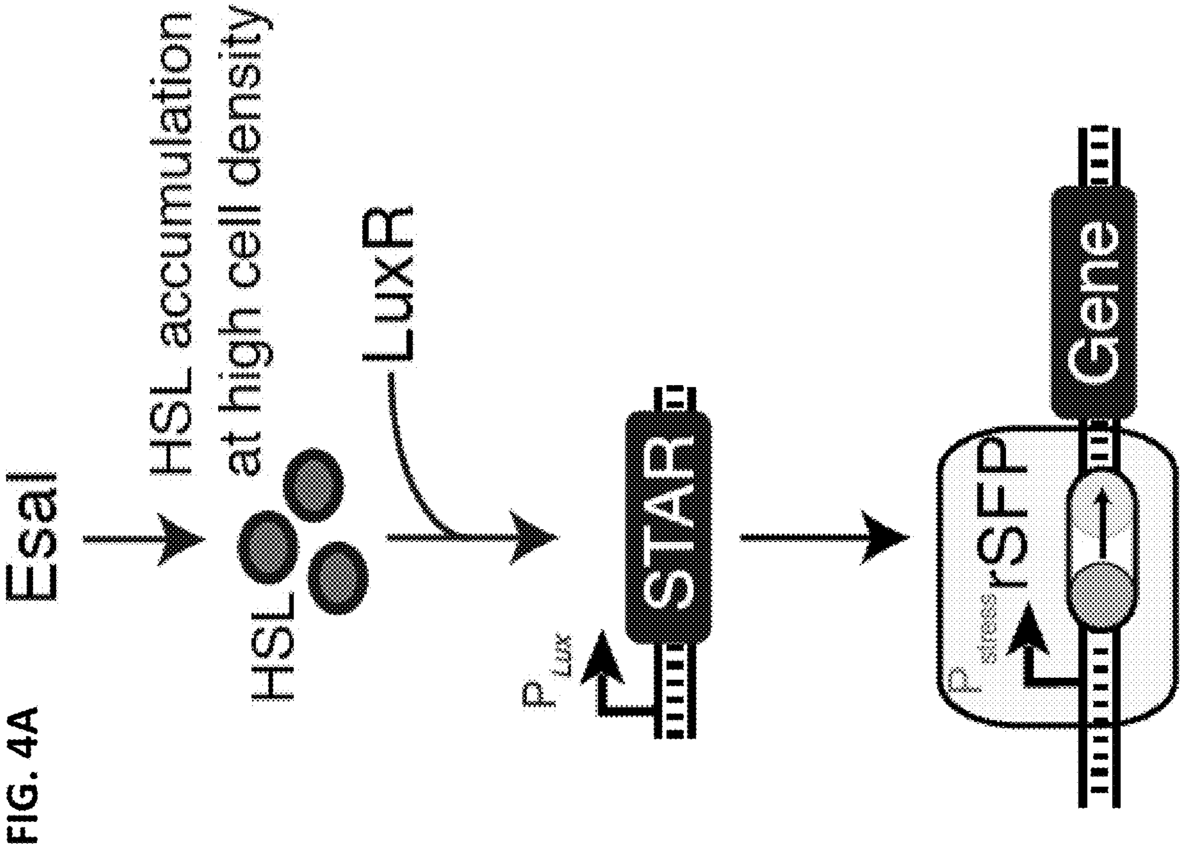
FIGS. 4A-4D show quorum sensing activation of rSFPs allows autonomous control of CYP725A4 expression.
Figure 4B:
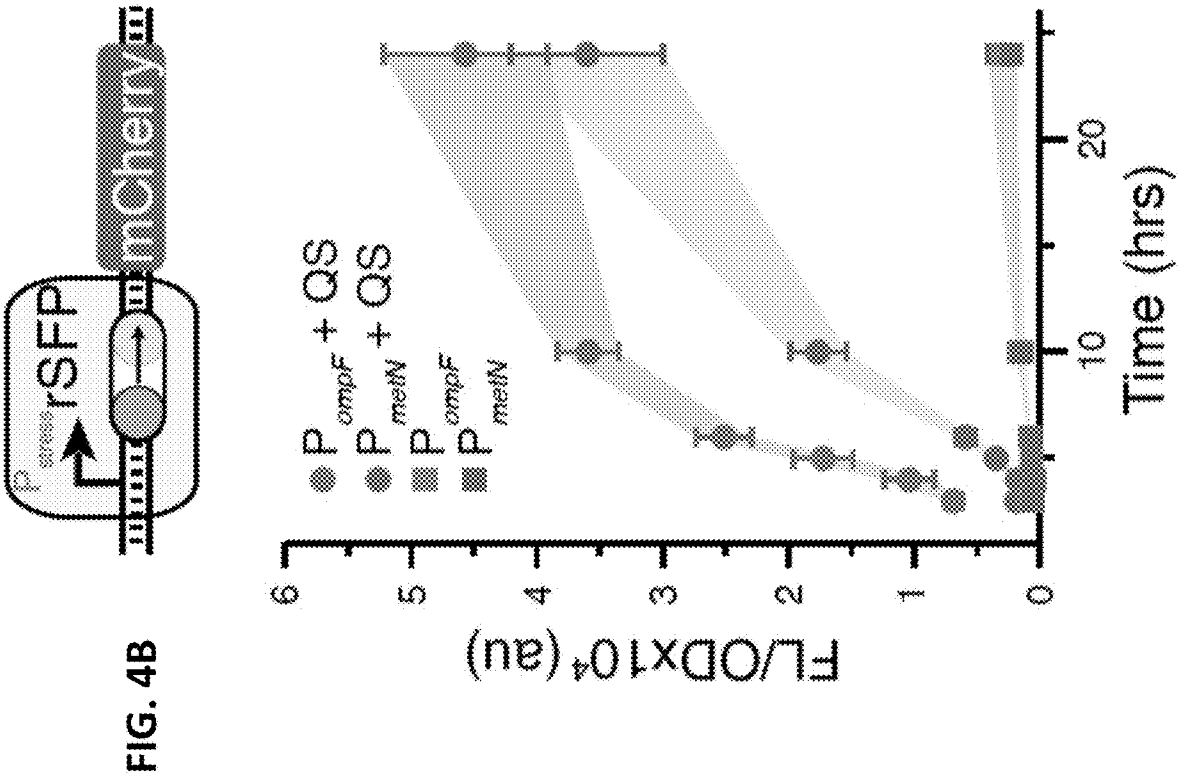

Quorum-sensing activated rSFPs allow autonomous regulation of pathway expression. Though inducible systems offer flexibility for screening of optimal induction timing, the cost of inducers can be prohibitive at an industrial scale[30,31], and several efforts have been carried out to design autonomous means of induction. Quorum-sensing (QS) systems that are activated in a cell-density dependent manner offer one such route to this behavior[32]. QS systems have been used with great utility in metabolic engineering to create a separation of cell growth and pathway production phases without the need for a chemical inducer, and provide a natural means for balancing carbon utilization with biomass production[33-35]. We therefore sought to utilize this strategy within our model pathway by leveraging the modularity of rSFPs to be easily configured to utilize different input systems. Specifically, we chose the $P_{Lux}$ promoter that is activated by the LuxR transcriptional activator upon sufficient production of the C6-homoserine lactone (HSL) signaling molecule[36]. We cloned a STAR under control of $p^{Lux}$ and integrated an operon with the EsaI HSL synthase[37] and LuxR into the genome of the *E. coli* Tax1 strain to create the Tax1-QS strain (FIG. 4A). When plasmids encoding the expression of $P_{Lux}$-STAR and the $P_{metN}$ Or $P_{ompF}$ rSFPs controlling mCherry expression were transformed into *E. coli* Tax1 or Tax1-QS, we found that activation only occurred in the engineered Tax1-QS strain containing EsaI and LuxR (FIG. 4B). These QS-activated rSFPs produced comparable fold activation to manual induction with $P_{L,TetO1}$ and exhibited a time dependent activation.

Figures 4C, 4D:
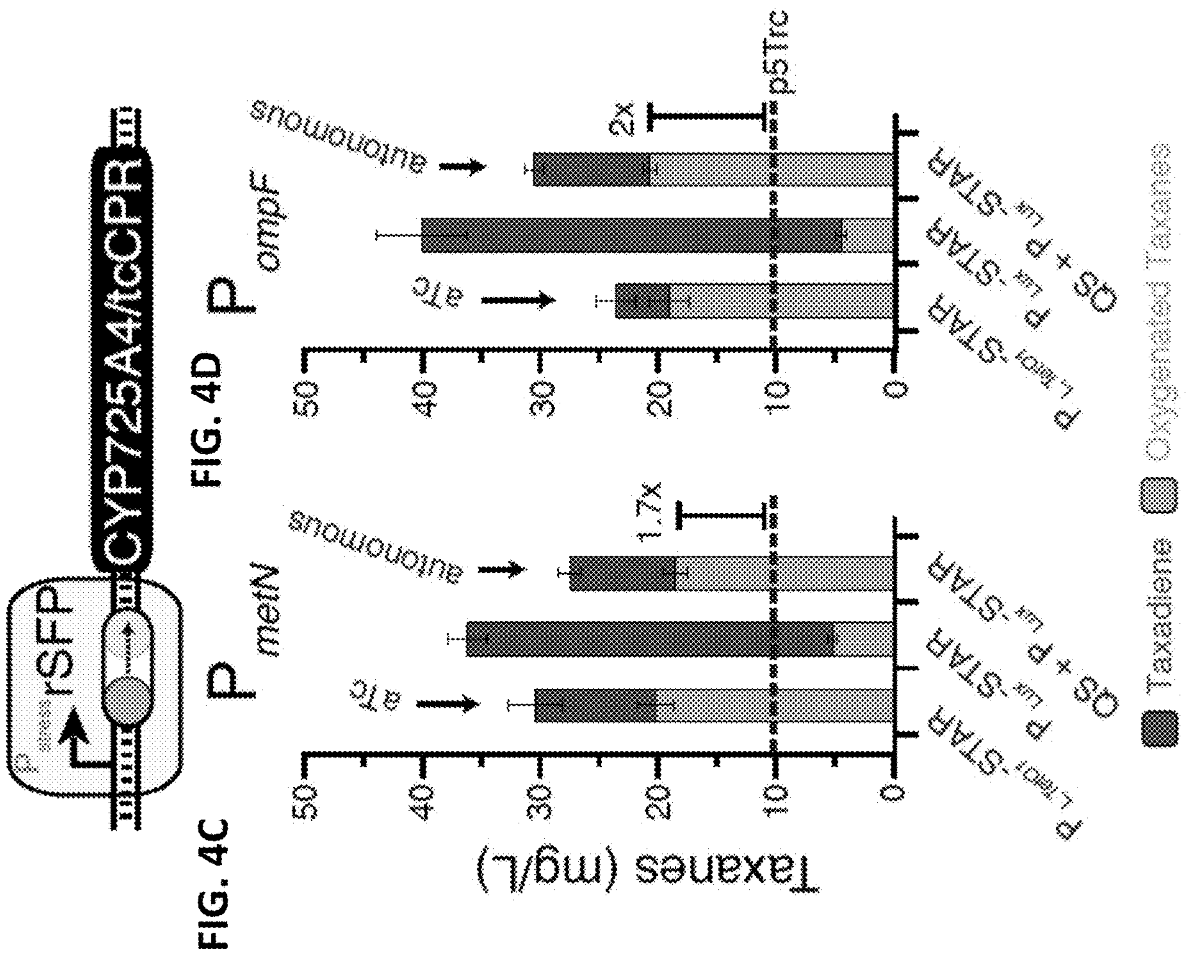

To demonstrate that QS-activated rSFPs could be used to autonomously control the expression of metabolic pathway enzymes, we applied the $P_{metN}$ and $P_{ompF}$ QS-activated rSFPs to control the expression of CYP725A4/tcCPR within the taxadiene oxygenation pathway. Fermentations were performed by inoculating cell cultures into media without addition of exogenous inducer. Upon fermentation and analysis, we found that QS-based activation resulted in comparable titers of oxygenated taxanes to those obtained from manual induction of rSFPs with aTc before optimization (FIG. 4C,D). Importantly, this represented 1.7× and 2× fold improvements, respectively, over the previous gold standard, and was achieved with a completely autonomous genetic feedback network without the need for costly inducers.

DISCUSSION

Here we report the development, characterization and application of switchable feedback promoters that enable an additional synthetic layer of control over natural stress-response promoters. Stress-response promoters are a promising route to achieving dynamic control of heterologous metabolic pathways by acting as sensor-actuators to stresses caused by pathway expression, intermediate metabolites and other fermentation conditions[17,18]. While stress-response promoters can improve production of desired chemicals by regulating expression in response to toxic pathway intermediates and enzymes, they are constrained by their complexity, leading to a lack of control over the timing and overall magnitude of their transcriptional output, which is essential to achieving a separation of growth phase and production phase in large-scale fermentations[38]. By design, the rSFP concept enables this control by introducing an additional regulatory layer within the natural stress-response pathway by gating stress-response promoter outputs with trans-acting RNA regulators. The use of an inducible promoter to control RNA regulator synthesis allows modification of the timing and overall magnitude of the natural stress-response promoter outputs. Furthermore, the use of QS systems allows the autonomous activation of rSFPs in a cell-density dependent manner. In this way, rSFPs have modularity both at the lever of their inputs and outputs, and the types of stresses they can respond to through changing of the regulated stress-response promoter. This offers the flexible implementation of controllable stress-response networks in a single compact locus.

In this work, we designed and implemented rSFPs and demonstrated that they are both modular and tunable—the rSFP concept can be applied to many unique stress-response promoters in a plug-and-play fashion, activator inputs can be easily interchanged, and activated output levels can be modulated by titrating inducer concentrations. Notably, we found that all 17 of the stress-response promoters that were inserted into rSFPs were activated significantly, strongly suggesting that rSFPs can be used with new stress-response promoters as they are discovered, and potentially that the rSFP concept can be used to easily regulate engineered promoter systems as well. These features allow rapid screening of rSFP libraries within combinatorial strain engineering procedures[39] that could be used by industry to identify effective implementations of dynamic control. In addition, the ability of rSFPs to naturally adapt to an optimal expression level may allow for rapid prototyping of potentially toxic enzymes and pathways without the requisite need to first balance expression levels with constitutive static regulators-speeding the pace of pathway construction for new chemical products.

To demonstrate their utility in the context of optimizing metabolic pathway production, we applied rSFPs to a synthetic Taxol precursor pathway in *E. coli*[25] by regulating expression of a problematic cytochrome P450 enzyme that causes a membrane stress detrimental to productivity[24]. By screening through a library of envelope-stress-response promoters in rSFPs, we identified variants that improved pathway productivity over a previous strain that had been optimized using a laborious trial-and-error approach. Furthermore, we showed that optimizing rSFP induction timing and magnitude in the fermentation enabled additional improvements, highlighting an advantage of the rSFP system to enable the control of pathway expression timing. We also showed that rSFPs can be controlled by QS systems that do not require addition of an external inducer, enabling fully autonomous control of pathway expression.

Dynamic pathway regulation is a promising strategy in metabolic engineering but can be difficult to implement. The rSFP strategy enables modular and tunable control of endogenous promoters that have evolved sophisticated transcriptional responses to a range of cellular stresses and fermentation conditions. Due to their simplicity, we envision that the rSFP concept will enable streamlined implementation of dynamic regulation into metabolic pathways. Furthermore, given their modularity, we imagine rSFPs will be useful for dynamic control in other applications, such as high-level expression of difficult or toxic proteins, living therapeutics[40], and cellular diagnostics[41] where endogenous promoters could be used as sensor-actuators for numerous environments.

Methods

Plasmid assembly. All plasmids used in this study can be found in Supplementary Table 1 with key sequences provided in Supplementary Tables 2 and 3. Gibson assembly and inverse PCR (iPCR) was used for construction of all plasmids. All assembled plasmids were verified using DNA sequencing.

Integration of QS operon into the *E. coli* genome. Strains containing genomic insertions of the EsaI-LuxR operon were created using the clonetegration[42] platform as summarized in Supplementary Table 4. The HK022 plasmid was used to integrate constructs into the attB site of the *E. coli* genome. Successful integrations were identified by antibiotic selection and colony PCR according to the published protocol.

Strains, growth media, in vivo bulk fluorescence measurements. Fluorescence characterization experiments for all envelope stress-response promoters were performed in *E. coli* strain Tax124 containing the synthetic pathway for taxadiene biosynthesis or modified Tax1-QS containing the QS operon. Experiments were performed for 7-9 biological replicates collected over three separate days. For each day of fluorescence measurements, plasmid combinations were transformed into chemically competent *E. coli* cells and plated on LB+Agar (Difco) plates containing combinations of 100 μg/mL carbenicillin, 34 μg/mL chloramphenicol and/or 50 μg/mL spectinomycin depending on plasmids used (see SI Table 1 for plasmids used in each experiment), and incubated approximately 17 hours (h) overnight at 37° C. Plates were taken out of the incubator and left at room temperature for approximately 7 h. Three colonies were used to inoculate three cultures of 300 μL of LB containing antibiotics at the concentrations described above in a 2 mL 96-well block (Costar), and grown for approximately 17 h overnight at 37° C. at 1,000 rpm in a VorTemp 56 (Labnet) bench top shaker. FIGS. 1*d*, 1*e:* 4 μL of each overnight culture were added to 196 μL (1:50 dilution) of supplemented M9 minimal media (1'M9 minimal salts, 1 mM thiamine hydrochloride, 0.4% glycerol, 0.2% casamino acids, 2 mM MgSO4, 0.1 mM CaCl2) containing the selective antibiotics and grown for 6 h at the same conditions as the overnight culture. Appropriate concentrations of anhydrotetracycline (Sigma) were added to culture media as indicated. FIG. 4*b:* 20 μL of each overnight culture were added to 980 μL of M9 minimal media containing selective antibiotics and grown for 24 h at 37C. Periodic samples of 10-200 μL of culture were collected for characterization by bulk fluorescence measurements. For all bulk fluorescence measurements: 10-200 μL of sampled culture were transferred to a 96-well plate (Costar) containing 0-190 μL of phosphate buffered saline (PBS). Fluorescence (FL) and optical density (OD) at 600 nm were then measured using a Synergy H1 plate reader (Biotek). The following settings were used: mCherry fluorescence (560 nm excitation, 630 nm emission).

Bulk fluorescence data analysis. On each 96-well block there were two sets of controls; a media blank and *E. coli* Tax1 cells transformed with combination of control plasmids JBL002 and JBL644 (blank cells) and thus not expressing mCherry (Supplementary Table 1). The block contained three replicates of each control. OD and FL values for each colony were first corrected by subtracting the corresponding mean values of the media blank. The ratio of FL to OD (FL/OD) was then calculated for each well (grown from a single colony) and the mean FL/OD of blank cells was subtracted from each colony's FL/OD value. Three biological replicates were collected from independent transformations, with three colonies characterized per transformation (9 colonies total). Occasional wells were discarded due to poor growth (OD<0.1 at measurement), however, all samples contained at least 7 replicates over the three experiments. Means of FL/OD were calculated over replicates and error bars represent standard deviations (s.d).

Small-scale "Hungate" fermentation. Small-scale fermentation assays were used to quantify oxygenated taxanes and taxadiene production in *E. coli* Tax1 or Tax1-QS. Experiments were performed with six biological replicates collected over three independent experiments (FIG. 2*c*, 2*d*) or four biological replicates collected over two independent experiments (FIG. 3*c*, 3*d*, 3*e*, 3*f*, 4*c*, 4*d*). For each experiment, plasmid combinations (SI Table 1) were transformed into chemically competent *E. coli* cells and plated on LB+Agar (Difco) plates containing appropriate antibiotics (100 μg/mL carbenicillin, 34 μg/mL chloramphenicol and/or 50 μg/mL spectinomycin). Plates were incubated approximately 17 hrs overnight at 30° C. Individual colonies were inoculated into culture tubes containing LB and appropriate antibiotics and incubated at 30° C. for roughly 16 hrs overnight to achieve an approximate OD600 of 3. For 2 mL batch fermentations, 50 μL of overnight cells were added to 1.95 mL of complete R-media (Supplementary Tables 5-7) and appropriate antibiotics in glass hungate tubes (Chem-Glass). 0.1 mM IPTG was added for induction of the upstream pathway enzymes and p5Trc/p10Trc expression. 16-100 ng/mL aTc was added, as indicated, to induce $P_{L,TetO1}$-STAR activated rSFPs. A 10% v/v dodecane layer (200 μL) was added in all fermentations. Hungate tubes were sealed with a rubber septa and plastic screw-cap (Chem-Glass). PrecisionGlide 18G hypodermic needles (BD) were inserted into the rubber septa to allow for gas exchange. Hungate tubes were incubated at 22° C. and 250 rpm for 96 hrs. After the fermentations were completed, the culture was centrifuged to collect the dodecane overlay. This overlay was subsequently diluted into hexane for analytical procedures described below.

GC-MS analysis. Dodecane samples collected from batch fermentations were diluted at a ratio of 1:40 in n-hexane containing 5 mg/L B-caryophyllene. The 5 mg/L scaryophyllene was utilized as a standard to calculate titer of taxadiene and oxygenated taxanes. GC-MS analysis was performed with an Agilent 7890 GC and Agilent HP-5 ms-UI column (Ultra Inert, 30 m, 0.25 mm, 025 μm, 7 in cage). Helium was utilized as a carrier gas at a flow rate of 1 mL/min and the sample injection volume was 1 μL. The splitless method begins at 50° C. hold for 1 minute followed by a 10° C./min ramp to 200° C. and a final 5° C./min ramp to 270° C. Mass spectroscopy data was collected for 22.5 minutes with an 11-minute solvent delay with an Agilent 7000 QQQ in scan mode using Electron Ionization (EI). m/z values ranging from 40-500 were scanned with a scan time of 528 ms. MassHunter Workstation Qualitative Analysis software (vB.06.00) was utilized to integrate peaks on the chromatograms and determine their respective mass spectrums. The ratio of peak area of taxadiene (m/z 272) to the standard β-caryophyllene (m/z 204) was used to calculate titer of taxadiene, while the ratio of the sum of all peaks of oxygenated taxanes (m/z 288) to β-caryophyllene was used to calculate titer of the oxygenated taxanes. Means of titers were calculated over replicates and error bars represent s.d.

REFERENCES

1. Keasling, J. D. Manufacturing molecules through metabolic engineering. Science (2010). doi: 10.1126/science.1193990.
2. Nielsen, J. & Keasling, J. D. Engineering Cellular Metabolism. Cell (2016). doi: 10.1016/j.cell.2016.02.004.
3. Biggs, B. W., De Paepe, B., Santos, C. N. S., De Mey, M. & Kumaran Ajikumar, P. Multivariate modular metabolic engineering for pathway and strain optimization. Current Opinion in Biotechnology (2014). doi: 10.1016/j.copbio.2014.05.005.
4. Sun, J., Jeffryes, J. G., Henry, C. S., Bruner, S. D. & Hanson, A. D. Metabolite damage and repair in metabolic engineering design. Metabolic Engineering (2017). doi: 10.1016/j.ymben.2017.10.006.
5. Farmer, W. R. & Liao, J. C. Improving lycopene production in *Escherichia coli* by engineering metabolic control. Nat. Biotechnol. (2000). doi: 10.1038/75398.
6. Venayak, N., Anesiadis, N., Cluett, W. R. & Mahadevan, R. Engineering metabolism through dynamic control. Current Opinion in Biotechnology (2015). doi: 10.1016/j.copbio.2014.12.022.
7. Brockman, I. M. & Prather, K. L. J. Dynamic metabolic engineering: New strategies for developing responsive cell factories. Biotechnol. J. (2015). doi: 10.1002/biot.201400422.
8. Tan, S. Z. & Prather, K. L. Dynamic pathway regulation: recent advances and methods of construction. Current Opinion in Chemical Biology (2017). doi: 10.1016/j.cbpa.2017.10.004.
9. Zhang, F., Carothers, J. M. & Keasling, J. D. Design of a dynamic sensorregulator system for production of chemicals and fuels derived from fatty acids. Nat. Biotechnol. (2012). doi: 10.1038/nbt.2149.
10. Xu, P., Li, L., Zhang, F., Stephanopoulos, G. & Koffas, M. Improving fatty acids production by engineering dynamic pathway regulation and metabolic control. Proc. Natl. Acad. Sci. U.S.A (2014). doi: 10.1073/pnas.1406401111.
11. Moser, F. et al. Dynamic control of endogenous metabolism with combinatorial logic circuits. Mol. Syst. Biol. 14, (2018).
12. Carothers, J. M., Goler, J. A., Juminaga, D. & Keasling, J. D. Model-driven engineering of RNA devices to quantitatively program gene expression. Science (2011). doi: 10.1126/science.1212209.
13. Tan, C., Marguet, P. & You, L. Emergent bistability by a growth-modulating positive feedback circuit. Nat. Chem. Biol. (2009). doi: 10.1038/nchembio.218.
14. Aertsen, A. & Michiels, C. W. Stress and how bacteria cope with death and survival. Critical Reviews in Microbiology (2004). doi: 10.1080/10408410490884757
15. Belliveau, N. M. et al. Systematic approach for dissecting the molecular mechanisms of transcriptional regulation in bacteria. Proc. Natl. Acad. Sci. (2018). doi: 10.1073/pnas.1722055115.
16. Ceroni, F. et al. Burden-driven feedback control of gene expression. Nat. Methods (2018). doi: 10.1038/nmeth.4635.
17. Dahl, R. H. et al. Engineering dynamic pathway regulation using stress-response promoters. Nat. Biotechnol. (2013). doi: 10.1038/nbt.2689.
18. Boyarskiy, S., Davis López, S., Kong, N. & Tullman-Ercek, D. Transcriptional feedback regulation of efflux protein expression for increased tolerance to and production of n-butanol. Metab. Eng. (2016). doi: 10.1016/j.ymben.2015.11.005.
19. Jones, J. A. et al. EPathOptimize: A combinatorial approach for transcriptional balancing of metabolic pathways. Sci. Rep. (2015). doi: 10.1038/srep11301.
20. Lutz, R. & Bujard, H. Independent and tight regulation of transcriptional units in *Escherichia coli* via the LacR/O, the TetR/O and AraC/11-12regulatory elements. Nucleic Acids Res. (1997). doi: 10.1093/nar/25.6.1203.

21. Chappell, J., Takahashi, M. K. & Lucks, J. B. Creating small transcription activating RNAs. Nat. Chem. Biol. (2015). doi: 10.1038/nchembio.1737.
22. Green, A. A., Silver, P. A., Collins, J. J. & Yin, P. Toehold switches: De-novodesigned regulators of gene expression. Cell (2014). doi: 10.1016/j.cell.2014.10.002.
23. Chappell, J., Westbrook, A., Verosloff, M. & Lucks, J. B. Computational design of small transcription activating RNAs for versatile and dynamic gene regulation. Nat. Commun. (2017). doi: 10.1038/s41467-017-01082-6.
24. Biggs, B. W. et al. Overcoming heterologous protein interdependency to optimize P450-mediated Taxol precursor synthesis in *Escherichia coli*. Proc. Natl. Acad. Sci. (2016). doi: 10.1073/pnas.1515826113.
25. Ajikumar, P. K. et al. Isoprenoid pathway optimization for Taxol precursor overproduction in *Escherichia coli*. Science (2010). doi: 10.1126/science.1191652.
26. Chang, M. C. Y., Eachus, R. A., Trieu, W., Ro, D. K. & Keasling, J. D. Engineering *Escherichia coli* for production of functionalized terpenoids using plant P450s. Nat. Chem. Biol. (2007). doi: 10.1038/nchembio875.
27. Leonard, E. & Koffas, M. A. G. Engineering of artificial plant cytochrome P450 enzymes for synthesis of isoflavones by *Escherichia coli*. Appl. Environ. Microbiol. (2007). doi: 10.1128/AEM.01411-07.
28. Valderrama-Rincon, J. D. et al. An engineered eukaryotic protein glycosylation pathway in *Escherichia coli*. Nat. Chem. Biol. (2012). doi: 10.1038/nchembio.921.
29. Glasscock, C. J. et al. A flow cytometric approach to engineering *Escherichia coli* for improved eukaryotic protein glycosylation. Metab. Eng. (2018). doi: 10.1016/j.ymben.2018.04.014.
30. Van Dien, S. From the first drop to the first truckload: Commercialization of microbial processes for renewable chemicals. Current Opinion in Biotechnology (2013). doi: 10.1016/j.copbio.2013.03.002.
31. Weber, W. & Fussenegger, M. Inducible product gene expression technology tailored to bioprocess engineering. Current Opinion in Biotechnology (2007). doi: 10.1016/j.copbio.2007.09.002.
32. Papenfort, K. & Bassler, B. L. Quorum sensing signal-response systems in Gramnegative bacteria. Nature Reviews Microbiology (2016). doi: 10.1038/nrmicro.2016.89.
33. Tsao, C. Y., Hooshangi, S., Wu, H. C., Valdes, J. J. & Bentley, W. E. Autonomous induction of recombinant proteins by minimally rewiring native quorum sensing regulon of *E. coli*. Metab. Eng. (2010). doi: 10.1016/j.ymben.2010.01.002.
34. Gupta, A., Reizman, I. M. B., Reisch, C. R. & Prather, K. L. J. Dynamic regulation of metabolic flux in engineered bacteria using a pathway-independent quorum-sensing circuit. Nat. Biotechnol. (2017). doi: 10.1038/nbt.3796.
35. Kim, E. M. et al. Autonomous control of metabolic state by a quorum sensing (QS)-mediated regulator for bisabolene production in engineered *E. coli*. Metab. Eng. (2017). doi: 10.1016/j.ymben.2017.11.004.
36. Engebrecht, J. & Silverman, M. Identification of genes and gene products necessary for bacterial bioluminescence. Proc. Natl. Acad. Sci. U.S.A (1984). doi: 10.1073/pnas.81.13.4154.
37. Minogue, T. D., Wehland-Von Trebra, M., Bernhard, F. & Von Bodman, S. B. The autoregulatory role of EsaR, a quorum-sensing regulator in *Pantoea stewartii* ssp. *stewartii*: Evidence for a repressor function. Mol. Microbiol. (2002). doi: 10.1046/j.1365-2958.2002.02987.x.
38. Malinowski, J. J. Two-phase partitioning bioreactors in fermentation technology. Biotechnology Advances (2001). doi: 10.1016/S0734-9750 (01) 00080-5.
39. Smanski, M. J. et al. Functional optimization of gene clusters by combinatorial design and assembly. Nat. Biotechnol. (2014). doi: 10.1038/nbt.3063.
40. Isabella, V. M. et al. Development of a synthetic live bacterial therapeutic for the human metabolic disease phenylketonuria. Nat. Biotechnol. (2018). doi: 10.1038/nbt.4222.
41. Watstein, D. M., McNerney, M. P. & Styczynski, M. P. Precise metabolic engineering of carotenoid biosynthesis in *Escherichia coli* towards a low-cost biosensor. Metab. Eng. (2015). doi: 10.1016/j.ymben.2015.06.007.
42. St-Pierre, F. et al. One-step cloning and chromosomal integration of DNA. ACS Synth. Biol. (2013). doi: 10.1021/sb400021j.

Tables

TABLE 1

Plasmids used in this study.

| Plasmid # | Plasmid architecture | Name | FIG. |
|---|---|---|---|
| pJBL002 | AmpR - ColE1 origin (Empty vector) | pJBL002 | 1d-e, 4b, 5, 7 |
| pJBL644 | SpcR - pCDF origin (Empty vecor) | pJBL644 | 1d-e, 4b, 5, 7 |
| pJBL6654 | $P_R$ - TetR - dblTerm - PL.TetO1 - STAR 8 - T500 - AmpR - ColE1 origin | $P_{L,TetO1}$-STAR | 1d-e, 2d, 3c-f, 4c-d, 5, 6, 7, 8, 9 |
| pJBL6655 | PLux - STAR 8 - 1500 - AmpR - ColE1 origin | $P_{Lux}$-STAR | 4b-c |
| pJBL6656 | PgntK - Target 8 - RBS 1 - mCherry - dblTerm - SpcR - pCDF origin | PgntK-mCherry | 1d, 5 |
| pJBL6657 | PompF - Target 8 - RBS 1 - mCherry - dblTerm - SpcR - pCDF origin | PompF-mCherry | 1d-e, 4b, 5, 7 |
| pJBL6658 | PyeeF - Target 8 - RBS 1 - mCherry - dblTerm - SpcR - pCDF origin | Pyeef-mCherry | 1d-e, 5 |
| pJBL6659 | PompT - Target 8 - RBS 1 - mCherry - dblTem - SpcR - pCDF origin | PompT-mCherry | 1d-e, 5 |
| pJBL6660 | PmetN - Target 8 - RBS 1 - mCherry - dblTerm - SpcR - pCDF origin | PmetN-mCherry | 1d-e, 4b, 5, 7 |
| pJBL6661 | Pb1762 - Target 8 - RBS 1 - mCherry - dblTerm - SpcR - pCDF origin | Pb1762-mCherry | 1d, 5 |
| pJBL6662 | PcarA - Target 8 - RBS 1 - mCherry - dblTerm - SpcR - pCDF origin | PcarA-mCherry | 1d, 5 |

TABLE 1-continued

Plasmids used in this study.

| Plasmid # | Plasmid architecture | Name | FIG. |
|---|---|---|---|
| pJBL6663 | PfadL - Target 8 - RBS 1 - mCherry - dblTerm - SpcR - pCDF origin | PfadL-mCherry | 1d, 5 |
| pJBL6664 | PfecA - Target 8 - RBS 1 - mCherry - dblTerm - SpcR - pCDF origin | PfecA-mCherry | 1d, 5 |
| pJBL6665 | PuraA - Target 8 - RBS 1 - mCherry - dblTerm - SpcR - pCDF origin | PuraA-mCherry | 1d, 5 |
| pJBL6666 | PgrxA - Target 8 - RBS 1 - mCherry - dblTerm - SpcR - pCDF origin | PgrxA-mCherry | 1d, 5 |
| pJBL6667 | PmtgA - Target 8 - RBS 1 - mCherry - dblTerm - SpcR - pCDF origin | PmtgA-mCherry | 1d, 5 |
| pJBL6668 | PybcU - Target 8 - RBS 1 - mCherry - dblTerm - SpcR - pCDF origin | PycbU-mCherry | 1d, 5 |
| pJBL6669 | PycbS - Target 8 - RBS 1 - mCherry - dblTerm - SpcR - pCDF origin | PycbS-mCherry | 1d, 5 |
| pJBL6670 | PyhjX - Target 8 - RBS 1 - mCherry - dblTerm - SpcR - pCDF origin | PyhjX-mCherry | 1d, 5 |
| pJBL6671 | PatoA - Target 8 - RBS 1 - mCherry - dblTerm - SpcR - pCDF origin | PatoA-mCherry | 1d, 5 |
| pJBL6672 | Pb2970 - Target 8 - RBS 1 - mCherry - dblTerm - SpcR - pCDF origin | Pb2970-mCherry | 1d, 5 |
| pJBL6673 | PecpD - Target 8 - RBS 1 - mCherry - dblTerm - SpcR - pCDF origin | PecpD-mCherry | 1d, 5 |
| pJBL6674 | PgntK - Target 8 - RBS 1 - CYP725A4-tcCPR - dblTerm - CmR - p15a origin | PgntK-P450 | 2d, 6 |
| pJBL6675 | PompF - Target 8 - RBS 1 - CYP725A4-tcCPR - dblTerm - CmR - P15a origin | PompF-P450 | 2d, 3d, 3f, 4d, 6, 9 |
| pJBL6676 | PyeeF - Target 8 - RBS 1 - CYP725A4-tcCPR - dblTerm - CmR - P15a origin | PyeeF-P450 | 2d, 6 |
| pJBL6677 | PompT - Target 8 - RBS 1 - CYP725A4-tcCPR - dblTerm - CmR - P15a origin | PompT-P450 | 2d, 6 |
| pJBL6678 | PmetN - Target 8 - RBS 1 - CYP725A4-tcCPR - dblTerm - CmR - P15a origin | PmetN-P450 | 2d, 3c, 3e, 4c, 6, 8 |
| pJBL6679 | Pb1762 - Target 8 - RBS 1 - CYP725A4-tcCPR - dblTerm - CmR - P15a origin | Pb1762-P450 | 2d, 6 |
| pJBL6680 | PcarA - Target 8 - RBS 1 - CYP725A4-tcCPR - dblTerm - CmR - P15a origin | PcarA-P450 | 2d, 6 |
| pJBL6681 | PfadL - Target 8 - RBS 1 - CYP725A4-tcCPR - dblTerm - CmR - P15a origin | PfadL-P450 | 6 |
| pJBL6682 | PfecA - Target 8 - RBS 1 - CYP725A4-tcCPR - dblTerm - CmR - P15a origin | PfecA-P450 | 6 |
| pJBL6683 | PuraA - Target 8 - RBS 1 - CYP725A4-tcCPR - dblTerm - CmR - P15a origin | PuraA-P450 | 6 |
| pJBL6684 | PgrxA - Target 8 - RBS 1 - CYP725A4-tcCPR - dblTerm - CmR - P15a origin | PgrxA-P450 | 6 |
| pJBL6685 | PmtgA - Target 8 - RBS 1 - CYP725A4-tcCPR - dblTerm - CmR - P15a origin | PmtgA-P450 | 6 |
| pJBL6686 | PybcU - Target 8 - RBS 1 - CYP725A4-tcCPR - dblTerm - CmR - P15a origin | PybcU-P450 | 6 |
| pJBL6687 | PycbS - Target 8 - RBS 1 - CYP725A4-tcCPR - dblTerm - CmR - P15a origin | PycbS-P450 | 6 |
| pJBL6688 | PyhjX - Target 8 - RBS 1 - CYP725A4-tcCPR - dblTerm - CmR - P15a origin | PyhjX-P450 | 6 |
| pJBL6689 | PatoA - Target 8 - RBS 1 - CYP725A4-tcCPR - dblTerm - CmR - P15a origin | PatoA-P450 | 6 |
| pJBL6690 | PecpD - Target 8 - RBS 1 - CYP725A4-tcCPR - dblTerm - CmR - P15a origin | PecpD-P450 | 6 |
| N/A | PTrc - CYP725A4-tcCPR - rrnB - SpcR - SC101 | P5Trc | 2c |
| N/A | PTrc - CYP725A4-tcCPR - rrnB - CmR - p15a | P10Trc | 2c |
| pJBL6691 | apFAB346 - apFAB682 - EsaI - LuxR - dblTerm - SpcR - SC101* | pQS | N/A |
| pJBL6692 | PJ23115 - Target 8 - RBS 1 - mCherry - dblTerm - SpcR - pCDF origin | PJ23115-mCherry | 7 |

apFAB parts were obtained from a previously published library of genetic parts1. Abbreviations are as follows: RBS 1 = ribosome binding site variant (see Supplementary Table 3), PR = tetR promoter2, PLTet, O1 = TetR repressible promoter3, PLux (BBa_R0062)* = LuxR inducible promoter4, mCherry = red fluorescent protein, LuxR (BBa_C0062)* = AHL inducible transcription factor4, tetR = tet repressor protein3, TrrnB = rrnB terminator, BBa_B0015* = B0015 terminator, T500 = T500 terminator, dblTerm = dblTerm terminator, PJ2315 = BBa_J23115 promoter from the iGEM Registry of Standard Biological Parts (parts.igem.org), CmR = chloramphenicol resistance cassette, AmpR = ampicillin resistance cassette, SpcR = spectinomycin resistance cassette, p15A = p15A origin of replication, ColE1 = ColE1 origin of replication and CDF = CDF origin of replication.

TABLE 2

Examples of DNA plasmid sequences. Abbreviations as in Table 1.

| Name | Sequence |
|---|---|
| PL,TetO1-STAR (PR-TetR-dblTerm-PL,TetO1-STAR8-T500) | GAATTCTAAAGATCTTTTTCTCTATCACTGATAGGGACGTGGTAAAA<br>TAACTCTATCAACGATAGAGTGTCAACAAAAATTAGGAATTAATG<br>ATGTCGAGATTAGATAAAAGTAAAGTGATTAACAGCGCATTAGAGCT<br>GCTTAATGAGGTCGGAATCGAAGGTTTAACAACCCGTAAACTCGCCC<br>AGAAGCTAGGTGTAGAGCAGCCTACATTGTATTGGCATGTAAAAAAT<br>AAGCGGGCTTTGCTCGACGCCTTAGCCATTGAGATGTTAGATAGGCA<br>CCATACTCACTTTTTGCCCTTTAGAAGGGGAAAGCTGGCAAGATTTTTT<br>ACGTAATAACGCTAAAAGTTTTAGATGTGCTTTTTACTAAGTCATCGCG<br>ATGGAGCAAAAGTACATTTAGGTACACGGCCTACAGAAAAACAGTA<br>TGAAACTCTCGAAAATCAATTAGCCTTTTTATGCCAACAAGGTTTTTTC<br>ACTAGAGAATGCATTATATGCACTCAGCGCTGTGGGGCATTTTACTTT<br>AGGTTGCGTATTGGAAGATCAAGAGCATCAAGTCGCTAAAGAAGAA<br>AGGGAAACACCTACTACTGATAGTATGCCGCCATTATTACGACAAGC<br>TATCGAATTATTTGATCACCAAGGTGCAGAGCCAGCCTTCTTATTCGG<br>CCTTGAATTGATCATATGCGGATTAGAAAAACAACTTAAATGTGAAA<br>GTGGGTCTTAATAACACTGATAGTGCTAGTGTAGATCACTACTAGAG<br>CCAGGCATCAAATAAAACGAAAGGCTCAGTCGAAAGACTGGGCCTTTCGT<br>TTTATCTGTTGTTTGTCGGTGAACGCTCTCTACTAGAGTCACACTGGCTCA<br>CCTTTCGGGTGGGCCTTTGTGCGTTTATATACTAGAGTCCCTATCAGTG<br>ATAGAGATTGACATCCCTATCAGTGATAGAGATACTGAGCACTGA<br>ACTGTATACATTCCCCGCAGGATAAGAGTAAGTGAGAGTAGGTAGAGA<br>TTGAGGATGGGGATCTCAAAGCCCGCCGAAAGGCGGGCTTTTTTTTGGA<br>TCCTTACTCGAGTCTAGACTGCAGGCTTCCTC (SEQ ID NO: 1) |
| PLux-STAR (PLux-STAR8-T500) | CTAAAGATCTATATACTAGAGACCTGTAGGATCGTACAGCGTTTTTACG<br>CAAGAAAATGGTTTTTGTTATAGTCGAATAAATGAACTGTATACATTC<br>CCCGCAGGATAAGAGTAAGTGAGAGTAGGTAGAGATTGAGGATGGGG<br>ATCTCAAAGCCCGCCGAAAGGCGGGCTTTTTTTTGGATCCTTACTCGAGT<br>CTAGACTGCAGGCTTCCTC (SEQ ID NO: 2) |
| Example rSFP Plasmid (PompF-TARGET 8-RBS1-mCherry (all lowercase) - dblTerm) | CGATCATCCTGTTACGGAATATTACATTGCAACATTTACGCGCAA<br>AAACTAATCCGCATTCTTATTGCGGATTAGTTTTTTCTTAGCTAA<br>TAGCACAATTTTCATACTATTTTTTGGCATTCTGGATGTCTGAAA<br>GAAGATTTTGTGCCAGGTCGATAAAGTTTCCATCAGAAACAAAAT<br>TTCCGTTTAGTTAATTTAAATATAAGGAAATCATATAAATAGATT<br>AAAATTGCTGTAAATATCATCACGTCTCTATGGAAATATGACGGT<br>GTTCACAAAGTTCCTTAAATTTTACTTTTGGTTACATATTTTTTCT<br>TTTTGAAACCAAATCTTTATCTTTGTAGCACTTTCACGGTAGCGA<br>AACGTTAGTTTGAATGGAAAGATGCCTGCAGACACATAAAGACA<br>CCAAACTCTCATCAATAGTTCCGTAAATTTTTATTGACAGAACTT<br>ATTGACGGCAGTGGCAGGTGTCATAAAAAAAACCATGAGGGTAA<br>TAAATACCATCCTCAATCTCTACCTACTCTCACTTACTCTTATCCT<br>GCGGGGAATGTATACAGTTCATGTATATATTCCCCGCTTTTTTTTT<br>TGGATCTAGGAGGAAGGATCTatggcgagtagcgaagacgttatca<br>aagagttcatgcgtttcaaagttcgtatggaaggttccgttaacgg<br>tcacgagttcgaaatcgaagctgaaggtgaaggtcgtccgtacgaag<br>gtacccagaccgctaaactgaaagttaccaaaggtcggtccgctgcc<br>ccgttcgcttgcgacatccctgtccccgcagttccagtacggttcca<br>aagcttacgttaaacacccggctgacatcccggactacctgaaactg<br>tccttcccggaaggtttcaaatgggaacgtgttatgaacttcgaaga<br>cggctcgtgttgttaccgttacccaggactcctccctgcaagacggt<br>gagttcatctacaaagttaaactgcgtggtaccaacttcccgtccga<br>cggtccgggttatgcagaaaaaaaccatgcggttgggaagcttccac<br>cgaacgtatgtacccggaagacggtgctctgaaaggtgaaatcaaaa<br>tgcgtctgaaactgaaagacggtggtcactacgacgctgaagttaaa<br>accacctacatgcctaaaaaaccggttcagctgccgggtgcttacaa<br>aaccgacatcaaactggacatcacctcccacaacgaagactacacca<br>tcgttgaacagtacgaacgtgctgaaggtcgtcactccaccggtgct<br>taaGGATCCAAACTCGAGTAAGGATCTCCAGGCATCAAATAAAACGA<br>AAGGCTCAGTCGAAAGACTGGGCCTTTCGTTTTATCTGTTGTTTG<br>TCGGTGAACGCTCTCTACTAGAGTCACACTGGCTCACCTTTCGGGTG<br>GGCCTTTTTCTGCGTTTATA (SEQ ID NO: 3) |
| CYP726A4/tc CPR fusion | ATGGCTCTGTTATTAGCAGTTTTTTTTAGCATCGCTTTGAGTGCAATT<br>GCCGGGATCTTGCTGTTGCTCCTGCTGTTTCGCTCGAAACGTCATAGT<br>AGCCTGAAATTACCTCCGGGCAAACTGGGCATTCCGTTTATCGGTGA<br>GTCCTTTATTTTTTTTTTTGCGCGCGCTGAGGAGCAATTCTCTGGAACAGTT<br>CTTTGATGAACGTGTGAAGAAGTTCGGCCTGGTATTTAAAACGTCCC<br>TTATCGGTCACCCGACGGTTGTCCTGTGCGGGCCCGCAGGTAATCGC<br>CTCATCCTGAGCAACGAAGAAAAGCTGGTACAGATGTCCTGGCCGGC<br>GCAGTTTATGAAGCTGATGGGAGAGAACTCAGTTGCGACCCGCCGTG<br>GTGAAGATCACATTGTTATGCGCTCCGCGTTGGCAGGCTTTTTCGGCC<br>CGGGAGCTCTGCAATCCTATATCGGCAAGATGAACACGGAAATCCAA<br>AGCCATATTAATGAAAAGTGGAAAGGGAAGGACGAGGTTAATGTCT<br>TACCCCTGGTGCGGGAACTGGTTTTTAACATCAGCGCTATTCTGTTCT<br>TTAACATTTACGATAAGCAGGAACAAGACCGTCTGCACAAGTTGTTA |

TABLE 2-continued

| Examples of DNA plasmid sequences. Abbreviations as in Table 1. | |
|---|---|
| Name | Sequence |
| | GAAACCATTCTGGTAGGCTCGTTTGCCTTACCAATTGATTTTACCGGGT<br>TTCGGGTTTCACCGCGCTTTTTACAAGGTCGTGCAAAACTCAATAAAAT<br>CATGTTGTCGCTTTTATTAAAAAACGTAAAGAGGACTTACAGTCGGGAT<br>CGGCCACCGCGACGCAGGACCTGTTGTCTGTGCTTCTGACTTTTTCCGTG<br>ATGATAAGGGCACCCCGTTTTAACCAATGACGAAATCCTGGACAACTTT<br>AGCTCACTGCTTCACGCCTCTTACGACACCACGACTAGTCCAATGGC<br>TCTGATTTTTTCAAATTACTGTCAAGTAACCCTGAATGCTATCAGAAAGT<br>CGTGCAAGAGCAACTCGAGATTCTGAGCAATAAGGAAGAAGGTGAA<br>GAAATTACCTGGAAAGATCTTAAGGCCATGAAATACACGTGGCAGGT<br>TGCGCAGGAGACACTTCGCATGTTTCCACCGGTGTTCGGGACCTTCC<br>GCAAAGCGATCACGGATATTCAGTATGACGGATACACAATCCCGAA<br>AGGTTGGAAACTGTTGTGGACTACCTATAGCACTCATCCTAAGGACC<br>TTTACTTCAACGAACCGGAGAAATTTATGCCTAGTCGTTTCGATCAG<br>GAAGGCAAACATGTTGCGCCCTATACCTTCCTGCCCTTTGGAGGCGG<br>TCAGCGGAGTTGTGTGGGTTGGGAGTTCTCTAAGATGGAGATTCTCC<br>TCTTCGTGCATCATTTCGTGAAAACATTTTCGAGCTATACCCCGGTCG<br>ATCCCGATGAAAAAATTTCCGGCGATCCACTGCCGCCGTTACCGAGC<br>AAAGGGTTTTCAATCAAACTGTTCCCTCGTCCGGGCAGCACCGGATC<br>CCGCCGTGGTGGAAGTGATACACAGAAGCCCGCCGTACGTCCCACAC<br>CTCTTGTTAAAGAAGAGGACGAAGAAGAAGAAGATGATAGCGCCAA<br>GAAAAAGGTCACAATATTTTTTGGCACCCAGACCGGCACCGCCGAAG<br>GTTTCGCAAAGGCCTTAGCTGAGGAAGCAAAGGCACGTTATGAAAA<br>GGCGGTATTTAAAGTCGTGGATTTGGATAACTATGCAGCGGATGACG<br>AACAGTACGAAGAGAAGTTGAAAAAGGAAAAGCTAGCGTTCTTCAT<br>GCTCGCCACCTACGGTGACGGCGAACCGACTGATAATGCCGCTCGCT<br>TTTATAAATGGTTTCTCGAGGGTAAAGAGCGCGAGCCATGGTTGTCA<br>GATCTGACTTATGGCGTGTTTGGCTTAGGTAACCGTCAGTATGAACA<br>CTTTAACAAGGTCGCGAAAGCGGTGGACGAAGTGCTCATTGAACAA<br>GGCGCCAAACGTCTGGTACCGGTAGGGCTTGGTGATGATGATCAGTG<br>CATTGAGGACGACTTCACTGCCTGGAGAGAACAAGTGTGGCCTGAGC<br>TGGATCAGCTCTTACGTGATGAAGATGACGAGCCGACGTCTGCGACC<br>CCGTACACGGCGGCTATTCCAGAATACCGGGTGGAAATCTACGACTC<br>AGTAGTGTCGGTCTATGAGGAAACCCATGCGCTGAAACAAAATGGA<br>CAAGCCGTATACGATATCCACCACCCGTGTCGCAGCAACGTGGCAGT<br>ACGTCGTGAGCTGCATACCCCGCTGTCGGATCGTAGTTGTATTCATCT<br>GGAATTCGATATTAGTGATACTGGGTTAATCTATGAGACGGGCGACC<br>ACGTTGGAGTTCATACCGAGAATTCAATTGAAACCGTGGAAGAAGCA<br>GCTAAACTGTTAGGTTACCAACTGGATACAATCTTCAGCGTGCATGG<br>GGACAAGGAAGATGGAACACCATTGGGCGGGAGTAGCCTGCCACCG<br>CCGTTTCCGGGGCCCTGCACGCTGCGGACGGCGCTGGCACGTTTACGC<br>GGACCTGCTGAACCCTCCGCGCAAAGCCGCCTTCCTGGCACTGGCCG<br>CACACGCGTCAGATCCGGCTGAAGCTGAACGCCTTAAATTTCTCAGT<br>TCTCCAGCCGGAAAAGACGAATACTCACAGTGGGTCACTGCGTCCCA<br>ACGCAGCCTCCTCGAGATTATGGCCGAATTCCCCAGCGCGAAACCGC<br>CGCTGGGAGTGTTTTTTCGCCGCAATAGCGCCGCGCTTGCAACCTAGG<br>TATTATAGCATCTCCTCCTCCCCGCGTTTTTCGCGCCGTCTCGTATCCAT<br>GTAACGTGCGCGCTGGTCTATGGTCCTAGCCCTACGGGGCGTATTCA<br>TAAAGGTGTGTGCAGCAACTGGATGAAGAATTCTTTGCCCTCCGAAG<br>AAACCCACGATTGCAGCTGGGCACCGGTCTTTGTGCGCCAGTCAAAC<br>TTTAAACTGCCGCGCCGATTCGACGACGCCAATCGTGATGGTTGGACC<br>TGGAACCGGCTTCGCTCCATTTCGCGGCTTCCTTCAGGAACGCGCAA<br>AACTGCAGGAAGCGGGCGAAAAATTGGGCCCGGCAGTGCTGTTTTTT<br>GGGTGCCGCAACCGCCAGATGGATTACATCTATGAAGATGAGCTTAA<br>GGGTTACGTTGAAAAAGGTATTCTGACGAATCTGATCGTTGCATTTTC<br>ACGAGAAGGCGCCACCAAAGAGTATGTTCAGCACAAGATGTTAGAG<br>AAAGCCTCCGACACGTGGTCTTTTAATCGCCCAGGGTGGTTATCTGTA<br>TGTTTGCGGTGATGCGAAGGGTATGGCCAGAGACGTACATCGCACCC<br>TGCATACAATCGTTCAGGAACAAGAATCCGTAGACTCGTCAAAAGCG<br>GAGTTTTTAGTCAAAAAGCTGCAAATGGATGGACGCTACTTACGGGA<br>TATTTGGTAA (SEQ ID NO: 4) |
| QS operon<br>(**apFAB346**-<br>*apFAB682*-<br>***Esal***-*B0034*-<br>**LuxR**-<br>dblTerm) | **TTGACAATTAATCATCCGGCTCGTAATGTTTGTGGA***GGGCCCAAGT*<br>*TCACTTAAAAAGGAGATCAACAATGAAAGCAATTTTTCGTACTGAAACATCTT*<br>*AATCATGCTAAGGAGGTTTTCTAAT****GATGCTTGAACTGTTTGACGTCAGT***<br>***TACGAAGAACTGCAAACCACCCGTTCAGAAGAACTTTTATAAACTTCGC***<br>***AAGAAAACATTTTAGCGATCGTCTGGGATGGGAAGTCATTTGCAGTCAG***<br>***GGAATGGAGTCCGATGAATTTGATGGGCCCGGTACACGTTATATTCTG***<br>***GGAATCTGCGAAGGACAATTAGTGTGCAGCGTACGTTTTACCAGCCTC***<br>***GATCGTCCCAACATGATCACGCACACTTTTCAGCACTGCTTCAGTGAT***<br>***GTCACCCTGCCCGCCTATGGTACCGAATCCAGCCGTTTTTTTTGTCGAC***<br>***AAAGCCCGCGCACGTGCGCTGTTAGGTGAGCACTACCCTATCAGCCAG***<br>***GTCCTGTTTTTAGCGATGGTGAACTGGGCGCAAAATAATGCCTACGGC***<br>***AATATCTATACGATTGTCAGCCGCGCGATGTTGAAAATTCTCACTCGCT***<br>***CTGGCTGGCAAATCAAAGTCATTAAAGAGGCTTTCCTGACCGAAAAGG***<br>***AACGTATCTATTTGCTGACGCTGCCAGCAGGTCAGGATGACAAGCAGC***<br>***AACTCGGTGGTGATGTGGTGTCACGTACGGGCTGTCCGCCCGTCGCAG*** |

TABLE 2-continued

Examples of DNA plasmid sequences. Abbreviations as in Table 1.

| Name | Sequence |
|---|---|
| | ***TCACTACCTGGCCGCTGACGCTGCCGGTCTGA***TACTAGAGA*AAGAGGA*<br>*GAAA*TACTAG**ATGAAAAACATAAATGCCGACGACACATACAGAAT**<br>**AATTAATAAAATTAAAGCTTGTAGAAGCAATAATGATATTAATCA**<br>**ATGCTTATCTGATATGACTAAAATGGTACATTGTGAATATTATTTTT**<br>**ACTCGCGATCATTTATCCTCATTCTATGGTTAAATCTTGATATTTTTC**<br>**AATCCTAGATAATTACCCTAAAAAATGGAGGCAATATTATGATGA**<br>**CGCTAATTTAATAAAATATGATCCTATAGTAGATTATTCTAACTC**<br>**CAATCATTCACCAATTAATTGGAATATATTTTTGAAAACAATGCTGT**<br>**AAATAAAAAATCTCCAAATGTAATTAAAGAAGCGAAAACATCAGG**<br>**TCTTATCACTGCGGTTTAGTTTCCCTATTCATACGGCTAACAATGG**<br>**CTTCGGAATGCTTAGTTTTGCACATTCAGAAAAAGACAACTATAT**<br>**AGATAGTTTATTTTTACATGCGTGTATGAACATACCATTAATTGT**<br>**TCCTTCTCTAGTTGATAATTATCGAAAAATAAATATAGCAAATAA**<br>**TAAATCAAACAACGATTTAACCAAAAGAGAAAAAGAATGTTTAGC**<br>**CGTGGGCATGCGAAGGAAAAAGCTCTTGGGATATTTCAAAAATAT**<br>**TAGGTTGCAGTGAGCGTACTGTCACTTTCCATTTAACCAATGCGC**<br>**AAATGAAACTCAATACAACAAACCGCTGCCAAAGTATTTCTAAAG**<br>**CAATTTTAACAGGAGCAATTGATTGCCCATACTTTAAAAATTAA**T<br>CTAGAGGATCCAAACTCGAGTAAGGATCTCCAGGCATCAAATAAAA<br>CGAAAGGCTCAGTCGAAAGACTGGGCCTTTTCGTTTTTATCTTTGTTGTTTG<br>TCGGTGAACGCTCTCTACTAGAGTCACACTGGCTCACCTTCGGGTGG<br>GCCTTTCTGCGTTTTTATACCTAGG (SEQ ID NO: 5) |

TABLE 3

Sequence of Promoter and RBS variants. Pstress promoters were PCR amplified from the *E. coli* K-12 MG1655 genome.

| Name | Sequence |
|---|---|
| RBS 1 | AGGAGGAA (SEQ ID NO:6) |
| B0034 RBS | AAGAGGAGAAA (SEQ ID NO:7) |
| $P_{LTetO-1}$ | TCCCTATCAGTGATAGAGATTGACATCCCTATCAGTGATAGAGATACTGAG<br>CAC (SEQ ID NO:8) |
| $P_{Lux}$ | ACCTGTAGGATCGTACAGGTTTACGCAAGAAAATGGTTTGTTATAGTCGAA<br>TAAA (SEQ ID NO:9) |
| PJ23115 | TTTATAGCTAGCTCAGCCCTTGGTACAATGCTAGC (SEQ ID NO: 10) |
| PgntK<br>(SEQ ID NO: 11) | AATCTGTGACACCGAAAATGTTAGATTTAGGTTTCACCTTGTCACCGGGCG<br>GATCTATTTAAGCCCACAAATTTGAAGTAGCTCACACTTATACACTTAAGG<br>CATGGATGGATATTGCTTCTGATATTGTCCGGCTGGAGAATGTTACCGATA<br>ACAGTTACCCGTAACATTTTTAATTCTTGTATTGTGGGGGCACCACT |
| PompF<br>(SEQ ID NO:1 2) | CGATCATCCTGTTACGGAATATTACATTGCAACATTTACGCGCAAAAACTA<br>ATCCGCATTCTTATTGCGGATTAGTTTTTTCTTAGCTAATAGCACAATTTTC<br>ATACTATTTTTTGGCATTCTGGATGTCTGAAAGAAGATTTTGTGCCAGGTC<br>GATAAAGTTTCCATCAGAAACAAAATTTCCGTTTAGTTAATTTAAATATAAG<br>GAAATCATATAAATAGATTAAAATTGCTGTAAATATCATCACGTCTCTATGG<br>AAATATGACGGTGTTCACAAAGTTCCTTAAATTTTACTTTTGGTTACATATTT<br>TTTCTTTTTGAAACCAAATCTTTATCTTTGTAGCACTTTCACGGTAGCGAAA<br>CGTTAGTTTGAATGGAAAGATGCCTGCAGACACATAAAGACACCAAACTCT<br>CATCAATAGTTCCGTAAATTTTTATTGACAGAACTTATTGACGGCAGTGGC<br>AGGTGTCATAAAAAAAACCATGAGGGTAATAAATA |
| PyeeF<br>(SEQ ID NO: 13) | ATTAGCGGCCTCGGCTGCGGCTATTTACCCCGTTATCTGGCGCAACGTTT<br>TCTCGATAGTGGCGCGTTAATCGAGAAGAAAGTGGTCGCCCAAACTCTCT<br>TTGAACCCGTCTGGATTGGCTGGAACGAACAGACCGCAGGACTTGCCAGT<br>GGCTGGTGGGGGGATGAAATTTTAGCAAATAGTGCGATCGCCGGTGTTTA<br>TGCAAAATCTGATGACGGAAAATCAGCCATTTAAAGAAAAATTATTCTGAC<br>AAGCCTCTCATTCTCTTGTCATTTCCCCCCCATTTAGGCACAATGCGCCGC<br>TGTCAAAAAATGACTAAAAACCGACGTTTCATCAGCGTCGGTTATTTTTTG<br>CTTCAAACCAATCATTCATACCAAGAGGCCGGGCTTCGTACCGGATAGAT<br>ATTTACTAAAAATCGAGAGTTGTTGTCGCTGAGGAATCGAAAAAAATGGGG<br>CAATTTTTTGCTTACGCGACGGTTATCACCGTAAAGGAGAATGACC |
| PompT<br>(SEQ ID NO: 14) | AACGGATAAGACGGGCATAAATGAGGAAGAAATGGCGCGCCCTGCAGGA<br>TTCGAACCTGCGGCCCACGACTTAGAAGTTCCTAGAACGACATTTTAAGTC<br>AACAACTTACCGCGCCATCTCTGCGCTCACACGTCCCACTACCTCAAAAC<br>ATGTAAAGCCTTGCAAGCCATTGCGAGGCCTTATGTGTCTCAGTTTTGTCC |

TABLE 3-continued

Sequence of Promoter and RBS variants. Pstress promoters were PCR amplified from the *E. coli* K-12 MG1655 genome.

| Name | Sequence |
|---|---|
| | CTCTTTTTTGTACTAAAAAACATAGTAATTGAGGATAAACCTCATGCTATTT<br>TCGCTTATATGCCTCTAAAGGCATGGCACTTAAATAGATAAAAGCACCACA<br>AAAGCATAAAAAAACCACACAGTAAAACCGAAATATGAAACAATAACAGAT<br>AATTAAACCAAAAACAGATAGCGCATTGTGATAATCATTCAATACTAAACAA<br>AATATAAACAGTGGAGCAATATGTAATTGACTCATTAAGTTAGATATAAAAA<br>ATACATATTCAATCATTAAAACGATTGAATGGAGAACTTTT |
| PmetN<br>(SEQ ID NO: 15) | GGCGAAACTCTTCAACACTACCCTGCGGATGATGCGGGCAATAATAGATA<br>CCATCCAGATCGACATCTCGGTCCGCCAGCGACCAGTCCATCCACTCGGT<br>CAGCGTTTCAAACTGTGCTTCGGTAAATTTACCGCGAGCAATGCCAGACT<br>GGTTGGTTACTACCACCAGCGCAAAGCCCATTTTTTTTAGCTCGCGCATG<br>GCGTCAATAACACCGTCGATAAATTCAAAGTIGTCGATCTCATGGACATAG<br>CCGTGATCGACATTAATGGTGCCATCACGGTCAAGAAAAATTGCGGGTAC<br>GCTCTTCGCCACCTTTTATAGCTCCTTAATAAGGCATGTGACGCTAGTATC<br>GCATGTTTCGACCTGCAAGAAAGTGCTCTTCGCATAAACCTGATTGATTTA<br>GACGTCTGGATGCCTTAACATCCATTTCATTGACGGCGTTGCCCGTTTCAG<br>GCATTCGAGATGCCACGACTAACTTAATGACGATAATAAATAATCA |
| Pb1762<br>(SEQ ID NO: 16) | GATTATTGAACTGTTGTTCAAGCGTGGTTTCCTGACCAAAAAAGGGCGCTA<br>TATCCACTCCACCGACGCCGGAAAAGCGCTATTCCATTCGCTGCCGGAGA<br>TGGCGACGCGACCGGACATGACCGCGCACTGGGAATCGGTGCTGACGCA<br>AATCAGCGAAAAGCAGTGTCGCTATCAGGACTTTATGCAGCCGCTGGTGG<br>GGACGCTATATCAGCTTATTGATCAAGCCAAACGTACGCCGGTGCGGCAG<br>TTTCGCGGCATTGTGGCTCCGGGCAGTGGTGGCAGTGCTGATAAGAAAAA<br>GGCTGCACCGCGTAAACGTAGTGCGAAAAAAAGTCCGCCAGCAGATGAA<br>GTCGGAAGCGGGGCGATAGCGTAAGCGAGTGAATCTTTCGTGCTATTCGA<br>GTCATATTCTGAAATATCCAGCGGATCAAGAAAATTCGTTGGATATTTTTTT<br>TGCATGGATAAAATTATCGCCTCTAAAGTATGTAATAACAGGGAATGTG |
| PcarA<br>(SEQ ID NO:17) | GGTCTTTTTGATATGCGAGATGTACTTGATCTCAATAATTTGTAACCACAAA<br>ATATTTGTTATGGTGCAAAAATAACACATTTAATTTATTGATTATAAAGGGC<br>TTTAATTTTTGGCCCTTTTATTTTTGGTGTTATGTTTTTAAATTGTCTATAAG<br>TGCCAAAAATTACATGTTTTGTCTTCTGTTTTTGTTGTTTTAATGTAAATTTT<br>GACCATTTGGTCCACTTTTTTCTGCTCGTTTTTATTTCATGCAATCTTCTTG<br>CTGCGCAAGCGTTTTCCAGAACAGGTTAGATGATCTTTTTGTCGCTTAATG<br>CCTGTAAAACATGCATGAGCCACAAAATAATATAAAAAATCCCGCCATTAA<br>GTTGACTTTTAGCGCCCATATCTCCAGAATGCCGCCGTTTGCCAGAAATTC<br>GTCGGTAAGCAGATTTGCATTGATTTACGTCATCATTGTGAATTAATATGCA<br>AATAAAGTGAGTGAATATTCTCTGGAGGGTGTT |
| PfadL<br>(SEQ ID NO: 18) | CGTTTGCTCTGCTTCTGCGCGGTTTGCAAACACGCGGCTGTAAGACGCGG<br>TGCAGTCGGAGTTGTCCATAATGGTGCCAACATCCATACAGCAGCAAACC<br>GGGGTTTCATCAGCACTACATTTACTCATCGTTGATTTCCTCTGTATGTGC<br>ACCCAAGGTGCCAGATAAACGTTGTGGATATTTTACGCTTCCGGAAAGTG<br>CTGCTCCAGTTGTTAATTCTGCAAAATCGGATAAGTGACCGAAATCACACT<br>TAAAAATGATCTAAAACAAAATTCACCCGAATCCATGAGTGCGCCACCTCC<br>AAATTTTGCCAGCTGGATCGCGTTTCTTAGATCATATTTGAAAAAAGATAGA<br>AACATACTTGCAACATTCCAGCTGGTCCGACCTATACTCTCGCCACTGGTC<br>TGATTTCTAAGATGTACCTCAGACCCTACACTTCGCGCTCCTGTTACAGCA<br>CGTAACATAGTTTGTATAAAAATAAATCATTGAGGTTATGGTC |
| PuraA<br>(SEQ ID NO: 19) | TACCGTTGTGCCAATTCTGCGTGCGGGTCTTGGTATGATGGACGGTGTGC<br>TGGAAAACGTTCCGAGCGCGCATCAGCGTTGTCGGTATGTACCGTAAT<br>GAAGAAACGCTGGAGCCGGTACCGTACTTCCAGAAACTGGTTTCTAACAT<br>CGATGAGCGTATGGCGCTGATCGTTGACCCAATGCTGGCAACCGGTGGTT<br>CCGTTATCGCGACCATCGACCTGCTGAAAAAAGCGGGCTGCAGCAGCATC<br>AAAGTTCTGGTGCTGGTAGCTGCGCCAGAAGGTATCGCTGCGCTGGAAAA<br>AGCGCACCCGGACGTCGAACTGTATACCGCATCGATTGATCAGGGACTGA<br>ACGAGCACGGATACATTATTCCGGGCCTCGGCGATGCCGGTGACAAAATC<br>TTTGGTACGAAATAAAGAATAAAAATAATTAAAGCCGACTTTAAGAGTCGG<br>CTTTTTTTTGAGTAAAGCGCCTATAACACATAATACAGAGGATAATACT |
| PgrxA<br>(SEQ ID NO: 20) | CGGAAATGGGTTCATCAGTGAAATGGCGAATGGAGCGATGGCCACAAATA<br>AGTTCAATGGTTGGCGTCATTATCTTTTTCTCTTTCTGAACGTGAATATTGC<br>GGTGGACGGTTCATCAGCTGTGGGGCAAGACGTTTTGCCACCTGAAGAAT<br>AACCACCACCGCAGCGGGAAGCATGAGCAAAACACCGAGAAAAATCATCA<br>GAATCTGCACTTCTGGCCGAGAAAATGGCTCAGGCAGCGACAGGGAGTC<br>GCTTACCGACAGCAGCGCCACCGCCAGTAGCATCATTCCGATAAATTCCA<br>GTATCAACACGCCTTTAGGCAATTTACCGATCGCGCGCATACGCTTCCCT<br>CTGCAAAGTGAGCCTTCAGTCTAAAACTTTTCACTGTATTGTGTTTAACAGT<br>TATAGCTTTTAGCAATTAATGCAACAGGTTAAACCTACTTTCAGCGAATACA<br>TTTTAGCGTGATCATTACAGGCATAAATCTATGAGGAGAGAAATA |
| PmtgA<br>(SEQ ID NO: 21) | CATTTAACTGGCGAAGCGATGACGGAAACGCGCAATGTGCTGATTGAAGC<br>GGCACGAATAACGCGCGGTGAAATCCGTCCTCTGGCCCAGGCCGATGCC |

TABLE 3-continued

Sequence of Promoter and RBS variants. Pstress promoters were PCR amplified from the *E. coli* K-12 MG1655 genome.

| Name | Sequence |
|---|---|
| | GCTGAACTGGATGCGTTGATTGTGCCGGGGGGGTTTGGCGCGGCGAAGA<br>ATTTAAGCAATTTTGCCAGTCTTGGTAGCGAATGCACCGTTGACCGTGAAT<br>TAAAGGCGCTGGCACAAGCGATGCATCAGGCCGGAAAACCGCTTGGTTTT<br>ATGTGTATTGCCCCGGCGATGCTGCCGAAAATTTTCGATTTCCCGCTGCG<br>TTTGACCATCGGTACTGATATCGATACCGCAGAAGTGCTGGAAGAGATGG<br>GCGCGGAGCATGTGCCGTGTCCTGTCGATGATATCGTGGTTGATGAAGAC<br>AATAAGATTGTCACCACCCCAGCATATATGCTGGCGCAGAACATTGCAGA<br>AGCGGCGAGCGGCATTGATAAGCTGGTTTCCCGCGTGCTGGTTCTGGCT<br>GA |
| PybcU<br>(SEQ ID NO:22) | TCAAGAAATACGCATCTTATAGAAACGTCCTATGATAGGTTGAAATCAAGA<br>GAAATCACATTTCAGCAATACAGGGAAAATCTTGCTAAAGCAGGAGTTTTC<br>CGATGGATTACAAATATCCACGAACATAAAAGATATTACTATACCTTTGATA<br>ATTCATTACTATTTACTGAGAGCATTCAGAACACTACACAAATCTTTCCACG<br>CTAAATCATAACGTCCGGTTTCTTCCGTGTCAGCACCGGGGTGTTGGCAT<br>AATACAATACATGTACGCGCTAAACCCTGTGTGCATCGTTTTTAATTATTCC<br>CGGACACTCCCGCAGAGAAGTTCCCCGTCAGGGCTGTGGACATAGTTAAT<br>CCGGGAATACAATGACGATTCATCGCACCTGGCATACATTAATAAATATTA<br>ACAATATGAAATTTCAACTCATTGTTTAGGGTTTGTTTAATTTTCTACACATA<br>CGATTCTGCGAACTTCAAAAAGCATCGGGAATAACACC |
| PycbS<br>(SEQ ID NO: 23) | CAGACTTTATTATTACACCACCGCTATTTGTGCTGAATCCGGCAAATGAGA<br>ATCTGTTACGCATTATGTACATTGGAGCGCCGTTGGCGAAAGACAGAGAA<br>ACCCTTTTCTTCACTAGCGTACGGGCAGTCCCTTCAACAACGAAGCGGAA<br>AGAGGGAAATACCCTGAAGATTGCCACACAAAGCGTCATCAAACTTTTCTG<br>GCGACCAAAAGGTTTAGCGTATCCCTTAGGCGAGGCTCCGGCGAAACTG<br>CGTTGCACTTCGTCAGCTGACATGGTTACGGTCAGTAACCCAACACCTTAT<br>TTCATTACCCTGACAGACCTGAAAATAGGTGGAAAAGTAGTTAAAAATCAA<br>ATGATTTCCCCCTTTGATAAATACCAATTTTCTCTGCCAAAGGGGGCCAAA<br>AATAGCAGCGTAACGTATCGAACCATCAATGACTAGGGGGGGGAAACGCC<br>GCAACTCAACTGTAAATCGTAAGCCGTCTTCAGTTAAGAGAGCGAG |
| PyhjX<br>(SEQ ID NO: 24) | TAGGCTGGCGTGTTGACTCCCGGCTTGGCGATCTCCGACCCTGGGCGCA<br>AATCAGCTATAACCAGCAATTTGGCGAGAATATCTGGAAGGCGCAATCAG<br>GCCTGAGCCGGATGACGGCGACAAACCAGAACGGCAACTGGCTGGATGT<br>CACCGTAGGCGCTGATATGTTGCTCAATCAAAATATTGCCGCCTATGCCG<br>CGCTAACTCAGGCAGAAAATACCACTAATAATAGCGACTATCTGTATACGA<br>TGGGGGTTAGCGCCAGATTTTAACGTAACAGTCACAATTGAAACCATTAAA<br>TAACAATAGTTGTGGCGATAGTGGGTGCTAACTTACCAAATAATAAATTTG<br>GTGAATAATTGTCGCGTCATTCATTCCTGAACTAAGGCATTTCATTCCGTT<br>CTGATGGCATTTCATGCCGTTTTTCCCCAGGCATAAAGTGCACTTCGTTAT<br>GGTTGTCGGCAGAGATTTTTCCTTTTTATTACTGCAGGAATACTGCC |
| PatoA<br>(SEQ ID NO: 25) | GCGTTTGTTGATACCGGCATCGGTCCGCTCATCGTCAATGGTCGAGTCCG<br>CAAAGTGATTGCTTCACATATCGGCACCAACCCGGAAACAGGTCGGCGCA<br>TGATATCTGGTGAGATGGACGTCGTTCTGGTGCCGCAAGGTACGCTAATC<br>GAGCAAATTCGCTGTGGTGGAGCTGGACTTGGTGGTTTTCTCACCCCAAC<br>GGGTGTCGGCACCGTCGTAGAGGAAGGCAAACAGACACTGACACTCGAC<br>GGTAAAACCTGGCTGCTCGAACGCCCACTGCGCGCCGACCTGGCGCTAA<br>TTCGCGCTCATCGTTGCGACACACTTGGCAACCTGACCTATCAACTTAGC<br>GCCCGCAACTTTAACCCCCTGATAGCCCTTGCGGCTGATATCACGCTGGT<br>AGAGCCAGATGAACTGGTCGAAACCGGCGAGCTGCAACCTGACCATATTG<br>TCACCCCTGGTGCCGTTATCGACCACATCATCGTTTCACAGGAGAGCAAA<br>TA |
| Pb2970<br>(SEQ ID NO:26) | GGATTATTAAGTGGCTGTGCCAGCCATAATGAAAATGCCAGTTTACTGGC<br>GAAAAAACAGGCGCAAAATATCAGCCAAAACCTGCCGATTAAATCTGCGG<br>GATATACCTTAGTGCTGGCGCAAAGTAGCGGCACAACGGTAAAAATGACC<br>ATTATCAGCGAAGCGGGTACACAAACCACGCAGACGCCTGACGCCTTTTT<br>AACCAGCTATCAACGACAAATGTGCGCTGACCCGACGGTGAAATTAATGA<br>TCACTGAGGGAATTAATTACAGCATAACGATTAATGATACACGTACAGGTA<br>ACCAGTATCAGCGGAAACTGGATCGTACCACCTGTGGAATAGTCAAAGCA<br>TAACGTCGGGTAGATATAAATTGGCGCGGGTTGTTTTTCGTGACGCACGA<br>ATTTATCTCATTCAATGGCTGACAAAAATTCGTCACACTCTTAACCAGAGAC<br>AATCTCTTAATACAGACAAAGAGCATCTGCGAAAAATTGCACGCGGG |
| PecpD<br>(SEQ ID NO:27) | CGGGCTGGAGGACGACGGTCAGATCAGCGCCAAAATCAACGGGGGGATT<br>TTCCCGCTTAACGGCAAGCGTAACTATCTCCCGCTCTCTCCCTATGGAAG<br>ATATGAGGTGGAGTTACAGAACAGCAAAAACTCACTCGACAGTTACGATAT<br>CGTCAGCGGCCGCAAAAGTCGTCTGACTCTCTATCCAGGCAATGTCGCTG<br>TCATTGAGCCAGAGGTGAAGCAGATGGTTACCGTCTCCGGTCGTATCCGT<br>GCGGAAGACGGCACACTGCTGGCTAACGCACGGATTAACAACCATATCG<br>GCCGAACCCGAACCGATGAAAACGGCGAGTTTGTCATGGACGTGGATAA<br>GAAATACCCCACTATCGATTTTCGCTACAGTGGCAATAAAACCTGCGAAGT<br>GGCTCTGGAACTCAACCAGGCGCGCGGTGCCGTCTGGGTCGGTGATGTG |

TABLE 3-continued

Sequence of Promoter and RBS variants. Pstress promoters were PCR amplified from the *E. coli* K-12 MG1655 genome.

| Name | Sequence |
|---|---|
| | GTCTGCAGCGGCCTCTCATCGTGGGGGGGGTGACGCAGACAGGAGAAG AGA |
| PfecA (SEQ ID NO:28) | GGGACAGAATTTACCGTCCGCCAGCAGGATAATTTCACGCAGCTTGACGT GCAGCAGCACGCTGTGGAAGTGCTTCTCGCCAGTGCCCCCGCGCAAAAA CGCATCGTGAACGCTGGTGAAAGCCTGCAGTTCAGCGCCTCTGAGTTTGG CGCAGTGAAACCGCTGGATGACGAGAGTACAAGCTGGACGAAGGACATC CTGAGCTTCAGCGATAAACCGCTGGGTGAGGTGATAGCCACGCTAACCC GTTACCGCAACGGCGTGCTGCGCTGCGATCCCGCCGTTGCCGGGCTGCG CCTGAGCGGGACGTTCCCGCTGAAAAATACCGATGCGATCCTGAACGTTA TCGCGCAAACGCTTCCCGTTAAAATTCAGTCTATTACGCGGTACTGGATAA ACATTTCACCACTGTAAGGAAAATAATTCTTATTTCGATTGTCCTTTTTACC CTTCTCGTTCGACTCATAGCTGAACACAACAAAAATGATGATGGGGAAGGT |

TABLE 4

Strains used in this study. Strains containing genomic insertions were created using the clonetegration platform to integrate the inserts using the HK022 plasmid into the attB site of the *E. coli* genome5. Successful integrations were identified by antibiotic selection and colony PCR according to the published protocol of St. Pierre et al. (2013).

| Strain | Strain Information | Genomic Insertion |
|---|---|---|
| E. coli Tax1 | *E. coli* containing genome integrated pathway enzymes for taxadiene biosynthesis (gift from Manus Bio) | N/A |
| *E. coli* Tax1-QS | Derived from *E. coli* Tax1 | attB::Esal-LuxR(apFAB346-apFAB382-Esal-LuxR-dblTerm - KmR) |

TABLE 5

Basal R-media recipe, per liter. Adapted from Biggs et al. 2016.

| Component | Final media concentration (g/l) |
|---|---|
| $KH_2PO_4$ | 13.3 |
| $(NH_4)_2HPO_4$ | 4 |
| Citric Acid Monohydrate | 1.7 |
| Yeast Extract | 5 |
| HEPES | 23.83 |

TABLE 6

1000× Trace Element (TE) solution, per liter. Adapted from Biggs et al. 2016.

| Component | Final media concentration (mg/l) |
|---|---|
| EDTA | 8.4 |
| $H_3BO_3$ | 3.0 |
| $Zn(CH_3COO)_2$ | 8.0 |
| $CoCl_2 \cdot 6H_2O$ | 4.6 |
| $CuCl2 \cdot 2H_2O$ | 1.9 |
| $MnCl_2 \cdot 4H_2O$ | 24.0 |
| $Na_2MoO_4 \cdot 2H_2O$ | 2.9 |

TABLE 7

Complete R-media compositions utilized for hungate tube fermentations. Adapted from Biggs et al. 2016.

| Component | Amount (mL) |
|---|---|
| Basal R-media | 35 |
| 32% v/v Glycerol | 1.3 |
| 1M $MgSO_4$ | 0.171 |
| 0.1M Ferric Citrate | 0.0858 |
| 1000× TE Solution | 0.035 |
| 1000× Antibiotic | 0.035 |
| 1M Thiamine HCl | 0.00047 |

SUPPLEMENTAL REFERENCES

1. Mutalik, V. K. et al. Precise and reliable gene expression via standard transcription and translation initiation elements. Nat. Methods (2013). doi: 10.1038/nmeth.2404.

2. Meier, I., Wray, L. V & Hillen, W. Differential regulation of the Tn10-encoded tetracycline resistance genes tetA and tetR by the tandem tet operators 01 and 02. EMBO J. (1988). doi: 10.1002/j.1460-2075.1988.tb02846.x.

3. Lutz, R. & Bujard, H. Independent and tight regulation of transcriptional units in *Escherichia coli* via the LacR/O, the TetR/O and AraC/11-12 regulatory elements. Nucleic Acids Res. (1997).doi: 10.1093/nar/25.6.1203.

4. Engebrecht, J. & Silverman, M. Identification of genes and gene products necessary for bacterial bioluminescence. Proc. Natl. Acad. Sci. U.S.A (1984). doi: 10.1073/pnas.81.13.4154.

5. St-Pierre, F. et al. One-step cloning and chromosomal integration of DNA. ACS Synth. Biol. (2013). doi: 10.1021/sb400021j.

6. Biggs, B. W. et al. Overcoming heterologous protein interdependency to optimize P450-mediated Taxol precursor synthesis in *Escherichia coli*. Proc. Natl. Acad. Sci. (2016). doi: 10.1073/pnas.1515826113.

Figure 11:
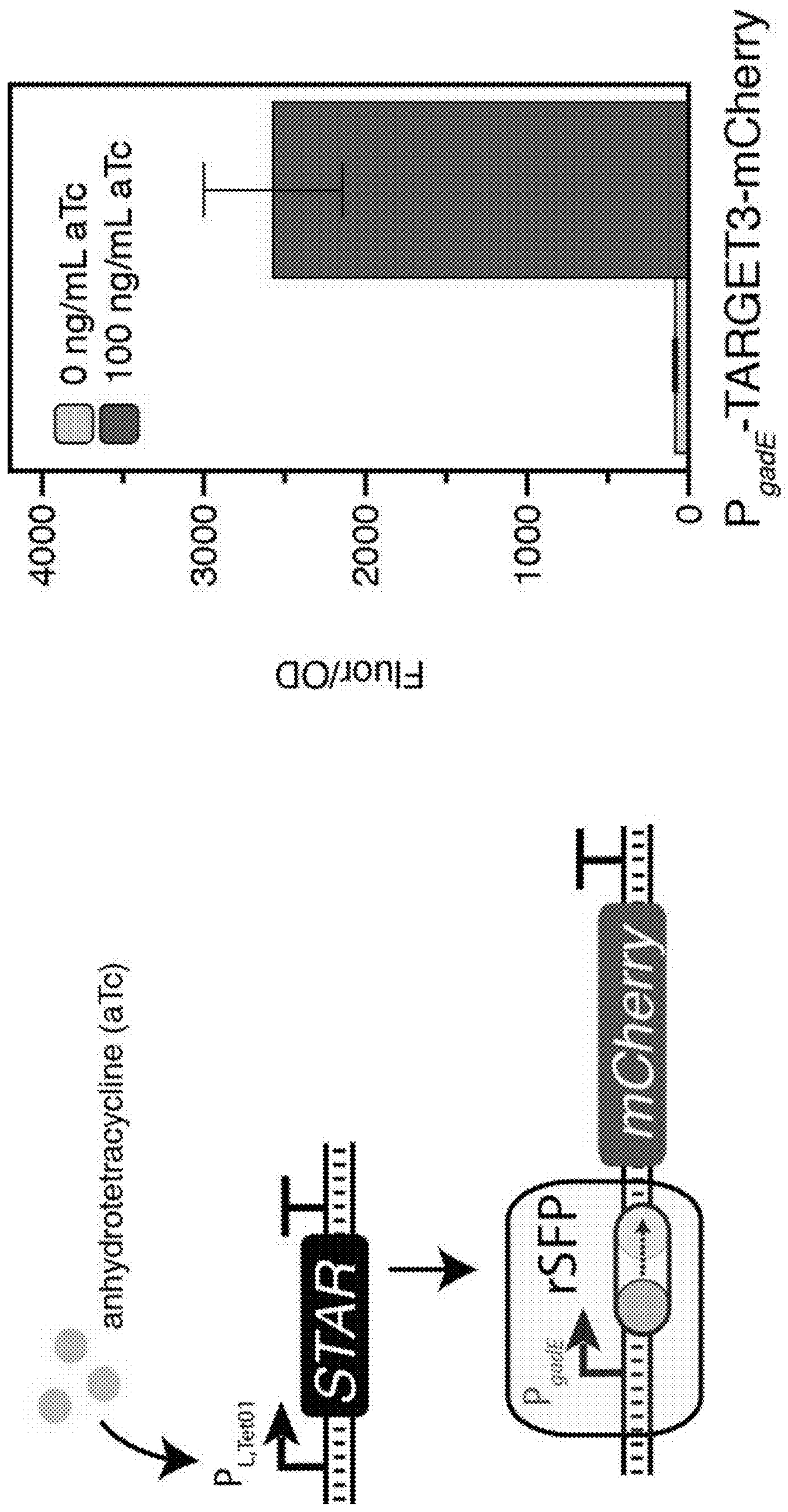
FIG. 11 shows activation of the PgadE stress-responsive promoter with the riboregulated switchable feedback promoter system. Characterization of the PgadE rSFP variant containing unique envelope stress-response promoters. $P_{L,TetO1}$ inducible STAR expression is used to activate the rSFPs containing the PgadE promoter upstream of a STAR Target sequence, a ribosome binding site, and a red fluorescent protein (mCherry) coding sequence. Fluorescence characterization was performed on *E. coli* transformed with plasmids encoding each rSFP controlling mCherry expression in the absence and presence of 100 ng/ml aTc.

Example 3-Preparation of a PadE Stress-Responsive Promoter System Including a Riboregulated Switchable Feedback Element (PgadE rSFP) and its Use to Improve an Amorphadiene Production Pathway We prepared an inducible system comprising a stress-responsive promoter for gadE ($P_{gadE}$) operatively linked to a riboregulated switch. (See FIG. 11). Addition of aTc enables ~31-fold activation of mCherry expression when $P_{gadE}$ is gated by a target sequence that is activated by a STAR RNA. Fluorescence characterization experiments for the $P_{gadE}$ rSFP were performed in *E. coli* strain DH1. Experiments were performed for 3 biological replicates. Plasmid combinations were transformed into chemically competent *E. coli* cells and plated on LB+Agar (Difco) plates containing combinations of 100 g/mL carbenicillin, 34 μg/mL chloramphenicol and 50 μg/mL spectinomycin, and incubated approximately 17 hours (h) overnight at 37° C. Plates were taken out of the incubator and left at room temperature for approximately 7 h. Three colonies were used to inoculate three cultures of 300 μL of LB containing antibiotics at the concentrations described above in a 2 mL 96-well block (Costar), and grown for approximately 17 h overnight at 37° C. at 1,000 rpm in a VorTemp 56 (Labnet) bench top shaker. 4 μL of each overnight culture were added to 196 μL of MOPS EZ Rich Defined media containing selective antibiotics and grown for 6 h at 37C. Periodic samples of 10-200 μL of culture were collected for characterization by bulk fluorescence measurements. For all bulk fluorescence measurements: 10-200 μL of sampled culture were transferred to a 96-well plate (Costar) containing 0-190 μL of phosphate buffered saline (PBS). Fluorescence (FL) and optical density (OD) at 600 nm were then measured using a Synergy H1 plate reader (Biotek). The following settings were used: mCherry fluorescence (560 nm excitation, 630 nm emission). On each 96-well block there were two sets of controls; a media blank and *E. coli* Tax1 cells transformed with combination of control plasmids JBL002 and JBL644 (blank cells) and thus not expressing mCherry. The block contained three replicates of each control. OD and FL values for each colony were first corrected by subtracting the corresponding mean values of the media blank. The ratio of FL to OD (FL/OD) was then calculated for each well (grown from a single colony) and the mean FL/OD of blank cells was subtracted from each colony's FL/OD value. Three biological replicates were collected. Means of FL/OD were calculated over replicates and error bars represent standard deviations (s.d).

Figure 12A:
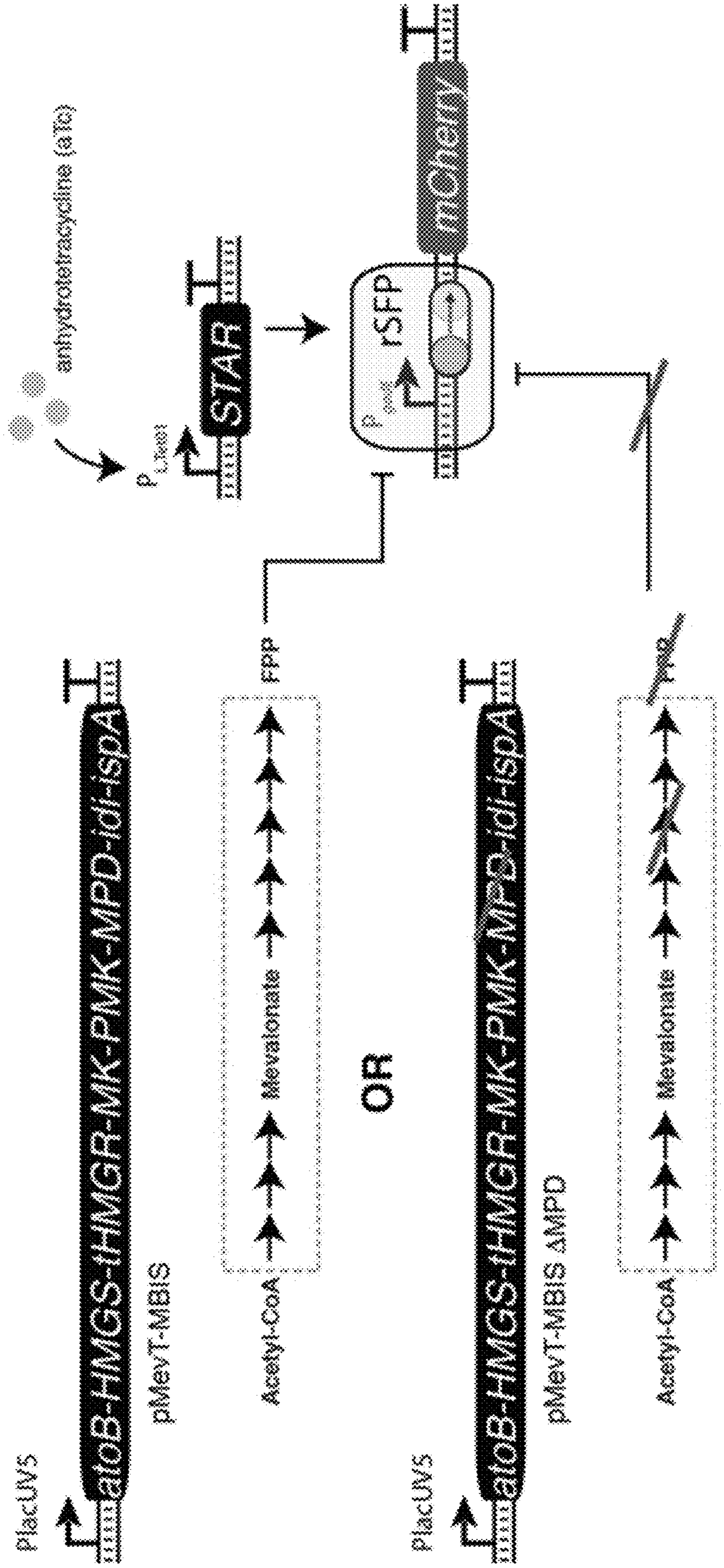
FIGS. 12A-12B show the PgadE stress-responsive promoter is responsive to farnesyl pyrophosphate (FPP) metabolite stress when regulated by a riboregulated switchable feedback promoter system. Experiments were performed as in FIG. 11 except *E. coli* cells contained an additional plasmid expressing the MevT-MBIS pathway or the MevT-MBIS ΔMPD mutant pathway (FIG. 12A). IPTG was added to the experiment for expression of MevT-MBIS genes that produce the toxic FPP molecule. Results show that PgadE rSFP expression was reduced in the presence of the MevT-MBIS pathway in comparison with the MevT-MBIS ΔMPD mutant pathway (FIG. 12B). When the PgadE promoter was replaced with a synthetic constitutive promoter there was no change in mCherry expression between the two pathway variants.
Figure 12B:
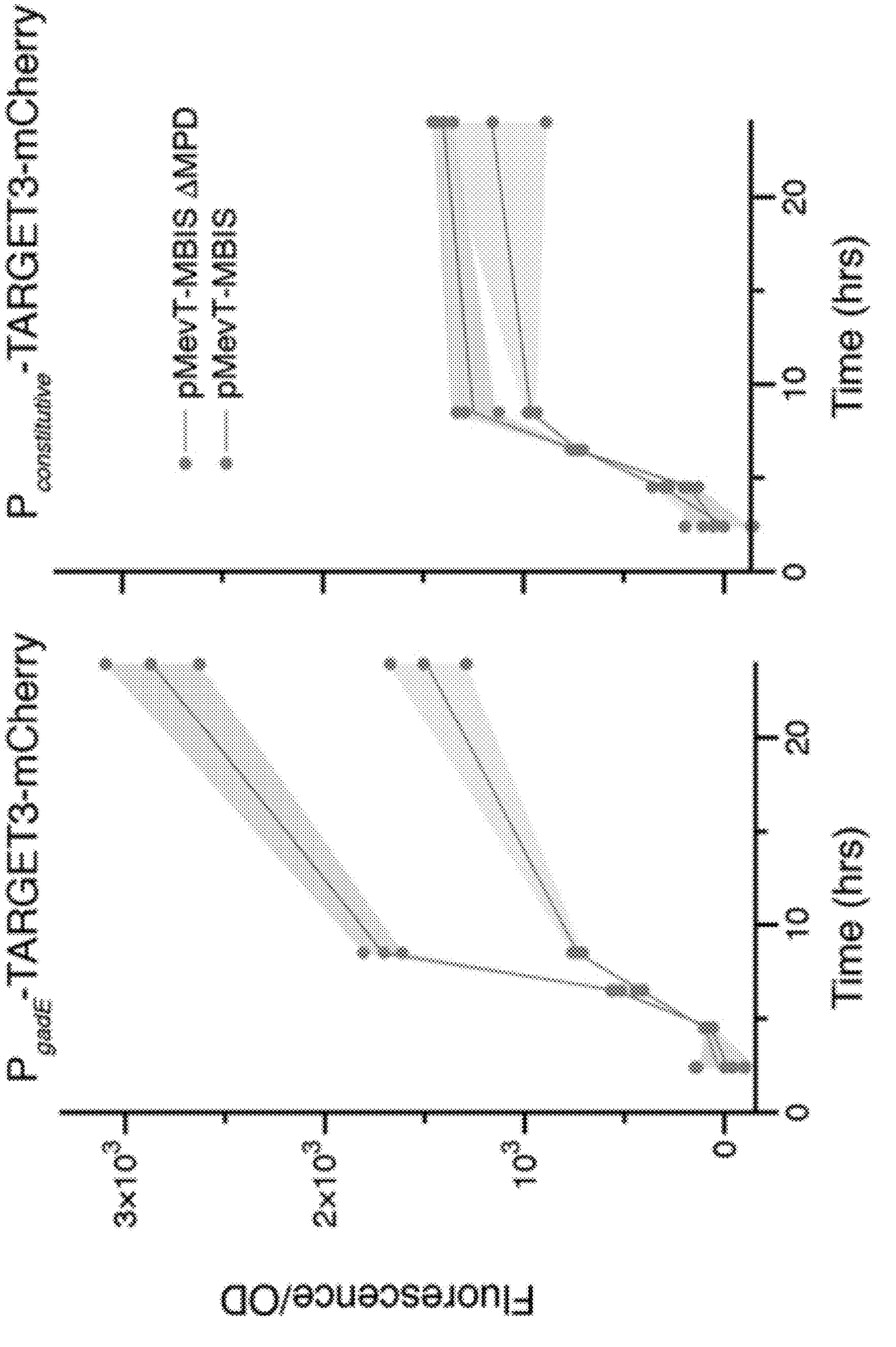
Figure 13A:
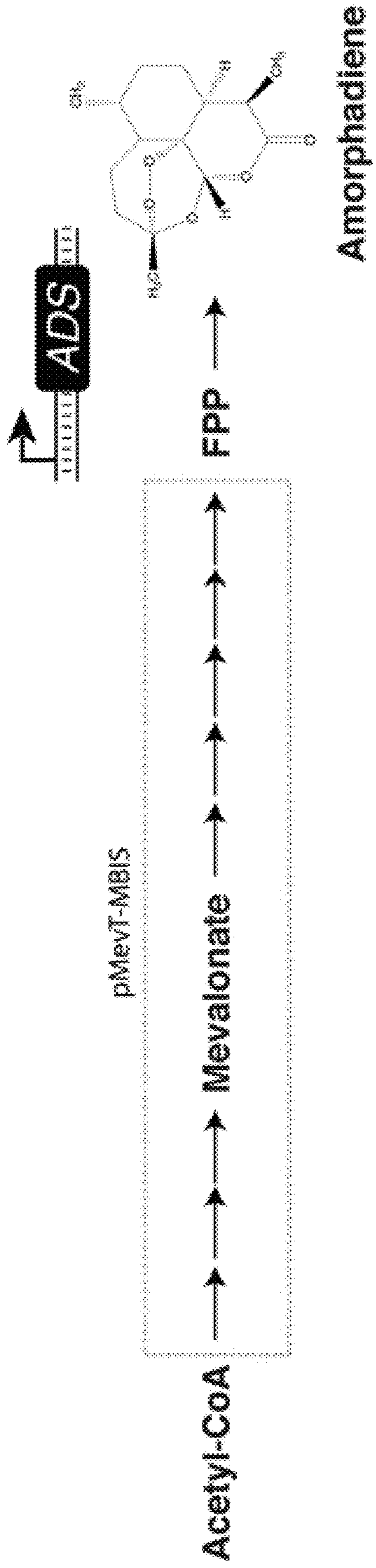
FIGS. 13A-13D show improvement in genetic stability of a PgadE stress-responsive promoter via inclusion of a riboregulated switchable feedback element (PgadE-rSFP). Fermentations were conducted with *E. coli* cells containing the pMevT-MBIS (FIG. 13A) under control of a PlacUV5 promoter, an unregulated PgadE promoter, and containing a PgadE-rSFP element (FIG. 13B). Additional plasmids included the $P_{L,TetO1}$ inducible STAR plasmid and a plasmid expressing the amorphadiene synthase (ADS) gene. For fermentations, overnight cultures of each strain were inoculated into MOPS EZ Rich Defined medium at 37C for 72 hrs in the presence or absence of 100 ng/ml aTc before analysis by GC-MS. Additional fermentations were run after subculturing the overnight cultures in LB medium at 37C 6 times over a period of 4 days before inoculating the fermentations (FIG. 13D). Fermentation experiments revealed significantly improved titers for the rSFP variant compared with the PlacUV5 variant and significantly improved genetic stability compared with the unregulated PgadE variant (FIG. 13C).
Figure 13B:
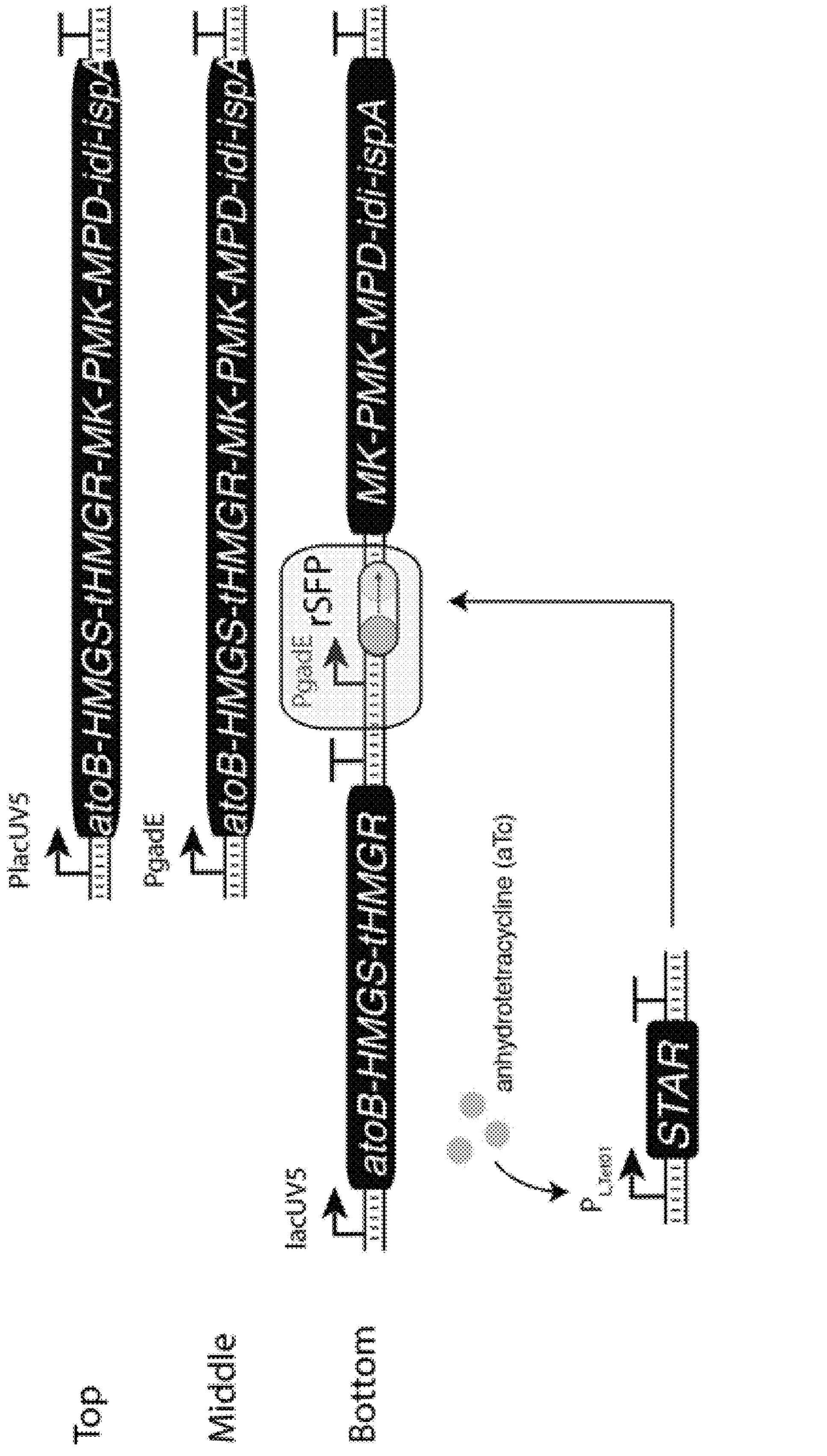
Figure 13C:
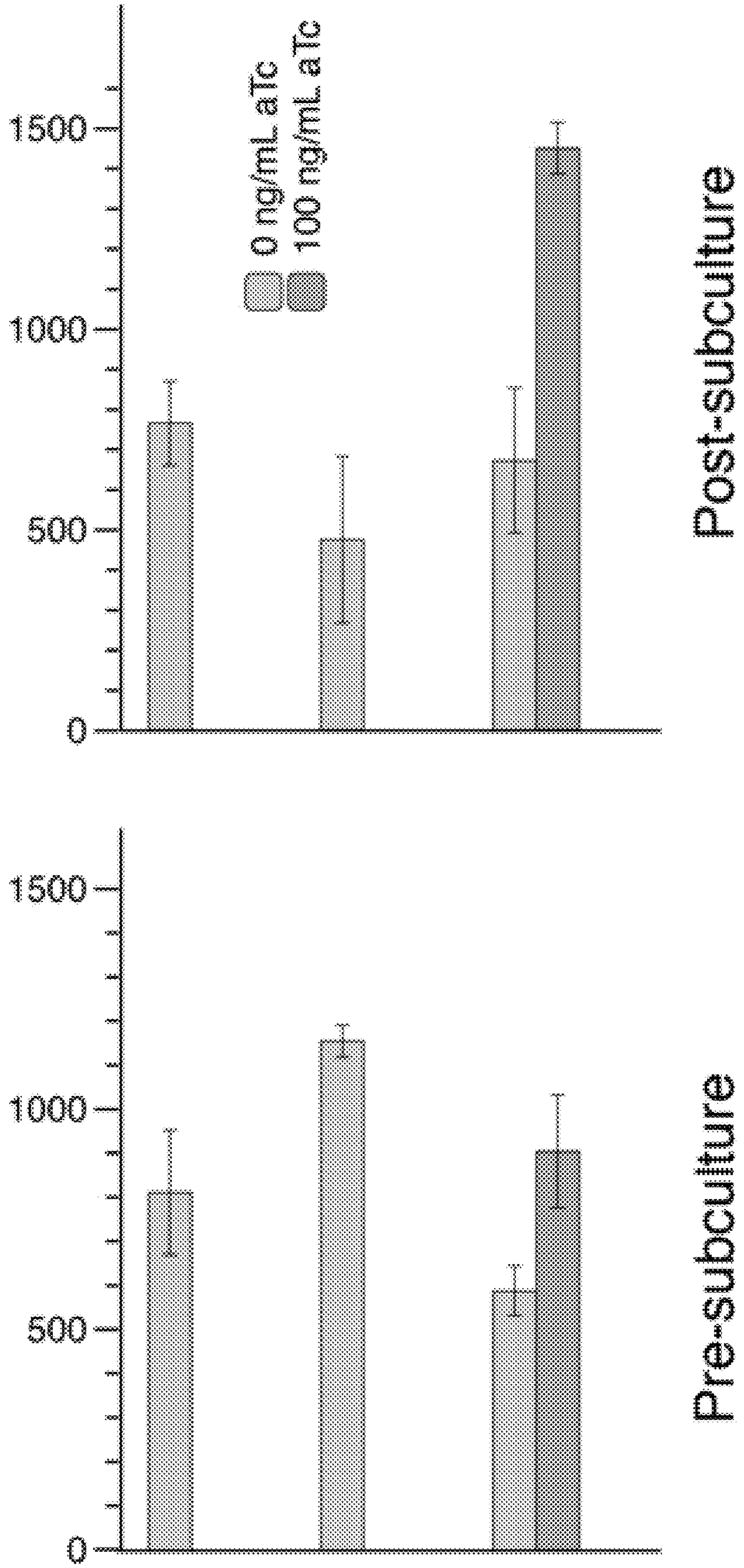
Figure 13D:
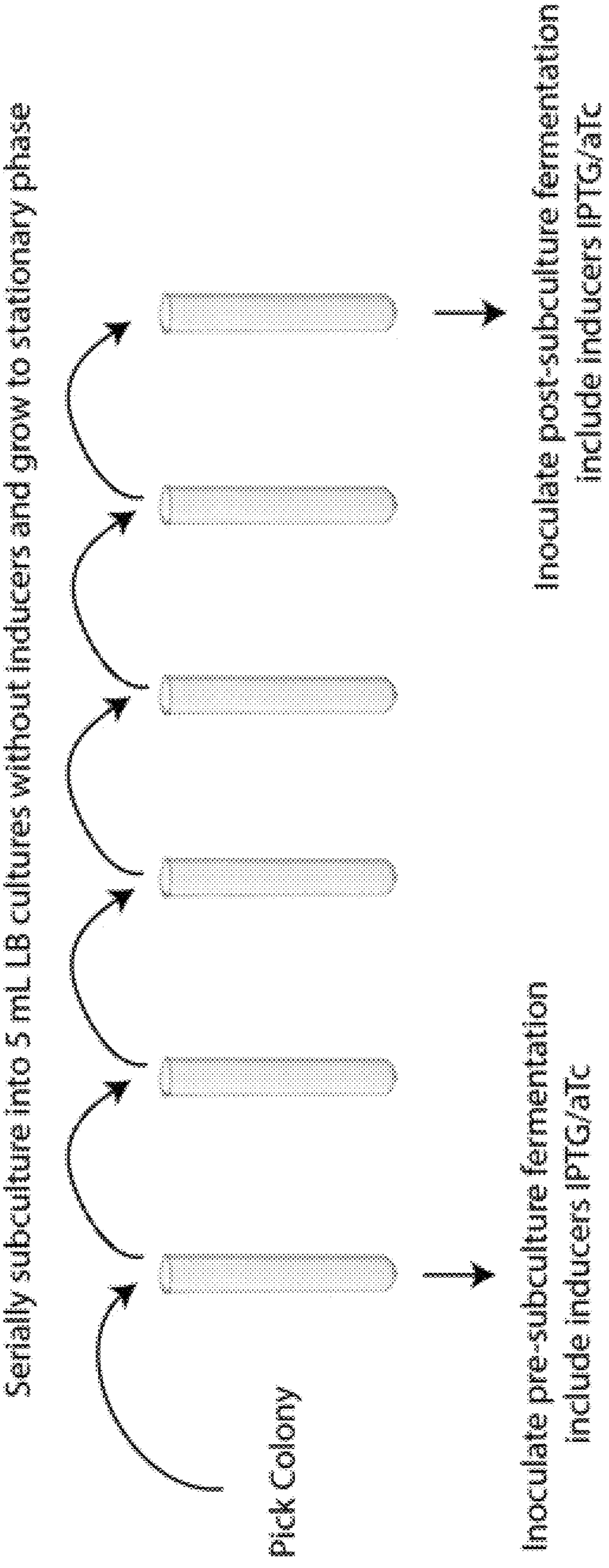

We next tested whether the $P_{gadE}$ stress-responsive promoter is responsive to farnesyl pyrophosphate (FPP) metabolite stress when regulated by a riboregulated switchable feedback promoter system. (See FIG. 2*). The pMevT-MBIS plasmid produces FPP when expressed in cells while the pMevT-MBIS ΔMPD plasmid does not produce FPP when produced in cells. The $P_{gadE}$ rSFP system produces less mCherry expression when co-expressed with pMevT-MBIS in comparison with pMevT-MBIS ΔMPD. (See FIG. 12). In contrast, when the $P_{gadE}$ stress-responsive promoter is replaced with a constitutive promoter ($P_{constitutive}$) there is only a negligible change in mCherry expression between two strains. (See FIG. 12). Fluorescence characterization experiments were performed as in paragraph [00128] except 20 μL of each overnight culture were added to 980 μL of MOPS EZ Rich Defined media containing selective antibiotics and grown for 24 h at 37C. Periodic samples of 10-200 μL of culture were collected for characterization by bulk fluorescence measurements.

Regulation of FPP production in an amorphadiene pathway improves production titers and genetic stability. Previous studies (Dahl et al., 2019, Nature Biotechnology) have shown that the $P_{gadE}$ stress-responsive promoter improves amorphadiene production when controlling the pMevT-MBIS plasmid for FPP production. (See FIG. 13, Top vs Middle). However, this requires expression to be "always on" which can lead to genetic instability by driving selection for mutations that decrease pathway expression. This is a major cause for failure for genetically engineered microbes in industry. Therefore, we tested whether a riboregulated switchable feedback promoter (rSFP) system can be used to prevent "always on" expression and allow induction only when it is required in a fermentation, reducing selection for escape mutants that reduce pathway expression. As illustrated in FIG. 13, the amorphadiene pathway controlled with an unregulated $P_{gadE}$ promoter is not genetically stable after 6 rounds of serial subculturing. (See FIG. 13, Middle). However, when we configured the amorphadiene pathway to include a $P_{gadE}$-rSFP expression cassette, fermentation titers remain unchanged after serial subculturing and led to significant improvements over both the unregulated $P_{gadE}$ promoter system and a pathway controlled by a conventional inducible ($P_{lacUV5}$) promoter. (See FIG. 13, Bottom). Small-scale fermentation assays were used to quantify amorphadiene production in *E. coli* DH1. Experiments were performed with 3 biological replicates. For each experiment, plasmid combinations were transformed into chemically competent *E. coli* cells and plated on LB+Agar (Difco) plates containing appropriate antibiotics (100 μg/mL carbenicillin, 34 μg/mL chloramphenicol and/or 50 μg/mL spectinomycin). Plates were incubated approximately 17 hrs overnight at 30° C. Individual colonies were inoculated into culture tubes containing LB and appropriate antibiotics and incubated at 37° C. for roughly 16 hrs overnight to achieve an approximate OD600 of 3. For 2 mL batch fermentations, 125 μL of overnight cells were added to 5 mL of MOPS EZ Rich medium and appropriate antibiotics. 0.5 mM IPTG and 100 ng/mL aTc was added, as indicated, to induce $P_{lacUV5}$, $P_{Trc}$ and $P_{LTetO1}$-STAR expression. Tubes were incubated at 37° C. and 250 rpm for 72 hrs. After the fermentations were completed, the culture was centrifuged to collect the dodecane overlay. This overlay was subsequently diluted into hexane for analytical procedures. Dodecane samples collected from batch fermentations were diluted at a ratio of 1:200 in n-hexane containing 5 mg/L B-caryophyllene. The 5 mg/L caryophyllene was utilized as a standard to calculate titer of amorphadiene. GC-MS analysis was performed with an Agilent 7890 GC and Agilent HP-5 ms-UI column (Ultra Inert, 30 m, 0.25 mm, 025 μm, 7 in cage). Helium was utilized as a carrier gas at a flow rate of 1 mL/min and the sample injection volume was 1 μL. The splitless method begins at 50° C. hold for 1 minute followed by a 10° C./min ramp to 200° C. Mass spectroscopy data was collected for 16 minutes with an 11-minute solvent delay with an Agilent 7000 QQQ in scan mode using Electron Ionization (EI). m/z values ranging from 40-500 were scanned with a scan time of 528 ms. MassHunter Workstation Qualitative Analysis software (vB.06.00) was utilized to integrate peaks on the chromatograms and determine their respective mass spectrums. The ratio of peak area of amorphadiene (m/z 204) to the standard B-caryophyllene (m/z 204) was used to calculate titer. Means of titers were calculated over replicates and error bars represent s.d.

Example 4. Dynamic Control of Gene Expression with Riboregulated Switchable Feedback Promoters Abstract. One major challenge in synthetic biology is the deleterious impacts of cellular stress caused by expression of heterologous pathways, sensors and circuits. Feedback control and dynamic regulation are broadly proposed strategies to mitigate this cellular stress by optimizing gene expression levels temporally and in response to biological cues. While a variety of approaches for feedback implementation exist, they are often complex and cannot be easily manipulated. Here, we report a strategy that uses RNA transcriptional regulators to integrate additional layers of control over the output of natural and engineered feedback responsive circuits. Called riboregulated switchable feedback promoters (rSFPs), these gene expression cassettes can be modularly activated using multiple mechanisms, from manual induction to autonomous quorum sensing, allowing control over the timing, magnitude and autonomy of expression. We develop rSFPs in *Escherichia coli* to regulate multiple feedback networks and apply them to control the output of two metabolic pathways. We envision that rSFPs will become a valuable tool for flexible and dynamic control of gene expression in metabolic engineering, biotherapeutic production, and many other applications.

Introduction. The fine tuning of gene expression to improve system performance is a long standing goal of synthetic biology for applications ranging from chemical synthesis via metabolic engineering[1,2] to advanced therapeutics[3] and diagnostics[4]. A nearly universal challenge within synthetic biology is the burden and toxicity engineered genetic systems place on host cells due to high levels of heterologous gene expression and possible accumulation of toxic biochemical intermediates[5,6]. This burden creates a selective pressure for mutations that can break the introduced genetic system and lead to loss of productivity, effectiveness, or entire function[7], creating a continuous need for strategies that alleviate or avoid these pitfalls. This is a nontrivial challenge, because each application presents unique sources of stresses that can change over time, making it difficult to find generalizable solutions.

Current approaches to solve expression-related challenges range from static tuning of gene expression to utilizing dynamic gene expression control systems[8-10]. For static control, promoter strength, ribosomal binding site (RBS) strength, plasmid copy number, or the location or number of genetic integrations are varied and screened to find an optimal solution[11-16]. Dynamic control systems can be implemented in multiple ways. For example, endogenous feedback networks can be harnessed by utilizing regulatory elements, such as stress-response promoters, that integrate signals from natural genetic networks to modulate mRNA synthesis in response to cellular cues like membrane, oxidative, pH extremes and nutrient deprivation stresses[17]. These have been incorporated to regulate heterologous genetic systems, leading to notable improvements to productivity and yield for protein expression[18] and engineered metabolic pathways for the production of the artemisinin precursor amorphadiene[19] and n-butanol[20] as examples. Alternatively, synthetic circuits can be built using ligand-inducible transcription factors[21-23] or ribozymes[24] that sense and respond to metabolic pathway intermediates so that expression can adapt dynamically to maintain optimal enzyme concentration over time[9,10,25,26]. Synthetic feedback circuits have also been constructed to enable additional useful features, such as engineered stabilized promoters that maintain constant gene expression regardless of changes or fluctuation in DNA copy number[27].

While each of the above strategies has moved the field of synthetic biology forward, there are still significant limitations. For example, hard-coded static solutions cannot adapt to stresses that vary in time, and may no longer be optimal upon inclusion of additional genetic components or within a new environment[8]. Natural dynamic feedback-responsive circuits such as stress-response promoters could resolve this but have not been widely adopted, as their unknown architecture and interconnectedness to native regulatory systems makes it difficult to fine-tune their behavior for specific applications. Synthetic feedback circuits that sense pathway intermediates are useful in specific contexts, but often do not respond to general aspects of the cellular environment such as growth phase, fermentation conditions and cellular stresses that are important sources of variation that affect system performance across many applications. A unifying limitation for both natural and synthetic feedback systems is the difficulty in integrating additional external points of control that can tune either the timing or overall magnitude of their transcriptional outputs-two key parameters for optimizing system performance[28].

To address this limitation, we created a new regulatory motif called a switchable feedback promoter (SFP) that combines the properties of natural and synthetic feedback-responsive promoter systems, with integrated regulators that offer additional control of the timing and overall magnitude of transcriptional outputs (FIG. 1A-D). The SFP concept is general, relying on a trans-acting synthetic regulator to gate the transcription of the feedback promoter system. Here, we focus on utilizing small transcription activating RNAs (STARs)[29] to make riboregulated SFPs (rSFPs) in *Escherichia coli*, as their well-defined composition rules enables them to be inserted into a gene expression construct without modification or disruption of the desired promoter sequence. This enables the rSFP output to be controlled with any strategy that can regulate the expression of the trans-acting RNA.

Results.

We report the creation and characterization of STAR-mediated feedback responsive promoters in *E. coli* using both natural stress-responsive promoters as well as engineered stabilized promoters[27]. First, we created a set of 18 stress-responsive rSFPs by interfacing STARs with natural *E. coli* stress-response promoters and placing trans-acting STAR production under control of an inducible promoter. We then characterized select rSFPs for their response to sources of cellular stress, including membrane protein expression and toxic metabolite accumulation. Second, we create stabilized rSFPs and show them to maintain constant gene expression over different plasmid copy numbers while simultaneously introducing inducible control. To demonstrate the applicability of rSFPs, we next apply them to regulate two important metabolic pathways, one for amorphadiene, a precursor to the antimalarial artemsinin, and the other for an oxygenated taxane precursor to the anticancer drug Taxol. Finally, to demonstrate the use of other control points for rSFPs, we engineer quorum sensing rSFPs that offer autonomous pathway expression regulation with titers similar to manual induction but without costly external inducers. Overall, rSFPs represent a novel and general strategy to add additional points of control to feedback-responsive gene regulation systems to enhance their use and optimizations for broad synthetic biology applications. The rSFP methodology works in multiple contexts and should be readily applied to many other engineered bacterial organisms.

rSFPs Enable Inducible Control of Feedback Responsive Promoters in *E. coli*

Figures 14A, 14B, 14C, 14D, 14E:
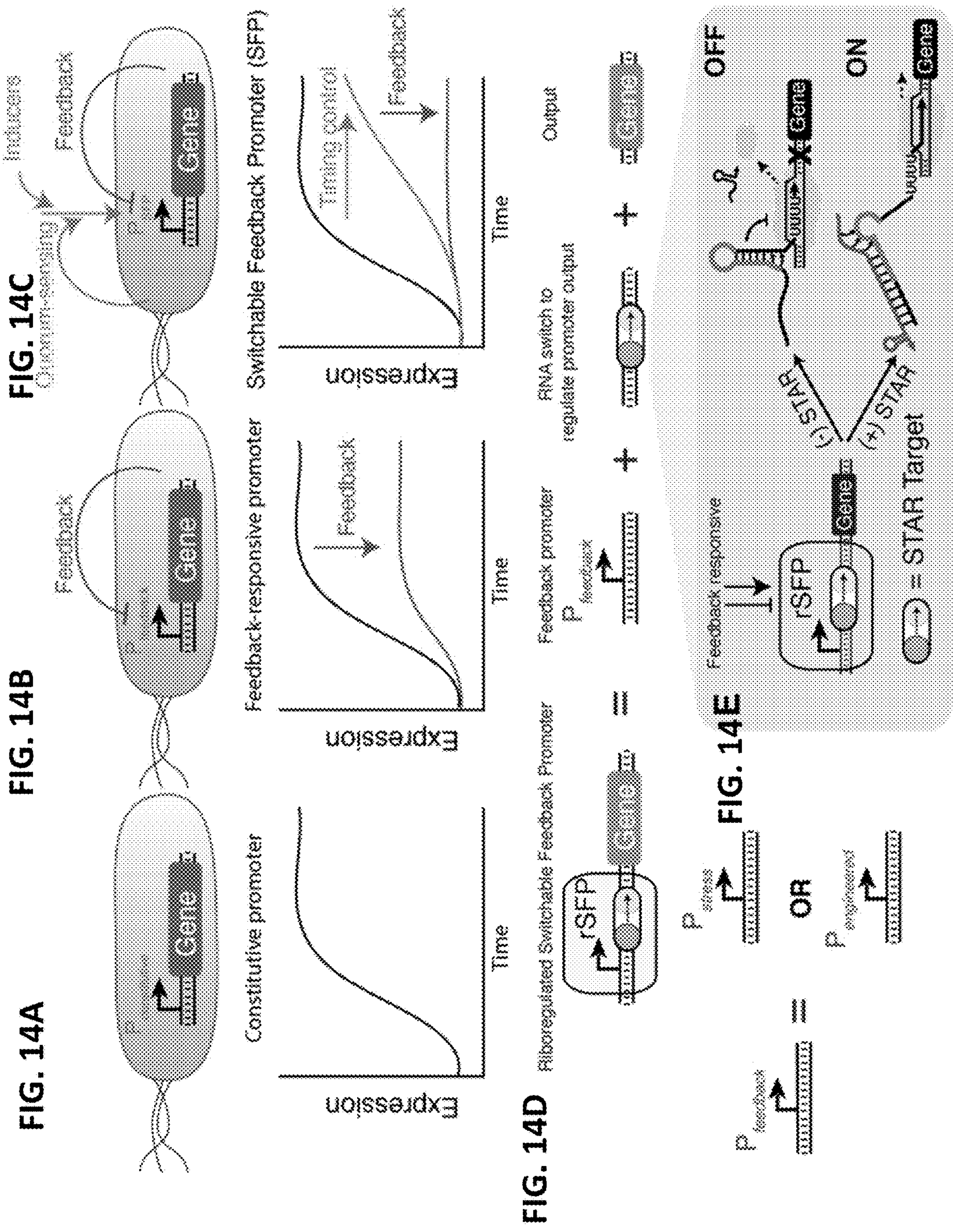
FIGS. 14A-14E show synthetic regulation of feedback responsive promoters enables combined control of gene expression timing and tuning with feedback regulation.

We used STARs to construct rSFPs because they exhibit low leak and high dynamic range comparable to exemplary protein-based regulators and can be computationally designed to not interfere with other RNA elements required for downstream gene expression[30]. STARs activate transcription by disrupting the folding pathway of a terminator hairpin sequence, called a target, that is placed upstream of the gene to be regulated (FIG. 14E). In the absence of a STAR, the target region folds into an intrinsic terminator hairpin which stops transcription before reaching the downstream gene. When present, a STAR RNA can bind to the 5' portion of the terminator hairpin, preventing its formation, and allowing transcription. rSFPs are then created by inserting a target sequence downstream of a candidate feedback-responsive promoter. In this way, the introduction of the STAR/target adds an additional layer of control, gating its transcriptional output through the regulation of STAR RNA expression, which can be controlled using a variety of mechanism.

Figure 15A:
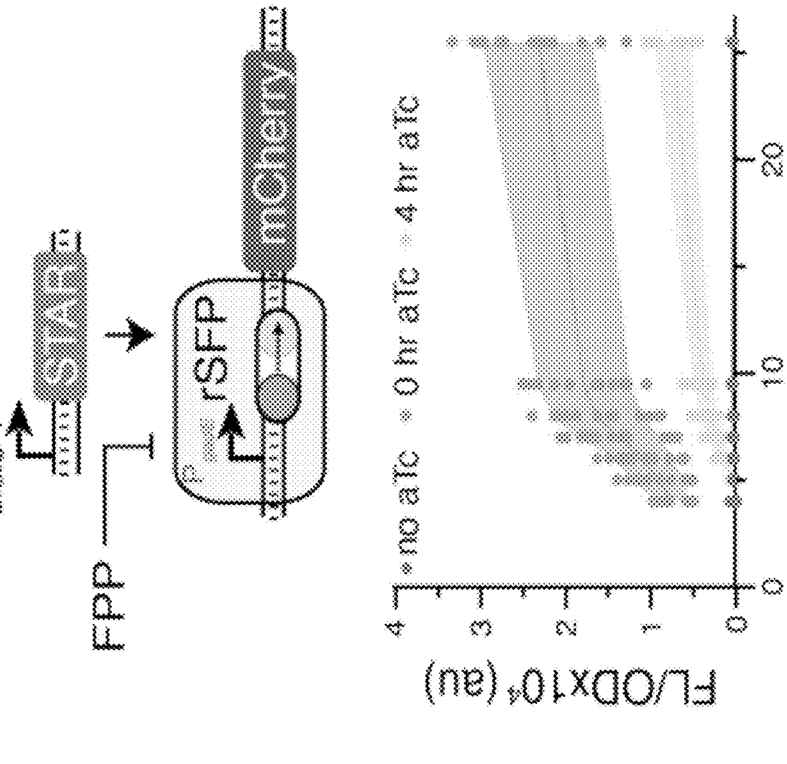
FIGS. 15A-15C show creation of the PgadE rSFP.

We began rSFP development with the previously characterized $P_{gadE}$ acid stress-response promoter that has been shown to improve amorphadiene pathway production by responding to accumulation of the toxic metabolite farnesyl pyrophosphate (FPP)[19]. Our initial rSFP design utilized a previously developed STAR[30] under the well-characterized inducible system TetR/$P_{LTetO\text{-}1}$[31] promoter to control its expression. This STAR was interfaced with the $P_{gadE}$ promoter by cloning a target sequence immediately after the promoter and 5' UTR, and directly before the start codon of the natural gene regulated by the stress-response promoter in *E. coli*. This sequence was followed by an mRNA region containing an RBS and mCherry. We found that induction of $P_{LTetO\text{-}1}$-STAR resulted in activation (~40×) from the P gadE stress-response promoter (FIG. 15A). Additionally, we found that timing control of $P_{gadE}$ expression could be achieved by delaying induction, albeit with lower endpoint expression levels (FIG. 15A). We characterized the transfer curve of the $P_{gadE}$ rSFP by titrating inducer levels and found that it exhibited a monotonically increasing induction profile (FIG. 15B), reflecting the properties of the $P_{LTetO\text{-}1}$ promoter system and providing evidence that other transfer curve profiles might be achieved by selecting different inducible promoter systems for STAR expression.

Figure 24A:
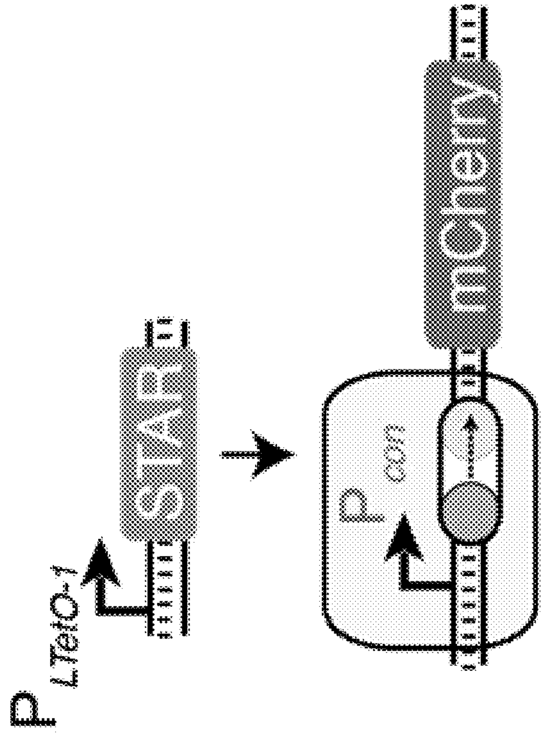
FIGS. 24A-24B show responsiveness of a STAR-regulated constitutive promoter ($P_{con}$) to FPP accumulation.
Figure 24B:
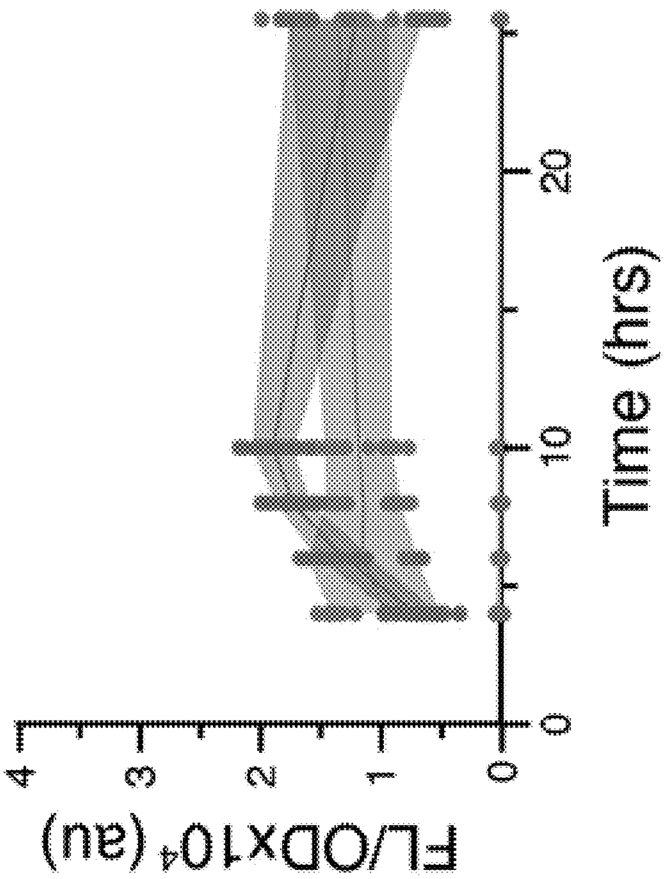

Next, we characterized downregulation of the $P_{gadE}$ rSFP by FPP accumulation. In addition to the $P_{gadE}$ rSFP and $P_{LTetO\text{-}1}$-STAR plasmid, we co-expressed either pMevT-MBIS that results in accumulation of FPP or pMevT-MBIS ΔMPD that is defective in pyrophosphate decarboxylase activity involved in conversion of mevalonate to FPP. We found the $P_{gadE}$ rSFP expression was repressed over time in the presence of pMevT-MBIS in comparison with pMevT-MBIS ΔMPD (FIG. 15C), while similar repression was not observed with a constitutive promoter replacing $P_{gadE}$ (FIG. 24).

Figure 16A:
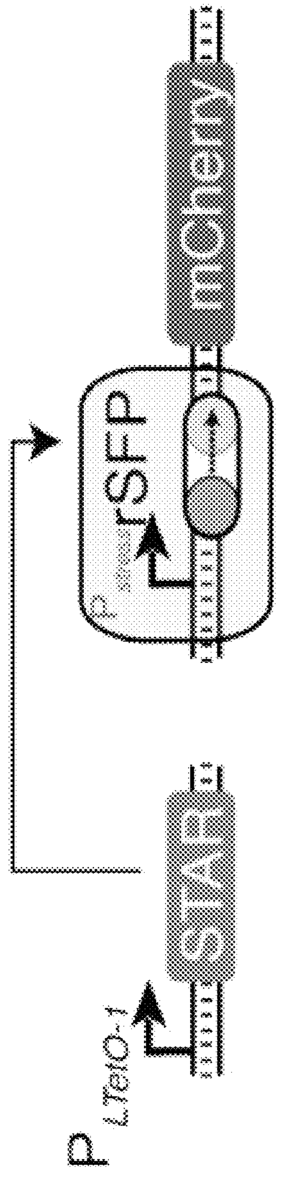
FIG. 16A-16B show creation of an rSFP library with unique envelope stress-responsive promoters.
Figure 16B:
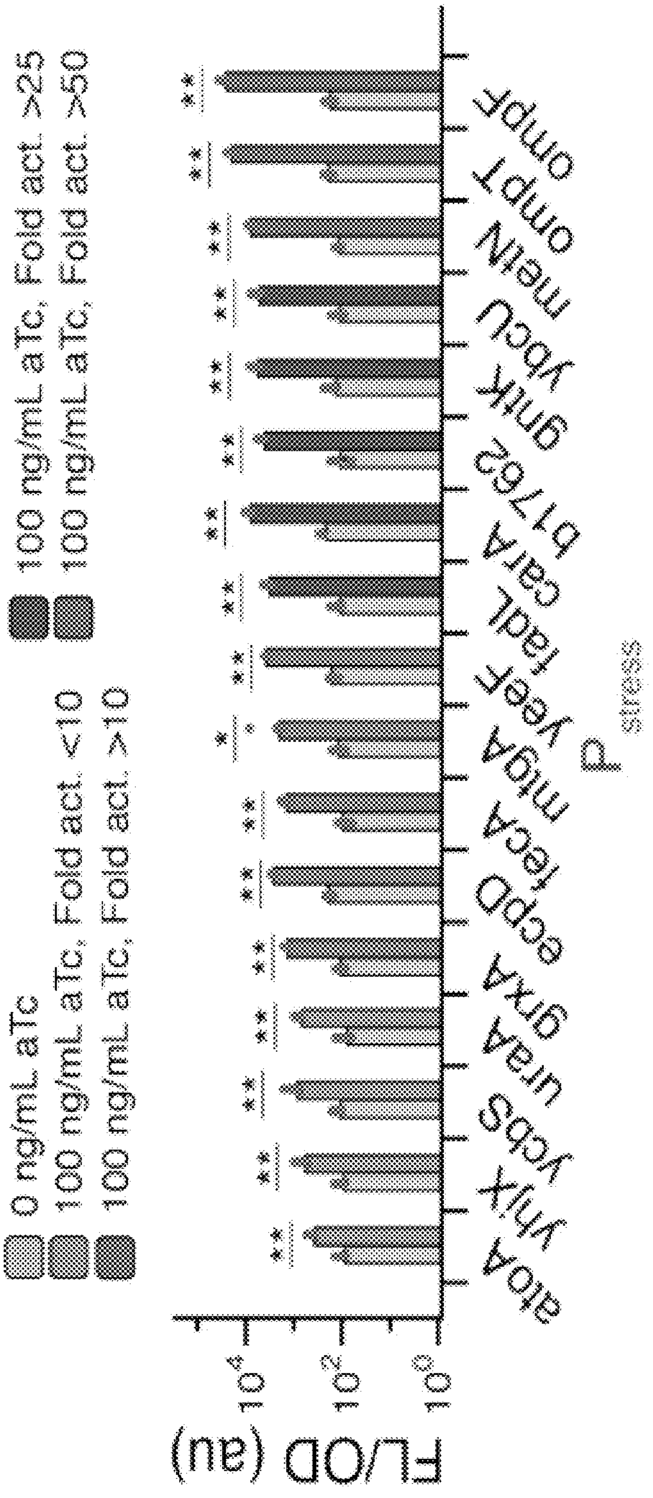
Figure 17A:
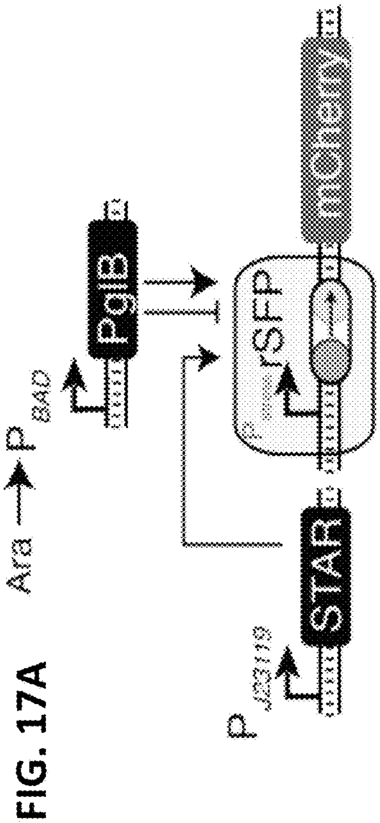
FIGS. 17A-17B show analysis of feedback-responsiveness of selected stress-response promoters to *C. jejuni* Pg1B-induced stress.
Figure 17B:
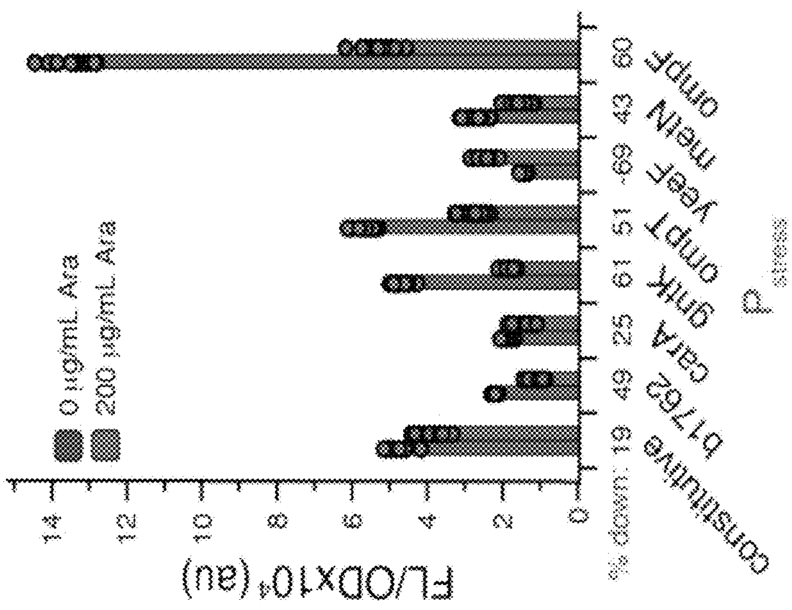
Figure 25:
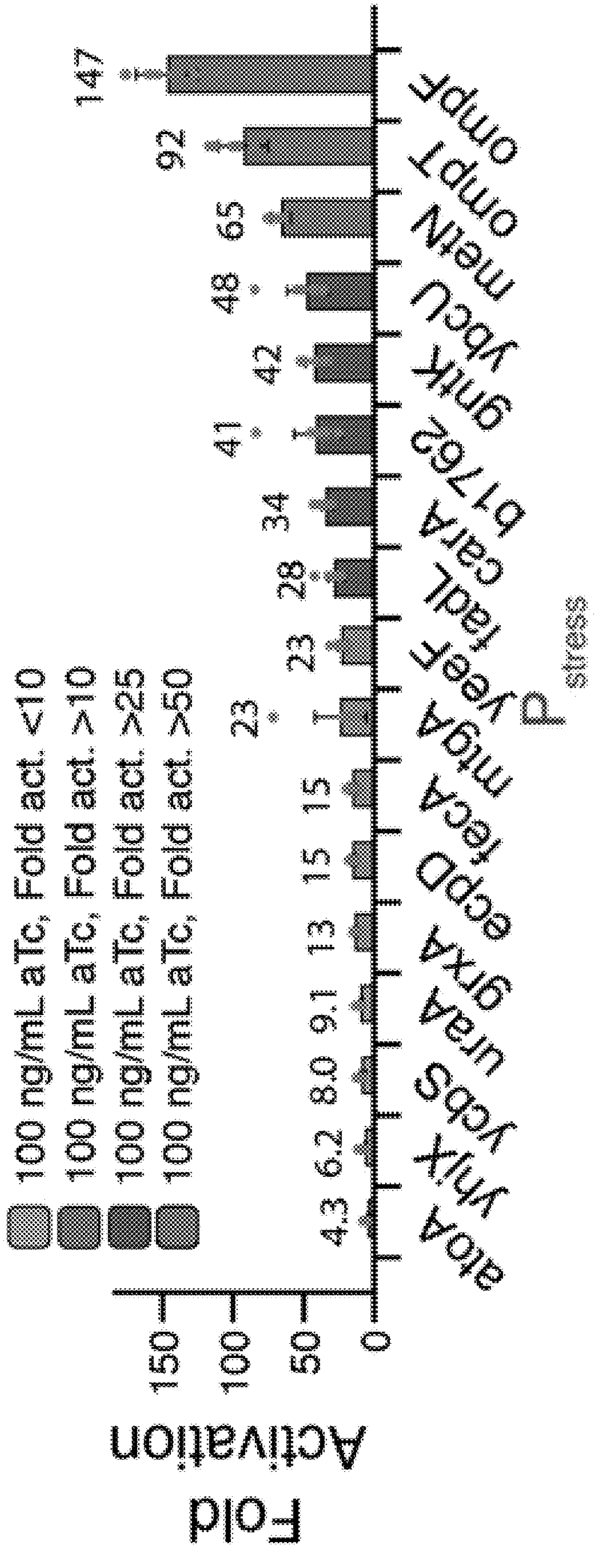
FIG. 25 shows fold activation (ON/OFF) of rSFP variants containing unique envelope stress-response promoters. Fluorescence characterization was performed on *E. coli* Tax1 transformed with plasmids encoding each rSFP controlling mCherry expression and $P_{LTetO\text{-}1}$-STAR in the absence and presence of 100 ng/mL aTc. Individual data points represent fold activation calculated as fluorescence/optical density (FL/OD) for each colony grown with 100 ng/mL aTc divided by FL/OD of the same colony without aTc. Bars represent mean fold activation and error bars represent s.d. of n=9 biological replicates. Mean fold activation for each rSFP variant is indicated above each bar.

We expanded the rSFP designs to include a library of 17 putative membrane stress-responsive promoters[20], chosen as several had been previously identified to regulate a biofuel transporter protein in *E. coli*[20] and could therefore be valuable for dynamic regulation of membrane proteins in metabolic pathways. We found that induction of $P_{LTetO\text{-}1}$-STAR resulted in activation from all members of the stress-response promoter library (FIG. 16A-B), exemplifying the modularity of the rSFP concept. Eight library members were activated by >25× fold upon induction, with a maximum activation of nearly 150× fold (FIG. 25). We characterized a subset of high-performing rSFPs for stress-responsiveness to a model stress from the oligosaccharyltransferase membrane protein Pg1B from *Campylobacter jejuni*[32] and for other features of their expression. The expression of each was affected by Pg1B, with PgntK and $P_{ompF}$ showing the largest repression (FIG. 17A-B). We examined the transfer curves of select rSFPs (FIG. 26A,B) and found that they were monotonically increasing.

Figures 26A, 26B, 26C:
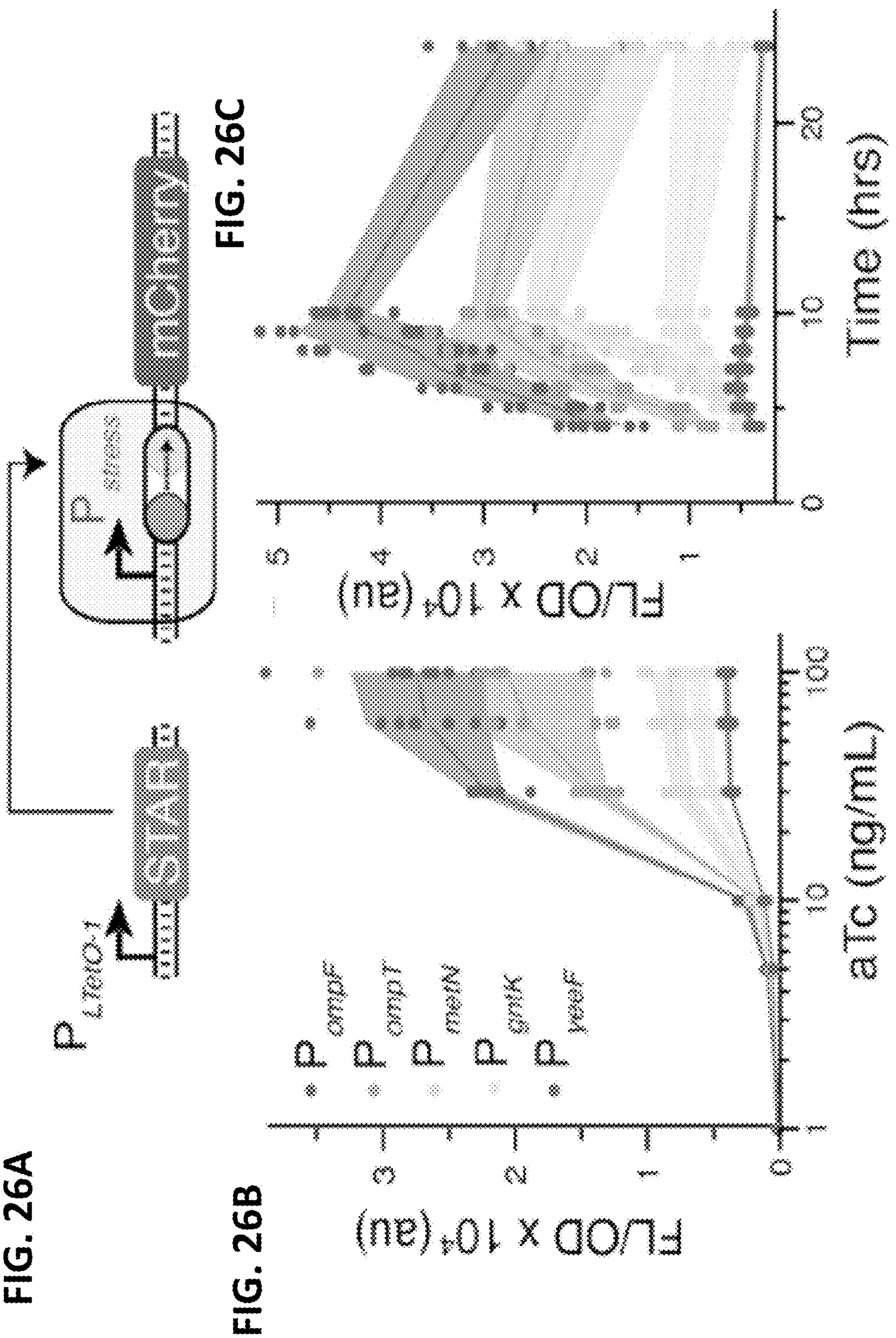
FIGS. 26A-26D show fluorescence characterization of rSFP variants containing unique envelope stress-response promoters from FIG. 3B.
Figure 26D:
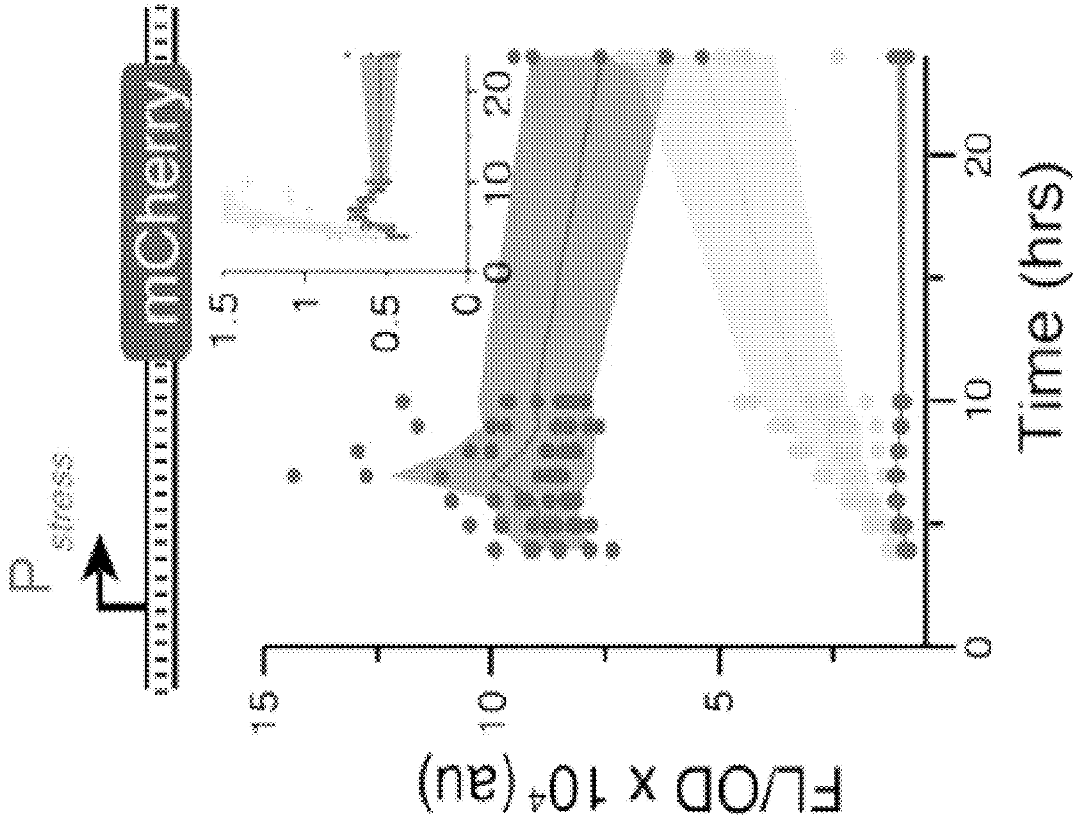

Characterization of the expression profile over time showed that all were activated at the earliest measured time point (4 hrs) and achieved maximal activation by ~10 hrs (FIG. 26C). Finally, comparison of select rSFPs with corresponding unregulated stress-response promoters revealed profiles with lower overall endpoint expression levels for rSFPs (FIG. 26D), due to the incorporation of the STAR target sequence that likely exhibits an inherent level of termination even upon STAR expression. Previous work[30] suggests that the overall rSFP expression could be further tuned by changing plasmid copy number or RBS strength as needed.

To demonstrate that rSFPs can be configured to control other feedback architectures, including engineered feedback promoter systems, we created rSFPs utilizing the recently developed stabilized promoter system that buffers gene expression from changes and fluctuations in DNA copy number using an incoherent feedforward loop (iFFL)[27]. Stabilized promoters work by configuring promoter expression to be responsive to a co-expressed transcription-activator-like effector (TALE) repressor. In this way, increased DNA copy number results in increased repressor expression, which interacts with the stabilized promoter to counter changes in gene expression. Stabilized promoters are of interest because they enable more precise control of gene expression by buffering against changes in DNA copy number that occur over time and between cells[34], in different host strains[35], and in different growth conditions such as medium[36,37], temperature[38], and growth rate[36]. Furthermore, stabilized promoter systems are useful to buffer genetic constructs from changes in copy number that are caused throughout the engineering/optimization process, such as adding new pathway enzymes[39-41], accumulating mutations that influence plasmid maintenance during a bioprocess[27], or integrating genes into the host genome[27].

Figure 18A:
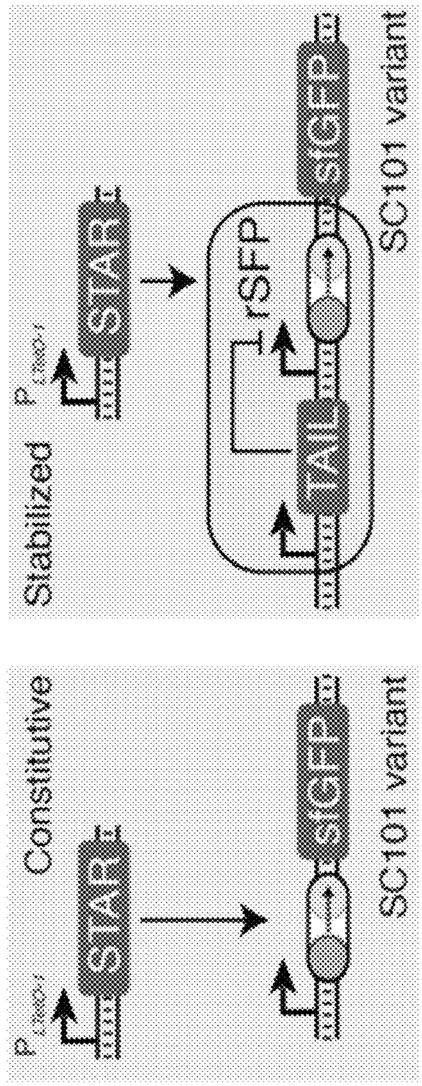
FIGS. 18A-18B show creation of stabilized rSFPs.
Figure 18B:
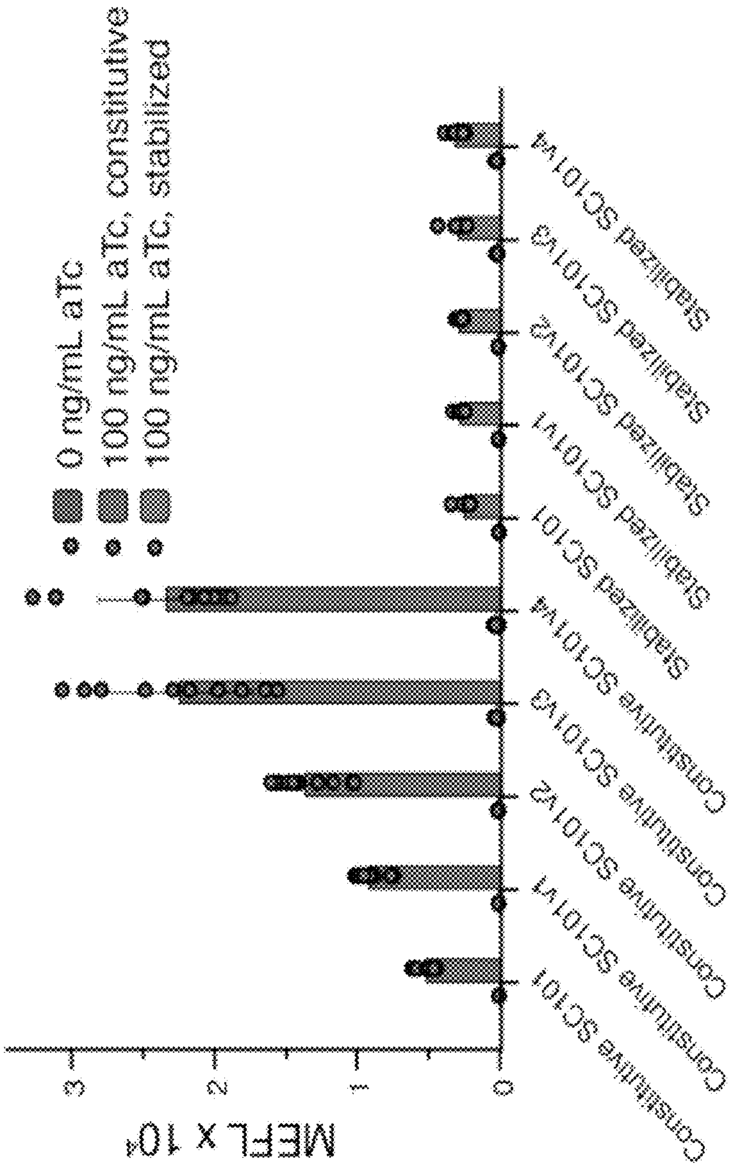
Figure 27A:
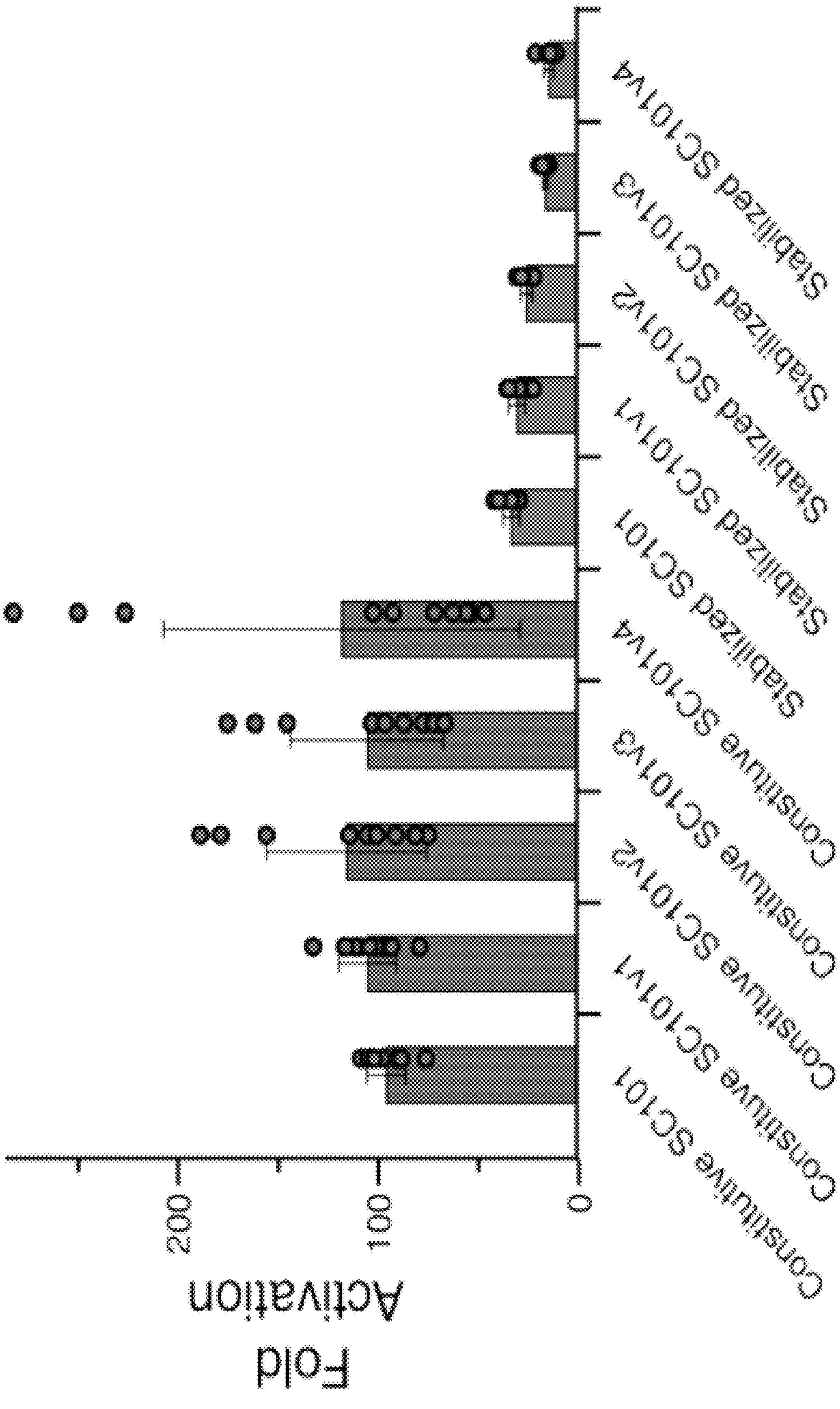
FIGS. 27A-27B show fold activation and analysis of cell-to-cell variability in stabilized rSFPs.

Much like natural stress-response promoters, stabilized promoters lack the ability to control gene expression timing, which is critical for creating a separation of growth and production phase in biomanufacturing processes[9]. Therefore, we applied the rSFP promoter gating concept to create stabilized promoter rSFPs. Similar to stress-response promoter rSFPs, a STAR target sequence was cloned immediately downstream of a stabilized promoter to regulate expression of an sfGFP reporter with the cognate $P_{LTetO\text{-}1}$-STAR construct (FIG. 18A). For comparison, a STAR-regulated constitutive promoter lacking the TALE repressor protein was also cloned to regulate expression of an sfGFP reporter with the same $P_{LTetO\text{-}1}$-STAR construct (FIG. 18A). We found that induction of $P_{LTetO\text{-}1}$-STAR resulted in activation of the stabilized promoter of ~33×-fold (FIG. 18B, 27A) and the STAR-regulated constitutive promoter lacking the TALE repressor protein of ~95×-fold (FIG. 18B, 27A). It is notable that the stabilized rSFP has lower overall expression levels than the constitutive STAR-regulated promoter system. This is an inherent feature of the previously developed iFFL[27] utilized here and could likely be compensated through tuning of RBS strength[16], promoter strength[27], or use of a STAR/TARGET pair with different expression level[30].

Figure 27B:
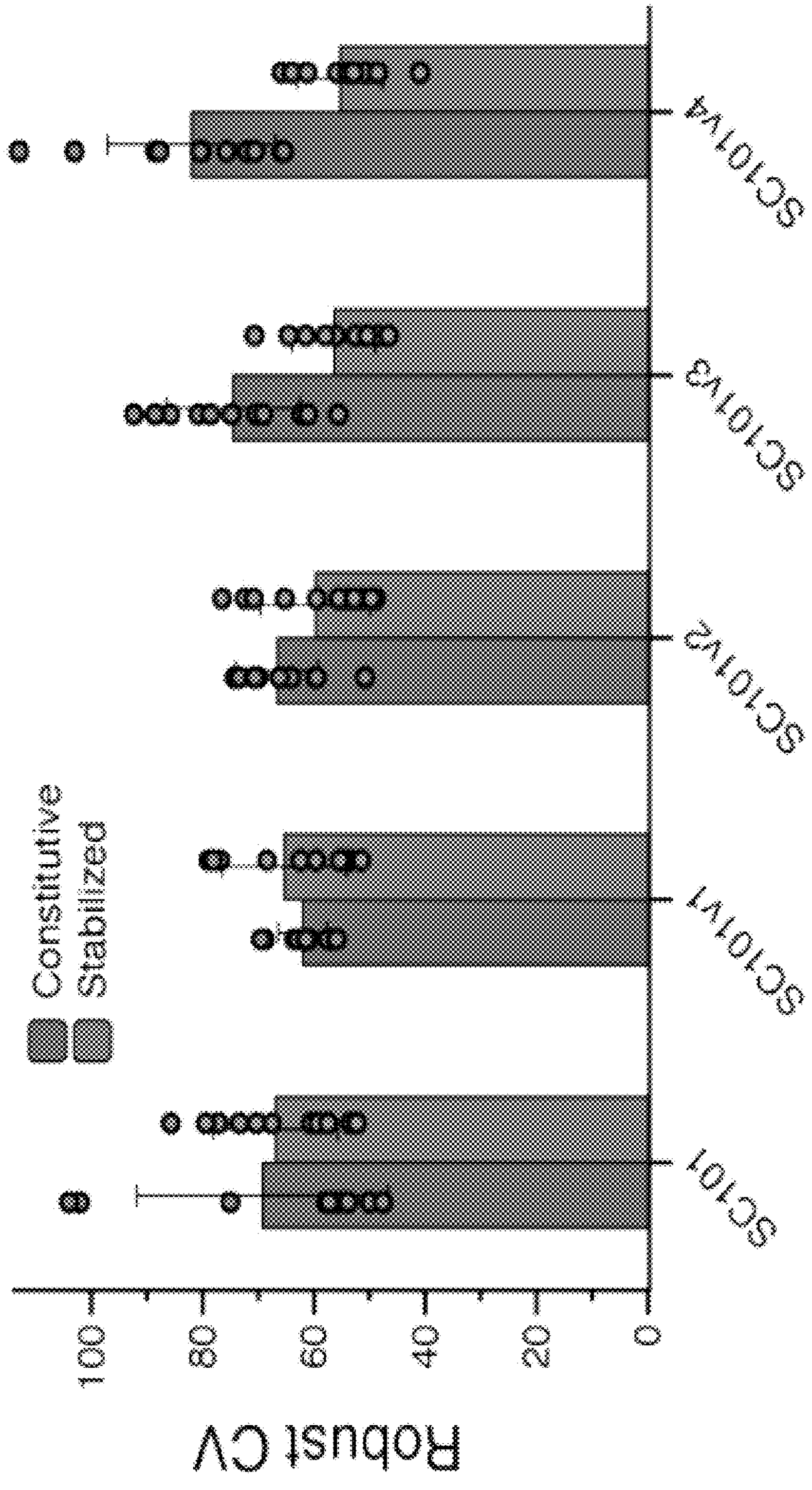

To demonstrate the effect of plasmid copy number on both a STAR-regulated constitutive promoter and the stabilized rSFP, we cloned mutants of the commonly used pSC101 plasmid backbone that exhibit a range of different copy numbers, between ~2 to ~30[27,33]. We observed that the STAR-regulated constitutive promoter system increased sfGFP expression as the pSC101 plasmid backbone increased in copy number, as expected. Importantly, there was negligible change in sfGFP expression when the stabilized rSFP was expressed from the various pSC101 mutant backbones (FIG. 18B). Interestingly, analysis of cell-to-cell variability observed across distributions of individual flow cytometry samples revealed lower variability for stabilized rSFPs compared with STAR-regulated constitutive promoters at high copy numbers (FIG. 27B), an anticipated feature of iFFLs[27].

Figure 19B:
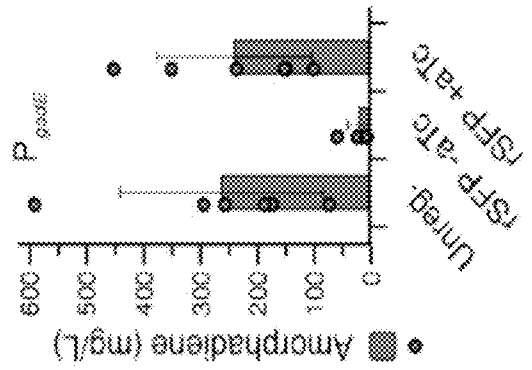
FIGS. 19A-19B show switchable control of an amorphadiene pathway with the PgadE rSFP.
Figure 19A:
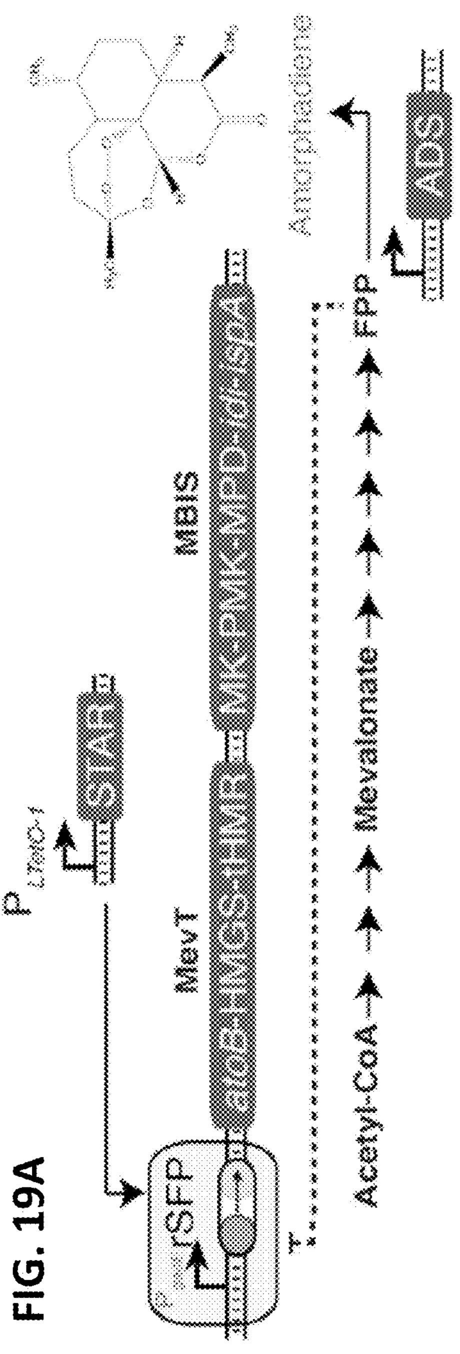
Figure 28B:
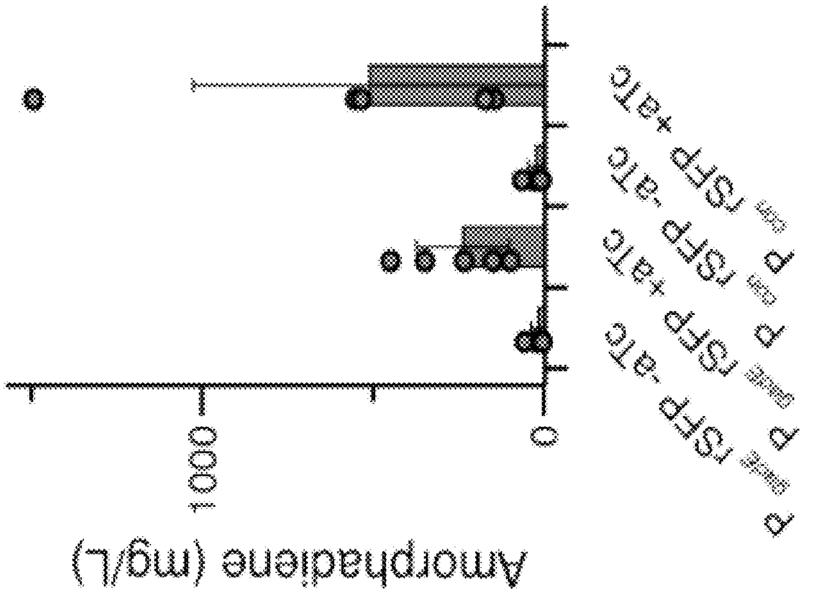
FIG. 28B shows titers of fermentations after 72 hrs with *E. coli* DH1 containing pADS and MevT-MBIS under control of either the PgadE rSFP or a STAR-regulated constitutive promoter. PLTet0-1-STAR was used to regulate PgadE or $P_{con}$ expression in the absence and presence of 100 ng/mL aTc added at inoculation. $P_{con}$=PapFAB45. Data corresponding to the PgadE conditions are the same as presented in FIG. 19B.
Figure 28A:
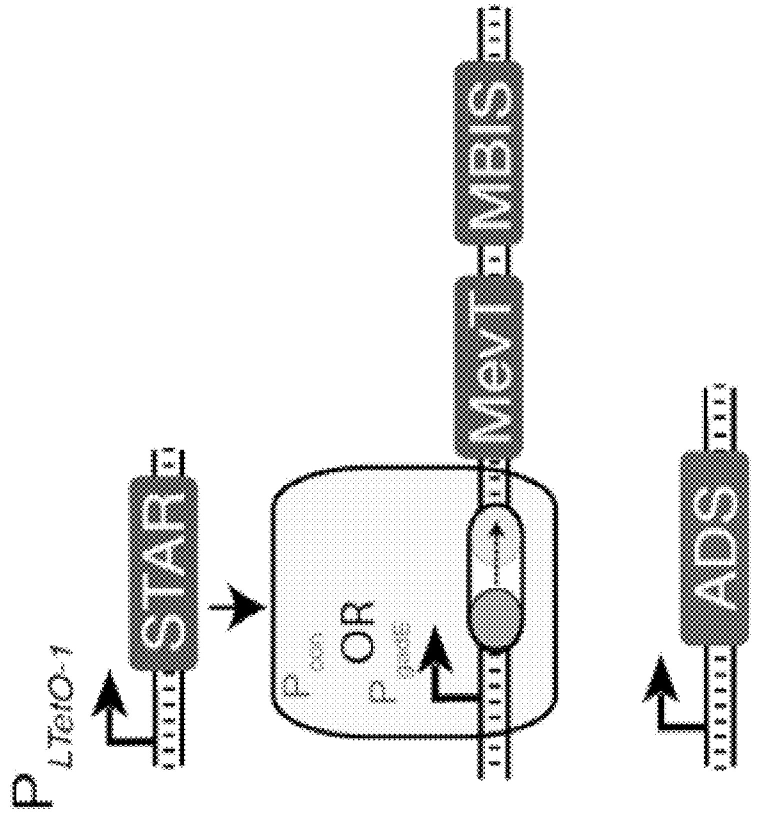
FIG. 28A is a schematic depicting configurations of the amorphadiene pathway containing pADS and MevT-MBIS under control of either the PgadE rSFP or a STAR-regulated constitutive promoter.
Figure 28D:
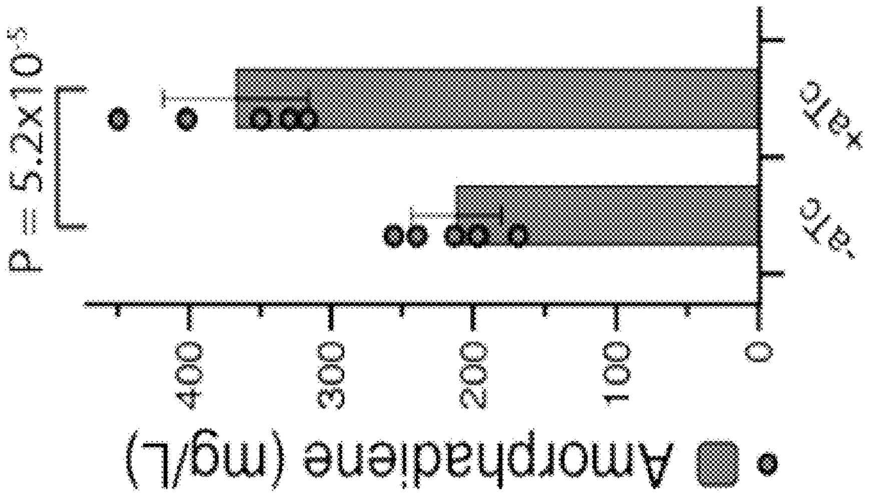
FIG. 28C is a schematic depicting configurations of the amorphadiene pathway containing pADS and MevT-MBIS under control of the stabilized rSFP. The stabilized rSFP is configured to activate by manual induction with PLTet0-1-STAR.
Figure 28C:
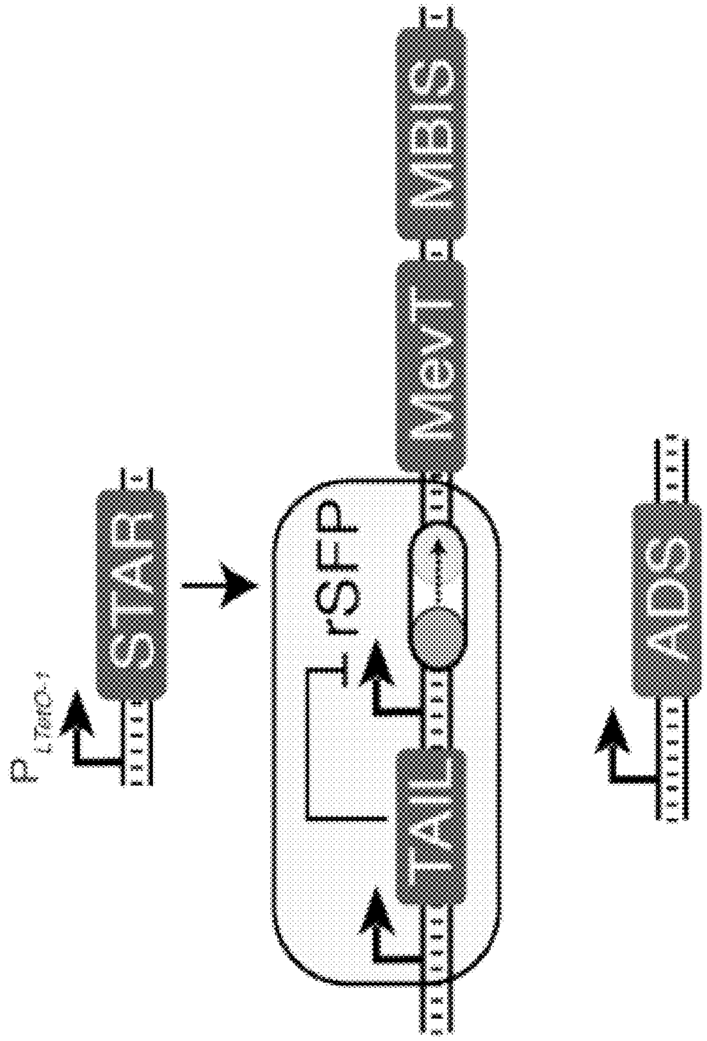

Overall, these results demonstrate our ability to leverage STARs to generate novel switchable feedback promoter circuits with different underlying feedback mechanisms. Our library provides tunable control of gene expression level by selecting different stress-response promoters or engineered promoter systems and manipulating inducer concentration. In addition, these rSFPs exhibit responsiveness to various sources of feedback (FPP and Pg1B stress[19,20], transcription factor repression[27]), suggesting that the additional layer of regulation does not interfere with the feedback-responsiveness of these promoters.

rSFPs Enable Switchable Control of Metabolic Pathway Genes with Stress-Response Promoters We next tested the ability of stress-response promoter rSFPs to regulate expression of metabolic pathway genes. First, we sought to regulate a pathway for amorphadiene biosynthesis that involves the toxic intermediate metabolite farnesyl pyrophosphate (FPP). In this pathway, FPP production is encoded by the previously engineered MevT-MBIS operon with final conversion by an amorphadiene synthase from *Artemisia annua* (ADS) 42 (FIG. 19A). Previous work showed that the $P_{gadE}$ stress-response promoter is down-regulated by FPP stress and that amorphadiene production is improved when $P_{gadE}$ is configured to control expression of the MevT-MBIS pathway for FPP synthesis[19]. We constructed a variant of the MevT-MBIS pathway under $P_{gadE}$ rSFP control and performed small-scale amorphadiene fermentations to compare these variants with MevT-MBIS under an unregulated $P_{gadE}$ promoter. Upon analysis, we found that the $P_{gadE}$ rSFP produced 238+/−136 mg/L of amorphadiene, which was comparable with the amorphadiene titer of the unregulated $P_{gadE}$ variant (260+/−178 mg/L) (FIG. 19B), but with the additional ability to regulate induction that can be essential in industrial scale-up[7]. In comparison, cultivations with MevT-MBIS under control of a STAR-regulated constitutive promoter showed more heterogeneity in production between biological replicates, but with greater average amorphadiene titers (FIG. 28A,B). While this system would require further optimization for eventual application, these results confirm the ability of rSFPs to enable inducible control of multi-gene metabolic pathway operons expressed from a stress-response promoter. We also found that the stabilized promoter rSFP can control the amorphadiene pathway with similar fermentation experiments (FIG. 28C,D), however delivers relatively weak induction.

Figures 20A, 20B, 20C:
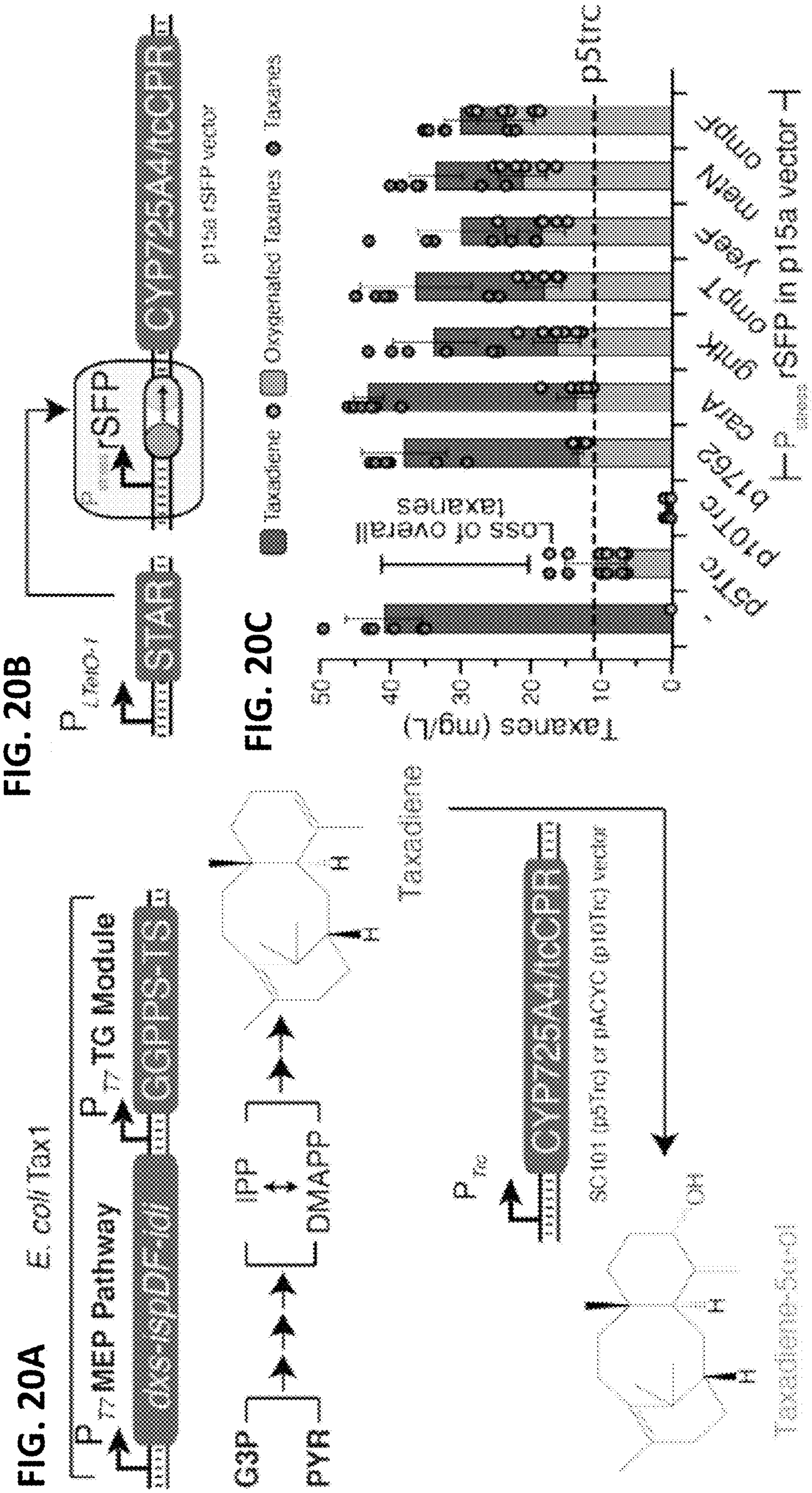
FIGS. 20A-20C show control of a taxadiene oxygenation pathway with rSFPs.

To demonstrate the modularity of rSFPs and their ability to improve pathway expression over a previous gold-standard, we next used them to regulate a portion of the anticancer drug paclitaxel's biosynthesis pathway that has been previously reconstituted in *E. coli*[43]. We focused on the first P450-mediated step where taxadiene is oxygenated by the membrane anchored cytochrome P450 CYP725A4 (FIG. 20A) and can be converted to Taxol through additional enzymatic or synthetic routes[44]. Previous work has shown that expression level of CYP725A4 and its reductase partner is critical to achieving high titers of oxygenated taxanes in *E. coli*[43]. A previously optimized low-copy expression vector (p5Trc-CYP725A4/tcCPR) (FIG. 20A) transformed into the *E. coli* Tax1 strain containing genomic modifications to maximize the synthesis of the taxadiene precursor, produces ~11 mg/L of oxygenated taxanes in our experiments (FIG. 20C). However, as found before, increasing expression of the enzyme using a medium copy expression vector (p10Trc) does not increase titer, but causes a complete loss of pathway productivity (FIG. 20C), presumably due to the enzyme's membrane stress crossing a critical threshold and triggering a global response.

Figure 29:
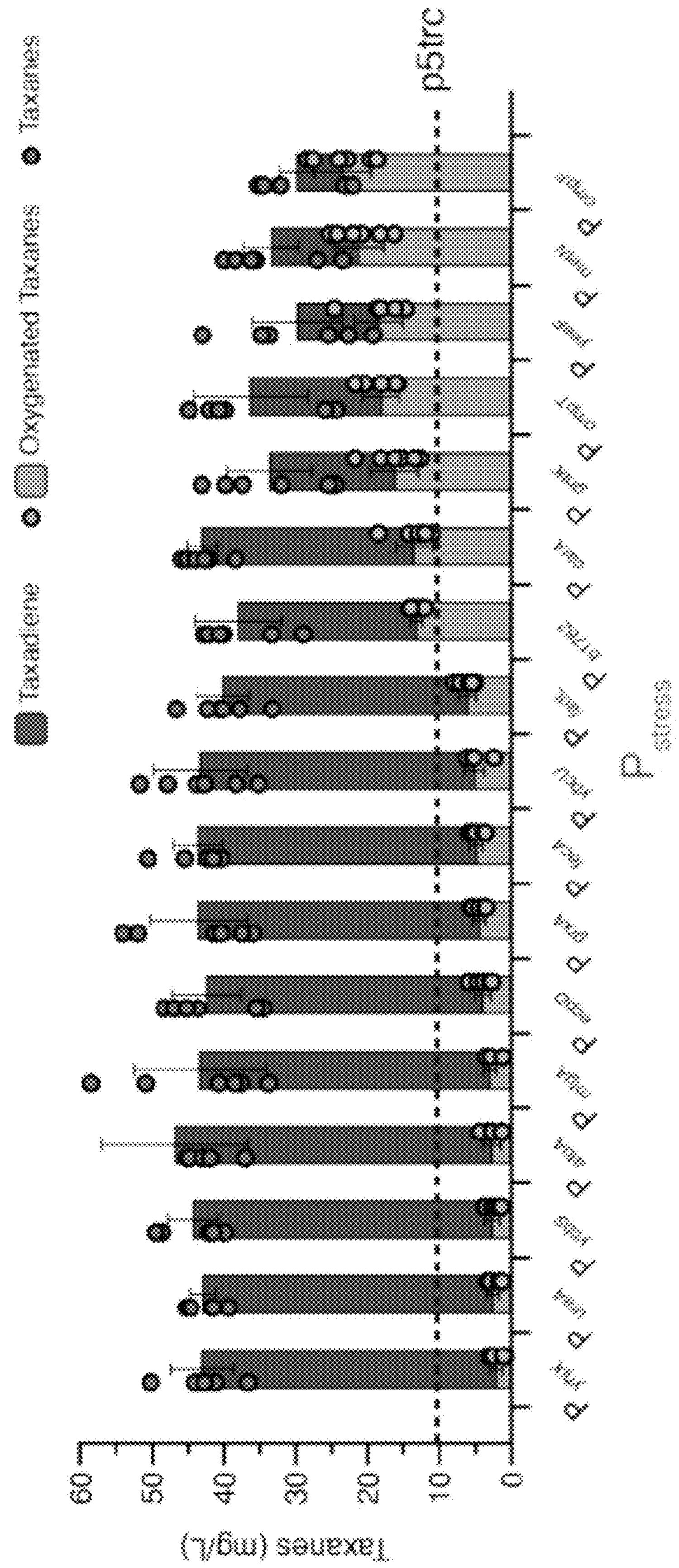
FIG. 29 shows taxane titers of fermentations after 96 hrs with *E. coli* Tax1 containing CYP725A4/tcCPR under control of an rSFP and PLTet0-1-STAR with addition of 100 ng/mL aTc at inoculation. Dashed line represents production of oxygenated taxanes from p5Trc in *E. coli* Tax1 in FIG. 20C. Bars represent mean values of taxane titers measured with GC-MS and error bars represent s.d. of at least n=5 biological replicates. Filled points represent individual data points of overall taxanes or individual data points of oxygenated taxanes.

We hypothesized we could achieve greater pathway productivity over the p5Trc benchmark strain by identifying relevant rSFPs for control of CYP725A4/tcCPR. To test this, the CYP725A4/tcCPR coding sequence was introduced into each of the 17 rSFP constructs (FIG. 20B). *E. coli* Tax1 was transformed with each rSFP construct and the $P_{LTetO\text{-}1}$-STAR plasmid and tested in the context of taxadiene oxygenation cultivations, with the STAR induced from inoculation. Using this approach, we found that several performed well against the p5Trc benchmark strain (FIG. 29). In particular, 7 of the rSFPs had greater titers of oxygenated taxanes than the p5Trc strain (FIG. 20C), with all also improving overall taxane production. Furthermore, the $P_{ompF}$ rSFP resulted in ~2.2× fold greater oxygenated taxanes (~23.5+/−4.0 mg/L) and ~2.8× fold greater overall taxanes (29.9+/−5.8 mg/L) than the p5Trc strain.

Figure 30A:
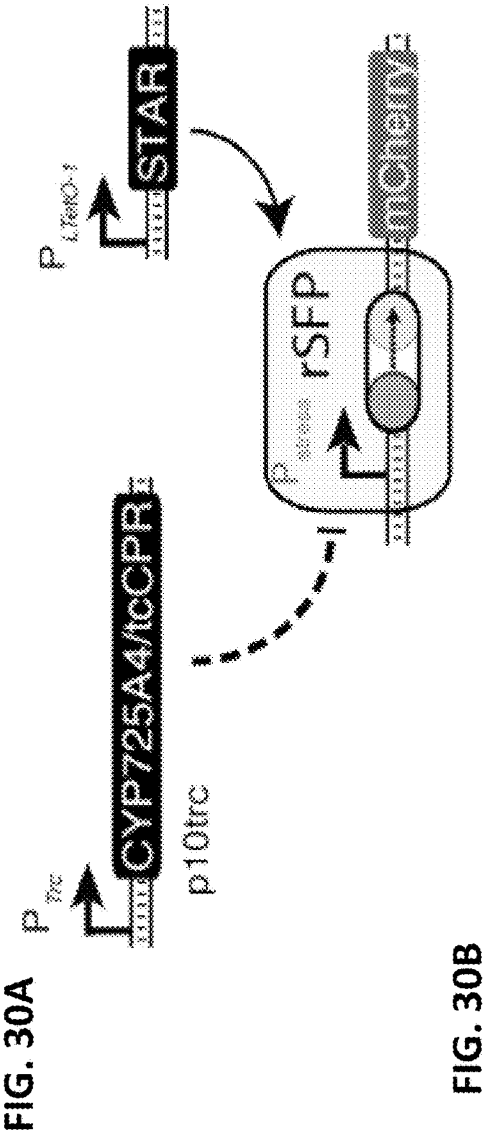
FIGS. 30A-30B show analysis of feedback-responsiveness of selected stress-response promoters to CYP725A4/tcCPR stress.
Figure 30B:
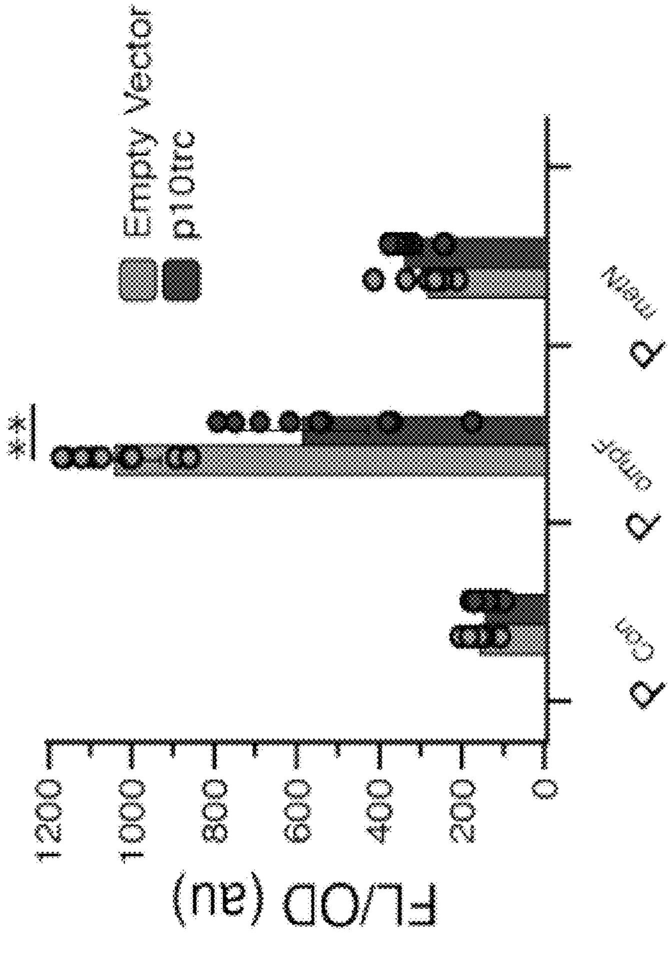

To confirm that rSFPs can indeed be feedback regulated by CYP725A4/tcCPR stress, we performed fluorescence analysis of *E. coli* cells containing plasmids for rSFP expression of an mCherry reporter and the p10Trc plasmid separately expressing CYP725A4/tcCPR, in order to monitor changes in rSFP expression caused by membrane stress (FIG. S7A). We observed reduced expression from $P_{ompF}$ when p10Trc was present in place of an empty vector (FIG. 30B), suggesting that it is indeed responsive to CYP725A4/tcCPR induced stress. A constitutive promoter control had no response as expected (FIG. 30B). Interestingly, the $P_{metN}$ rSFP did not exhibit responsiveness to CYP725A4/tcCPR expression, despite our earlier observation that it did respond to Pg1B expression (FIG. 17). This finding indicates that not all rSFPs respond to stresses in the same way and that CYP725A4/tcCPR presents a unique stress compared to Pg1B, highlighting the need to pair different stresses to appropriate stress-response promoters.

Figures 31A, 31B, 31C:
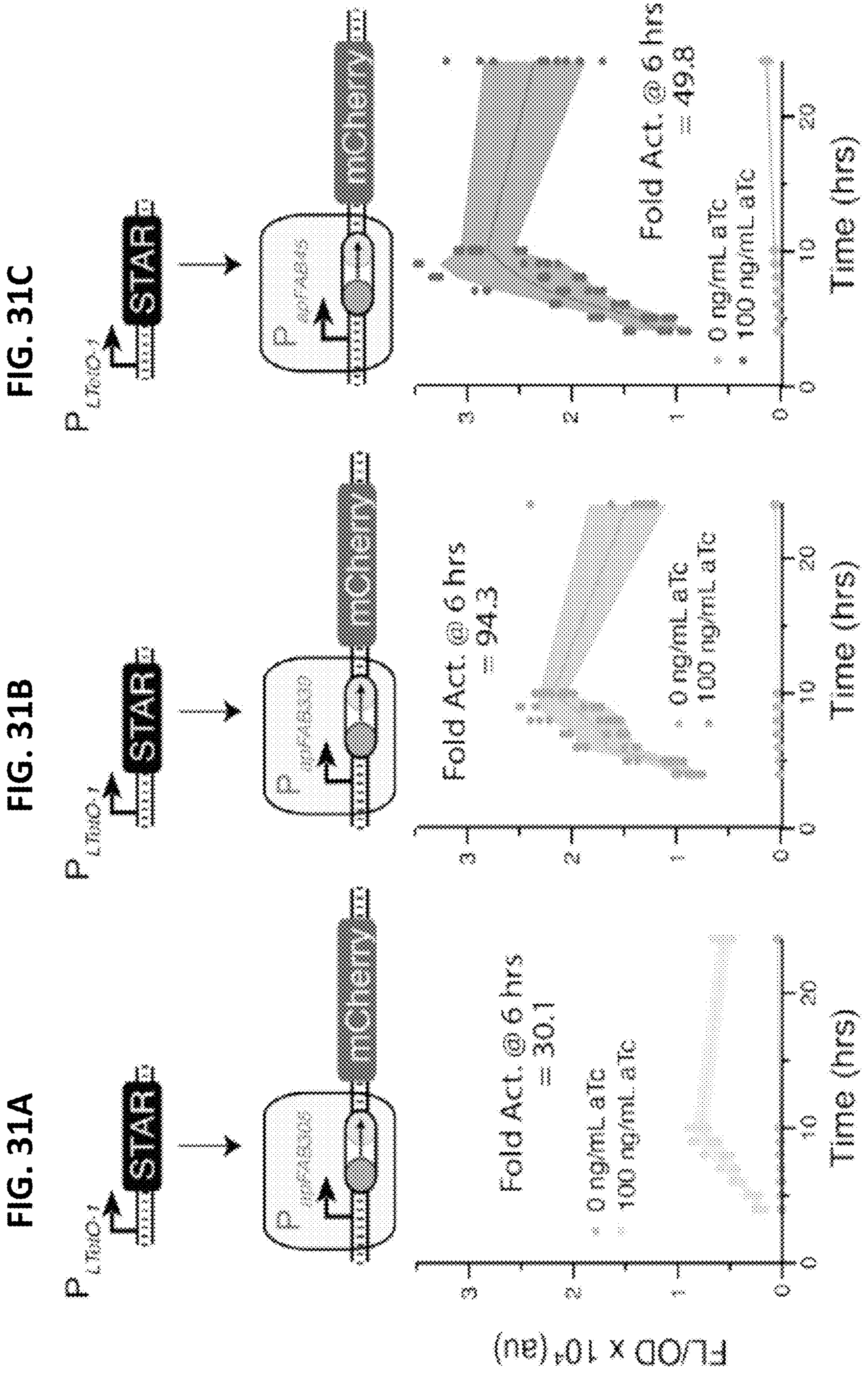
FIG. 31A shows fluorescence characterization of the weak $P_{apFAB305}$ promoter over time. Fluorescence characterization was performed on *E. coli* Tax1 transformed with plasmids encoding the STAR-regulated constitutive promoter controlling mCherry expression and $P_{LTetO\text{-}1}$-STAR in the absence and presence of 100 ng/ml aTc added at 0 hrs.
FIG. 31B shows fluorescence characterization of the medium $P_{apFAB339}$ promoter.
FIG. 31C shows fluorescence characterization of the strong $P_{apFAB45}$ promoter.
Figure 31D:
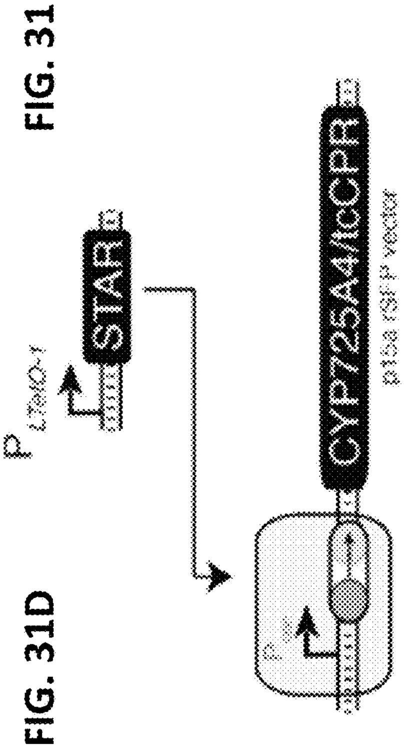
FIG. 31D shows architecture of STAR-regulated constitutive promoters controlling CYP725A4/tcCPR.
Figure 31E:
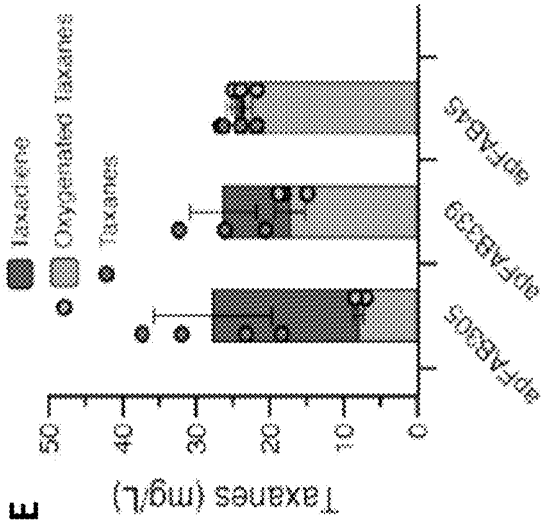
FIG. 31E shows titers of fermentations after 96 hrs with *E. coli* Tax1 containing CYP725A4/tcCPR under control of each STAR-regulated constitutive promoter and $P_{LTetO\text{-}1}$-STAR with addition of 100 ng/ml aTc at inoculation.
Figure 31F:
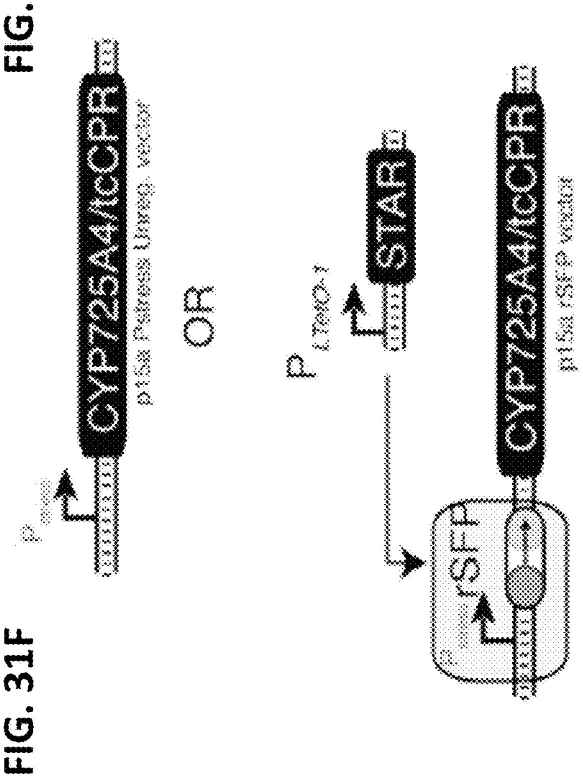
FIG. 31F shows architecture of unregulated stress-response promoters controlling CYP725A4/tcCPR or an rSFP controlling the same gene cluster and activated by PLTet0-1-STAR.
Figure 31G:
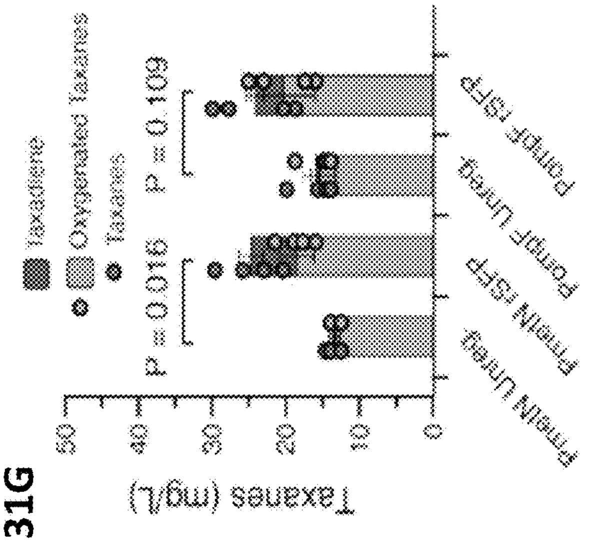
FIG. 31G shows titers of fermentations after 96 hrs with *E. coli* Tax1 containing CYP725A4/tcCPR under control of an unregulated stress-response promoter or an rSFP and $P_{LTetO\text{-}1}$-STAR with addition of 100 ng/mL aTc at inoculation. Individual data points in a, b, c represent fluorescence measurements in units of arbitrary fluorescence/optical density (FL/OD). Lines in a, b, c represent mean values of FL/OD and shaded areas represent mean +/−s.d. of n=9 biological replicates. Bars in e, g represent mean values of taxane and oxygenated taxane titers measured with GC-MS and error bars represent s.d. of n=4 biological replicates. Filled points in e, g represent individual data points of overall taxanes or individual data points of oxygenated taxanes. P indicates results of a Welch's t-test (two-tailed, unequal variances) comparing the oxygenated titers between the unregulated and rSFP regulated conditions.
Figure 32A:
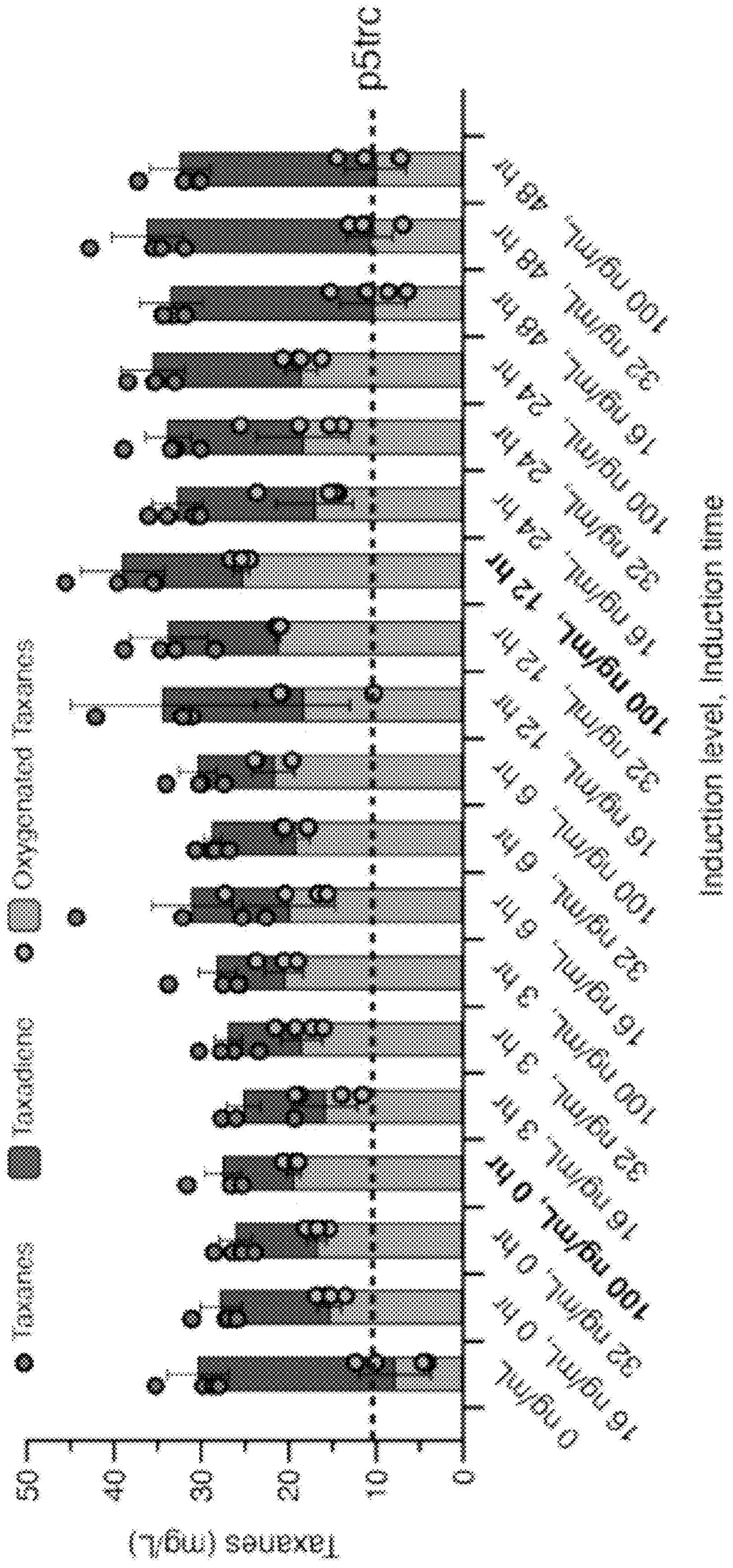
FIG. 32A shows titers of fermentations after 96 hrs with *E. coli* Tax1 containing CYP725A4/tcCPR controlled by the $P_{metN}$ rSFP and PLTet0-1-STAR under each induction condition. Data presented as a heatmap in FIG. 7B.
Figure 32B:
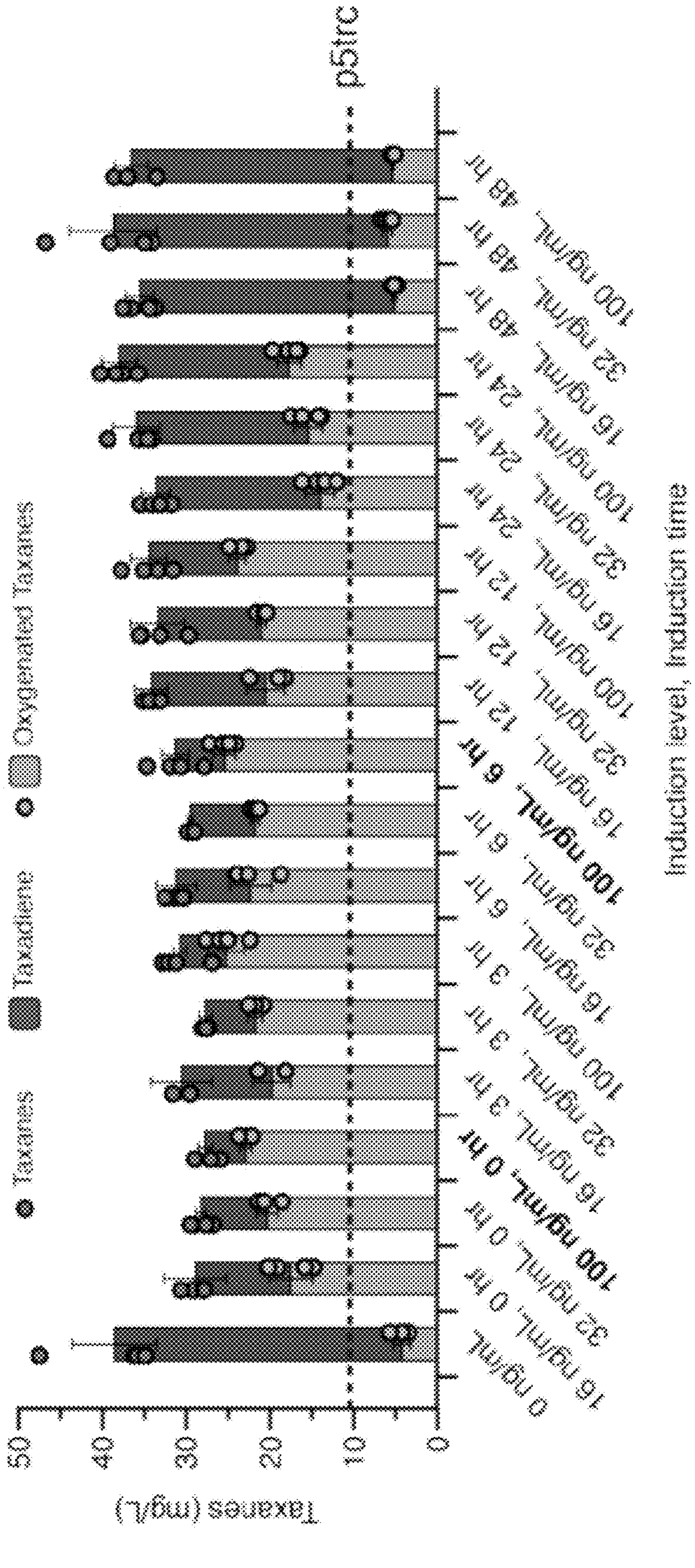
FIG. 32B shows titers of fermentations after 96 hrs with *E. coli* Tax1 containing CYP725A4/tcCPR controlled by the $P_{ompF}$ ISFP and $P_{LTetO\text{-}1}$-STAR under each induction condition. Data presented as a heatmap in FIG. 20C. Bold conditions indicate 100 ng/mL aTc induction at inoculation and the optimal time point. Dashed line represents production of oxygenated taxanes from p5Trc in *E. coli* Tax1 in FIG. 20C. Bars represent mean values of taxane and oxygenated taxane titers measured with GCMS after 96 hrs and error bars represent s.d. of at least n=3 biological replicates. Filled points represent individual data points of overall taxanes or individual data points of oxygenated taxanes.

Controls with varied strength constitutive promoters regulated by STARs were also run and one combination was found to achieve similar titers to the $P_{ompF}$ rSFP (FIG. 31A-E). This suggests that in this pathway the introduction of a STAR to control promoter output may help contribute to improved pathway performance but requires the highest strength promoter ($P_{apFAB45}$). To further explore the impact of introducing STAR regulation, we performed fermentations with unregulated $P_{metN}$ and $P_{ompF}$ promoters replacing the corresponding rSFPs (FIG. 31F). We observed that rSFPs outperformed unregulated stress-response promoters in both cases with regards to total taxane production and, in the case of the $P_{metN}$ rSFP, oxygenated taxane production (FIG. 31G).

Figure 8:
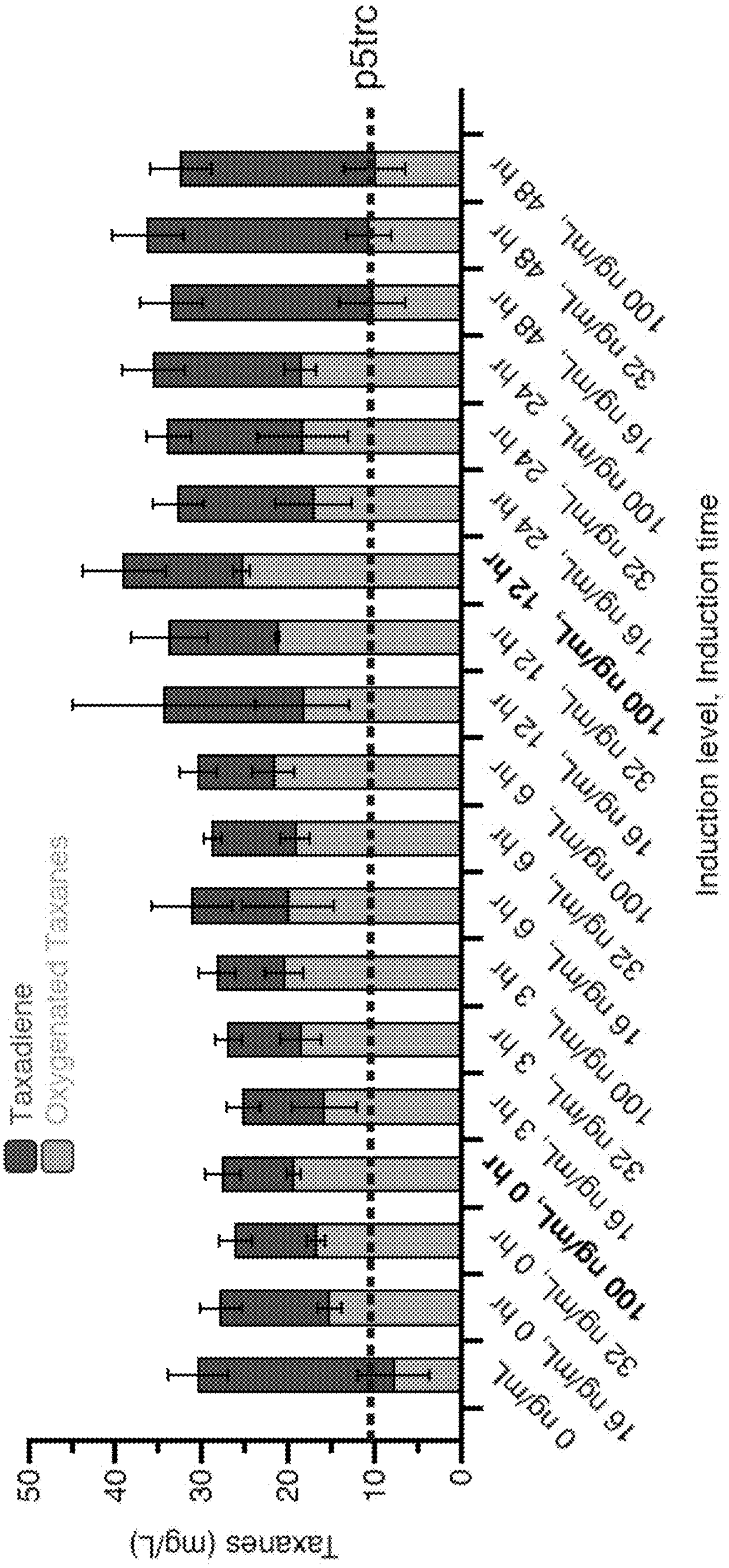
FIG. 8 shows titers of fermentations after 96 hrs with *E. coli* Tax1 containing CYP725A4/tcCPR controlled by the $P_{metN}$ rSFP and $P_{L,TetO1}$-STAR under each induction condition. Dashed line represents production of oxygenated taxanes from p5Trc in FIG. 2C. Data represent mean values of fermentation titers and error bars represent s.d. of at least n=3 biological replicates. Bold conditions indicate 100 ng/mL aTc induction at inoculation and the optimal inductions.
Figures 21A, 21B, 21C:
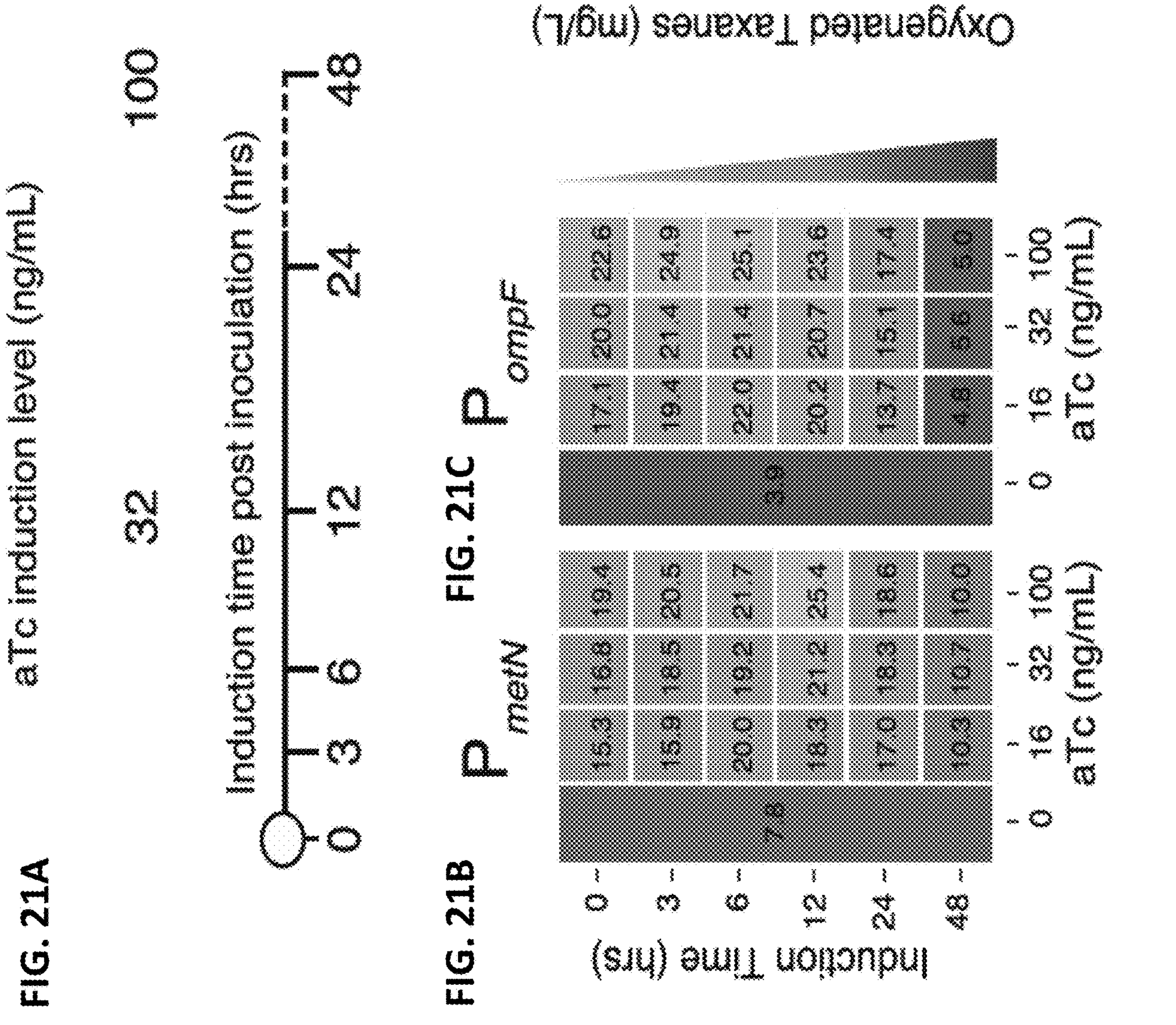
Figure 21E:
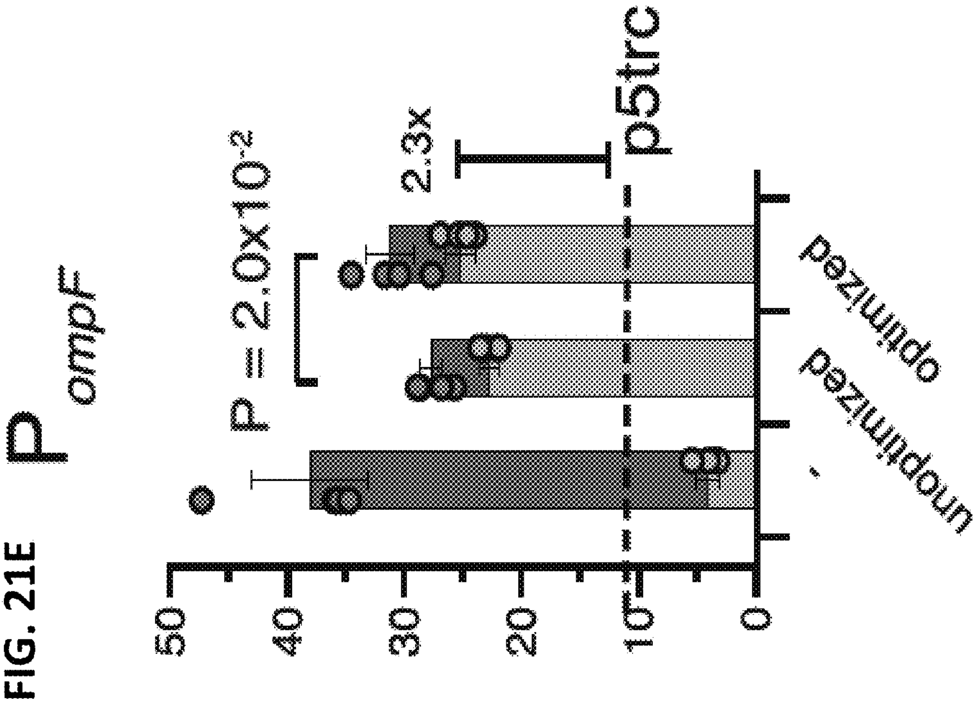
(FIG. 21D, FIG. 21E) Fermentation titers with *E. coli* Tax1 containing the (d) $P_{metN}$ or (e) $P_{ompF}$ rSFP without aTc induction, with aTc induction before optimization (100 ng/mL aTc at 0 hrs), and with aTc induction after optimization. Dashed line represents production of oxygenated taxanes from p5Trc in FIG. 20C. Bars in d, e represent mean values of taxane titers measured with GCMS after 96 hrs of fermentation and error bars represent s.d. of at least n=4 biological replicates. Filled points represent individual data points of overall taxanes or individual data points of oxygenated taxanes. P-values indicate a statistically significant difference in oxygenated taxane production by a Welch's t-test (two-tailed, unequal variances) between the unoptimized and optimized conditions.
Figure 21D:
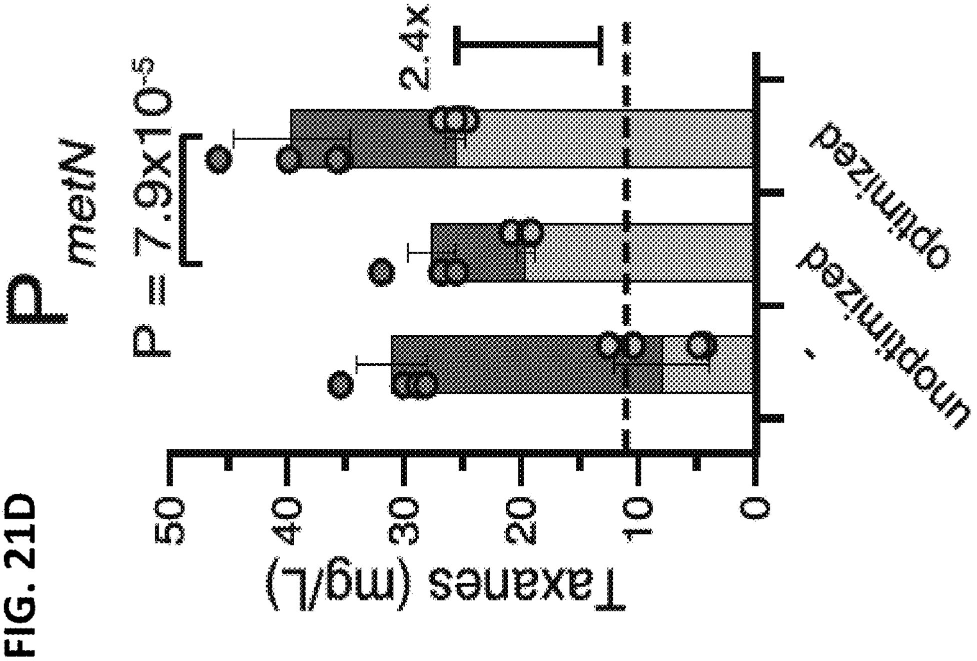

We next explored how the external control offered by rSFPs can be used to further optimize induction level and timing of stress-response promoter activity. To test this, we selected the two best rSFP systems and performed a matrix of aTc induction at four levels (0, 16, 32, and 100 ng/mL aTc), which were added at six different induction times (0, 3, 6, 12, 24, 48 hrs) post inoculation (FIG. 21A). We found that oxygenated taxane production with both rSFPs was sensitive to induction level and timing (FIG. 8B,C, S9A,B) and that optimizing induction of $P_{metN}$ and $P_{ompF}$ rSFPs could improve final titers of oxygenated taxanes further to 25.4+/−0.9 and 25.1+/−1.3 mg/L, respectively, and overall taxanes to 39.0+/−4.8 and 31.0+/−2.9 mg/L (FIG. 21D,E), representing an overall 2.4× and 2.3× fold improvement over the previous gold standard benchmark in terms of oxygenated taxanes, and 3.6× and 2.9× fold improvements in terms of overall taxanes, demonstrating potential performance advantages of inducible control in rSFPs.

Overall, we demonstrate that the rSFP regulation concept is modular, effectively enabling inducible control and optimization of metabolic pathway production using different stress-response promoters and different metabolic pathways. Importantly, rSFPs enable tuning of expression timing and overall magnitude of stress-response promoter output to further enhance fermentation titers.

Quorum-Sensing Activated rSFPs Allow Autonomous Regulation of Pathway Expression.

Figure 9:
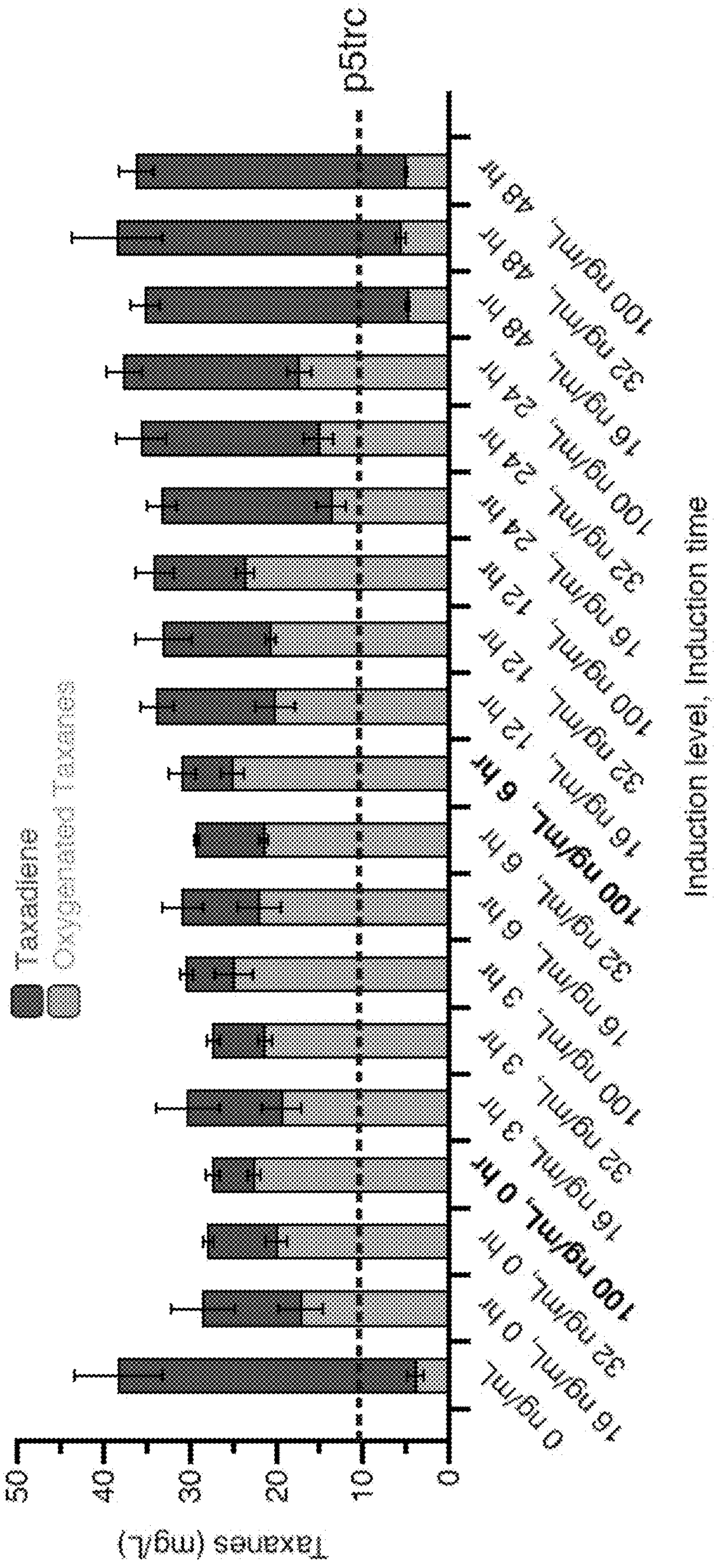
FIG. 9 shows titers of fermentations after 96 hrs with *E. coli* Tax1 containing CYP725A4/tcCPR controlled by the $P_{ompF}$ rSFP and $P_{L,TetO1}$-STAR under each induction condition. Dashed line represents production of oxygenated taxanes from p5Trc in FIG. 2C. Data represent mean values of fermentation titers and error bars represent s.d. of at least n=3 biological replicates. Bold conditions indicate 100 ng/mL aTc induction at inoculation and the optimal inductions.
Figure 10:
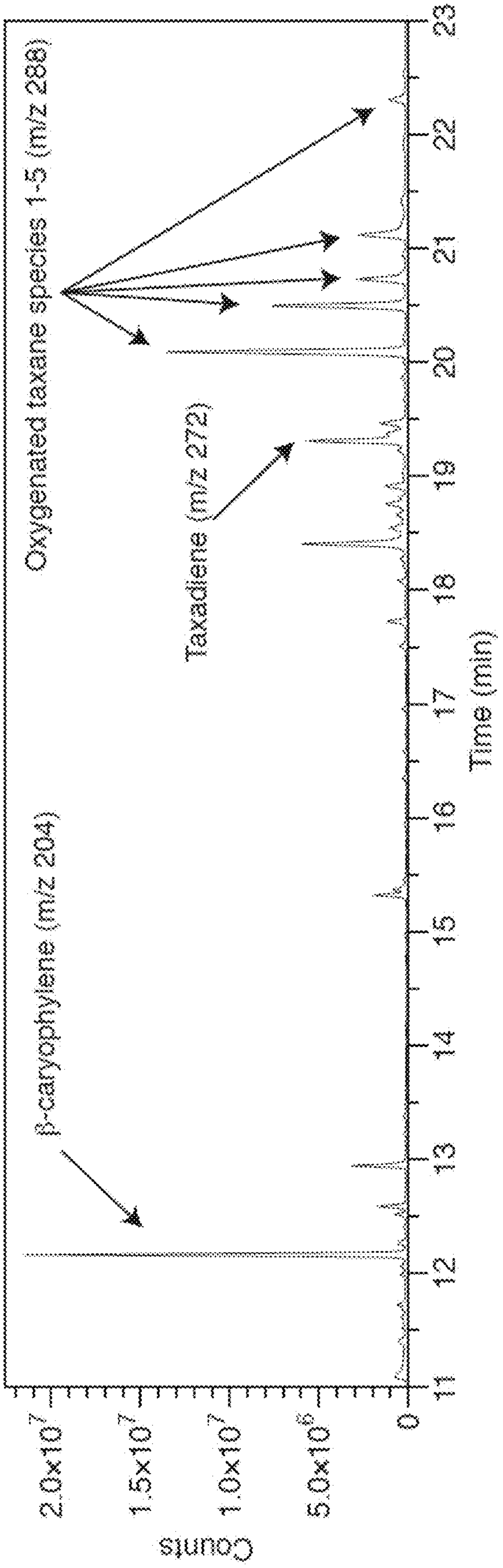
FIG. 10 shows an example GC chromatogram for analysis of taxadiene and oxygenated taxane fermentations. Taxadiene and oxygenated taxane peaks were previously described in Biggs, B. W. et al. "Overcoming heterologous protein interdependency to optimize P450-mediated Taxol precursor synthesis in *Escherichia coli*." Proc. Natl. Acad. Sci. (2016). doi: 10.1073/pnas.1515826113.
Figures 22A, 22B, 22C:
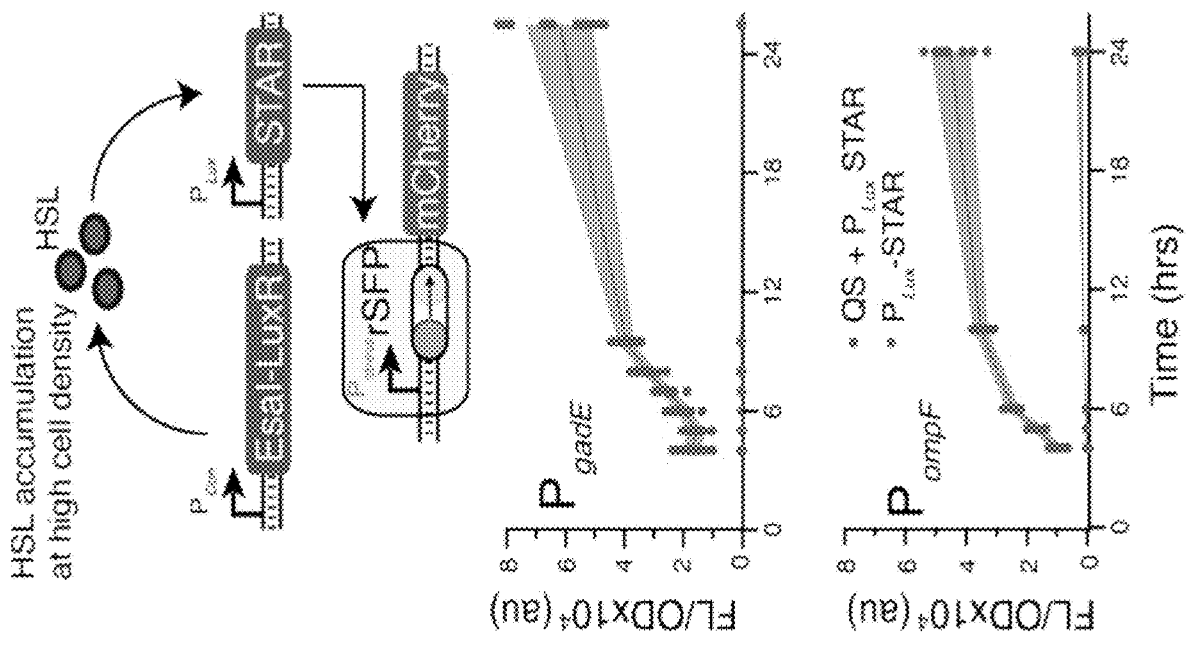
FIGS. 22A-22C show characterization of autonomous quorum-sensing rSFPs.

Though inducible systems offer flexibility for screening of optimal induction timing, the cost of inducers can be prohibitive at an industrial scale[45,46], and several efforts have been carried out to design autonomous means of induction. Quorum-sensing (QS) systems that are activated in a cell-density dependent manner offer one such route to this behavior[47]. QS systems have been used with great utility in metabolic engineering to create a separation of cell growth and pathway production phases without the need for a chemical inducer and provide a natural means for balancing carbon utilization with biomass production[48-50]. We therefore utilized this strategy within our model pathways by leveraging the modularity of rSFPs to be easily configured to utilize different input systems. Specifically, we chose the $P_{Lux}$ promoter that is activated by the LuxR transcriptional activator upon sufficient production of the C6-homoserine lactone (HSL) signaling molecule[51], since we had previously used $P_{Lux}$/LuxR to control STAR production[30]. In addition, we chose the EsaI HSL synthase[52] because it had previously been used successfully in metabolic engineering applications[49]. We cloned a STAR under control of $P_{Lux}$ and integrated an operon with the EsaI and LuxR into the genome of the *E. coli* DH1 or Tax1 to create DH1-QS and Tax1-QS strains (FIG. 22A). When plasmids encoding the expression of $P_{Lux}$-STAR and the $P_{gadE}$ rSFP controlling mCherry expression were transformed into *E. coli* DH1 or DH1-QS, we found that activation only occurred in the engineered DH1-QS strain containing EsaI and LuxR (FIG. 22B). Similarly, transformation of a $P_{Lux}$-STAR vector and the $P_{ompF}$ rSFP into *E. coli* Tax1 or Tax1-QS resulted in mCherry fluorescence activation only in Tax1-QS (FIG. 9C). These QS-activated rSFPs produced mCherry autonomously over time with comparable fold activation to manual induction with $P_{LTetO\text{-}1}$.

Figures 23A, 23B, 23C:
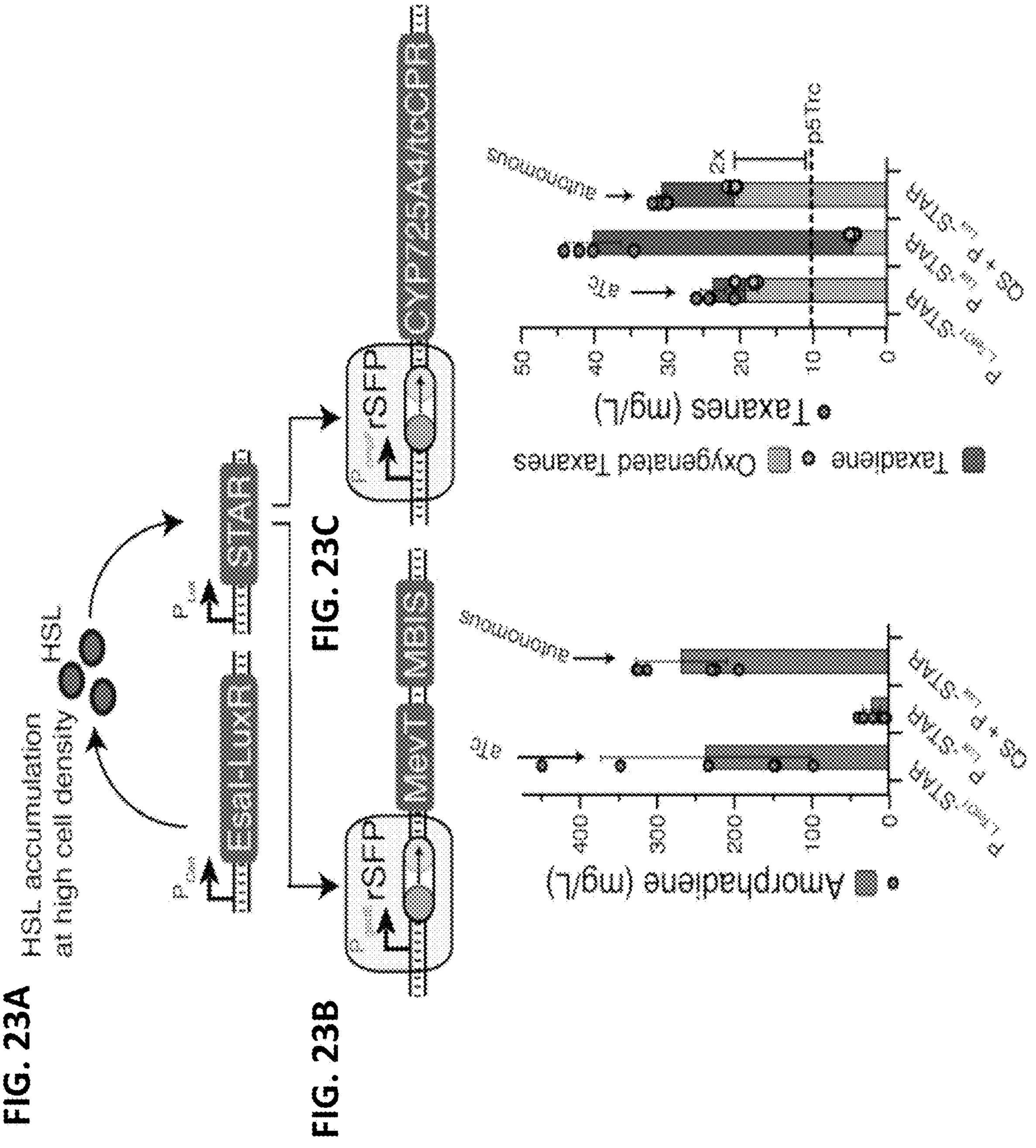
FIGS. 23A-23C show autonomous control of metabolic pathways with quorum-sensing rSFPs.

To demonstrate that QS-activated rSFPs could be used to autonomously control the expression of metabolic pathway enzymes, we applied the $P_{gadE}$ QS-activated rSFP to control expression of MevT-MBIS within the amorphadiene pathway and the $P_{ompF}$ QS-activated rSFP to control CYP725A4/tcCPR expression within the taxadiene oxygenation pathway. Cultivations were performed by inoculating cell cultures into media without addition of exogenous inducer. Upon cultivation and analysis, we found that QS-based activation in both systems resulted in comparable titers of amorphadiene or oxygenated taxanes to those obtained from manual induction (FIG. 23). Importantly, this was achieved with a completely autonomous genetic feedback network without the need for costly inducers and, for the oxygenated taxane pathway, this represented a 2×-fold improvement over the previous gold standard. These results demonstrate the composability of rSFPs, showing that QS systems can be configured to autonomously activate expression of rSFPs to regulate metabolic pathways with favorable performance when compared to manually induced rSFP configurations.

DISCUSSION

Here we report the development, characterization and application of switchable feedback promoters that enable an additional synthetic layer of control over natural stress-response promoters and engineered feedback promoter systems. Stress-response promoters are a promising route to achieving dynamic control of heterologous metabolic pathways by acting as sensor-actuators to stresses caused by pathway expression, intermediate metabolites and other fermentation conditions[19,20]. While stress-response promoters have previously been shown to improve production of desired chemicals by regulating expression in response to toxic pathway intermediates and enzymes, their use is constrained by their complexity in terms of their specific signaling pathways and regulatory architecture, which may not be fully understood. This has led to a lack of control over the timing and overall magnitude of their transcriptional output, which is essential to achieving a separation of growth phase and production phase in large-scale fermentations[7,53]. This same limitation is also true of many engineered promoter systems, including stabilized promoters that buffer gene expression from changes in copy number[27].

By design, the rSFP concept enables switchable control by introducing an additional regulatory layer within the natural or engineered feedback pathway by gating stress-response promoter outputs with trans-acting RNA regulators. The use of an exogenous small molecule-inducible system to control RNA regulator synthesis allows modification of the timing and overall magnitude of the feedback promoter outputs. Furthermore, the use of QS systems allows the autonomous activation of rSFPs in a cell-density dependent manner. In this way, rSFPs are a composable element and have modularity at the level of their activation inputs, gene expression outputs, and the types of stresses they can respond to through changing of the regulated feedback promoter. By utilizing transcriptional RNA regulators, rSFPs offer the flexible implementation of controllable feedback networks in a single compact locus that is convenient for expression of operons. However, translational RNA regulators such as toehold switches[54] or antisense RNAs[55], configured to appropriately regulate the individual genes within an operon, could be used with similar results. Although transcriptional activation is expected to be optimal in many applications, an additional benefit of the rSFP system is the flexible ability to swap transcriptional activation of STARs with alternative modalities for transcriptional repression[56,57]. Alternative technologies, such as CRISPR interference[58], would be difficult to implement to control stress-response promoter outputs in metabolic pathways due to the need for expressing additional burdensome components (e.g. dCas9) and the reliance on repression, rather than activation afforded by STARs. Along these lines, technologies such as the burden-driven feedback controller that leverages stress-response promoters to dynamically regulate CRISPR gRNAs[18] could be enhanced by our rSFP approach by enabling inducible control of gRNA expression while maintaining burden-driven feedback.

We demonstrate that rSFPs are both modular and tunable—the rSFP concept can be applied to many unique stress-response promoters as well as the engineered stabilized promoter system in a plug-and-play fashion, activator inputs can be easily interchanged, and activated output levels can be modulated by titrating inducer concentrations. To demonstrate their utility in the context of optimizing metabolic pathway production, we applied rSFPs to regulate expression of a multi-gene operon in amorphadiene biosynthesis and a toxic cytochrome P450 enzyme in a synthetic Taxol precursor pathway in *E. coli*[43,59], enabling inducible control of pathway expression and improvements in production of the desired oxygenated taxane. We also showed that optimizing rSFP induction timing and magnitude in the oxygenated taxane fermentation enabled additional improvements, highlighting an advantage of the rSFP system to enable the control of pathway expression timing. We next showed that rSFPs can be controlled by QS systems that do not require addition of an exogenous inducer, enabling fully autonomous control of pathway expression. We developed rSFPs in *E. coli* and the system is likely adaptable to bacterial metabolic engineering hosts such as *Pseudomonas putida, Bacillus subtilis*, or *Acinetobacter* baylyi. However, future development of RNA transcriptional regulators or implementing rSFPs with other types of genetic control could be used to adapt the concept for yeast or other organisms.

Notably, we found that all 18 of the stress-response promoters, and the stabilized promoter, were activated significantly, strongly suggesting that the concept can be used with new feedback promoters as they are discovered in nature or engineered. In the case where an individual promoter does not perform well in rSFPs, which can be caused by extra 5' UTR sequence downstream of the stress-response promoter, alternative STAR/target pairs[30] may be screened or the extra 5' UTR may be trimmed for improved fold activation. Characterization of selected promoters under stress caused by buildup of a toxic intermediate metabolite or expression of toxic proteins showed that rSFPs remain responsive to stress as expected based on the behavior of unregulated stress-response promoters. These features allow rapid screening of rSFP libraries within combinatorial strain engineering procedures[60] that could be used by industry to identify effective implementations of dynamic control by capturing the unique temporal profiles and feedback responsiveness of different stress-response promoters. In addition, the ability of rSFPs to naturally adapt to an optimal expression level may allow for rapid prototyping of potentially toxic enzymes and pathways without the requisite need to first balance expression levels with constitutive static regulators—speeding the pace of pathway construction for new chemical products, especially if rSFPs become well characterized for use with specific types of stress.

Dynamic pathway regulation is a promising approach in the construction of genetic systems but can be difficult to implement. The rSFP strategy enables modular and tunable control of natural and engineered feedback-responsive promoters that have sophisticated transcriptional responses to a range of cellular stresses and cues. Due to their simplicity, we envision that the rSFP concept will enable streamlined implementation of dynamic regulation into metabolic pathways. Furthermore, given their modularity, we imagine rSFPs will be useful for dynamic control in other applications, such as high-level expression of difficult or toxic proteins, living therapeutics[3], and cellular diagnostics[4] where endogenous and engineered promoters could be used as sensor-actuators for numerous environments.

Methods

Plasmid assembly. All plasmids used in this study can be found in Table S13 with key sequences provided in Tables S13 and S14. Gibson assembly and inverse PCR (iPCR) was used for construction of all plasmids. All assembled plasmids were verified using DNA sequencing. rSFPs for the 17 envelope stress-response promoters and the stabilized promoter all used STAR/target variant 8 and the P gadE SFP used STAR/target variant 3. The downstream end of each stress-response promoter was defined as the 5' adjacent nucleotide to the start codon of its endogenously regulated gene. Cognate STARs were cloned in a second PLTet0-1 or $P_{Lux}$ plasmid.

Integration of QS operon into the *E. coli* genome. Strains containing genomic insertions of the EsaI-LuxR operon were created using the clonetegration[61] platform for creation of *E. coli* Tax1-QS or 2 Red recombineering[62] for *E. coli* DH1-QS as summarized in Table S15. For clonetegration, the HK022 plasmid was used to integrate constructs into the attB site of the *E. coli* genome. Successful integrations were identified by antibiotic selection and colony PCR according to the published protocol. For recombineering, double-stranded DNA fragments flanked upstream and downstream by 40 bp of homology to the attB site were generated for both the cat-sacB cassette and the EsaI-LuxR operon. Homology to the attB site was included in oligos and appended to each insert via PCR. The cat-sacB cassette was amplified from a purified *E. coli* TUC01 genome. *E. coli* DH1 carrying the pSIM6 plasmid was subjected to two rounds of recombineering according to the published protocol[62]. The first round inserted the cat-sacB cassette at the attB locus, and the second round replaced the cat-sacB cassette with the EsaI-LuxR operon. Successful integrations were identified by resistance to chloramphenicol (first round) or growth on sucrose and colony PCR (second round). Insertion of the complete EsaI-LuxR operon was confirmed by Sanger sequencing.

Figure 15B:
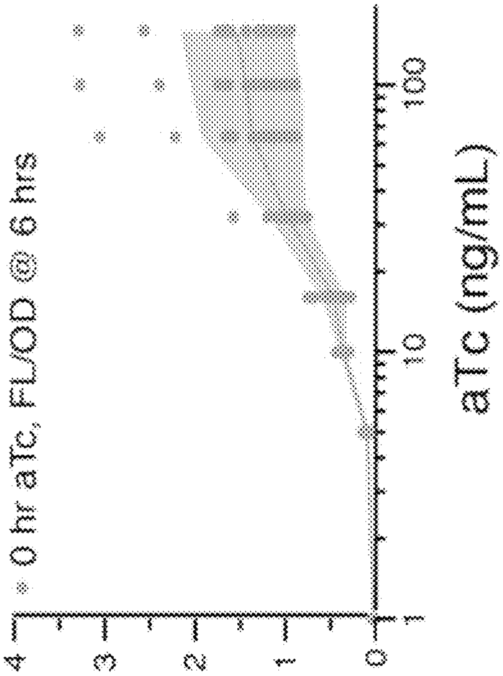
Figure 15C:
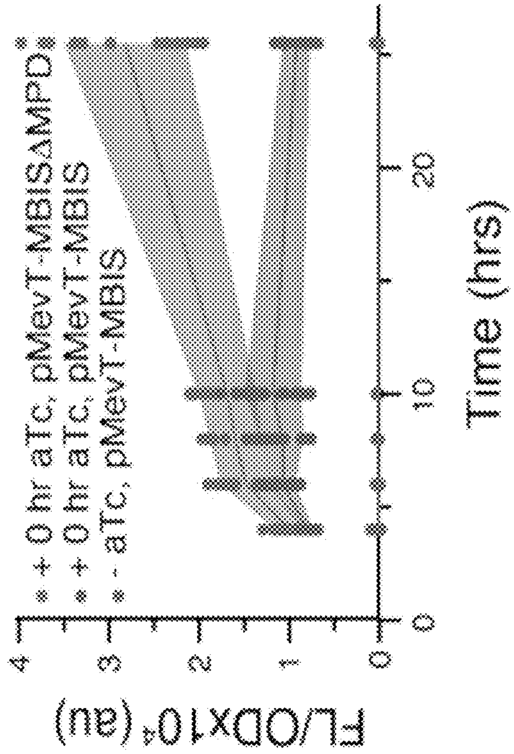

Strains, growth media, in vivo bulk fluorescence measurements. Fluorescence characterization experiments for all envelope stress-response promoters (FIG. 16B, 17B, 22C) were performed in *E. coli* strain Tax1[43] containing the synthetic pathway for taxadiene biosynthesis or modified Tax1-QS containing the QS operon. Experiments involving the $P_{gadE}$ promoter (FIG. 15A-C, 22B) were performed in *E. coli* strain DH1 (F-2-endAl recAl relAl gyrA96 thi-1 glnV44 hsdR17 (rK-mK-)) or modified DH1-QS containing the QS operon. Experiments were performed for at least 7 biological replicates collected over two separate days. For each day of fluorescence measurements, plasmid combinations were transformed into chemically competent *E. coli* cells and plated on LB+Agar (Difco) plates containing combinations of 100 μg/mL carbenicillin, 34 μg/mL chloramphenicol and/or 50 μg/mL spectinomycin depending on plasmids used (see Table 13 for plasmids used in each experiment), and incubated approximately 17 hours (h) overnight at 37° C. Plates were taken out of the incubator and left at room temperature for approximately 7 h. Three colonies were used to inoculate three cultures of 300 μL of LB containing antibiotics at the concentrations described above in a 2 mL 96-well block (Costar), and grown for approximately 17 h overnight at 37° C. at 1,000 rpm in a VorTemp 56 (Labnet) bench top shaker. FIG. 15B, 16B: 4 μL of each overnight culture were added to 196 μL (1:50 dilution) of supplemented M9 minimal media (1×M9 minimal salts, 1 mM thiamine hydrochloride, 0.4% glycerol, 0.2% casamino acids, 2 mM $MgSO_4$, 0.1 mM $CaCl_2$)) containing the selective antibiotics and grown for 6 h at the same conditions as the overnight culture. Appropriate concentrations of anhydrotetracycline (Sigma) were added to culture media as indicated. FIG. 15A, 15C, 22B, 22C: 20 μL of each overnight culture were added to 980 μL of M9 minimal media containing selective antibiotics and grown for 24 h at 37° C.

Periodic samples of 10-200 μL of culture were collected for characterization by bulk fluorescence measurements. FIG. 17B: 4 μL of each overnight culture were added to 196 μL of LB media containing selective antibiotics and grown for 2.5 h at 37° C. 200 mg/mL L-arabinose was added to appropriate conditions at 2.5 h. After another 4 hrs of growth at 37C, 100 μL were sampled for characterization by bulk fluorescence measurements. For all bulk fluorescence measurements: 10-200 μL of sampled culture were transferred to a 96-well plate (Costar) containing 0-190 μL of phosphate buffered saline (PBS). Fluorescence (FL) and optical density (OD) at 600 nm were then measured using a Synergy H1 plate reader (Biotek). The following settings were used: mCherry fluorescence (560 nm excitation, 630 nm emission).

Bulk fluorescence data analysis. On each 96-well block there were two sets of controls; a media blank and *E. coli* Tax1 cells transformed with combination of control plasmids JBL002 and JBL644 (blank cells) and thus not expressing mCherry (Table 8). The block contained three replicates of each control. OD and FL values for each colony were first corrected by subtracting the corresponding mean values of the media blank. The ratio of FL to OD (FL/OD) was then calculated for each well (grown from a single colony) and the mean FL/OD of blank cells was subtracted from each colony's FL/OD value. Three biological replicates were collected from independent transformations, with three colonies characterized per transformation (9 colonies total). Occasional wells were discarded due to poor growth (OD<0.1 at measurement), however, all samples contained at least 7 replicates over the three experiments. Means of FL/OD were calculated over replicates and error bars represent standard deviations (s.d). Fold activation was calculated as FL/OD for each colony grown with 100 ng/mL aTc over the same colony with 0 ng/ml aTc. Means of fold activation were calculated over replicates and error bars represent standard deviations (s.d).

Flow cytometry data collection and analysis for sfGFP fluorescence analysis of stabilized rSFP variants. All flow cytometry experiments were performed in *E. coli* strain TG1 (F'traD36 lacIq Delta (lacZ) M15 pro A+B+/supE Delta (hsdM-mcrB) 5 (rk-mk-McrB-) thi Delta (lac-proAB)). Plasmid combinations were transformed into chemically competent *E. coli* cells, plated on Difco LB+Agar plates containing 100 μg/mL carbenicillin and 34 μg/mL chloramphenicol (see Table S12 for plasmids used in each experiment), and grown overnight at 37° C. Following overnight incubation, plates were left at room temperature for approximately 7 h. Individual colonies were grown overnight in LB, then diluted 1:50 into M9 minimal media. After 6 h, cells were diluted 1:100 in 1x Phosphate Buffered Saline (PBS) containing 2 mg/mL kanamycin. A BD Accuri C6 Plus flow cytometer fitted with a high-throughput sampler was then used to measure sfGFP fluorescence. Measurements were taken for 11 biological replicates collected over two separate experiments on different days.

Flow cytometry data analysis was performed using FlowJo (v10.4.1). Cells were gated by FSC-A and SSC-A, and the same gate was used for all samples prior to calculating the geometric mean fluorescence for each sample. All fluorescence measurements were converted to Molecules of Equivalent Fluorescein (MEFL) using CS&T RUO Beads (BD cat #661414). The average fluorescence (MEFL) over replicates of cells expressing empty plasmids (pJBL001 and pJBL002) was then subtracted from each measured fluorescence value. Robust CV was calculated for each measurement using FlowJo (v10.7.1).

Amorphadiene fermentation. Small-scale batch fermentations were used to evaluate amorphadiene production. Experiments were performed with at least 5 biological replicates over two independent experiments. *E. coli* DH1 cells were transformed with $P_{Trc}$-ADS (subcloned into the pCDF vector), the appropriate MevT-MBIS plasmid, and the $P_{LTetO\text{-}1}$-STAR or $P_{Lux}$-STAR plasmid as appropriate. An inadvertent T303N mutation was present in the MK gene of all MevT-MBIS plasmid variants used in this study. Individual colonies were inoculated into culture tubes containing LB and appropriate antibiotics and incubated at 37° C. for roughly 16 hrs overnight to achieve an approximate OD600 of 3. 125 μL of overnight cells were inoculated into tubes of 4.875 mL supplemented M9 minimal media (1×M9 minimal salts, 1 mM thiamine hydrochloride, 0.2% casamino acids, 2 mM $MgSO_4$, 0.1 mM $CaCl_2$)) with 1% glucose and a 10% dodecane overlay to capture amorphadiene. Cultures were induced with 0.5 mM IPTG and 100 ng/mL aTc as appropriate. Tubes were incubated at 37° C. and 250 rpm for 72 hrs. After the fermentations were complete, the cultures were centrifuged to collect the dodecane overlay. These overlays were subsequently diluted into hexane for analytical procedures described below.

Small-scale "Hungate" fermentation. Small-scale fermentation assays were used to quantify oxygenated taxanes and taxadiene production in *E. coli* Tax1 or Tax1-QS. Experiments were performed with six biological replicates collected over three independent experiments (FIG. 20C) or four biological replicates collected over two independent experiments (FIG. 21B, 21C, 21D, 21E, 23C). For each experiment, plasmid combinations (Table 8) were transformed into chemically competent *E. coli* cells and plated on LB+Agar (Difco) plates containing appropriate antibiotics (100 μg/mL carbenicillin, 34 μg/mL chloramphenicol and/or 50 μg/mL spectinomycin). Plates were incubated approximately 17 hrs overnight at 30° C. Individual colonies were inoculated into culture tubes containing LB and appropriate antibiotics and incubated at 30° C. for roughly 16 hrs overnight to achieve an approximate OD600 of 3. For 2 mL batch fermentations, 50 μL of overnight cells were added to 1.95 mL of complete R-media (Tables 12-14) and appropriate antibiotics in glass hungate tubes (ChemGlass). 0.1 mM IPTG was added for induction of the upstream pathway enzymes and p5Trc/p10Trc expression. 16-100 ng/mL aTc was added, as indicated, to induce PLTet0-1-STAR activated rSFPs. A 10% v/v dodecane layer (200 μL) was added in all fermentations. Hungate tubes were sealed with a rubber septum and plastic screwcap (ChemGlass). PrecisionGlide 18G hypodermic needles (BD) were inserted into the rubber septa to allow for gas exchange. Hungate tubes were incubated at 22° C. and 250 rpm for 96 hrs. After the fermentations were completed, the culture was centrifuged to collect the dodecane overlay. This overlay was subsequently diluted into hexane for analytical procedures described below.

Figure 33A:
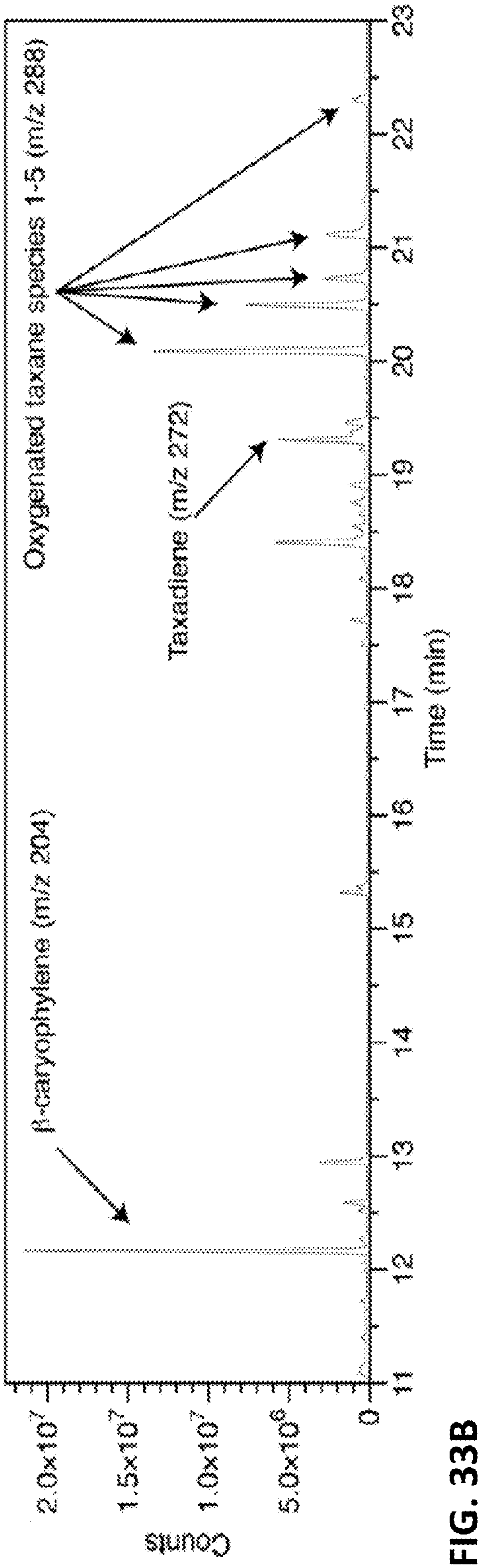
FIG. 33A is an example GC chromatogram for analysis of taxadiene and oxygenated taxane fermentations. Taxadiene and oxygenated taxane peaks were previously described in Biggs et al.[43] of example 4.
Figure 33B:
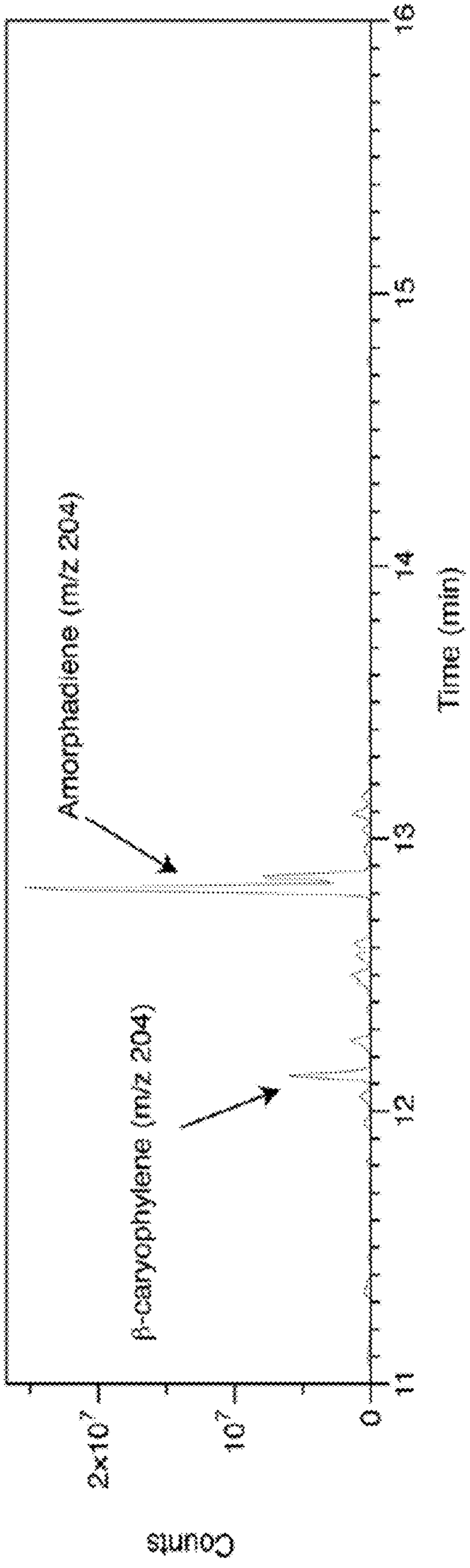
FIG. 33B is an example GC chromatogram for analysis of amorphadiene fermentations.

GC-MS analysis. Dodecane samples collected from batch fermentations were diluted at a ratio of 1:20 (for taxadiene fermentations) or 1:200 (for amorphadiene fermentations) in n-hexane containing 5 mg/L β-caryophyllene. The 5 mg/L β-caryophyllene was utilized as a standard to calculate titer of taxadiene and oxygenated taxanes. GC-MS analysis was performed with an Agilent 7890 GC and Agilent HP-5 ms-UI column (Ultra Inert, 30 m, 0.25 mm, 025 μm, 7 in cage). Helium was utilized as a carrier gas at a flow rate of 1 mL/min and the sample injection volume was 1 μL. The splitless method begins at 50° C. hold for 1 minute followed by a 10° C./min ramp to 200° C. and a final 5° C./min ramp to 270° C. (final ramp excluded for amorphadiene analysis). Mass spectroscopy data was collected for 22.5 minutes with an 11-minute solvent delay. m/z values ranging from 40-500 were scanned with a scan time of 528 ms. MassHunter Workstation Qualitative Analysis software (vB.06.00) was utilized to integrate peaks on the chromatograms and determine their respective mass spectrums (FIG. 33). The ratio of peak area of taxadiene (m/z 272) and amorphadiene (m/z 204) to the standard β-caryophyllene (m/z 204) was used to calculate titer of taxadiene and amorphadiene, while the ratio of the sum of all peaks of oxygenated taxanes (m/z 288) to β-caryophyllene was used to calculate titer of the oxygenated taxanes. Overall taxanes were calculated by summing taxadiene and oxygenated taxane titers for each sample. Means of titers were calculated over replicates and error bars represent s.d.

Abbreviations: rSFP, riboregulated switchable feedback promoter; RBS, ribosomal binding site; STAR, small transcription activating RNA; FPP, farnesyl pyrophosphate; aTc, anhydrotetracycline; HSL, homoserine lactone; IPP, isopentenyl diphosphate, DMAPP, dimethylallyl diphosphate; MEP, methylerythritol phosphate; GGPP, geryanlgeranyl diphosphate G3P, glyceraldehyde-3-phosphate; PYR, pyruvate.

Tables for Example 4

Table 8. Plasmids used in this study. apFAB parts were obtained from a previously published library of genetic parts[15]. Abbreviations are as follows: RBS 1=ribosome binding site variant, PR=tetR promoter[63], $P_{LTei,O1}$=TetR repressible promoter[31], $P_{Lux}$ (BBa_R0062) *=LuxR inducible promoter[51], mCherry=red fluorescent protein, LuxR (BBa_C0062) *=AHL inducible transcription factor[30], tetR=tet repressor protein[31], TrrnB=rmB terminator, BBa_B0015*=B0015 terminator, T500=T500 terminator, dblTerm=dblTerm terminator, PJ2315=BBa_J23115 promoter from the iGEM Registry of Standard Biological Parts (parts.igem.org), CmR=chloramphenicol resistance cassette, AmpR=ampicillin resistance cassette, SpcR=spectinomycin resistance cassette, p15A=p15A origin of replication, ColEl=ColEl origin of replication and CDF=CDF origin of replication.

TABLE 8

| Plasmid # | Plasmid architecture | Name | FIG. |
|---|---|---|---|
| pJBL002 | AmpR - ColE1 origin (Empty vector) | pJBL002 | 15a-c, 16b, 17b, 22b-c, 24-26 |
| pJBL644 | SpcR - pCDF origin (Empty vector) | pJBL644 | 15a-c, 16b, 17b, 22b-c, 24-26 |
| pJBL001 | CmR - p15a origin (Empty Vector) | pJBL001 | 18b, 27 |
| pJBL6654 | $P_R$ - TetR - dblTerm - PLTetO - 1 - STAR 8 - T500 - AmpR - ColE1 origin | $P_{LTetO}$-1-STAR8 | 16b, 17b, 20c, 21b-e, 22c, 25-27, 29-32 |
| pJBL6714 | $P_R$ - TetR - dblTerm - PLTetO - 1 - STAR 3 - T500 - AmpR - ColE1 origin | $P_{LTetO}$-1-STAR3 | 15a-c, 19b, 22b, 24, 28 |
| pJBL5809 | PJ23119 - STAR 8 - T500 - AmpR - ColE1 origin | PJ23119-STAR8 | 17b |
| pJBL6655 | PLux - STAR 8 - T500 - AmpR - ColE1 origin | $P_{Lux}$-STAR8 | 22c, 23c |
| pJBL6715 | PLux - STAR 3 - T500 - AmpR - ColE1 origin | $P_{Lux}$-STAR3 | 22b, 23b |
| pJBL6656 | PgntK - Target 8 - RBS 1 - mCherry - dblTerm - SpcR - pCDF origin | PgntK-TARGET8-mCherry | 16b, 17b, 25-26 |
| pJBL6657 | PompF - Target 8 - RBS 1 - mCherry - dblTerm - SpcR - pCDF origin | PompF-TARGET8-mCherry | 16b, 17b, 22c, 25-26, 30 |
| pJBL6658 | PyeeF - Target 8 - RBS 1 - mCherry - dblTerm - SpcR - pCDF origin | PyeeF-TARGET8-mCherry | 16b, 178b, 25-26 |
| pJBL6659 | PompT - Target 8 - RBS 1 - mCherry - dblTerm - SpcR - pCDF origin | PompT-TARGET8-mCherry | 16b, 17b, 25-26 |
| pJBL6660 | PmetN - Target 8 - RBS 1 - mCherry - dblTerm - SpcR - pCDF origin | PmetN-TARGET8-mCherry | 16b, 17b, 25-26, 30 |
| pJBL6661 | Pb1762 - Target 8 - RBS 1 - mCherry - dblTerm - SpcR - pCDF origin | Pb1762-TARGET8-mCherry | 16b, 17b, 25 |
| pJBL6662 | PcarA - Target 8 - RBS 1 - mCherry - dblTerm - SpcR - pCDF origin | PcarA-TARGET8-mCherry | 16b, 17b, 25 |
| pJBL6663 | PfadL - Target 8 - RBS 1 - mCherry - dblTerm - SpcR - pCDF origin | PfadL-TARGET8-mCherry | 16b, 17b, 25 |
| pJBL6664 | PfecA - Target 8 - RBS 1 - mCherry - dblTerm - SpcR - pCDF origin | PfecA-TARGET8-mCherry | 16b, 17b, 25 |
| pJBL6665 | PuraA - Target 8 - RBS 1 - mCherry - dblTerm - SpcR - pCDF origin | PuraA-TARGET8-mCherry | 16b, 17b, 25 |
| pJBL6666 | PgrxA - Target 8 - RBS 1 - mCherry - dblTerm - SpcR - pCDF origin | PgrxA-TARGET8-mCherry | 16b, 17b, 25 |

TABLE 8-continued

| Plasmid # | Plasmid architecture | Name | FIG. |
|---|---|---|---|
| pJBL6667 | PmtgA - Target 8 - RBS 1 - mCherry - dblTerm - SpcR - pCDF origin | PmtgA-TARGET8-mCherry | 16b, 17b, 25 |
| pJBL6668 | PybcU - Target 8 - RBS 1 - mCherry - dblTerm - SpcR - pCDF origin | PycbU-TARGET8-mCherry | 16b, 17b, 25 |
| pJBL6669 | PycbS - Target 8 - RBS 1 - mCherry - dblTerm - SpcR - pCDF origin | PycbS-TARGET8-mCherry | 16b, 17b, 25 |
| pJBL6670 | PyhjX - Target 8 - RBS 1 - mCherry - dblTerm - SpcR - pCDF origin | PyhjX-TARGET8-mCherry | 16b, 17b, 25 |
| pJBL6671 | PatoA - Target 8 - RBS 1 - mCherry - dblTerm - SpcR - pCDF origin | PatoA-TARGET8-mCherry | 16b, 17b, 25 |
| pJBL6672 | Pb2970 - Target 8 - RBS 1 - mCherry - dblTerm - SpcR - pCDF origin | Pb2970-TARGET8-mCherry | 16b, 17b, 25 |
| pJBL6673 | PecpD - Target 8 - RBS 1 - mCherry - dblTerm - SpcR - pCDF origin | PecpD-TARGET8-mCherry | 16b, 17b, 25 |
| pJBL6717 | PgadE - Target 3 - RBS 1 - mCherry - dblTerm - SpcR - pCDF origin | PgadE-TARGET3-mCherry | 15a-c, 22b |
| pJBL6718 | PompF - RBS 2 - mCherry - dblTerm - SpcR - pCDF origin | PompF-mCherry | 26 |
| pJBL6719 | PmetN - RBS 2 - mCherry - dblTerm - SpcR - pCDF origin | PmetN-mCherry | 26 |
| pJBL6720 | PyeeF - RBS 2 - mCherry - dblTerm - SpcR - pCDF origin | PyeeF-mCherry | 26 |
| pJBL6721<br>pJBL6733<br>pJBL6734<br>pJBL6735<br>pJBL6736 | DNsp1 - TARGET8 - sfGFP - CmR - SC101, SC101v1, SC101v2, SC101v3, SC101v4 origin | DNsp1-TARGET8-mCherry | 18b, 27 |
| pJBL6722<br>pJBL6737<br>pJBL6738<br>pJBL6739<br>pJBL6740 | TAIL1 - UPsp1 - TARGET - sfGFP - CmR - SC101, SC101v1, SC101v2, SC101v3, SC101v4 origin | Pstabilized-TARGET8-mCherry | 18b, 27 |
| pJBL6674 | PgntK - Target 8 - RBS 1 - CYP725A4-tcCPR - dblTerm - CmR - p15a origin | PgntK-TARGET8-P450 | 20c, 32 |
| pJBL6675 | PompF - Target 8 - RBS 1 - CYP725A4-tcCPR - dblTerm - CmR - P15a origin | PompF-TARGET8-P450 | 20c, 21c, 21e, 23c, 29, 31-32 |
| pJBL6676 | PyeeF - Target 8 - RBS 1 - CYP725A4-tcCPR - dblTerm - CmR - P15a origin | PyeeF-TARGET8-P450 | 20c, 29 |
| pJBL6677 | PompT - Target 8 - RBS 1 - CYP725A4-tcCPR - dblTerm - CmR - P15a origin | PompT-TARGET8-P450 | 20c, 29 |
| pJBL6678 | PmetN - Target 8 - RBS 1 - CYP725A4-tcCPR - dblTerm - CmR - P15a origin | PmetN-TARGET8-P450 | 20c, 21b, 21d, 29, 31-32 |
| pJBL6679 | Pb1762 - Target 8 - RBS 1 - CYP725A4-tcCPR - dblTerm - CmR - P15a origin | Pb1762-TARGET8-P450 | 20c, 29 |
| pJBL6680 | PcarA - Target 8 - RBS 1 - CYP725A4-tcCPR - dblTerm - CmR - P15a origin | PcarA-TARGET8-P450 | 20c, 29 |
| pJBL6681 | PfadL - Target 8 - RBS 1 - CYP725A4-tcCPR - dblTerm - CmR - P15a origin | PfadL-TARGET8-P450 | 29 |
| pJBL6682 | PfecA - Target 8 - RBS 1 - CYP725A4-tcCPR - dblTerm - CmR - P15a origin | PfecA-TARGET8-P450 | 29 |
| pJBL6683 | PuraA - Target 8 - RBS 1 - CYP725A4-tcCPR - dblTerm - CmR - P15a origin | PuraA-TARGET8-P450 | 29 |
| pJBL6684 | PgrxA - Target 8 - RBS 1 - CYP725A4-tcCPR - dblTerm - CmR - P15a origin | PgrxA-TARGET8-P450 | 29 |
| pJBL6685 | PmtgA - Target 8 - RBS 1 - CYP725A4-tcCPR - dblTerm - CmR - P15a origin | PmtgA-TARGET8-P450 | 29 |

TABLE 8-continued

| Plasmid # | Plasmid architecture | Name | FIG. |
|---|---|---|---|
| pJBL6686 | PybcU - Target 8 - RBS 1 - CYP725A4-tcCPR - dblTerm - CmR - P15a origin | PybcU-TARGET8-P450 | 29 |
| pJBL6687 | PycbS - Target 8 - RBS 1 - CYP725A4-tcCPR - dblTerm - CmR - P15a origin | PycbS-P450 | 29 |
| pJBL6688 | PyhjX - Target 8 - RBS 1 - CYP725A4-tcCPR - dblTerm - CmR - P15a origin | PyhjX-TARGET8-P450 | 29 |
| pJBL6689 | PatoA - Target 8 - RBS 1 - CYP725A4-tcCPR - dblTerm - CmR - P15a origin | PatoA-P450 | 29 |
| pJBL6690 | PecpD - Target 8 - RBS 1 - CYP725A4-tcCPR - dblTerm - CmR - P15a origin | PecpD-TARGET8-P450 | 29 |
| pJBL6723 | PapFAB305 - Target 8 - RBS 1 - CYP725A4-tcCPR - dblTerm - CmR - P15a origin | PapFAB305-TARGET8-mCherry | 31 |
| pJBL6724 | PapFAB339 - Target 8 - RBS 1 - CYP725A4-tcCPR - dblTerm - CmR - P15a origin | PapFAB339-TARGET8-mCherry | 31 |
| pJBL6725 | PapFAB45 - Target 8 - RBS 1 - CYP725A4-tcCPR - dblTerm - CmR - P15a origin | PapFAB45-TARGET8-mCherry | 31 |
| pJBL6726 | PompF - RBS 2 - CYP725A4-tcCPR - dblTerm - CmR - P15a origin | PompF-P450 | 31 |
| pJBL6727 | PmetN - RBS 2 - CYP725A4-tcCPR - dblTerm - CmR - P15a origin | PmetN-P450 | 31 |
| N/A | PLacUV5 - MevT - MBIS - CmR - P15a origin[19] | pMevT-MBIS | 15c, 24 |
| pJBL6728 | PLacUV5 - MevT - MBIS □MPD - CmR - P15a origin[19] | pMevT-MBIS □MPD | 15c, 24 |
| N/A | PgadE - MevT - MBIS - P15a origin[19] | PgadE-MevT-MBIS | 19b |
| N/A | PTrc - ADS - pCDF origin[19] | PTrc-ADS | 19b, 23b, 28 |
| pJBL6729 | PgadE - Target 3 - MevT - MBIS - P15a origin | PgadE-TARGET3-MevT-MBIS | 19b, 23b, 28 |
| pJBL6730 | PapFAB45 - TARGET 3 - MevT - MBIS - P15a origin | PapFAB45-TARGET3-MevT-MBIS | 28b |
| pJBL6731 | TAIL1 - UPsp1 - TARGET8 - MevT - MBIS - P15a origin | Pstabilized-TARGET8-MevT-MBIS | 28d |
| N/A | PTrc - CYP725A4-tcCPR - rrnB - SpcR - SC101 origin | P5Trc | 20c |
| N/A | PTrc - CYP725A4-tcCPR - rrnB - CmR - p15a origin | P10Trc | 20c |
| pJBL6691 | apFAB346 - apFAB682 - Esal - - LuxR - dblTerm - SpcR - SC101* | pQS | N/A |
| pJBL6692 | PJ23115 - Target 8 - RBS 1 - mCherry - dblTerm - SpcR - pCDF origin | PJ23115-TARGET8-mCherry | 30 |
| pJBL6693 | PapFAB45 - Target 8 - RBS 1 - mCherry - dblTerm - SpcR - pCDF origin | PapFAB45-TARGET8-mCherry | 31 |
| pJBL6693 | PapFAB339 - Target 8 - RBS 1 - mCherry - dblTerm - SpcR - pCDF origin | PapFAB339-TARGET8-mCherry | 31 |
| pJBL6693 | PapFAB305 - Target 8 - RBS 1 - mCherry - dblTerm - SpcR - pCDF origin | PapFAB305-TARGET8-mCherry | 31 |
| pJBL6732 | PapFAB339 - Target 3 - RBS 1 - mCherry - dblTerm - SpcR - pCDF origin | PapFAB339-TARGET3-mCherry | 24 |
| N/A | PBAD - CjPglB - AmpR - pBR322 origin[32] | PBAD-CjPglB | 17b |

Table 9. Examples of DNA plasmid sequences used in Example 4 (abbreviations are described above in Table 8).

TABLE 9

| Name | Sequence |
|---|---|
| PLTetO-1-STAR8 | GAATTCTAAAGATCTTTTTCTCTATCACTGATAGGGAGTGGTAAAATAA CTCTATCAACGATAGAGTGTCAACAAAAATTAGGAATTAATGATGTCGA |

TABLE 9-continued

| Name | Sequence |
|---|---|
| ($P_R$-TetR-dblTerm-PLTetO-1-STAR8-T500) | GATTAGATAAAAGTAAAGTGATTAACAGCGCATTAGAGGTGCTTAATG AGGTCGGAATCGAAGGTTTAACAACCCGTAAACTCGCCCAGAAGCTA GGTGTAGAGCAGCCTACATTGTATTGGCATGTAAAAAATAAGCGGGCT TTGCTCGACGCCTTAGCCATTGAGATGTTAGATAGGCACCATACTCAC TTTTGCCCTTTAGAAGGGGAAAGCTGGCAAGATTTTTTACGTAATAAC GCTAAAAGTTTTAGATGTGCTTTACTAAGTCATCGCGATGGAGCAAAA GTACATTTAGGTACACGGCCTACAGAAAAACAGTATGAAACTCTCGAA AATCAATTAGCCTTTTTATGCCAACAAGGTTTTTCACTAGAGAATGCAT TATATGCACTCAGCGCTGTGGGGCATTTTACTTTAGGTTGCGTATTGG AAGATCAAGAGCATCAAGTCGGTAAAGAAGAAAGGGAAACACCTACTA CTGATAGTATGCCGCCATTATTACGACAAGCTATCGAATTATTTGATCA CCAAGGTGGAGAGGCAGCCTTCTTATTCGGCCTTGAATTGATCATATG GGGATTAGAAAAAGAAGTTAAATGTGAAAGTGGGTCTTAATAACACTG ATAGTGCTAGTGTAGATCACTACTAGAGCCAGGCATCAAATAAAACGA AAGGCTCAGTCGAAAGACTGGGCCTTTCGTTTTATGTGTTGTTTGTCG GTGAACGCTCTACTAGAGAGTCACACTGGCTCACCTTCGGGTGGGCC TTTCTGCGTATATACTAGAGTCCCTATCAGTGATAGAGATTGACATC CCTATCAGTGATAGAGATACTGAGCACTGAACTGTATACATTCCCCGC AGGATAAGAGTAAGTGAGAGTAGGTAGAGATTGAGGATGGGGATCTC AAAGCCCGCCGAAAGGCGGGCTTTTTTTTGGATCCTTACTCGAGTCTA GACTGCAGGCTTCCTC (SEQ ID NO: 1) |
| PLTetO-1-STAR8 ($P_R$-TetR-dblTerm-PLTetO-1-STAR3-T500) | GAATTCTAAAGATCTTTTTCTCTATCACTGATAGGGAGTGGTAAAATAA CTCTATCAACGATAGAGTGTCAACAAAAATTAGGAATTAATGATGTCGA GATTAGATAAAAGTAAAGTGATTAAGAGCGCATTAGAGCTGCTTAATG AGGTCGGAATCGAAGGTTTAACAACCCGTAAACTCGCCCAGAAGCTA GGTGTAGAGCAGCCTACATTGTATTGGCATGTAAAAAATAAGGGGGGT TTGCTCGACGCCTTAGCCATTGAGATGTTAGATAGGGAGGATACTCAC TTTTGCCCTTTAGAAGGGGAAAGCTGGCAAGATTTTTTACGTAATAAC GCTAAAAGTTTTAGATGTGCTTTACTAAGTCATCGCGATGGAGCAAAA GTACATTTAGGTACACGGCCTACAGAAAAACAGTATGAAACTCTCGAA AATCAATTAGCCTTTTTATGCCAACAAGGTTTTTCACTAGAGAATGCAT TATATGCACTCAGGGCTGTGGGGGATTTTACTTTAGGTTGCGTATTGG AAGATCAAGAGCATCAAGTCGCTAAAGAAGAAAGGGAAACACCTACTA CTGATAGTATGCCGCCATTATTACGACAAGCTATCGAATTATTTGATCA CCAAGGTGCAGAGCCAGCCTTCTTATTCGGCCTTGAATTGATCATATG CGGATTAGAAAACAACTTAAATGTGAAAGTGGGTCTTAATAACACTG ATAGTGCTAGTGTAGATCACTACTAGAGCCAGCCATCAAATAAAAGGA AAGGCTCAGTCGAAAGACTGGGCCTTTCGTTTTATGTGTTGTTTGTCG GTGAACGCTCTCTACTAGAGTCACACTGGCTCACCTTGGGGTGGGCC TTTCTGCGTTTATATACTAGAGTCCCTATCAGTGATAGAGATTGACATC CCTATCAGTGATAGAGATACTGAGCACTGAACTGTATACATTCCCCGC AAAGACACAGGACAGGACAGGCAGATAGATAGGATAGAGGGGATCTC AAAGCCCGCCGAAAGGGGGGCTTTTTTTTGGATCCTTACTCGAGTCTA GACTGCAGGCTTCCTC (SEQ ID NO: 29) |
| PLux-STAR (PLux-STAR8-T500) | CTAAAGATCTATATACTAGAGACCTGTAGGATCGTACAGGTTTACGCA AGAAAATGGTTTGTTATAGTCGAATAAATGAACTGTATACATTCCCCGC AGGATAAGAGTAAGTGAGAGTAGGTAGAGATTGAGGATGGGGATCTC AAAGCCCGCCGAAAGGGGGCTTTTTTTTGGATCCTTACTCGAGTCTA GACTGCAGGCTTCCTC (SEQ ID NO: 2) |
| PLux-STAR (PLux-STAR3-T500) | CTAAAGATCTATATACTAGAGACCTGTAGGATCGTACAGGTTTACGCA AGAAAATGGTTTGTTATAGTCGAATAAATGAACTGTATACATTCCCCGC AAAGACACAGGACAGGCACAGGCAGATAGATAGGATAGAGGGGATCTC AAAGCCCGCCGAAAGGGGGGCTTTTTTTTGGATCCTTACTCGAGTCTA GACTGCAGGCTTCCTC (SEQ ID NO: 30) |
| Example rSFP Plasmid (PompF-TARGET 8-RBS 1-mCherry-dblTerM) | CGATCATCCTGTTACGGAATATTACATTGCAACATTTACGCGCAAAAA CTAATCCGCATTCTTATTGCGGATTAGTTTTTTCTTAGCTAATAGCACA ATTTTCATACTATTTTTTGGCATTCTGGATGTCTGAAAGAAGATTTTGT GCCAGGTCGATAAAGTTTCCATCAGAAACAAAATTTCCGTTTAGTTAAT TTAAATATAAGGAAATCATATAAATAGATTAAAATTGCTGTAAATATCAT CACGTCTCTATGGAAATATGACGGTGTTCACAAAGTTCCTTAAATTTTA CTTTTGGTTACATATTTTTTCTTTTTGAAACCAAATCTTTATCTTTGTAG CACTTTCACGGTAGCGAAACGTTAGTTTGAATGGAAAGATGCCTGCAG ACACATAAAGACACCAAACTCTCATCAATAGTTCCGTAAATTTTTATTG ACAGAACTTATTGAGGGCAGTGGCAGGTGTCATAAAAAAAAACCATGAG GGTAATAAATACCATCCTCAATCTCTACCTACTCTCACTTACTCTTATC CTGCGGGGAATGTATACAGTTCATGTATATATTCCCCGCTTTTTTTTTG GATCTAGGAGGAAGGATCTATGGCGAGTAGCGAAGACGTTATCAAAG AGTTCATGCGTTTCAAAGTTCGTATGGAAGGTTCCGTTAACGGTCACG AGTTCGAAATCGAAGGTGAAGGTGAAGGTCGTCCGTACGAAGGTACC CAGACCGCTAAACTGAAAGTTACCAAAGGTGGTCCGCTGCCGTTCGC TTGGGACATCCTGTCCCCGCAGTTCCAGTACGGTTCCAAAGCTTACGT TAAACACCCGGCTGACATCCCGGACTACCTGAAACTGTCCTTCCCGG AAGGTTTCAAATGGGAACGTGTTATGAACTTCGAAGACGGTGGTGTTG TTACCGTTACCCAGGACTCCTCCCTGCAAGACGGTGAGTTCATCTACA |

TABLE 9-continued

| Name | Sequence |
|---|---|
| | AAGTTAAACTGCGTGGTACCAACTTCCCGTCCGACGGTCCGGTTATG<br>CAGAAAAAAACCATGGGTTGGGAAGCTTCCACCGAACGTATGTACCC<br>GGAAGACGGTGCTCTGAAAGGTGAAATCAAAATGCGTCTGAAACTGA<br>AAGACGGTGGTCACTACGACGCTGAAGTTAAAACCACCTACATGGCT<br>AAAAAACCGGTTCAGCTGCCGGGTGCTTACAAAACCGACATCAAACT<br>GGACATCACCTCCCACAACGAAGACTACACCATCGTTGAACAGTACG<br>AACGTGCTGAAGGTCGTCACTCCACCGGTGCTTAAGGATCCAAACTC<br>GAGTAAGGATCTCCAGGCATCAAATAAAACGAAAGGCTCAGTCGAAA<br>GACTGGGCCTTTCGTTTTATCTGTTGTTTGTCGGTGAACGCTCTCTAC<br>TAGAGTCACACTGGCTCACCTTCGGGTGGGCCTTTCTGCGTTTATA<br>(SEQ ID NO: 3) |
| Example rSFP Plasmid (PgadE-TARGET 3-RBS 1-mCherry-dblTerm) | TTAATACTCTCTCCGCTACGCAGTGTTGTAGATCAATTGCGCACTATC<br>ATTGAAATAATTACCTGCTAGTGATTATTTCAACCTACTGAATTTCATCT<br>AATTTTTTTCACTCTATGGCAAATTAGCCATTTCAAACATTATCATGGCT<br>GATATTTTCCGTAGTCAGGTTTAATGTTTTAAAAGTGCTGTGGGAAAGT<br>GAACAAAGAGTTCCGTAAGCGTTGATGCTATGGGGGGTTAAATAAGTA<br>ATCCGGETTCATTTTTTTGCAACTGGCGTTGATTACATTGCATAAATAT<br>CCGTGTCTCCAGACGCTATATAAAAACCTGAAGACATGAATGCGTTAT<br>TTACTCAGGTAATTTCAATGCGTTAAAAGAAAGCTGGCAATCCAATTG<br>CCAGCTTAAGTCGAAACAAGGAGACTCGATATTTAAATCGGATTACAT<br>TTTAACTTTAGTAATATTCTTCAGAGATCACAAACTGGTTATTGATAACT<br>TATTCTTGGGCAGTAATCCGCAAACGTTAACTTTTTGTTTGCTATTTAC<br>AAGCTGATAACAACCAGGAATCTTACTTAGGATCAATATATGGAGTGC<br>GTGATGGATAAATCTGAAGTATTGATTAGTGTTAATAGACGTATTAGTT<br>CACGAAGGGTAAAGTTCTTATAGGCGTTTACTATATTGAACAACGATT<br>CGGACAAGGATGTAAATAATGAAAAGGATGACATATTCGAAACGACCT<br>CTATCCTATCTATCTGCCTGTCCTGTCCTGTGTCTTTGCGGGGAATGT<br>ATACAGTTCATGTATATATTCCCCGCTTTTTTTTTTGGATCTAGGAGGAA<br>GGATCTATGGCGAGTAGCGAAGACGTTATCAAAGAGTTCATGCGTTTC<br>AAAGTTCGTATGGAAGGTTCCGTTAACGGTCACGAGTTCGAAATCGAA<br>GGTGAAGGTGAAGGTCGTCCGTACGAAGGTACCCAGACCGCTAAACT<br>GAAAGTTACCAAAGGTGGTCCGCTGCCGTTCGCTTGGGACATCCTGT<br>CCCCGCAGTTCCAGTACGGTTCCAAAGCTTACGTTAAACACCCGGCT<br>GACATCCCGGACTACCTGAAACTGTCCTTCCCGGAAGGTTTCAAATG<br>GGAACGTGTTATGAACTTCGAAGACGGTGGTGTTGTTACCGTTACCCA<br>GGACTCCTCCCTGCAAGACGGTGAGTTCATCTACAAAGTTAAACTGCG<br>TGGTACCAACTTCCCGTCCGACGGTCCGGTTATGCAGAAAAAAACCAT<br>GGGTTGGGAAGCTTCCACCGAACGTATGTACCCGGAAGACGGTGCTC<br>TGAAAGGTGAAATCAAAATGCGTCTGAAACTGAAAGACGGTGGTCACT<br>ACGACGCTGAAGTTAAAACCACCTACATGGCTAAAAAACCGGTTCAGC<br>TGCCGGGTGCTTACAAAACCGACATCAAACTGGACATCACCTCCCAC<br>AACGAAGACTACACCATCGTTGAACAGTACGAACGTGCTGAAGGTCG<br>TCACTCCACCGGTGCTTAAGGATCCAAACTCGAGTAAGGATCTCCAG<br>GCATCAAATAAAACGAAAGGCTCAGTCGAAAGACTGGCCTTTCGTTT<br>TATCTCTTGTTTGTCGGTGAACGCTCTCTACTAGAGTCACACTGGCTC<br>ACCTTCCGGTGGCGCTTTCTGCGTTTATA (SEC TD NC: 31) |
| CYP725A4/ tcCPR fusion | ATGGCTCTGTTATTAGCAGTTTTTTTAGCATCGCTTTGAGTGCAATTG<br>CCGGGATCTTGCTGTTGCTCCTGCTGTTTCGCTCGAAACGTCATAGTA<br>GCCTGAAATTACCTCCGGGCAAACTGGGCATTCCGTTTATCGGTGAG<br>TCCTTTATTTTTTTGCGCGCGCTGAGGAGCAATTCTCTGGAACAGTTC<br>TTTGATGAACGTGTGAAGAAGTTCGGCCTGGTATTTAAAACGTCCCTT<br>ATCGGTCACCCGACGGTTGTCCTGTGCGGGCCCGCAGGTAATCGCCT<br>CATCCTGAGCAACGAAGAAAAGCTGGTACAGATGTCCTGGCCGGCGC<br>AGTTTATGAAGCTGATGGGAGAGAACTCAGTTGCGACCCGCCGTGGT<br>GAAGATCACATTGTTATGCGCTCCGCGTTGGCAGGCTTTTTCGGCCC<br>GGGAGCTCTGCAATCCTATATCGGCAAGATGAACACGGAAATCCAAA<br>GCCATATTAATGAAAAGTGGAAAGGGAAGGACGAGGTTAATGTCTTAC<br>CCCTGGTGCGGGAACTGGTTTTTAACATCAGCGCTATTCTGTTCTTTA<br>ACATTTACGATAAGCAGGAACAAGACCGTCTGCACAAGTTGTTAGAAA<br>CCATTCTGGTAGGCTCGTTTGCCTTACCAATTGATTTACCGGGTTTCG<br>GGTTTCACCGCGCTTTACAAGGTCGTGCAAAACTCAATAAAATCATGT<br>TGTCGCTTATTAAAAAACGTAAAGAGGACTTACAGTCGGGATCGGCCA<br>CCGCGACGCAGGACCTGTTGTCTGTGCTTCTGACTTTCCGTGATGATA<br>AGGGCACCCCGTTAACCAATGACGAAATCCTGGACAACTTTAGCTCAC<br>TGCTTCACGCCTCTTACGACACCACGACTAGTCCAATGGCTCTGATTT<br>TCAAATTACTGTCAAGTAACCCTGAATGCTATCAGAAAGTCGTGCAAG<br>AGCAACTCGAGATTCTGAGCAATAAGGAAGAAGGTGAAGAAATTACCT<br>GGAAAGATCTTAAGGCCATGAAATACACGTGGCAGGTTGCGCAGGAG<br>ACACTTCGCATGTTTCCACCGGTGTTCGGGACCTTCCGCAAAGCGAT<br>CACGGATATTCAGTATGACGGATACACAATCCCGAAAGGTTGGAAACT<br>GTTGTGGACTACCTATAGCACTCATCCTAAGGACCTTTACTTCAACGA<br>ACCGGAGAAATTTATGCCTAGTCGTTTCGATCAGGAAGGCAAACATGT<br>TGCGCCCTATACCTTCCTGCCCTTTGGAGGCGGTCAGCGGAGTTGTG<br>TGGGTTGGGAGTTCTCTAAGATGGAGATTCTCCTCTTCGTGCATCATT<br>TCGTGAAAACATTTTCGAGCTATACCCCGGTCGATCCCGATGAAAAAA<br>TTTCCGGCGATCCACTGCCGCCGTTACCGAGCAAAGGGTTTTCAATC<br>AAACTGTTCCCTCGTCCGggcagcaccggatccCGCCGTGGTGGAAGTGAT |

TABLE 9-continued

| Name | Sequence |
|---|---|
| | ACACAGAAGCCCGCCGTACGTCCCACACCTCTTGTTAAAGAAGAGGA<br>CGAAGAAGAAGAAGATGATAGCGCCAAGAAAAAGGTCACAATATTTTT<br>TGGCACCCAGACCGGCACCGCCGAAGGTTTCGCAAAGGCCTTAGCT<br>GAGGAAGCAAAGGCACGTTATGAAAAGGCGGTATTTAAAGTCGTGGA<br>TTTGGATAACTATGCAGCGGATGACGAACAGTACGAAGAGAAGTTGAA<br>AAAGGAAAAGCTAGCGTTCTTCATGCTCGCCACCTACGGTGACGGCG<br>AACCGACTGATAATGCCGCTCGCTTTTATAAATGGTTTCTCGAGGGTA<br>AAGAGCGCGAGCCATGGTTGTCAGATCTGACTTATGGCGTGTTTGGC<br>TTAGGTAACCGTCAGTATGAACACTTTAACAAGGTCGCGAAAGCGGTG<br>GACGAAGTGCTCATTGAACAAGGCGCCAAACGTCTGGTACCGGTAGG<br>GCTTGGTGATGATGATCAGTGCATTGAGGACGACTTCACTGCCTGGA<br>GAGAACAAGTGTGGCCTGAGCTGGATCAGCTCTTACGTGATGAAGAT<br>GACGAGCCGACGTCTGCGACCCCGTACACGGCGGCTATTCCAGAATA<br>CCGGGTGGAAATCTACGACTCAGTAGTGTCGGTCTATGAGGAAACCC<br>ATGCGCTGAAACAAAATGGACAAGCCGTATACGATATCCACCACCCGT<br>GTCGCAGCAACGTGGCAGTACGTCGTGAGCTGCATACCCCGCTGTCG<br>GATCGTAGTTGTATTCATCTGGAATTCGATATTAGTGATACTGGGTTAA<br>TCTATGAGACGGGCGACCACGTTGGAGTTCATACCGAGAATTCAATTG<br>AAACCGTGGAAGAAGCAGCTAAACTGTTAGGTTACCAACTGGATACAA<br>TCTTCAGCGTGCATGGGGACAAGGAAGATGGAACACCATTGGGGG<br>GAGTAGCCTGCCACCGCCGTTTCCGGGGCCCTGCACGCTGCGGACG<br>GCGCTGGCACGTTACGCGGACCTGCTGAACCCTCCGCGCAAAGCCG<br>CCTTCCTGGCACTGGCCGCACACGCGTCAGATCCGGCTGAAGCTGAA<br>CGCCTTAAATTTCTCAGTTCTCCAGCCGGAAAAGACGAATACTCACAG<br>TGGGTCACTGCGTCCCAACGCAGCCTCCTCGAGATTATGGCCGAATT<br>CCCCAGCGCGAAACCGCCGCTGGGAGTGTTTTTCGCCGCAATAGCG<br>CCGCGCTTGCAACCTAGGTATTATAGCATCTCCTCCTCCCCGCGTTTC<br>GCGCCGTCTCGTATCCATGTAACGTGCGCGCTGGTCTATGGTCCTAG<br>CCCTACGGGGCGTATTCATAAAGGTGTGTGCAGCAACTGGATGAAGA<br>ATTCTTTGCCCTCCGAAGAAACCCACGATTGCAGCTGGGCACCGGTC<br>TTTGTGCGCCAGTCAAACTTTAAACTGCCCGCCGATTCGACGACGCC<br>AATCGTGATGGTTGGACCTGGAACCGGCTTCGCTCCATTTCGCGGCT<br>TCCTTCAGGAACGCGCAAAACTGCAGGAAGCGGGCGAAAAATTGGGC<br>CCGGCAGTGCTGTTTTTTGGGTGCCGCAACCGCCAGATGGATTACAT<br>CTATGAAGATGAGCTTAAGGGTTACGTTGAAAAAGGTATTCTGACGAA<br>TCTGATCGTTGCATTTTCACGAGAAGGCGCCACCAAAGAGTATGTTCA<br>GCACAAGATGTTAGAGAAAGCCTCCGACACGTGGTCTTTAATCGCCC<br>AGGGTGGTTATCTGTATGTTTGCGGTGATGCGAAGGGTATGGCCAGA<br>GACGTACATCGCACCCTGCATACAATCGTTCAGGAACAAGAATCCGTA<br>GACTCGTCAAAAGCGGAGTTTTTAGTCAAAAAGCTGCAAATGGATGGA<br>CGCTACTTACGGGATATTTGGTAA (SEQ ID NO: 32) |
| (PgadE-TARGET 3-MevT-MBIS) | TTAATACTCTCTCCGCTACGCAGTGTTGTAGATGAATTGCGCACTATC<br>ATTGAAATAATTACCTGCTAGTGATTATTTCAACCTACTGAATTTCATCT<br>AATTTTTTTCACTCTATGGCAAATTAGCCATTTCAAACATTATCATGGCT<br>GATATTTTCCGTAGTCAGGTTTAATGTTTTAAAAGTGCTGTGGGAAAGT<br>GAACAAAGAGTTCCGTAAGCGTTGATGCTATGGGGGGTTAAATAAGTA<br>ATCGGGGTTCATTTTTTTGCAACTGGCGTTGATTACATTGCATAAATAT<br>CCGTGTCTCCAGACGCTATATTAAAAAGCTGAAGACATGAATGGGTTAT<br>TTACTCAGGTAATTTCAATGCGTTAAAAGAAAGCTGGCAATCCAATTG<br>CCAGCTTAAGTCGAAACAAGGAGACTCGATATTTAAATCGGATTACAT<br>TTTAACTTTAGTAATATTCTTCAGAGACACAAACTGGTTATTGATAACT<br>TATTCTTGGGCAGTAATCCGCAAACGTTAACTTTTTGTTTGCTATTTAC<br>AAGCTGATAACAACCAGGAATCTTACTTAGGATCAATATATGGAGTGC<br>GTGATGGATAAATCTGAAGTATTGATTAGTGTTAATAGACGTATTAGTT<br>CACGAAGGCTAAAGTTCTTATAGGCGTTTACTATATTGAACAACGATT<br>CGGACAAGGATGTAAATAATGAAAAGGATGACATATTCGAAACGACCT<br>CTATCCTATCTATCTGCCTGTCCTGTCCTGTGTCTTTGGGGGGAATGT<br>ATACAGTTCATGTATATATTCCCCGCTTTTTTTTTGGATGTTAGGAGGA<br>ATATAAAATGAAAAATTGTGTCATCGTCAGTGGGGTACGTACTGCTAT<br>GGGTAGTTTTAACCGTTCACTCGCTTCCACCAGCCGGATCGAGGTGC<br>GGGCGACAGTAATTAAAGCCGCCATTGAACGTGCAAAAATCGATTCAC<br>AACACGTTGATGAAGTGATTATGGGTAACGTGTTACAAGGGGGGCTG<br>GGGGAAAATGGGGGGGGTCAGGCACTGTTAAAAAGGGGGCTGGGAG<br>AAACGGTGTGCGGATTCACGCTCAATAAAGTATGTGGTTCGGGTCTTA<br>AAAGTGTGGCGCTTGCCGCCCAGGCCATTCAGGCAGGTCAGGCGGA<br>GAGGATTGTGGGGGGGGGTATGGAAAATATGAGTTTAGGCCCCTACT<br>TACTCGATGCAAAAGCACGCTCTGGTTATCGTCTTGGAGACGGACAG<br>GTTTATGACGTAATCCTGCGCGATGGGCTGATGTGGGCCACCGATGG<br>TTATCATATGGGGATTACCCCCGAAAACGTGGCTAAAGAGTACGGAAT<br>TACCCGTGAAATGCAGGATGAACTGGCGCTAGATTCACAGCGTAAAG<br>CGGCAGCGGCAATTGAGTCCGGTGCTTTTACAGGGGAAATCGTCGCC<br>GTAAATGTTGTCACTCGAAAGAAAACCTTCGTCTTCAGTCAAGACGAG<br>TTCCCGAAAGCGAACTCAACGGCTGAAGCGTTAGGTGCATTGCGCCC<br>GGCCTTCGATAAAGCAGGAACAGTCACCGCTGGGAACGCGTCTGGTA<br>TTAACGACGGTGCTGCCGCTCTGGTGATTATGGAAGAATGTGGGGCG<br>CTGGGAGCAGGCCTTACCCCCGTCGCTCGCATTAAAAGTTATGCCAC<br>CGGTGGCGTGCCCCCCGCATTGATGGGTATGGGGCCAGTACCTGCC |

TABLE 9-continued

| Name | Sequence |
|---|---|
| | ACGGAAAAAGCGTTACAACTGGGGGGGGTGCAACTGGGGGATATTGA |
| | TCTCATTGAGGCTAATGAAGCATTTGCTGCACAGTTCCTTGGGGTTGG |
| | GAAAAACCTGGGCTTTGATTCTGAGAAAGTGAATGTCAACGGCGGGG |
| | CCATGGCGCTCGGGCATCCTATCGGTCGGAGTGGTCCTCGTATTCTG |
| | GTCACACTATTACATGCCATGCAGGCACGCGATAAAACGCTGGGGCT |
| | GGCAACACTGTGCATTGGGGGGGGTCAGGGAATTGCGATGGTGATTG |
| | AACGGTTGAATTGAGGATCTTGAATTAAGGAGGACAGCTAAATGAAAC |
| | TCTCAACTAAACTTTGTTGGTGTGGTATTAAAGGAAGACTTAGGCCGC |
| | AAAAGCAACAACAATTACACAATACAAACTTGCAAATGACTGAACTAAA |
| | AAAAGAAAAGACCGCTGAACAAAAAACCAGACGTCAAAATGTCGGTAT |
| | TAAAGGTATCCAAATTTACATCCCAACTCAATGTGTCAACCAATCTGAG |
| | CTAGAGAAATTTGATGGCGTTTCTCAAGGTAAATACACAATTGGTCTG |
| | GGCCAAACCAACATGTCTTTTGTCAATGACAGAGAAGATATCTACTCG |
| | ATGTCCCTAACTGTTTTGTCTAAGTTGATCAAGAGTTAGAACATGGACA |
| | CGAACAAAATTCGTAGATTAGAAGTCGGTAGTGAAAGTGTGATTGACA |
| | AGTCCAAGTGTGTCAAGTGTGTGTTGATGCAATTGTTTGGTGAAAAGA |
| | CTGACGTCGAAGGTATTGACACGCTTAATGCCTGTTACGGTGGTACCA |
| | ACGGGTTGTTCAACTCTTTGAACTGGATTGAATCTAACGCATGGGATG |
| | GTAGAGACGCCATTGTAGTTTGCGGTGATATTGCCATCTACGATAAGG |
| | GTGCCGCAAGACCAACCGGTGGTGCCGGTACTGTTGCTATGTGGATC |
| | GGTCCTGATGCTCCAATTGTATTTGAGTCTGTAAGAGCTTCTTACATG |
| | GAACACGCCTACGATTTTTACAAGCCAGATTTCACCAGCGAATATCCT |
| | TACGTCGATGGTCATTTTTCATTAACTTGTTACGTCAAGGCTCTTGATC |
| | AAGTTTACAAGAGTTATTCGAAGAAGGCTATTTCTAAAGGGTTGGTTA |
| | GCGATCCCGGTGGTTCGGATGCTTTGAAGGTTTTGAAATATTTCGACT |
| | ACAACGTTTTCCATGTTCCAACCTGTAAATTGGTCACAAAATCATAGGG |
| | TAGATTACTATATAAGGATTTGAGACGGAATCCTGAATTGTTCCCAGAA |
| | GTTGACGCCGAATTAGCTACTCGCGATTATGACGAATCTTTAACCGAT |
| | AAGAACATTGAAAAAACTTTTGTTAATGTTGCTAAGCCATTCCACAAAG |
| | AGAGAGTTGGCCAATCTTTGATTGTTCCAACAAACACAGGTAACATGT |
| | ACACCGCATGTGTTTATGCCGCCTTTGCATCTCTATTAAACTATGTTCG |
| | ATGTGAGGACTTACAAGGGAAGCGTGTTGGTTTATTTTGTTAGGGTTC |
| | CGGTTTAGCTGCATCTCTATATTGTTGCAAAATTGTTGGTGACGTCCAA |
| | CATATTATCAAGGAATTAGATATTACTAACAAATTAGCCAAGAGAATCA |
| | CCGAAACTCCAAAGGATTACGAAGCTGCCATCGAATTGAGAGAAAATG |
| | CCCATTTGAAGAAGAACTTCAAACCTCAAGGTTCCATTGAGCATTTGC |
| | AAAGTGGTGTTTACTACTTGACCAACATCGATGACAAATTTAGAAGATC |
| | CTACGATGTTAAAAAATGAGGATGTAAAATAAGGAGGATTACACTATC |
| | GTTTTAAGGAATAAAACAGTCATTTGTGGATGGAAAGTGAAAAGTTTAT |
| | CATCTGCGCAATCGAGCTCATCAGGACCTTCATCATCTAGTGAGGAAG |
| | ATGATTCCGGCGATATTGAAAGCTTGGATAAGAAAATACGTCGTTTAG |
| | AAGAATTAGAAGCATTATTAAGTAGTGGAAATACAAAACAATTGAAGAA |
| | CAAAGAGGTCGCTGCCTTGGTTATTCACGGTAAGTTACCTTTGTAGGC |
| | TTTCGAGAAAAAATTAGGTGATACTACGAGAGGGGTTGCCGTACGTA |
| | GGAAGGCTCTTTCAATTTTGGCAGAAGCTCCTGTATTAGCATCTGATC |
| | GTTTAGCATATAAAAATTATGACTAGGACCGCGTATTTGGCGCTTGTTG |
| | TGAAAATGTTATAGGTTACATGCCTTTGCCCGTTGGTGTTATAGGCCC |
| | CTTGGTTATCGATGGTAGATCTTATCATATACCAATGGCAACTACAGA |
| | GGGTTGTTTGGTAGCTTCTGCCATGCGTGGCTGTAAGGCAATCAATG |
| | CTGGCGGTGGTGCAACAACTGTTTTAACTAAGGATGGTATGACAAGA |
| | GGCCCAGTAGTCCGTTTCCCAACTTTGAAAAGATCCGGTGCGTGTAA |
| | GATATGGTTAGACTCAGAAGAGGGACAAAACGCAATTAAAAAAGCTTT |
| | TAACTCTACATCAAGATTTGCACGTCTGCAACATATTCAAACTTGTCTA |
| | GCAGGAGATTTACTCTTCATGAGATTTAGAACAACTACTGGTGACGCA |
| | ATGGGTATGAATATGATTTCTAAAGGTGTCGAATACTCATTAAAGCAAA |
| | TGGTAGAAGAGTATGGCTCGGAAGATATGGACGTTGTCTCCGTTTCT |
| | GGTAAGTACTGTACGGACAAAAAACCAGCTGCCATCAACTGGATCGAA |
| | GGTCGTGGTAAGAGTGTCGTCGCAGAAGCTACTATTCCTGGTGATGT |
| | TGTCAGAAAAGTGTTAAAAAGTGATGTTTCCGCATTGGTTGAGTTGAA |
| | CATTGCTAAGAATTTGGTTGGATCTGGAATGGCTGGGTCTGTTGGTGG |
| | ATTTAACGCACATGCAGCTAATTTAGTGACAGCTGTTTTCTTGGCATTA |
| | GGACAAGATCCTGCACAAAATGTTGAAAGTTCGAAGTGTATAACATTC |
| | ATGAAAGAAGTGGACGGTGATTTGAGAATTTCCGTATCCATGGCATCG |
| | ATCGAAGTAGGTACCATCGGTGGTGGTACTGTTCTAGAACCACAAGG |
| | TGCCATGTTGGACTTATTAGGTGTAAGAGGCCCGGATGCTACCGCTC |
| | CTGGTACCAAGGCACGTCAATTAGCAAGAATAGTTGCCTGTGCCGTCT |
| | TCGGAGGTGAATTATCCTTATGTGCTGCCCTAGCAGCCGGCCATTTG |
| | GTTCAAAGTCATATGACCCACAACAGGAAACGTGGTGAACGAACAAAA |
| | CCTAACAATTTGGACGCCACTGATATAAATCGTTTGAAAGATGGGTCC |
| | GTCACCTGCATTAAATCCTGAGGATCTAGGAGGTTAATTGGATGTCAT |
| | TACCGTTCTTAACTTCTGCACCGGGAAAGGTTATTATTTTTGGTGAACA |
| | CTCTGCTCTCTACAACAAGCCTGCCGTCGCTGCTAGTGTGTCTGCGT |
| | TGAGAACCTACCTGCTAATAAGCGAGTCATCTGCACCAGATACTATTG |
| | AATTGGACTTCCCGGACATTAGCTTTAATCATAAGTGGTCCATCAATG |
| | ATTTCAATGCCATCACCGAGGATCAAGTAAACTCCCAAAAATTGGCCA |
| | AGGCTCAACAAGCCACCGATGGCTTGTCTCAGGAACTCGTTAGTCTTT |
| | TGGACCCGTTGTTAGCTCAACTATCCGAATCCTTCCACTACCATGCAG |
| | CGTTTTGTTTCCTGTATATGTTTGTTTGCCTATGCCCCCATGCGAAGAA |

TABLE 9-continued

| Name | Sequence |
|---|---|
| | TATTAAGTTTTCTTTAAAGTCTACTTTAGCCATCGGTGGTGGGTTGGGG<br>TCAAGCGCSTCTATTTCTGTATCACTGGGGTTAGCTATCGCCTACTTG<br>GGGGGGTTAATAGGATCTAATGACTTGGAAAAGCTGTCAGAAAACGAT<br>AAGCATATAGTGAATGAATGGGCCTTCATAGGTGAAAAGTGTATTCAC<br>GGTACCCCTTCAGGAATAGATAACGCTGTGGCCACTTATGGTAATGCC<br>CTGCTATTTGAAAAAGACTCACATAATGGAAGAATAAACACAAACAATT<br>TTAAGTTCTTAGATGATTTCGGAGCCATTCCAATGATCGTAACCTATAC<br>TAGGATTCGAAGGTCTACAAAAGACCTTGTTGCTGGCGTTCGTGTGTT<br>GGTCACCGAGAAATTTCCTGAAGTTATGAAGCCAATTCTAGATGCCAT<br>GGGTGAATGTGCCCTACAAGGCTTAGAGATCATGACTAAGTTAAGTAA<br>ATGTAAAGGCACCGATGACGAGGCTGTAGAAACTAATAATGAACTGTA<br>TGAACAACTATTGGAATTGATAAGAATAAATCATGGACTGCTTGTCTCA<br>ATGQGTGTTTCTCATCGTGGATTAGAACTTATTAAAAATCTGAGGGATG<br>ATTTGAGAATTGGCTCCACAAAACTTACCGGTGCTGGTGGGGGGGGT<br>TGCTCTTTGAGTTTGTTACGAAGAGACATTACTGAAGAGCAAATTGACA<br>GCTTCAAAAAGAAATTGCAAGATGATTTTAGTTACGAGACATTTGAAAC<br>AGACTTGGGGGGACTGGCTGCTGTTTGTTAAGCGCAAAAAATTTGAA<br>TAAAGACCTTAAAATCAAATCCCTAGTATTCCAATTATTTGAAAATAAAA<br>CTACCAGAAAGCAACAAATTGACGATCTATTATTGCCAGGAAAGACGA<br>ATTTACCATGGACTTCATAGGGATCTTAAGGAGGATACCCTATGTCAG<br>AGTTGAGAGCCTTCAGTGCCCCAGGGAAAGCGTTACTAGCTGGTGGA<br>TATTTAGTTTTAGATACAAAATATGAAGCATTTGTAGTCGGATTATCGG<br>CAAGAATGCATGGTGTAGCCCATCCTTACGGTTCATTGCAAGGGTCTG<br>ATAAGTTTGAAGTGCGTGTGAAAAGTAAACAATTTAAAGATGGGGAGT<br>GGCTGTACCATATAAGTCCTAAAAGTGGCTTGATTCCTGTTTCGATAG<br>GCGGATCTAAGAACCCTTTCATTGAAAAAGTTATCCGTAAGGTATTTAG<br>CTACTTTAAACCTAACATGGACGACTACTGCAATAGAAACTTGTTCGTT<br>ATTGATATTTTCTCTGATGATGCCTACCATTCTCAGGAGGATAGCGTTA<br>CCGAAGATCGTGGCAACAGAAGATTGAGTTTTCATTCGCACAGAATTG<br>AAGAAGTTCCCAAAACAGGGCTGGGCTCCTCGGCAGGTTTAGTCAçA<br>GTTTTAACTACAGCTTTCGCCTCCTTTTTTGTATCGGACCTCGAAAATA<br>ATGTAGACAAATATAGAGAAGTTATTCATAATTTAGCACAAGTTGGTCA<br>TTGTCAAGCTCAGGGTAAAATTGGAAGGGGGTTTGATGTAGGGGGGG<br>CAGCATATGGATCTATCAGATATAGAAGATTCCCACCCGCATTAATCT<br>CTAATTTGCCAGATATTGGAAGTGCTACTTACGGCAGTAAACTGGCGC<br>ATTTGGTTGATGAAGAAGACTGGAATATTACGATTAAAAGTAACCATTT<br>ACCTTCGGGATTAACTTTATGGATGGGGGATATTAAGAATGCTTGAGA<br>AACAGTAAAACTGGTCCAGAAGGTAAAAAATTGGTATGATTCGCATAT<br>GCCAGAAAGCTTGAAAATATATACAGAACTCGATCATGCAAATTCTAG<br>ATTTATGGATGGACTATCTAAACTAGATCGCTTACACGAGACTCATGA<br>CGATTACAGCGATCAGATATTTGAGTCTCTTGAGAGGAATGACTGTAC<br>CTGTCAAAAGTATCCTGAAATCACAGAAGTTAGAGATGCAGTTGCCAC<br>AATTAGACGTTCCTTTAGAAAAATAACTAAAGAATGTGGTGCCGATATG<br>GAACCTCCCGTACAAACTAGCTTATTGGATGATTGCCAGACCTTAAAA<br>GGAGTTCTTACTTGCTTAATACCTGGTGCTGGTGGTTATGACGCCATT<br>GCAGTGATTACTAAGCAAGATGTTGATCTTAGGGGTCAAACCGCTAAT<br>GACAAAAGATTTTCTAAGGTTCAATGGCTGGATGTAACTCAGGCTGAC<br>TGGGGTGTTAGGAAAGAAAAAGATCCGGAAACTTATCTTGATAAATAG<br>GGATCTAGGAGGATTATGAGATGACCGTTTAGACAGCATCCGTTACCG<br>CACCCGTCAACATCGCAACCCTTAAGTATTGGGGGAAAAGGGACACG<br>AAGTTGAATCTGCCCACCAATTCGTCCATATCAGTGACTTTATCGCAA<br>GATGACCTCAGAACGTTGACCTCTGCGGCTACTGCACCTGAGTTTGA<br>ACGCGACACTTTGTGGTTAAATGGAGAACCACACAGCATCGAGAATGA<br>AAGAACTCAAAATTGTGTGGGCGACCTACGCCAATTAAGAAAGGAAAT<br>GGAATGGAAGGAGGCCTCATTGCCCACATTATGTCAATGGAAACTGGA<br>CATTGTCTCCGAAAATAACTTTCCTACAGCAGCTGGTTTAGCTTCCCTC<br>CGCTGCTGGCTTTGCTGCATTGGTGTCTGCAATTGGTAAGTTATACCA<br>ATTACCACAGTCAACTTCAGAAATATCTAGAATAGCAAGAAAGGGGTC<br>TGCTTCAGCTTGTAGATCGTTGTTTGGGGGATACGTGGCCTGGGAAA<br>TCGGAAAAGCTGAAGATGGTCATGATTCCATGGCAGTACAAATCGGA<br>GACAGCTCTGACTGGCCTCAGATGAAAGCTTGTGTCCTAGTTGTCAG<br>CGATATTAAAAAGGATGTGAGTTCCACTCAGGGTATGCAATTGACCGT<br>GGCAACCTCCGAACTATTTAAAGAAAGAATTGAACATGTCGTACCAAA<br>GAGATTTGAAGTCATGCGTAAAGCCATTGTTGAAAAAGATTTCGCCAG<br>CTTTGCAAAGGAAACAATGATGGATTCCAACTCTTTCCATGCCACATG<br>TTTGGACTCTTTCCCTCCAATATTCTACATGAATGAGACTTCCAAGCGT<br>ATCATGAGTTGGTGCCACACCATTAATCAGTTTTAGGGAGAAACAATC<br>GTTGCATACACGTTTGATGCAGGTCCAAATGCTGTGTTGTACTACTTA<br>GCTGAAAATGAGTCGAAACTCTTTGCATTTATCTATAAATTGTTTGGCT<br>CTGTTCCTGGATGGGAGAAGAAATTTACTACTGAGCAGCTTGAGGCTT<br>TCAACCATCAATTTGAATCATCTAACTTTACTGCACGTGAATTGGATCT<br>TGAGTTGCAAAAGGATGTTGCCAGAGTGATTTTAACTCAAGTCCGTTG<br>AGGCCCACAAGAAACAAAGGAATCTTTGATTGAGGCAAAGACTGGTCT<br>ACCAAAGGAATAAGGATCTAGGAGGTAATGATAATGCAAACGGAACAC<br>GTCATTTTATTGAATGCACAGGGAGTTCCCAGGGGTAGCTGGAAAA<br>GTATGCCGCACACACGGCAGACACCCGCTTACATCTCGCGTTCTCCA<br>GTTGGCTCTTTAATGCCAAAGGACAATTATTAGTTACCCGCCGCGGAC<br>TGAGGAAAAAAGCATGGGGGGCGTGTGGACTAACTCGGTTTGTGGG |

TABLE 9-continued

| Name | Sequence |
|---|---|
| | CACCCACAACTGGGAGAAAGCAACGAAGAGGCAGTGATGGGGGGTTC<br>CCGTTATGAGCTTGGCGTCGAAATTACGCCTCCTGAATCTATCTATCC<br>TGACTTTCGCTACCGCGCCACCGATCCGAGTGGCATTGTGGAAAATG<br>AAGTGTGTCCGGTATTTGGGGCACGCACCACTAGTGCGTTACAGATC<br>AATGATGATGAAGTGATGGATTATCAATGGTGTGATTTAGCAGATGTA<br>TTACAGGGTATTGATGCCACGCCGTGGGGGTTCAGTCCGTGGATGGT<br>GATGCAGGCGACAAATCGCGAAGCCAGAAAACGATTATCTGCATTTAC<br>CCAGCTTAAATAAGGATCTAGGAGGTTACTCATATGGACTTTCCGCAG<br>CAACTCGAAGCCTGCGTTAAGCAGGCCAACCAGGGGCTGAGGGGTTT<br>TATCGCCCCACTGCCCTTTCAGAACACTCCCGTGGTCGAAACCATGC<br>AGTATGGCGCATTATTAGGTGGTAAGCGCCTGCGACCTTTCCTGGTTT<br>ATGCCACCGGTCATATGTTCGGCGTTAGCACAAAGAGGCTGGACCCA<br>CCCGCTGCCGCCGTTGAGTGTATCCACGCTTACTCATTAATTCATGAT<br>GATTTACCGGCAATGGATGATGACGATCTGCGTCGGGGTTTGCCAAC<br>CTGCCATGTGAAGTTTGGCGAAGCAAAGCGATTCTGGCTGGCGACG<br>CTTTACAAACGCTGGCGTTCTCGATTTTAAGCGATGCCGATATGCCGC<br>AAGTGTCGGACCGCGACAGAATTTGGATGATTTCTGAACTGGGGAGC<br>GCCAGTGGTATTGCCGGAATGTGCGGTGGTCAGGGATTAGATTTAGA<br>CGCGGAAGGCAAACACGTACCTCTGGACGCGCTTGAGCGTATTCATC<br>GTCATAAAACCGGCGCATTGATTCGCGCCGCCGTTCGCCTTGGTGCA<br>TTAAGCGGGGGAGATAAAGGACGTCGTGCTCTGCCGGTACTCGACAA<br>GTATGAGAGAGCATCCGCCTTCCCTTCCAGGTTCAGGATGACATCC<br>TGGATGTGGTGGGAGATACTGCAAGGTTGGGAAAACGCGAGGGTGC<br>GGACCAGCAATTGGTAAAAGTACCTACCGTGGACTTCTGGGTCTTGA<br>GCAAGCCCGGAAGAAAGCCCGGGATCTGATCGACGATGCCCGTCAG<br>TCGCTGAAACAACTGGCTGAACAGTCACTCGATACCTCGGGAGTGGA<br>AGCGCTAGCGGACTACATCATCCAGCGTAATAAATAA<br>(SEQ ID NO: 33) |
| QS operon<br>(apFAB346-<br>apFAB682-<br>Esal-B0034-<br>LuxR-<br>dblTerm) | TTGACAATTAATCATCCGGCTCGTAATGTTTGTGGAGGGCCCAAGTTC<br>ACTTAAAAAGGAGATCAAGAATGAAAGCAATTTTCGTACTGAAACATCT<br>TAATCATGCTAAGGACGTTTTCTAATGATGCTTGAACTGTTTGACGTCA<br>CTTACGAAGAACTCCAAACCACCCGTTCAGAAGAACTTTATAAACTTC<br>GCAAGAAAACATTTAGCGATCGTCTGGGATGGGAAGTCATTTGCAGTC<br>AGGGAATGGAGTCCGATGAATTTGATGGGGGGGTACACGTTATATT<br>CTGGGAATCTGCGAAGCACAATTAGTGTGCAGCGTACGTTTTACCAG<br>QCTCGATCGTCCCAACATGATCACCCACACTTTTCAGCACTGCTTCAG<br>TGATGTCACCCTCCCCGCCTATGGTACCGAATCCAGCCGTTTTTTTGT<br>CGACAAAGCCCGCGTCACGTGCGCTGTTAGGTGAGCACTACCCTATCA<br>GCCAGGTCCTGTTTTTAGCGATGGTGAACTGGGCGCAAAATAATGCC<br>TACGGCAATATCTATACGATTGTCAGCCGGGGGATGTTGAAAATTCTC<br>ACTCGCTCTCGCTGGCAAATCAAAGTCATTAAAGAGCCTTTCCTGACC<br>GAAA AGGAACGTATCTATTTGCTGACGCTGCCAGCAGGTCAGGATGA<br>CAAGCAGCAACTCGGTGGTGATGTGGTGTCACGTACGCGCTGTCGGC<br>CCGTCGCAGTCACTACCTGGCCGCTGACGCTGCCGGTCTGATACTAG<br>AGAAAGAGGAGAAATACTAGATGAAAAACATAAATGCCGACGACACAT<br>ACAGAATAATTAATAAAATTAAAGCTTGTAGAAGCAATAATGATATTAAT<br>CAATGCTTATCTGATATGACTAAAATGGTACATTGTGAATATTATTTACT<br>CGCGATCATTTATCCTCATTCTATGGTTAAATCTGATATTTCAATCCTA<br>GATAATTACCCTAAAAAATGGAGGCAATATTATGATGACGCTAATTTAA<br>TAAAATATGATCCTATAGTAGATTATTCTAACTCCAATCATTCACCAATT<br>AATTGGAATATATTTGAAAACAATGCTGTAAATAAAAAATCTCCAAATG<br>TAATTAAAGAAGCGAAAACATCAGGTCTTATCACTGGGTTTAGTTTCCC<br>TATTCATACGGCTAACAATGGCTTCGGAATGCTTAGTTTTGCACATTCA<br>GAAAAAGACAACTATATAGATAGTTTATTTTTACATGCGTGTATGAACA<br>TACCATTAATTGTTCCTTCTCTAGTTGATAATTATCGAAAAATAAATATA<br>GCAAATAATAAATCAAACAACGATTTAACCAAAAGAGAAAAAGAATGTT<br>TAGCGTGGGCATGCGAAGGAAAAAGCTCTTGGGATATTTCAAAAATAT<br>TAGGTTGCAGTGAGCGTACTGTCACTTTCCATTTAACCAATGCGCAAA<br>TGAAACTCAATACAACAAACCGCTGCCAAAGTATTTCTAAAGCAATTTT<br>AACAGGAGCAATTGATTGCCCATACTTTAAAAATTAATCTAGAGGATCC<br>AAACTCGAGTAAGGATCTCCAGGCATCAAATAAAACGAAAGGCTCAGT<br>CGAAAGACTGGGCCTTTCGTTTTATGTGTTGTTTGTCGGTGAACGCTC<br>TCTACTAGAGTCACACTGGCTCACCTTCGGGTGGGCCTTTCTGCGTTT<br>ATACCTAGG (SEQ ID NOW: 5) |
| Stabilized<br>rSFP<br>(TAIL1-<br>UPsp1-<br>TARGET8) | CTCGGTACCAAATTCCAGAAAAGAGGCCTCCCGAAAGGGGGGCCTTT<br>TTTCGTTTTGGTCCTACTGGCGCGCCTCAGTCAGAGTATTGACTTAAA<br>GTCTAACCTATAGGACCGTTACAGCCATCGAGAGCTGCGAGACTGTC<br>GCCGGATGTGTATCCGACCTGACGATGGCCCAAAAGGGCCGAAACA<br>GTCCTCTACAAATAATTTTGTTTAAATCAATTCACCTGCGTGAAAATGG<br>TAGATTTAAGAACTTTAGGATATTCACAGCAGCAACAGGAAAAGATCA<br>AGCCCAAAGTTAGGTCGACAGTCGCGCAGCATCACGAAGCGCTGGTT<br>GGTCATGGGTTTACACATGCCCACATCGTAGCCTTATCGCAGCACCCT<br>GCAGCCCTTGGCACGGTCGCCGTCAAGTACCAGGACATGATTGCGG<br>CGTTGCCGGAAGCCACACATGAGGCGATCGTCGGTGTGGGGAAACA<br>GTGGAGCGGAGCCCGAGCGCTTGAGGCCCTGTTGACGGTCGCGGGA<br>GAGCTGAGAGGGCCTCCCCTTCAGCTGGACACGGCCAGTTGCTGA |

TABLE 9-continued

| Name | Sequence |
|---|---|
| | AGATCGCGAAGCGGGGAGGAGTCACGGCGGTCGAGGCGGTGCACG<br>CGTGGCGCAATGCGCTCACGGGAGCACCCCTCAATCTGACCCCGGA<br>TCAGGTGGTTGCGATCGCCAGTAATGGGGGAGGCAAACAAGCACTCG<br>AAACTGTACAGCGCCTCCTGCCGGTACTGTGCCAAGATCATGGCTTG<br>ACGCCTGAGCAAGTCGTAGCTATTGCATCAAACATCGGTGGTAAACA<br>GGCGCTGGAAACCGTACAACGATTACTCCCTGTCTTATGCCAGGCAC<br>ACGGTCTGACCCCCGACCAAGTTGTAGCCATTGCGTCTAATGGGGGC<br>GGGAAACAGGCCCTGGAAACGGTCCAACGTCTGTTACCCGTTCTGTG<br>TCAGGCTCACGGTCTGACCCCTGCCCAGGTAGTTGCAATTGCCAGCA<br>ACATCGGCGGGAAACAAGCGCTGGAGACTGTGCAGCGTCTGCTCCCT<br>GTGTTATGCCAAGATCATGGGCTCACTCCGGATCAGGTGGTGGCCAT<br>CGCTTCCAATATTGGGGGTAAACAGGCGCTGGAGACAGTGCAACGAC<br>TTTTACCTGTTCTCTGCCAGGATCATGGTCTAACTCCCGAGCAGGTCG<br>TCGCCATCGCCTCTCATGACGGCGGGAAACAAGCGTTGGAAACTGTC<br>CAGCGACTCCTGCCGGTTTTGTGCCAGGCCCACGGGCTTACTCCTGA<br>CCAGGTAGTTGCGATCGCGTCAAATGGGGGTGGCAAACAAGCCCTCG<br>AAACCGTGCAACGCCTGCTGCCCGTCTTGTGCCAAGCTCATGGGCTG<br>ACTCCGGCGCAAGTAGTCGCGATTGCGAGCCACGATGGGGGTAAGC<br>AGGCACTGGAAACGGTTCAGCGCCTGCTCCCGGTTCTATGCCAGGAT<br>CACGGCCTGACCCCGGACCAGGTCGTCGCGATCGCGTCAAATATCG<br>GTGGCAAACAAGCTTTGGAGACAGTACAGCGCCTGTTACCAGTGCTT<br>TGCCAGGACCATGGTCTGACCCCTGAGCAAGTAGTGGCGATCGCTTC<br>TAATATTGGGGGCAAACAAGCGCTGGAAACAGTACAGCGTCTGTTAC<br>CGGTCCTATGCCAGGCACATGGCCTGACCCCTGATCAGGTGGTAGCC<br>ATTGCCAGTCATGATGGGGGTAAACAGGCGCTTGAGACTGTCCAACG<br>TCTGCTGCCGGTCCTCTGTCAGGCTCATGGCCTGACGCCAGCTCAAG<br>TCGTGGCTATCGCTTCGCATGATGGCGGAAAACAGGCACTGGAGACT<br>GTGCAGCGACTGTTGCCAGTTCTGTGTCAGGATCACGGTTTAACTCC<br>GGACCAGGTGGTCGCTATTGCGTCGAATGGGGGGGGTAAACAAGCG<br>CTGGAAACTGTGCAACGTTTGCTCCCAGTTCTGTGCCAGGACCATGG<br>GCTGACTCCGGAACAGGTAGTGGCCATTGCTTCTAATATTGGTGGGA<br>AACAGGCGCGCTGGAAACCGTGCAGCGCCTGCTTCCAGTGCTTTGCCAG<br>GCCCATGGCCTGACGCCAGATCAGGTGGTTGCTATAGCCAGCAATGG<br>CGGCGGTAAACAGGCCCTCGAAACCGTCCAGCGCCTGCTCCCTGTG<br>CTGTGCCAGGCCCATGGGCTTACCCCAGCGCAAGTAGTGGGGATTGC<br>GTCTAATATTGGTGGTAAACAGGCGTTGGAGACTGTACAACGCCTGCT<br>GCCAGTTTTATGCCAAGATCATGGTCTGACCCCTGAGCAGGTAGTGG<br>CTATTGCATCCAACAACGGGGGCAGACCCGCACTGGAGTCAATCGTG<br>GCCCAGCTTTCGAGGCCGGACCCCGCGCTGGCCGCACTCACTAATG<br>ATCATCTTGTAGCGCTGGCCTGCCTCGGCGGACGACCCGCCTTGGAT<br>GCGGTGAAGAAGGGGCTCCCGCACGCGCCTGCATTGATTAAGCGGA<br>CCAACAGAAGGATTCCCGAGAGGACATCACATCGAGTGGCAGATCAC<br>GCGCAAGTGGTCCGCGTGCTCGGATTCTTCCAGTGTCACTCCCACCC<br>CGCACAAGCGTTCGATGACGCCATGACTCAATTTGGTATGTCGAGAC<br>ACGGACTGCTGCAGCTCTTTCGTAGAGTCGGTGTCACAGAACTCGAG<br>GCCCGCTGGGGCACACTGCCTCCCGCCTCCCAGCGGTGGGACAGGA<br>TTCTCCAAGCGAGCGGTATGAAACGCGCGAAGCCTTCACCTACGTCA<br>ACTCAGACACCTGACCAGGCGAGCCTTCATGCGTTCGGAGACTCGCT<br>GGAGAGGGATTTGGACGCGCCCTCGCCCATGCATGAAGGGGACCAA<br>ACTCGCGCGTCATAATAGGTTTCAGCCAAAAAACTTAAGACCGCCGGT<br>CTTGTCCACTACCTTGCAGTAATGCGGTGGACAGGATCGGGGGTTTT<br>CTTTTCTCTTCTCAAGCTT<br>ATCCCGAAAATTTATCAAAAAGAGTATTGACTTATAACTCAACCTATAG<br>GATACTTACAGCC<br>ATCGAGAGCTGGGCCATCCTCAATGTCTACCTACTCTCACTTAGTCTT<br>ATCCTGCGGGGAATGTATACAGTTCATGTATATATTCCCCGCTTTTTTT<br>TT (SEQ ID NO: 34) |

Table 10. Sequence of Promoter and RBS variants. Pstress promoters were PCR amplified from the *E. coli* K-12 MG1655 genome.

TABLE 10

| Name | Sequence |
|---|---|
| RBS 1 | AGGAGGAA (SEQ ID NO: 6) |
| RBS 2 | TTTAAGAAGGAGATATACAT (SEQ ID NO: 35) |
| B0034 RBS | AAGAGGAGAAA (SEQ ID NO: 7) |
| $P_{LTetO-1}$ | TCCCTATCAGTGATAGAGATTGACATCCCTATCAGTGATA<br>GAGATACTGAGCAC (SEQ ID NO: 8) |

TABLE 10-continued

| Name | Sequence |
|---|---|
| $P_{Lux}$ | ACCTGTAGGATCGTACAGGTTTACGCAAGAAAATGGTTT GTTATAGTCGAATAAA (SEQ ID NO: 9) |
| PJ23115 | TTTATAGCTAGCTCAGCCCTTGGTACAATGCTAGC (SEQ ID NO: 10) |
| PJ23119 | TTGACAGCTAGCTCAGTCCTAGGTATAATACTAGT (SEQ ID NO: 36) |
| PapFAB305 | AAAAAGAGTATTGACTTCGCATCTTTTTGTACCTATAATG TGTGG (SEQ ID NO: 37) |
| PapFB339 | TTGACAATTAATCATCCGGCTCGTAATTTATGTGG (SEQ ID NO: 38) |
| PapFAB45 | TTGACAATTAATCATCCGGCTCGTAATTTATGTGG (SEQ ID NO: 38) |
| PgntK | AATCTGTGACACCGAAAATGTTAGATTTAGGTTTCACCTT GTCACCGGGCGGATCTATTTAAGCCCACAAATTTGAAGT AGCTCACACTTATACACTTAAGGCATGGATGGATATTGCT TCTGATATTGTCCGGCTGGACAATGTTACCGATAACAGT TACCCGTAACATTTTTAATTCTTGTATTGTGGGGGCACCA CT (SEQ ID NO: 11) |
| PompF | CGATCATCCTGTTACGGAATATTACATTGCAACATTTACG CGCAAAAACTAATCCGCATTCTTATTGCGGATTAGTTTTT TCTTAGCTAATAGCACAATTTTCATACTATTTTTTGGCATT CTGGATGTCTGAAAGAAGATTTTGTGCCAGGTCGATAAA GTTTCCATCAGAAACAAAATTTCCGTTTAGTTAATTTAAAT ATAAGGAAATCATATAAATAGATTAAAATTGCTGTAAATAT CATCACGTCTCTATGGAAATATGACGGTGTTCACAAAGTT CCTTAAATTTTACTTTTGGTTACATATTTTTTCTTTTTGAAA CCAAATCTTTATCTTTGTAGCACTTTCACGGTAGCGAAAC GTTAGTTTGAATGGAAAGATGCCTGCAGACACATAAAGA CACCAAACTCTCATCAATAGTTCCGTAAATTTTTATTGAC AGAACTTATTGACGGCAGTGGCAGGTGTCATAAAAAAAA CCATGAGGGTAATAAATA (SEQ ID NO: 12) |
| PyeeF | ATTAGCGGCCTCGGCTGCGGCTATTTACCCCGTTATCTG GCGCAACGTTTTCTCGATAGTGGCGCGTTAATCGAGAAG AAAGTGGTCGCCCAAACTCTCTTTGAACCCGTCTGGATT GGCTGGAACGAACAGACCGCAGGACTTGCCAGTGGCTG GTGGCGGGATGAAATTTTAGCAAATAGTGCGATCGCCG GTGTTTATGCAAAATCTGATGACGGAAAATCAGCCATTTA AAGAAAAAATTATTCTGACAAGCCTCTCATTCTCTTGTCAT TTCCCCCCCATTTAGGCACAATGCGCCGCTGTCAAAAAA TGACTAAAAACCGACGTTTCATCAGCGTCGGTTATTTTTT GCTTCAAACCAATCATTCATACCAAGAGGCCGGGCTTCG TACCGGATAGATATTTACTAAAAATCGACAGTTGTTGTCG CTGAGGAATCCAAAAAAATGGGGCAATTTTTTGCTTACG CGACGGTTATCACCGTAAAGGAGAATGACC (SEQ ID NO: 13) |
| PompT | AACGGATAAGACGGGCATAAATGAGGAAGAAATGGCGC GCCCTGCAGGATTCGAACCTGCGGCCCACGACTTAGAA GTTCCTAGAACGACATTTTAAGTCAACAACTTACCGCGC CATCTCTGCGCTCACACGTCCCACTACCTCAAAACATGT AAAGCCTTGCAAGCCATTGCGAGGCCTTATGTGTCTCAG TTTTGTCCCTCTTTTTTGTACTAAAAAACATAGTAATTGAG GATAAACCTCATGCTATTTTCGCTTATATGCCTCTAAAGG CATGGCACTTAAATAGATAAAAGCACCACAAAAGCATAAA AAAACCACACAGTAAAACCGAAATATGAAACAATAACAGA TAATTAAACCAAAAACAGATAGCGCATTGTGATAATCATT CAATACTAAACAAAATATAAACAGTGGAGCAATATGTAAT TGACTCATTAAGTTAGATATAAAAAATACATATTCAATCAT TAAAACGATTGAATGGAGAACTTTT (SEQ ID NO: 14) |
| PmetN | GGCGAAACTCTTCAACACTACCCTGCGGATGATGCGGG CAATAATAGATACCATCCAGATCGACATCTCGGTCCGCC AGCGACCAGTCCATCCACTCGGTCAGCGTTTCAAACTGT GCTTCGGTAAATTTACCGCGAGCAATGCCAGACTGGTTG GTTACTACCACCAGCGCAAAGCCCATTTTTTTTAGCTCG CGCATGGCGTCAATAACACCGTCGATAAATTCAAAGTTG TCGATCTCATGGACATAGCCGTGATCGACATTAATGGTG CCATCACGGTCAAGAAAAATTGCGGGTACGCTCTTCGCC ACCTTTTATAGCTCCTTAATAAGGCATGTGACGCTAGTAT CGCATGTTTCGACCTGCAAGAAAGTGCTCTTCGCATAAA |

TABLE 10-continued

| Name | Sequence |
|---|---|
| | CCTGATTGATTTAGACGTCTGGATGCCTTAACATCCATTT CATTGACGGCGTTGCCCGTTTCAGGCATTCGAGATGCCA CGACTAACTTAATGACGATAATAAATAATCA (SEQ ID NO: 15) |
| Pb1762 | GATTATTGAACTGTTGTTCAAGCGTGGTTTCCTGACCAAA AAAGGGCGCTATATCCACTCCACCGACGCCGGAAAAGC GCTATTCCATTCGCTGCCGGAGATGGCGACGCGACCGG ACATGACCGCGCACTGGGAATCGGTGCTGACGCAAATC AGCGAAAAGCAGTGTCGCTATCAGGACTTTATGCAGCCG CTGGTGGGGACGCTATATCAGCTTATTGATCAAGCCAAA CGTACGCCGGTGCGGCAGTTTCGCGGCATTGTGGCTCC GGGCAGTGGTGGCAGTGCTGATAAGAAAAAGGCTGCAC CGCGTAAACGTAGTGCGAAAAAAAGTCCGCCAGCAGAT GAAGTCGGAAGCGGGGCGATAGCGTAAGCGAGTGAATC TTTCGTGCTATTCGAGTCATATTCTGAAATATCCAGCGGA TCAAGAAAATTCGTTGGATATTTTTTTTGCATGGATAAAAT TATCGCCTCTAAAGTATGTAATAACAGGGAATGTG (SEQ ID NO: 16) |
| PcarA | GGTCTTTTTGATATGCGAGATGTACTTGATCTCAATAATT TGTAACCACAAAATATTTGTTATGGTGCAAAAATAACACA TTTAATTTATTGATTATAAAGGGCTTTAATTTTTGGCCCTT TTATTTTTGGTGTTATGTTTTTAAATTGTCTATAAGTGCCA AAAATTACATGTTTTGTCTTCTGTTTTTGTTGTTTTAATGT AAATTTTGACCATTTGGTCCACTTTTTTCTGCTCGTTTTTA TTTCATGCAATCTTCTTGCTGCGCAAGCGTTTTCCAGAAC AGGTTAGATGATCTTTTTGTCGCTTAATGCCTGTAAAACA TGCATGAGCCACAAAATAATATAAAAAATCCCGCCATTAA GTTGACTTTTAGCGCCCATATCTCCAGAATGCCGCCGTT TGCCAGAAATTCGTCGGTAAGCAGATTTGCATTGATTTAC GTCATCATTGTGAATTAATATGCAAATAAAGTGAGTGAAT ATTCTCTGGAGGGTGTT (SEQ ID NO: 17) |
| PfadL | CGTTTGCTCTGCTTCTGCGCGGTTTGCAAACACGCGGCT GTAAGACGCGGTGCAGTCGGAGTTGTCCATAATGGTGC CAACATCCATACAGCAGCAAACCGGGGTTTCATCAGCAC TACATTTACTCATCGTTGATTTCCTCTGTATGTGCACCCA AGGTGCCAGATAAACGTTGTGGATATTTTACGCTTCCGG AAAGTGCTGCTCCAGTTGTTAATTCTGCAAAATCGGATAA GTGACCGAAATCACACTTAAAAATGATCTAAAACAAAATT CACCCGAATCCATGAGTGCGCCACCTCCAAATTTTGCCA GCTGGATCGCGTTTCTTAGATCATATTTGAAAAAAGATAG AAACATACTTGCAACATTCCAGCTGGTCCGACCTATACT CTCGCCACTGGTCTGATTTCTAAGATGTACCTCAGACCC TACACTTCGCGCTCCTGTTACAGCACGTAACATAGTTTGT ATAAAAATAAATCATTGAGGTTATGGTC (SEQ ID NO: 18) |
| PuraA | TACCGTTGTGCCAATTCTGCGTGCGGGTCTTGGTATGAT GGACGGTGTGCTGGAAAACGTTCCGAGCGCGCGCATCA GCGTTGTCGGTATGTACCGTAATGAAGAAACGCTGGAGC CGGTACCGTACTTCCAGAAACTGGTTTCTAACATCGATG AGCGTATGGCGCTGATCGTTGACCCAATGCTGGCAACC GGTGGTTCCGTTATCGCGACCATCGACCTGCTGAAAAAA GCGGGCTGCAGCAGCATCAAAGTTCTGGTGCTGGTAGC TGCGCCAGAAGGTATCGCTGCGCTGGAAAAAGCGCACC CGGACGTCGAACTGTATACCGCATCGATTGATCAGGGAC TGAACGAGCACGGATACATTATTCCGGGCCTCGGCGAT GCCGGTGACAAAATCTTTGGTACGAAATAAAGAATAAAA ATAATTAAAGCCGACTTTAAGAGTCGGCTTTTTTTTGAGT AAAGCGCCTATAACACATAATACAGAGGATAATACT (SEQ ID NO: 19) |
| PgrxA | CGGAAATGGGTTCATCAGTGAAATGGCGAATGGAGCGA TGGCCACAAATAAGTTCAATGGTTGGCGTCATTATCTTTT TCTCTTTCTGAACGTGAATATTGCGGTGGACGGTTCATC AGCTGTGGGGCAAGACGTTTTGCCACCTGAAGAATAACC ACCACCGCAGCGGGAAGCATGAGCAAAACACCGAGAAA AATCATCAGAATCTGCACTTCTGGCCGAGAAAATGGCTC AGGCAGCGACAGGGAGTCGCTTACCGACAGCAGCGCCA CCGCCAGTAGCATCATTCCGATAAATTCCAGTATCAACA CGCCTTTAGGCAATTTACCGATCGCGCGCATACGCTTCC CTCTGCAAAGTGAGCCTTCAGTCTAAAACTTTTCACTGTA TTGTGTTTAACAGTTATAGCTTTTAGCAATTAATGCAACA GGTTAAACCTACTTTCAGCGAATACATTTTAGCGTGATCA TTACAGGCATAAATCTATGAGGAGAGAAATA (SEQ ID NO 20) |

TABLE 10-continued

| Name | Sequence |
|---|---|
| PmtgA | CATTTAACTGGCGAAGCGATGACGGAAACGCGCAATGT GCTGATTGAAGCGGCACGAATAACGCGCGGTGAAATCC GTCCTCTGGCCCAGGCCGATGCCGCTGAACTGGATGCG TTGATTGTGCCGGGGGGGTTTGGCGCGGCGAAGAATTT AAGCAATTTTGCCAGTCTTGGTAGCGAATGCACCGTTGA CCGTGAATTAAAGGCGCTGGCACAAGCGATGCATCAGG CCGGAAAACCGCTTGGTTTTATGTGTATTGCCCCGGCGA TGCTGCCGAAAATTTTCGATTTCCCGCTGCGTTTGACCA TCGGTACTGATATCGATACCGCAGAAGTGCTGGAAGAGA TGGGCGCGGAGCATGTGCCGTGTCCTGTCGATGATATC GTGGTTGATGAAGACAATAAGATTGTCACCACCCCAGCA TATATGCTGGCGCAGAACATTGCAGAAGCGGCGAGCGG CATTGATAAGCTGGTTTCCCGCGTGCTGGTTCTGGCTGA (SEQ ID NO: 21) |
| PybcU | TCAAGAAATACGCATCTTATAGAAACGTCCTATGATAGGT TGAAATCAAGAGAAATCACATTTCAGCAATACAGGGAAA ATCTTGCTAAAGCAGGAGTTTTCCGATGGATTACAAATAT CCACGAACATAAAAGATATTACTATACCTTTGATAATTCA TTACTATTTACTGAGAGCATTCAGAACACTACACAAATCT TTCCACGCTAAATCATAACGTCCGGTTTCTTCCGTGTCA GCACCGGGGTGTTGGCATAATACAATACATGTACGCGCT AAACCCTGTGTGCATCGTTTTTAATTATTCCCGGACACTC CCGCAGAGAAGTTCCCCGTCAGGGCTGTGGACATAGTT AATCCGGGAATACAATGACGATTCATCGCACCTGGCATA CATTAATAAATATTAACAATATGAAATTTCAACTCATTGTT TAGGGTTTGTTTAATTTTCTACACATACGATTCTGCGAAC TTCAAAAAGCATCGGGAATAACACC (SEQ ID NO: 22) |
| PycbS | CAGACTTTATTATTACACCACCGCTATTTGTGCTGAATCC GGCAAATGAGAATCTGTTACGCATTATGTACATTGGAGC GCCGTTGGCGAAAGACAGAGAAACCCTTTTCTTCACTAG CGTACGGGCAGTCCCTTCAACAACGAAGCGGAAAGAGG GAAATACCCTGAAGATTGCCACACAAAGCGTCATCAAAC TTTTCTGGCGACCAAAAGGTTTAGCGTATCCCTTAGGCG AGGCTCCGGCGAAACTGCGTTGCACTTCGTCAGCTGAC ATGGTTACGGTCAGTAACCCAACACCTTATTTCATTACCC TGACAGACCTGAAAATAGGTGGAAAAGTAGTTAAAAATC AAATGATTTCCCCCTTTGATAAATACCAATTTTCTCTGCC AAAGGGGGCCAAAAATAGCAGCGTAACGTATCGAACCAT CAATGACTACGGGGCGGAAACGCCGCAACTCAACTGTA AATCGTAAGCCGTCTTCAGTTAAGAGAGCGAG (SEQ ID NO: 23) |
| PyhjX | TAGGCTGGCGTGTTGACTCCCGGCTTGGCGATCTCCGA CCCTGGGCGCAAATCAGCTATAACCAGCAATTTGGCGAG AATATCTGGAAGGCGCAATCAGGCCTGAGCCGGATGAC GGCGACAAACCAGAACGGCAACTGGCTGGATGTCACCG TAGGCGCTGATATGTTGCTCAATCAAAATATTGCCGCCT ATGCCGCGCTAACTCAGGCAGAAAATACCACTAATAATA GCGACTATCTGTATACGATGGGGGTTAGCGCCAGATTTT AACGTAACAGTCACAATTGAAACCATTAAATAACAATAGT TGTGGCGATAGTGGGTGCTAACTTACCAAATAATAAATTT GGTGAATAATTGTCGCGTCATTCATTCCTGAACTAAGGC ATTTCATTCCGTTCTGATGGCATTTCATGCCGTTTTTCCC CAGGCATAAAGTGCACTTCGTTATGGTTGTCGGCAGAGA TTTTTCCTTTTTATTACTGCAGGAATACTGCC (SEQ ID NO: 24) |
| PatoA | GCGTTTGTTGATACCGGCATCGGTCCGCTCATCGTCAAT GGTCGAGTCCGCAAAGTGATTGCTTCACATATCGGCACC AACCCGGAAACAGGTCGGCGCATGATATCTGGTGAGAT GGACGTCGTTCTGGTGCCGCAAGGTACGCTAATCGAGC AAATTCGCTGTGGTGGAGCTGGACTTGGTGGTTTTCTCA CCCCAACGGGTGTCGGCACCGTCGTAGAGGAAGGCAAA CAGACACTGACACTCGACGGTAAAACCTGGCTGCTCGAA CGCCCACTGCGCGCCGACCTGGCGCTAATTCGCGCTCA TCGTTGCGACACACTTGGCAACCTGACCTATCAACTTAG CGCCCGCAACTTTAACCCCCTGATAGCCCTTGCGGCTGA TATCACGCTGGTAGAGCCAGATGAACTGGTCGAAACCG GCGAGCTGCAACCTGACCATATTGTCACCCCTGGTGCC GTTATCGACCACATCATCGTTTCACAGGAGAGCAAATA (SEQ ID NO: 25) |
| Pb2970 | GGATTATTAAGTGGCTGTGCCAGCCATAATGAAAATGCC AGTTTACTGGCGAAAAAACAGGCGCAAAATATCAGCCAA AACCTGCCGATTAAATCTGCGGGATATACCTTAGTGCTG GCGCAAAGTAGCGGCACAACGGTAAAAATGACCATTATC |

TABLE 10-continued

| Name | Sequence |
|---|---|
| | AGCGAAGCGGGTACACAAACCACGCAGACGCCTGACGC<br>CTTTTTAACCAGCTATCAACGACAAATGTGCGCTGACCC<br>GACGGTGAAATTAATGATCACTGAGGGAATTAATTACAG<br>CATAACGATTAATGATACACGTACAGGTAACCAGTATCA<br>GCGGAAACTGGATCGTACCACCTGTGGAATAGTCAAAGC<br>ATAACGTCGGGTAGATATAAATTGGCGCGGGTTGTTTTT<br>CGTGACGCACGAATTTATCTCATTCAATGGCTGACAAAA<br>ATTCGTCACACTCTTAACCAGAGACAATCTCTTAATACAG<br>ACAAAGAGCATCTGCGAAAAATTGCACGCGGG (SEQ ID<br>NO: 26) |
| PecpD | CGGGCTGGAGGACGACGGTCAGATCAGCGCCAAAATCA<br>ACGGGCGGATTTTCCCGCTTAACGGCAAGCGTAACTATC<br>TCCCGCTCTCTCCCTATGGAAGATATGAGGTGGAGTTAC<br>AGAACAGCAAAAACTCACTCGACAGTTACGATATCGTCA<br>GCGGCCGCAAAAGTCGTCTGACTCTCTATCCAGGCAATG<br>TCGCTGTCATTGAGCCAGAGGTGAAGCAGATGGTTACC<br>GTCTCCGGTCGTATCCGTGCGGAAGACGGCACACTGCT<br>GGCTAACGCACGGATTAACAACCATATCGGCCGAACCC<br>GAACCGATGAAAACGGCGAGTTTGTCATGGACGTGGATA<br>AGAAATACCCCACTATCGATTTTCGCTACAGTGGCAATAA<br>AACCTGCGAAGTGGCTCTGGAACTCAACCAGGCGCGCG<br>GTGCCGTCTGGGTCGGTGATGTGGTCTGCAGCGGCCTC<br>TCATCGTGGGCGGCGGTGACGCAGACAGGAGAAGAGA<br>(SEQ ID NO: 27) |
| PfecA | GGGACAGAATTTACCGTCCGCCAGCAGGATAATTTCACG<br>CAGCTTGACGTGCAGCAGCACGCTGTGGAAGTGCTTCT<br>CGCCAGTGCCCCCGCGCAAAAACGCATCGTGAACGCTG<br>GTGAAAGCCTGCAGTTCAGCGCCTCTGAGTTTGGCGCA<br>GTGAAACCGCTGGATGACGAGAGTACAAGCTGGACGAA<br>GGACATCCTGAGCTTCAGCGATAAACCGCTGGGTGAGG<br>TGATAGCCACGCTAACCCGTTACCGCAACGGCGTGCTG<br>CGCTGCGATCCCGCCGTTGCCGGGCTGCGCCTGAGCG<br>GGACGTTCCCGCTGAAAAATACCGATGCGATCCTGAACG<br>TTATCGCGCAAACGCTTCCCGTTAAAATTCAGTCTATTAC<br>GCGGTACTGGATAAACATTTCACCACTGTAAGGAAAATA<br>ATTCTTATTTCGATTGTCCTTTTTACCCTTCTCGTTCGACT<br>CATAGCTGAACACAACAAAAATGATGATGGGGAAGGT<br>(SEQ ID NO: 28) |
| PgadE | TTAATACTCTCTCCGCTACGCAGTGTTGTAGATCAATTGC<br>GCACTATCATTGAAATAATTACCTGCTAGTGATTATTTCA<br>ACCTACTGAATTTCATCTAATTTTTTTCACTCTATGGCAAA<br>TTAGCCATTTCAAACATTATCATGGCTGATATTTTCCGTA<br>GTCAGGTTTAATGTTTTAAAAGTGCTGTGGGAAAGTGAA<br>CAAAGAGTTCCGTAAGCGTTGATGCTATGGGCGGTTAAA<br>TAAGTAATCCGGGTTCATTTTTTTGCAACTGGCGTTGATT<br>ACATTGCATAAATATCCGTGTCTCCAGACGCTATATAAAA<br>ACCTGAAGACATGAATGCGTTATTTACTCAGGTAATTTCA<br>ATGCGTTAAAAGAAAGCTGGCAATCCAATTGCCAGCTTA<br>AGTCGAAACAAGGAGACTCGATATTTAAATCGGATTACAT<br>TTTAACTTTAGTAATATTCTTCAGAGATCACAAACTGGTTA<br>TTGATAACTTATTCTTGGGCAGTAATCCGCAAACGTTAAC<br>TTTTTGTTTGCTATTTACAAGCTGATAACAACCAGGAATC<br>TTACTTAGGATCAATATATGGAGTGCGTGATGGATAAATC<br>TGAAGTATTGATTAGTGTTAATAGACGTATTAGTTCACGA<br>AGGGTAAAGTTCTTATAGGCGTTTACTATATTGAACAACG<br>ATTCGGACAAGGATGTAAATAATGAAAAGGATGACATATT<br>CGAAACGA (SEQ ID NO: 31) |

Table 11. Strains used in this study. Strains containing genomic insertions were created using the clonetegration platform[61] to integrate the inserts using the HK022 plasmid into the attB site of the *E. coli* genome. The *E. coli* DH1 QS strain was generated using 2 Red recombineering[62] to insert the EsaI-LuxR operon at the attB site.

TABLE 11

| Strain | Strain Information | Genomic Insertion |
|---|---|---|
| *E. coli* Tax1 | *E. coli* containing genome integrated pathway enzymes for taxadiene biosynthesis (gift from Manus Bio) | N/A |
| *E. coli* Tax1-QS | Derived from *E. coli* Tax1 | attB::EsaI-LuxR(apFAB346-apFAB382-EsaI-LuxR-dblTerm - KmR) |
| *E. coli* DH1 | F-λ-endA1 recA1 relA1 gyrA96 thi-1 glnV44 hsdR17(rK-mK-) | N/A |
| *E. coli* DH1 QS | Derived from *E. coli* DH1 | attB::EsaI-LuxR(apFAB346-apFAB382-EsaI-LuxR-dblTerm - KmR) |

TABLE 11-continued

| Strain | Strain Information | Genomic Insertion |
|---|---|---|
| *E. coli* TG1 | glnV44 thi-1 Δ(lac-proAB) galE15 galK16 R(zgb-210::Tn10) TetS endA1 fhuA2 Δ(mcrB-hsdSM)5, (rK-mK-) F'[traD36 proAB+ laclq lacZΔM15] | N/A |

Table 12. Basal R-media recipe, per liter. Adapted from Biggs et al., 2016.43

TABLE 12

| Component | Final media concentration (g/l) |
|---|---|
| $KH_2PO_4$ | 13.3 |
| $(NH_4)_2HPO_4$ | 4 |
| Citric Acid Monohydrate | 1.7 |
| Yeast Extract | 5 |
| HEPES | 23.83 |

Table 13. 1000X Trace Element (TE) solution, per liter. Adapted from Biggs et al., 201643.

TABLE 13

| Component | Final media concentration (mg/l) |
|---|---|
| EDTA | 8.4 |
| $H_3BO_3$ | 3.0 |
| $Zn(CH_3COO)_2$ | 8.0 |
| $CoCl_2$•$6H_2O$ | 4.6 |
| CuCl2•$2H_2O$ | 1.9 |
| $MnCl_2$•$4H_2O$ | 24.0 |
| $Na_2MoO_4$•$2H_2O$ | 2.9 |

Table 14. Complete R-media compositions utilized for hungate tube fermentations. Adapted from Biggs et al., 201643

TABLE 14

| Component | Amount (mL) |
|---|---|
| Basal R-media | 35 |
| 32% v/v Glycerol | 1.3 |
| 1M $MgSO_4$ | 0.171 |
| 0.1M Ferric Citrate | 0.0858 |
| 1000× TE Solution | 0.035 |
| 1000× Antibiotic | 0.035 |
| 1M Thiamine HCl | 0.00047 |

Table 15. P values for Welch's t-tests (Two-tailed. Unequal variances) in FIG. 16B.

TABLE 15

| Condition | P value |
|---|---|
| PatoA | 2.4E−09 |
| PyhjX | 5.7E−07 |
| PycbS | 2.6E−06 |
| PuraA | 5.4E−09 |
| PgrxA | 1.3E−09 |
| PfecA | 1.4E−11 |
| PecpD | 7.9E−08 |
| PmtgA | 6.3E−03 |
| PyeeF | 7.8E−11 |
| PfadL | 4.6E−09 |
| PcarA | 4.0E−09 |
| Pb1762 | 3.5E−09 |
| PgntK | 1.5E−08 |
| PybcU | 1.2E−07 |

TABLE 15-continued

| Condition | P value |
|---|---|
| PmetN | 6.3E−09 |
| PompT | 2.9E−06 |
| PompF | 2.1E−07 |

REFERENCES FOR EXAMPLE 4

1. Keasling, J. D. (2010) Manufacturing molecules through metabolic engineering. Science 330, 1355-1358. doi: 10.1126/science.1193990.
2. Nielsen, J. and Keasling, J. D. (2016) Engineering Cellular Metabolism. Cell 164, 1185-1197. doi: 10.1016/j.cell.2016.02.0043.
3. Isabella, V. M., Ha, B. N., Castillo, M. J., Lubkowicz, D. J., Rowe, S. E., Millet, Y. A., Anderson, C. L., Li, N., Fisher, A. B., West, K. A., Reeder, P. J., Momin, M. M., Bergeron, C. G., Guilmain, S. E., Miller, P. F., Kurtz, C. B., and Falb, D. (2018) Development of a synthetic live bacterial therapeutic for the human metabolic disease phenylketonuria. Nat. Biotechnol. 36, 857-864. doi: 10.1038/nbt.4222.
4. Watstein, D. M., McNerney, M. P. and Styczynski, M. P. (2015) Precise metabolic engineering of carotenoid biosynthesis in *Escherichia coli* towards a low-cost biosensor. Metab. Eng. 31, 171-180. doi: 10.1016/j.ymben.2015.06.007.
5. Biggs, B. W., De Paepe, B., Santos, C. N. S., De Mey, M. and Ajikumar, P.K. (2014) Multivariate modular metabolic engineering for pathway and strain optimization. Curr. Opin. Biotechnol. 29, 156-162. doi: 10.1016/j.copbio.2014.05.005.
6. Sun, J., Jeffryes, J. G., Henry, C. S., Bruner, S. D. and Hanson, A. D. (2017) Metabolite damage and repair in metabolic engineering design. Metab. Eng. 44, 150-159. doi: 10.1016/j.ymben.2017.10.006.
7. Rugbjerg, P. and Sommer, M. O. A. (2019) Overcoming genetic heterogeneity in industrial fermentations. Nat. Biotechnol. 37, 869-876. doi: 10.1038/s41587-019-0171-6.
8. Holtz, W. J. and Keasling, J. D. (2010) Engineering Static and Dynamic Control of Synthetic Pathways. Cell 140, 19-23. doi: 10.1016/j.cell.2009.12.029.
9. Brockman, I. M. and Prather, K. L. J. (2015) Dynamic metabolic engineering: New strategies for developing responsive cell factories. Biotechnol. J. 10, 1360-1369. doi: 10.1002/biot.201400422.
10. Tan, S. Z. and Prather, K. L. (2017) Dynamic pathway regulation: recent advances and methods of construction. Curr. Opin. Chem. Biol. 41, 28-35. doi: 10.1016/j.cbpa.2017.10.004.
11. Alper, H., Fischer, C., Nevoigt, E. and Stephanopoulos, G. (2005) Tuning genetic control through promoter engineering. Proc. Natl. Acad. Sci. 102, 12678-12683. doi: 10.1073/pnas.0504604102.
12. Jensen, P. R. and Hammer, K. (1998) The sequence of spacers between the consensus sequences modulates the strength of prokaryotic promoters. Appl. Environ. Microbiol. 64, 82-87. doi: 10.1128/AEM.64.1.82-87.1998.
13. Pfleger, B. F., Pitera, D. J., Smolke, C. D. and Keasling, J. D. (2006) Combinatorial engineering of intergenic regions in operons tunes expression of multiple genes. Nat. Biotechnol. 24, 1021-2032. doi: 10.1038/nbt1226.

14. Barrick, D., Villanueba, K., Childs, J., Kalil, R., Schneider, T. D., Lawrence, C. E., Gold, L., and Stormo, G. D. (1994) Quantitative analysis of ribosome binding sites in *E. coli*. Nucleic Acids Res. 22, 1287-1295. doi: 10.1093/nar/22.7.1287.
15. Mutalik, V. K. Guimaraes, J. C., Cambray, G., Lam, C., Christoffersen, M. J., Mai, Q. A., Tran, A. B., Paul, M., Keasling, J. D., Arkin, A. P., and Endy, D. (2013) Precise and reliable gene expression via standard transcription and translation initiation elements. Nat. Methods. doi: 10.1038/nmeth.2404.
16. Salis, H. M., Mirsky, E. A. and Voigt, C. A. (2009) Automated design of synthetic ribosome binding sites to control protein expression. Nat. Biotechnol. 27, 946-950. doi: 10.1038/nbt.1568.
17. Gottesman, S. (2019) Trouble is coming: Signaling pathways that regulate general stress responses in bacteria. J. Biol. Chem. 294, 11685-11700. doi: 10.1074/jbc.REV119.005593.
18. Ceroni, F. Boo, A., Furini, S., Gorochowski, T. E., Borkowski, O., Ladak, Y. N., Awan A. R., Gilbert, C., Stan, G. B., and Ellis, T. (2018) Burden-driven feedback control of gene expression. Nat. Methods 15, 387-393. doi: 10.1038/nmeth.463519.
19. Dahl, R. H. Zhang, F., Alonso-Gutierrez, J., Baidoo, E., Batth, T. S., Redding-Johanson, A. M., Petzold, C. J., Mukhopadhyay, A., Lee, T. S., Adams, P. D., and Keasling, J. D. (2013) Engineering dynamic pathway regulation using stress-response promoters. Nat. Biotechnol. 31, 1039-1046. doi: 10.1038/nbt.2689.
20. Boyarskiy, S., Davis López, S., Kong, N. and Tullman-Ercek, D. (2016) Transcriptional feedback regulation of efflux protein expression for increased tolerance to and production of n-butanol. Metab. Eng. 33, 130-137. doi: 10.1016/j.ymben.2015.11.00521.
21. Zhang, F., Carothers, J. M. and Keasling, J. D. (2012) Design of a dynamic sensor-regulator system for production of chemicals and fuels derived from fatty acids. Nat. Biotechnol. 30, 354-359. doi: 10.1038/nbt.2149.
22. Xu, P., Li, L., Zhang, F., Stephanopoulos, G. and Koffas, M. (2014) Improving fatty acids production by engineering dynamic pathway regulation and metabolic control. Proc. Natl. Acad. Sci. U.S.A. 111, 11299-11304. doi: 10.1073/pnas.1406401111.
23. Moser, F. Borujeni, A. E., Ghodasara, A. N., Cameron, E., Park, Y., and Voigt, C. A. (2018) Dynamic control of endogenous metabolism with combinatorial logic circuits. Mol. Syst. Biol. 14, e8605. doi: 10.15252/msb.20188605.
24. Carothers, J. M., Goler, J. A., Juminaga, D. and Keasling, J. D. (2011) Model-driven engineering of RNA devices to quantitatively program gene expression. Science 334, 1716-1719. doi: 10.1126/science.1212209.
25. Farmer, W. R. and Liao, J. C. (2000) Improving lycopene production in *Escherichia coli* by engineering metabolic control. Nat. Biotechnol. 1 18, 533-537. doi: 10.1038/75398.
26. Venayak, N., Anesiadis, N., Cluett, W. R. and Mahadevan, R. (2015) Engineering metabolism through dynamic control. Curr. Opin. Biotechnol. 34, 142-152. doi: 10.1016/j.copbio.2014.12.022
27. Segall-Shapiro, T. H., Sontag, E. D. and Voigt, C. A. (2018) Engineered promoters enable constant gene expression at any copy number in bacteria. Nat. Biotechnol. 36, 352-358. doi: 10.1038/nbt.4111.
28. Jones, J. A., Vernacchio, V. R., Lachance, D. M., Leboish, M., Fu, Li., Shirke, A. N., Schultz, V. L., Cress, B., Linhardt, R. J., and Koffas, M. A. G. (2015) EPathOptimize: A combinatorial approach for transcriptional balancing of metabolic pathways. Sci. Rep. 5, 11301. doi: 10.1038/srep11301.
29. Chappell, J., Takahashi, M. K. and Lucks, J. B. (2015) Creating small transcription activating RNAs. Nat. Chem. Biol. 11, 214-220. doi: 10.1038/nchembio.1737.
30. Chappell, J., Westbrook, A., Verosloff, M. and Lucks, J. B. (2017) Computational design of small transcription activating RNAs for versatile and dynamic gene regulation. Nat. Commun. 8, 1051. doi: 10.1038/s41467-017-01082-6.
31. Lutz, R. and Bujard, H. (1997) Independent and tight regulation of transcriptional units in *Escherichia coli* via the LacR/O, the TetR/O and AraC/11-12regulatory elements. Nucleic Acids Res. 25, 1203-1210. doi: 10.1093/nar/25.6.1203.
32. Feldman, M. F., Wacker, M., Hernandez, M., Hitchen, P. G., Marolda, C. L., Kowarik, M., Morris, H. R., Dell, A., Valvano, M. A., and Aebi, M. (2005) Engineering N-linked protein glycosylation with diverse O antigen lipopolysaccharide structures in *Escherichia coli*. Proc. Natl. Acad. Sci. U.S.A. 102, 3016-3021. doi: 10.1073/pnas.0500044102.
33. Wong Ng, J., Chatenay, D., Robert, J. and Poirier, M. G. (2010) Plasmid copy number noise in monoclonal populations of bacteria. Phys. Rev. E. Stat. Nonlin. Soft. Matter Phys. 81, e011909. doi: 10.1103/PhysRevE.81.011909.
34. Lopilato, J., Bortner, S. and Beckwith, J. (1986) Mutations in a new chromosomal gene of *Escherichia coli* K-12, pcnB, reduce plasmid copy number of pBR322 and its derivatives. Mol. Genet. Genomics 205, 285-290. doi: 10.1007/BF00430440.
35. Lin-Chao, S. & Bremer, H. Effect of the bacterial growth rate on replication control of plasmid pBR322 in *Escherichia coli*. Mol. Genet. Genomics 203, 143-149 (1986). doi: 10.1007/BF00330395
36. Wegrzyn, G. (1999) Replication of plasmids during bacterial response to amino acid starvation. Plasmid 41, 1-16. doi: 10.1006/plas. 1998.1377.
37. Lin-Chao, S., Chen, W.-T and Wong, T.-T. (1992) High copy number of the pUC plasmid results from a Rom/Rop-suppressible point mutation in RNA II. Mol. Microbiol. 6, 3385-3393. doi: 10.1111/j.1365-2958.1992.tb02206.x.
38. Cheah, U. E., Weigand, W. A. and Stark, B. C. (1987) Effects of recombinant plasmid size on cellular processes in *Escherichia coli*. Plasmid 18, 127-134. doi: 10.1016/0147-619X (87) 90040-0.
39. Corchero, J. L. and Villaverde, A. (1998) Plasmid maintenance in *Escherichia coli* recombinant cultures is dramatically, steadily, and specifically influenced by features of the encoded proteins. Biotechnol. Bioeng. 58, 625-632. doi: 10.1002/(SICI) 1097-0290 (19980620) 58:6<625::AID-BIT8>3.0.CO;2-K.
40. Stueber, D. and Bujard, H. (1982) Transcription from efficient promoters can interfere with plasmid replication and diminish expression of plasmid specified genes. EMBO J. 1, 1399-1404. doi: 10.1002/j.1460-2075.1982.tb01329.x.
41. Peterson, J. and Phillips, G. J. (2008) New pSC101-derivative cloning vectors with elevated copy numbers. Plasmid 59, 193-201. doi: 10.1016/j.plasmid.2008.01.004.
42. Martin, V. J. J., Pitera, D. J., Withers, S. T., Newman, J. D. and Keasling, J. D. (2003) Engineering a mevalonate pathway in *Escherichia coli* for production of terpenoids. Nat. Biotechnol. 21, 796-802. doi: 10.1038/nbt833.

43. Biggs, B. W., Lim, C. G., Sagliani, K., Shankar, S., Stephanopoulos, G., De Mey, M., and Ajikumar, P. K. (2016) Overcoming heterologous protein interdependency to optimize P450-mediated Taxol precursor synthesis in *Escherichia coli*. Proc. Natl. Acad. Sci. U.S.A. 113, 3209-3214. doi: 10.1073/pnas.1515826113.
44. Kanda, Y., Nakamura, H., Umemiya, S., Puthukanoori, R. K., Appala, V. R. M., Gaddamaniugu, G. K., Paraselli, B. R., and Baran, P. S. (2020) Two-Phase Synthesis of Taxol. J. Am. Chem. Soc. 142, 10526-10533. doi: 10.1021/jacs.0c03592
45. Van Dien, S. (2013) From the first drop to the first truckload: Commercialization of microbial processes for renewable chemicals. Curr. Opin. Biotechnol. 24, 1061-1068. doi: 10.1016/j.copbio.2013.03.002.
46. Weber, W. and Fussenegger, M. (2007) Inducible product gene expression technology tailored to bioprocess engineering. Curr. Opin. Biotechnol. 18, 399-410. doi: 10.1016/j.copbio.2007.09.00.
47. Papenfort, K. and Bassler, B. L. (2016) Quorum sensing signal-response systems in Gram-negative bacteria. Nat. Rev. Microbiol. 14, 576-588. doi: 10.1038/nrmicro.2016.89
48. Tsao, C. Y., Hooshangi, S., Wu, H. C., Valdes, J. J. and Bentley, W. E. (2010) Autonomous induction of recombinant proteins by minimally rewiring native quorum sensing regulon of *E. coli*. Metab. Eng. 12, 291-297. doi: 10.1016/j.ymben.2010.01.002.
49. Gupta, A., Reizman, I. M. B., Reisch, C. R. and Prather, K. L. J. (2017) Dynamic regulation of metabolic flux in engineered bacteria using a pathway-independent quorum-sensing circuit. Nat. Biotechnol. 35, 273-279. doi: 10.1038/nbt.3796.
50. Kim, E. M. Woo, H. M., Tian, T., Yilmaz, S., Javidpour, P., Keasling, J. D., and Lee, T. S. (2017) Autonomous control of metabolic state by a quorum sensing (QS)-mediated regulator for bisabolene production in engineered *E. coli*. Metab. Eng. 44, 325-336. doi: 10.1016/j.ymben.2017.11.004.
51. Engebrecht, J. and Silverman, M. (1984) Identification of genes and gene products necessary for bacterial bioluminescence. Proc. Natl. Acad. Sci. U.S.A. 81, 4154-4158. doi: 10.1073/pnas.81.13.4154.
52. Minogue, T. D., Wehland-Von Trebra, M., Bernhard, F. and Von Bodman, S. B. (2002) The autoregulatory role of EsaR, a quorum-sensing regulator in *Pantoea stewartii* ssp. *stewartii*: Evidence for a repressor function. Mol. Microbiol. 44, 1625-1635. doi: 10.1046/j.1365-2958.2002.02987.x.
53. Malinowski, J. J. (2001) Two-phase partitioning bioreactors in fermentation technology. Biotechnol. Adv. 19, 525-538. doi: 10.1016/S0734-9750 (01) 00080-5.
54. Green, A. A., Silver, P. A., Collins, J. J. and Yin, P. (2014) Toehold switches: De-novo-designed regulators of gene expression. Cell 159, 925-939. doi: 10.1016/j.cell.2014.10.002
55. Na, D., Yoo, S. M., Chung, H., Park, H., Park, J. H., and Lee, S. Y. (2013) Metabolic engineering of *Escherichia coli* using synthetic small regulatory RNAs. Nat. Biotechnol. 31, 170-174. doi: 10.1038/nbt.2461
56. Takahashi, M. K. and Lucks, J. B. (2013) A modular strategy for engineering orthogonal chimeric RNA transcription regulators. Nucleic Acids Res. 41, 7577-7588. doi: 10.1093/nar/gkt452
57. Westbrook, A. M. and Lucks, J. B. (2017) Achieving large dynamic range control of gene expression with a compact RNA transcription-translation regulator. Nucleic Acids Res. 45, 5614-5624. doi: 10.1093/nar/gkx215
58. Qi, L. S., Larson, M. H., Gilbert, L. A., Doudna, J. A., Weissman, J. S., Arkin, A. P., and Lim, W. A. (2013) Repurposing CRISPR as an RNA-guided platform for sequence-specific control of gene expression. Cell 152, 1173-1183. doi: 10.1016/j.cell.2013.02.022.
59. Ajikumar, P. K., Xiao, W. H., Tyo, K. E. J., Wang, Y., Simeon, F., Leonard, E. Much, O., Phon, T. H., Pfeifer, B., and Stephanopoulos, G. (2010) Isoprenoid pathway optimization for Taxol precursor overproduction in *Escherichia coli*. Science 330, 70-74. doi: 10.1126/science.1191652.
60. Smanski, M. J., Bhatia, S., Zhao, D., Park. Y. J., Woodruff, L. B. A., Giannoukos, G., Ciulla, D., Busby, M., Calderon, J., Nicol,, R., Gordon, D. B., Densmore, D., and Voigt, C. A. (2014) Functional optimization of gene clusters by combinatorial design and assembly. Nat. Biotechnol. 32, 1241-1249. doi: 10.1038/nbt.3063.
61. St-Pierre, F., Cui, L. Priest, D. G., Endy, D., Dodd, I. B., and Shearwin, K. E. (2013) One-step cloning and chromosomal integration of DNA. ACS Synth. Biol. 2, 537-541. doi: 10.1021/sb400021j.
62. Thomason, L. C., Sawitzke, J. A., Li, X., Costantino, N. and Court, D. L. (2014) Recombineering: Genetic engineering in bacteria using homologous recombination. Curr. Protoc. Mol. Biol. 106, 1-39. doi: 10.1002/0471142727. mb0116s106.
63. Meier, I., Wray, L. V and Hillen, W. (1988) Differential regulation of the Tn10-encoded tetracycline resistance genes tetA and tetR by the tandem tet operators $O_1$ and 02. EMBO J. 7, 567-572. doi: 10.1002/j.1460-2075.1988.tb02846.x.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A riboregulated switchable feedback promoter system comprising:

(a) an expression cassette comprising a stress responsive promoter operably linked to DNA encoding an RNA switch located 3' of the promoter, and a target gene or operon located 3' of the DNA encoding the RNA switch, wherein the RNA switch comprises a transcriptional terminator and a target sequence for a small transcription activating RNA (STAR RNA), wherein the stress responsive promoter is transcriptionally regulated by an endogenous temporal gene expression network; and (b) an inducible promoter operably linked to DNA encoding the STAR RNA.

2. The system of claim 1, wherein the stress responsive promoter is selected from promoters for any of gntK, yhjX, uraA, ycbS, ataA, mtgA, ecpD, grxA, ybcU, fecA, fadL, b1762, carA, ompT, yeeF, metN, ompF, and gadE.

3. The system of claim 1, wherein the stress responsive promoter is regulated by an effector selected from the group consisting of metabolites, responses to cellular conditions, extracellular quorum-sensing signals, membrane stresses, unfolded protein stress responses, and stresses caused by reactive oxygen species (ROS).

4. The system of claim 1, wherein the inducible promoter operably linked to the DNA encoding the STAR RNA is contained in a second expression cassette.

5. The system of claim 1, wherein the inducible promoter operably linked to the DNA encoding the STAR RNA is induced by an effector selected from the group consisting of a chemical inducer, cell density, light, temperature, pH, $O_2$ levels, and substrate accumulation, and an endogenous temporal gene expression network.

6. The system of claim 5, wherein the effector is selected from n-butanol accumulation, glucose depletion, geranylgeranyl pyrophosphate accumulation, farnesyl pyrophosphate accumulation, anhydrotetracycline (aTc), isopropyl β-D-1-thiogalactopyranoside (IPTG), L-arabinose, light, temperature, $O_2$, pH, light, ion levels, membrane stresses, unfolded protein stress responses, stress caused by reactive oxygen species (ROS), and N-acyl-homoserine lactone (AHL) accumulation at high cell density.

7. The system of claim 1, wherein the expression cassette is present in one or more vectors.

8. A cell comprising the system of claim 1.

9. The cell of claim 8, wherein the cell is a prokaryotic cell.

10. The cell of claim 8, wherein the system is integrated into the genome of the cell.

* * * * *